US010682399B2

(12) United States Patent
Hunt et al.

(10) Patent No.: US 10,682,399 B2
(45) Date of Patent: Jun. 16, 2020

(54) TARGET PEPTIDES FOR COLORECTAL CANCER THERAPY AND DIAGNOSTICS

(71) Applicants: University of Virginia Patent Foundation, Charlottesville, VA (US); The University of Birmingham, Birmingham (GB)

(72) Inventors: Donald F. Hunt, Charlottesville, VA (US); Jeffrey Shabanowitz, Charlottesville, VA (US); Jennifer G. Abelin, Sommers, CT (US); Mark Cobbold, Birmingham (GB); Sarah Amy Penny, Birmingham (GB)

(73) Assignees: The University of Birmingham, Birmingham (GB); University of Virginia Patent Foundation, Charlottesville, VA (US)

( * ) Notice: Subject to any disclaimer, the term of this patent is extended or adjusted under 35 U.S.C. 154(b) by 0 days.

(21) Appl. No.: 14/425,946

(22) PCT Filed: Sep. 5, 2013

(86) PCT No.: PCT/US2013/058255
§ 371 (c)(1),
(2) Date: Mar. 4, 2015

(87) PCT Pub. No.: WO2014/039675
PCT Pub. Date: Mar. 13, 2014

(65) Prior Publication Data
US 2015/0328297 A1 Nov. 19, 2015

Related U.S. Application Data

(60) Provisional application No. 61/697,274, filed on Sep. 5, 2012, provisional application No. 61/712,807, filed on Oct. 12, 2012, provisional application No. 61/736,466, filed on Dec. 12, 2012.

(51) Int. Cl.
*A61K 39/00* (2006.01)
*G01N 33/574* (2006.01)

(52) U.S. Cl.
CPC .... *A61K 39/0011* (2013.01); *G01N 33/57419* (2013.01); *A61K 2039/555* (2013.01)

(58) Field of Classification Search
CPC .............................................. A61K 2039/555
See application file for complete search history.

(56) References Cited

U.S. PATENT DOCUMENTS

| 6,309,863 | B1 | 10/2001 | Anderson et al. |
|---|---|---|---|
| 7,067,110 | B1 | 6/2006 | Gillies et al. |
| 7,166,573 | B1 | 1/2007 | Obata |
| 7,449,548 | B2 * | 11/2008 | Raitano ................. C07K 16/30 530/350 |
| 8,124,741 | B2 | 2/2012 | Raitano et al. |
| 8,217,144 | B2 | 7/2012 | Jakobsen et al. |
| 8,283,446 | B2 | 10/2012 | Jakobsen et al. |
| 8,519,100 | B2 | 8/2013 | Jakobsen et al. |
| 2004/0086506 | A1 | 5/2004 | Haynes et al. |
| 2005/0277161 | A1 | 12/2005 | Engelhard et al. |
| 2006/0204509 | A1 | 9/2006 | Harty et al. |
| 2006/0251666 | A1 | 11/2006 | Nakatsura et al. |
| 2008/0292647 | A1 | 11/2008 | Kawakami et al. |
| 2009/0074800 | A1 | 3/2009 | Nakatsura et al. |
| 2009/0258378 | A1 | 10/2009 | Wang et al. |
| 2011/0059463 | A1 | 3/2011 | Moritz et al. |
| 2011/0293637 | A1 | 12/2011 | Hacohen et al. |
| 2011/0318380 | A1 | 12/2011 | Brix et al. |
| 2012/0021432 | A1 | 1/2012 | Yu et al. |
| 2012/0129776 | A1 | 5/2012 | Cohen et al. |
| 2012/0177669 | A1 | 7/2012 | Topalian et al. |
| 2013/0259883 | A1 | 10/2013 | Hunt et al. |
| 2015/0224182 | A1 | 8/2015 | Hunt et al. |
| 2016/0000893 | A1 | 1/2016 | Hunt et al. |
| 2017/0333541 | A1 | 11/2017 | Hunt et al. |
| 2019/0015494 | A1 | 1/2019 | Hunt et al. |

FOREIGN PATENT DOCUMENTS

| EP | 1 536 006 A1 | 6/2005 |
|---|---|---|
| WO | WO1996/040789 | 12/1996 |
| WO | WO2000/073801 | 12/2000 |
| WO | WO2007/017201 A1 | 2/2007 |
| WO | WO2007/127335 | 11/2007 |
| WO | WO 2009/134883 | 11/2009 |

(Continued)

OTHER PUBLICATIONS

Engelhard, Current Opinion in Immunology vol. 6 p. 13 (1994).*
Guo, et al Nature vol. 360 p. 384 (1992).*
Rammensee et al, Immunogenetics vol. 41 p. 178 (1995).*
Shastri et al J. Immunol. vol. 1995 vol. 155 p. 4339.*
Ezzell (J. NIH Res. 1995 7:46) (Year: 1995)*
Spitler (Cancer Biotherapy, 1995, 10:1-3) (Year: 1995).*
Boon (Adv. Can. Res. 1992 58:177-210) (Year: 1992).*
Klebanoff et al, Immunol Rev vol. 239(1): 27-44 (Jan. 2011) (Year: 2011).*
"CUL4A Antibody" Cell Signaling Technology, Inc. Sep. 16, 2010. <http://www.cellsignal.com/pdf/2699.pdf>.

(Continued)

*Primary Examiner* — Sheela J. Huff
(74) *Attorney, Agent, or Firm* — Jenkins, Wilson, Taylor & Hunt, P.A.

(57) ABSTRACT

A set of target peptides are presented by HLA A*0201, B*0301, B*0702 and B*2705 on the surface of disease cells. They are envisioned to, among other things, stimulate an immune response to the proliferative disease, e.g., colorectal cancer, to function as immunotherapeutics in adoptive T cell therapy or as a vaccine, facilitate antibody recognition of tumor boundaries in surgical pathology samples, act as biomarkers for early detection and/or diagnosis of the disease, and/or act as targets in the generation antibody-like molecules which recognize the target-peptide/MHC complex.

101 Claims, 8 Drawing Sheets

Specification includes a Sequence Listing.

(56) References Cited

FOREIGN PATENT DOCUMENTS

| WO | WO2010/129537 | | 11/2010 |
|---|---|---|---|
| WO | 2011149909 | * | 12/2011 |
| WO | WO2011/149909 | | 12/2011 |
| WO | WO2013/177593 | | 11/2013 |
| WO | 2014/036562 | * | 3/2014 |
| WO | WO 2014/039675 | | 3/2014 |
| WO | WO 2017/192969 A1 | | 11/2017 |

OTHER PUBLICATIONS

Altschul S.F. et al., "Basic Local Alignment Search Tool," *Journal of Molecular Biology*, 215:403-410, (1990).

Bullock et al. "Manipulation of avidity to improve effectiveness of adoptively transferred CD8(+) T cells for melanoma immunotherapy in human MHC class I-transgenic mice," J Immunol 167:5824-5831 (2001).

Bystryn et al. "Double-blind trial of a polyvalent, shed-antigen, melanoma vaccine" Clin Cancer Res 7:1882-1887 (2001).

Castelli et al., "T-Cell Recognition of Melanoma-Associated Antigens," *J Cell Physiol*, 182:323-331 (2000).

Chianese-Bullock et al. "Multi-peptide vaccines vialed as peptide mixtures can be stable reagents for use in peptide-based immune therapies" Vaccine 27:1764-1770 (2009).

Cottine, J., et al., "Identification of Novel Class I MHC-Restricted Phosphopeptides for Use as Cancer Immunotherapeutics," 58th Annual ASMS Conference on Mass Spectrometry and Allied Topics, Presentation, May 23-27, 2010, Salt Lake City, Utah.

Engelhard, "Identification of phosphorylated peptide antigens displayed on cancer cells and prospects for their use as immunotherapeutics," Powerpoint Presentation, Eleventh international conference on progress vaccination against cancer (PIVAC-11), Oct. 10-13, 2011, Copenhagen, Denmark.

Engelhard, "The contributions of mass spectrometry to understanding of immune recognition by T lymphocytes," Int J Mass Spectrom 259:32-39 (2007).

Evans, A.M., et al., "Differential Comparison of Phosphorylated MHC Class I HLA-A2.1 Peptides from Three Different Cancer Call Lines," Poster, 50th Annual ASMS Conference on Mass Spectrometry and Allied Topics, Jun. 2-6, 2002, Orlando, Florida.

Ferguson et al. "Strategies and challenges in eliciting immunity to melanoma," Immunol Rev 222:28-42 (2008).

Ficarro, S. B., et al., "Identification of Phosphorylated Peptides Associated with Class I MHC Molecules and Implications for Immunotherapy," Poster, 48th Annual ASMS Conference on Mass Spectrometry and Allied Topics, Jun. 11-15, 2000, Long Beach, California.

Goldman et al. "The cancer vaccine roller coaster," Nat Biotechnol 27:129-139 (2009).

Hawkins, O. E. et al., "Identification of Breast Cancer Peptide Epitopes Presented by HLA-A*0201," *Journal of Proteome Research*, 7:1445-1457 (2008).

Hida et al. A simple culture protocol to detect peptide-specific cytotoxic T lymphocyte precursors in the circulation. Cancer Immunol Immunother 51:219-228 (2002).

Hojlund et al., "In vivo phosphoproteome of human skeletal muscle revealed by phosphopeptide enrichment and HPLC-ESI-MS/MS," *J Proteome Res.*, 8(11):4954-4965 (2009).

Hopkins, L.M., "Sequence analysis of HLA-B7 peptides by ETD mass spectrometry: Comparative analysis of phosphopeptides on cancer and non-cancer cells," Poster, 53rd Annual ASMS Conference on Mass Spectrometry and Allied Topics, Jun. 5-9, 2005, San Antonio, Texas.

Hung et al., "Cul4A is an oncogene in malignant pleural mesothelioma," *J. Cell Mol Med.*, 15(2):350-8 (2011).

Hunt et al. "Characterization of peptides bound to the class I MHC molecule HLA-A2.1 by mass spectrometry," Science 255:1261-1263 (1992).

James, P.F., et al., "Analysis of HLA-A2 MHC Phosphopeptides with Titanium Dioxide, IMAC, Peptide Derivatization and Electron Transfer Dissociation," Poster, 58th Annual ASMS Conference on Mass Spectrometry and Allied Topics, May 23-27, 2010, Salt Lake City, Utah.

Jia et al., "SCF E3 ubiquitin ligases as anticancer targets," *Curr Cancer Drug Targets*, 11(3):347-56 (2011).

Lee et al., "Pathogenic Role of the CRL4 Ubiquitin Ligase in Human Disease," *Front Oncol.*, 2:21:1-7, (2012).

Liu et al., "CUL4A abrogation augments DNA damage response and protection against skin carcinogenesis," *Mol Cell*, 34(4):451-60 (2009).

Mackensen et al. "Phase I study in melanoma patients of a vaccine with peptide-pulsed dendritic cells generated in vitro from CD34(+) hematopoietic progenitor cells," Int J Cancer 86:385-392 (2000).

Meyer et al. (2009) Identification of natural MHC class II presented phosphopeptides and tumor-derived MHC class I phospholigands. J Proteome Res 8:3666-3674.

Morin et al. (1997) Activation of beta-catenin-Tcf signaling in colon cancer by mutations in beta-catenin or APC. Science 275:1787-1790.

Noguchi et al. "Personalized peptide vaccination: a new approach for advanced cancer as therapeutic cancer vaccine," Cancer Immunol Immunother 62:919-929. (2013), Epub Nov. 30, 2012.

Norris, A., "Identification of MHC Class I Phospho-peptide Antigens from Breast Cancer Utilizing sHLA Technology and Complementary Enrichment Strategies," Poster, 58th Annual ASMS Conference on Mass Spectrometry and Allied Topics, May 23-27, 2010, Salt Lake City, Utah.

Norris, A., et al., "The Identification of MHC Class II Peptides Expressed in vivo by B-Cell Leukemias and Lymphomas," Poster, 56th Annual ASMS Conference on Mass Spectrometry and Allied Topics, Jun. 1-8, 2008, Denver, Colorado.

Norris, A., et al., "Utilizing secreted MHC molecules (sHLA) to investigate the phosphor-immuno-peptidome of breast cancer," Poster, 57th Annual ASMS Conference on Mass Spectrometry and Allied Topics, May 31-Jun. 4, 2009, Philadelphia, Pennsylvania.

Ostankovitch et al. "N-glycosylation enhances presentation of a MHC class I-restricted epitope from tyrosinase," J Immunol 182:4830-4835 (2009).

Polefrone, J.M., et al., "Differential Expression of Class I, HLA-A2 Phosphopeptides on Tumor Cells: Characterization of Potential Candidates for Immunotherapy or a Cancer Vaccine," Poster, 53rd Annual ASMS Conference on Mass Spectrometry and Allied Topics, Jun. 5-9, 2005, San Antonio, Texas.

Qian, J., et al., "Analysis of HLA-DR4 restricted peptides by electron transfer dissociation tandem mass spectrometry," Poster, 54th Annual ASMS Conference on Mass Spectrometry and Allied Topics, May 28-Jun. 1, 2006, Seattle, Washington.

Qian, J., et al., "Class I and II MHC restricted phosphopeptides as cancer immunotherapeutics or diagnostics," Poster, 55th Annual ASMS Conference on Mass Spectrometry and Allied Topics, Jun. 3-7, 2007, Indianapolis, Indiana.

Ren et al., "Oncogenic CUL4A determines the response to thalidomide treatment in prostate cancer," *J Mol Med* (Berl), 90(10):1121-32 (2012).

Rock and Goldberg, "Degradation of Cell Proteins and the Generation of MHC Class I-Presented Peptides," *Annu Rev Immunol*, 17:739-779 (1999).

Schwartzentruber et al. "gp100 peptide vaccine and interleukin-2 in patients with advanced melanoma," N Engl J Med 364:2119-2127 (2011).

Slingluff "Immunity to melanoma antigens: from self-tolerance to immunotherapy," Adv Immunol 90:243-295 (2006).

Slingluff "Peptide approaches to melanoma vaccines: innovations and challenges," iSTBc/CVC workshop, Alexandria, VA (2005).

Slingluff "The present and future of peptide vaccines for cancer: single or multiple, long or short, alone or in combination?" Cancer J 17:343-350 (2011).

Slingluff et al. "Clinical and immunologic results of a randomized phase II trial of vaccination using four melanoma peptides either administered in granulocyte-macrophage colony-stimulating factor in adjuvant or pulsed on dendritic cells," J Clin Oncol 21:4016-4026 (2003).

(56) References Cited

OTHER PUBLICATIONS

The UniProt Consortium, The Universal Protein Resource (UniProt) in 2010, Nucleic Acids Research, 15:D142-D148 (2010).
Tyagi et al. "MAGRIT: the largest-ever phase III lung cancer trial aims to establish a novel tumor-specific approach to therapy," Clin Lung Cancer 10:371-374 (2009).
Wang "Extensive crosstalk between O-GlcN Acylation and phosphorylation regulates cytokinesis," Sci Signal 3:ra2 (2010).
Watts, C., "Capture and Processing of Exogenous Antigens for Presentation on MHC Molecules," *Annu Rev Immunol*, 15:821-850 (1997).
Zarling et al., "Abstract 1584: MHC-restricted phosphopeptides as broad-based immunotherapeutic targets for cancer," Poster Presentations—Tumor Vaccine Development, Proceedings: AACR 103rd Annual Meeting Mar. 31-Apr. 4, 2012; Chicago, IL, *Cancer Research*, 72(8):Supplement 1 (2012).
Andersen et al. (2001) Induction of Systemic CTL Responses in Melanoma Patients by Dendritic Cell Vaccination: Cessation of CTL Responses is Associated with Disease Progression. Int. J. Cancer, vol. 94 pp. 820-824 (2001).
Bins et al. (2007) Phase I clinical study with multiple peptide vaccines in combination with tetanus toxoid and GM-CSF in advanced-stage HLA-A*0201-positive melanoma patients. J. Immunther. 30(2):234-9.
Cobbold et al. (2005) Adoptive transfer of cytomegalovirus-specific CTL to stem cell transplant patients after selection by HLA-peptide tetramers. J Exp Med 202:379-386.
Cobbold et al. (2013) MHC Class I-Associated Phosphopepetides are the Targets of Memory-like Immunity in Leukemia. Science Translational Medicine, vol. 5, No. 203:203ra125 (Sep. 18, 2013).
Depontieu et al. (2009) Supplemental Information for "Identification of tumor-associated, MHC class II-restricted phosphopeptides as targets or immunotherapy." Proc Natl Acad Sci U S A 106. DOI:10.1073/pnas.0903852106 (7 pages).
Depontieu et al. (2009) Identification of tumor-associated, MHC class II-restricted phosphopeptides as targets for immunotherapy. Proc Natl Acad Sci U S A 106:12073-12078.
Hogan et al. (1998) The peptide recognized by HLA-A68.2-restricted, squamous cell carcinoma of the lung-specific cytotoxic T lymphocytes is derived from a mutated elongation factor 2 gene. Cancer Res 58:5144-5150.
Kielhorn et al. (2003) Tissue microarray-based analysis shows phospho-beta-catenin expression in malignant melanoma is associated with poor outcome. Int J Cancer 103:652-656.
Mohammed et al. (2008) Phosphorylation-dependent interaction between antigenic peptides and MHC class I: a molecular basis for the presentation of transformed self. Nat Immunol 9:1236-1243.
Notification Concerning Transmittal of International Preliminary Report on Patentability (Chapter 1 of the Patent Cooperation Treaty) corresponding to PCT/US2013/057856 dated Mar. 12, 2015.
Notification Concerning Transmittal of International Preliminary Report on Patentability (Chapter 1 of the Patent Cooperation Treaty) corresponding to PCT/US2013/058255 dated Apr. 30, 2015.
Notification Concerning Transmittal of International Preliminary Report on Patentability (Chapter 1 of the Patent Cooperation Treaty) corresponding to PCT/US2013/075073 dated Jun. 25, 2015.
Notification of Transmittal of the International Search Report and the Written Opinion of the International Searching Authority, or the Declaration, corresponding to PCT/US2013/057856 dated Feb. 28, 2014.
Notification of Transmittal of the International Search Report and the Written Opinion of the International Searching Authority, or the Declaration, corresponding to PCT/US2013/058255 dated Feb. 21, 2014.
Notification of Transmittal of the International Search Report and the Written Opinion of the International Searching Authority, or the Declaration, corresponding to PCT/US2013/058477 dated Dec. 20, 2013.
Notification of Transmittal of the International Search Report and the Written Opinion of the International Searching Authority, or the Declaration, corresponding to PCT/US2013/075073 dated May 20, 2014.
Petersen et al. (2009) Phosphorylated self-peptides alter human leukocyte antigen class I-restricted antigen presentation and generate tumor-specific epitopes. *Proc Natl Acad Sci U S A* 106:2776-2781.
Slingluff et al. (2011) Randomized multicenter trial of the effects of melanoma-associated helper peptides and cyclophosphamide on the immunogenicity of a multipeptide melanoma vaccine. J Clin Oncol 29(21):2924-2932.
Utz et al. (1997) Proteins phosphorylated during stress-induced apoptosis are common targets for autoantibody production in patients with systemic lupus erythematosus. J Exp Med 185:843-854.
Zarling et al. (2000) Phosphorylated peptides are naturally processed and presented by MHC class I molecules in vivo. J Exp Med 192:1755-1762.
Zarling et al. (2006) Identification of class I MHC associated phosphopeptides as targets for cancer immunotherapy. Proc Natl Acad Sci U S A 103:14889-14894.
European Search Report corresponding to European Patent Application No. 13832812.5-1403/2897631 dated Apr. 28, 2016.
Office Action corresponding to U.S. Appl. No. 14/424,702 dated March 14, 2016.
Office Action (Restriction Requirement) corresponding to U.S. Appl. No. 14/424,702 dated Nov. 20, 2015.
Communication pursuant to Rule 164(1) EPC for European Patent Application No. 13835570.6 dated Jul. 4, 2016.
Communication of the extended European search report for European Patent Application No. 13862491.1 dated Sep. 19, 2016.
Office Action corresponding to U.S. Appl. No. 14/424,702 dated Jun. 24, 2016.
Cobbold et al. (2013) Sci. Transl. Med. 5(203):1-23.
Examination Report No. 1 for standard patent application corresponding to Australian Patent Application No. 2013312529 dated May 22, 2017.
Interview Summary for U.S. Appl. No. 14/424,702 dated Sep. 15, 2016.
Notice of Allowance and Fee(s) due corresponding to U.S. Appl. No. 14/424,702 dated Oct. 13, 2016.
Notification of Transmittal of the International Search Report and the Written Opinion of the International Searching Authority, or the Declaration corresponding to International Application No. PCT/US2011/037699 dated Feb. 9, 2012.
Office Action corresponding to U.S. Appl. No. 13/699,563 dated Oct. 11, 2016.
Restriction Requirement corresponding to U.S. Appl. No. 13/699,563 dated Mar. 16, 2016.
Storkus et al., "Reversal of natural killing susceptibility in target cells expressing transfected class 1 HLA genes," PNAS USA, vol. 86, No. 7, pp. 2361-2364 (Apr. 1989).
Communication of the extended European search report corresponding to European Patent Application No. 15780107.7 dated Oct. 23, 2017.
Notification of Transmittal of International Preliminary Report on Patentability (Chapter 1 of the Patent Cooperation Treaty) corresponding to PCT/US2015/025942 dated Oct. 16, 2015.
Notification of Transmittal of the International Search Report and the Written Opinion of the International Searching Authority, or the Declaration, corresponding to PCT/US2016/045852 dated Nov. 26, 2016.
Notification of Transmittal of the International Search Report and the Written Opinion of the International Searching Authority, or the Declaration, corresponding to PCT/US2015/025942 dated Oct. 19, 2015.
Notification of Transmittal of the International Search Report and the Written Opinion of the International Searching Authority, or the Declaration corresponding to International Application No. PCT/US2017/031266 dated Aug. 24, 2017.
Office Action corresponding to U.S. Appl. No. 14/651,932 dated Jun. 23, 2017.

(56) References Cited

OTHER PUBLICATIONS

Office Action corresponding to U.S. Appl. No. 14/651,932 dated Feb. 6, 2018.
Office Action corresponding to Australian Patent Application No. 2013359001 dated Jul. 28, 2017.
Office Action corresponding to Australian Patent Application No. 2013308409 dated May 17, 2017.
Office Action corresponding to European Patent Application Serial No. 13 832 812.5 dated Jul. 11, 2017.
Office Action corresponding to European Patent Application Serial No. 13 862 491.1 dated Dec. 13, 2017.
Office Action corresponding to European Patent Application No. 13 385 570.6 dated Feb. 21, 2018.
Pages et al. (2009) In situ cytotoxic and memory T cells predict outcome in the patients with early-stage colorectal cancer. Journal of clinical oncology 27(35):5944-5951.
Weihrauch et al. (2005) Phase I/II Combined Chemoimmunotherapy With Carcinoembryonic Antigen-Derived HLA-A2-restricted CAP-1 Peptide and Irinotecan, 5-Fluorouracil, and Leucovorin in Patients With Primary Metastatic Colorectal Cancer. Clin Cancer Res 11(16):5993-6001.
Blaydes et al. (2000) Methods in Molecular Biology, Stress Response Methods and Protocols. Humana Press. vol. 99, Chapter 14 "The Development and Use of Phospho-Specific Antibodies to Study Protein Phosphorylation", pp. 177-189.
Hart et al. (2011) Cross talk between O-GlcNAcylation and phosphorylation: roles in signaling, transcription, and chronic disease. Annu Rev Biochem 80:825-858.
Haurum et al. (1994) Recognition of carbohydrate by major histocompatibility complex class I-restricted, glycopeptide-specific cytotoxic T lymphocytes. J Exp Med 180(2): 739-744.
Haurum et al. (1995) Peptide anchor residue glycosylation: effect on class I major histocompatibility complex binding and cytotoxic T lymphocyte recognition. Eur. J Immunol 25(12):3270-3276.
Haurum et al. (1999) Presentation of cytosolic glycosylated peptides by human class I major histocompatibility complex molecules in vivo. J Exp Med 190(1): 145-150.
Kastrup et al. (2000) Lectin purified human class I MHC-derived peptides: evidence for presentation of glycopeptides in vivo. Tissue Antigens 56(2): 129-135.
Office Action (Restriction Requirement) corresponding to U.S. Appl. No. 15/388,896 dated Jun. 6, 2018.
Office Action corresponding to U.S. Appl. No. 14/651,932 dated Oct. 10, 2018.
Office Action corresponding to U.S. Appl. No. 15/303,677, dated Aug. 29, 2018/.
Slawson and Hart (2011) O-GlcNAc signaling: implications for cancer biology. Nat Rev Cancer 11:678-684.
Wang et al. (2010a) Enrichment and site-mapping of O-linked N-acetylglucosamine by a combination of chemical/enzymatic tagging, photochemical cleavage, and electron transfer dissociation (ETD) mass spectrometry. Mol Cell Proteomics 9(1):153-160.
Wells et al. (2004) O-GlcNAc transferase is in a functional complex with protein phosphatase 1 catalytic subunits. J Biol Chem 279(37):38466-38470.
Wolfert and Boons (2013) Adaptive immune activation: glycosylation does matter. Nature Chem Biol 9:776-784.
Examination Report corresponding to Australian Patent Application No. 2018203355 dated Apr. 7, 2019.
Examination Report corresponding to Australian Patent Application No. 2018203542 dated Mar. 29, 2019.
Extended European Search Report corresponding to European Patent Application No. 16835708.5 dated Feb. 21, 2019.
Garcia et al., Cell, vol. 122, 333-336, Aug. 12, 2005. (Year: 2005).
Li etal., JMB, vol. 399, 2010, pp. 596-603. (Year: 2010).
Manning etal., Immunity, vol. 8, 413-425, Apr. 1998. (Year: 1998).
Natarajan etal., 2016, Cell Reports 14, 2833-2845 (Year: 2016).
Office Action corresponding to European Patent Application No. 13835570.6 dated May 9, 2019.
Office Action corresponding to U.S. Appl. No. 15/388,896, dated Dec. 17, 2018.
Office Action corresponding to U.S. Appl. No. 15/388,896, dated Dec. 3, 2018.
Office Action corresponding to U.S. Appl. No. 15/388,896, dated Jul. 1, 2019.
Office Action corresponding to U.S. Appl. No. 14/651,932, dated Apr. 19, 2019.
Office Action corresponding to U.S. Appl. No. 15/303,677, dated Jun. 6, 2019.
Portolano et al., J Immunol Feb. 1, 1993; 150(3):880-7. (Year: 1993).
Robins et al., Blood. 2009; 114:4099-4107. (Year: 2009).
Subbramanian et al. (Nat Biotechnol. Nov. 2004;22(11):1429-34. (Year: 2004).
Summons to Attend Oral Proceedings corresponding to European Patent Application No. 13862491.1. dated Mar. 6, 2019.
Woodsworth et al., Genome Medicine 2013, 5:98. (Year: 2013).
Examination Report corresponding to Australian Patent Application No. 2018208738 dated Jul. 12, 2019.

* cited by examiner

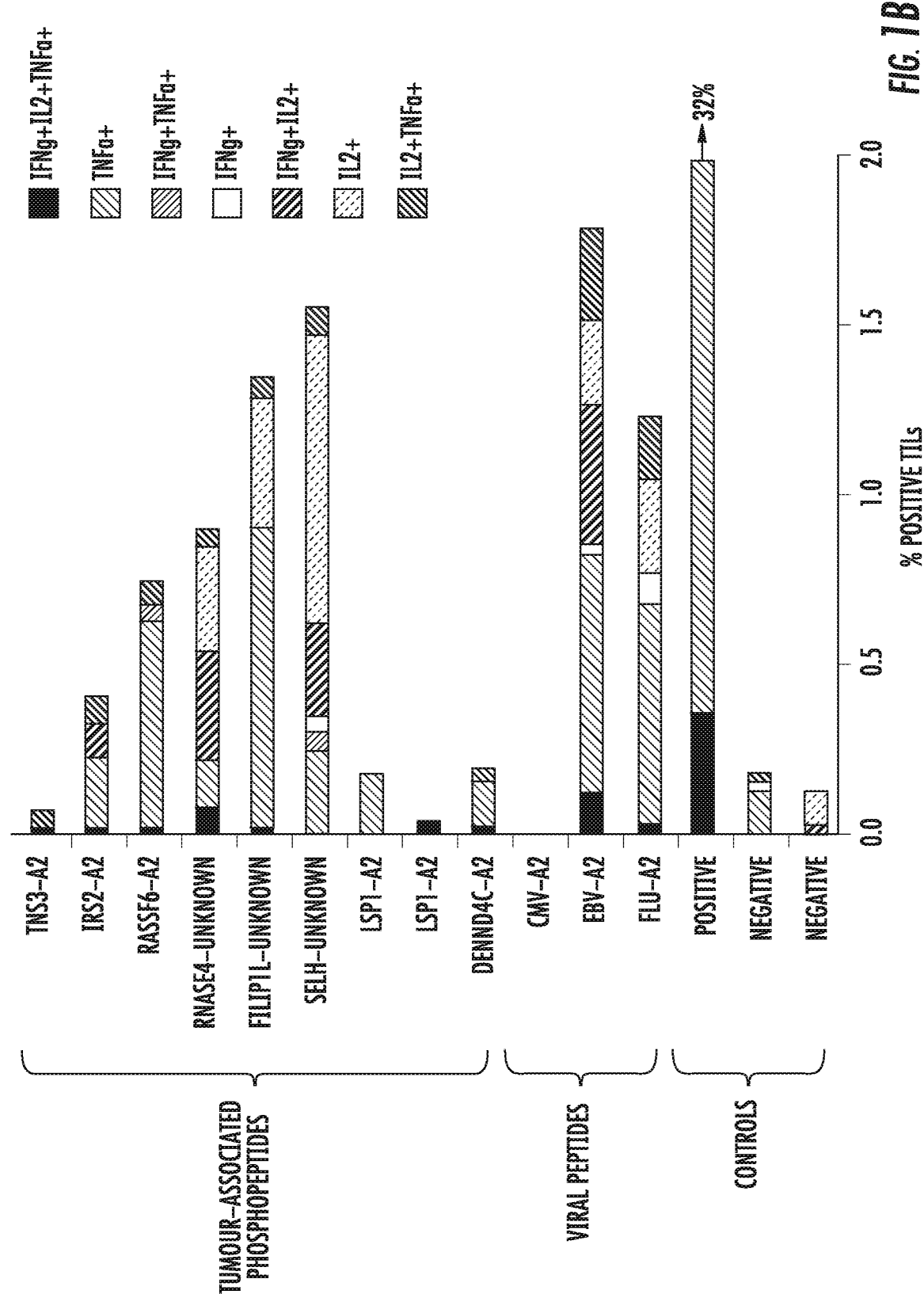

|  | HLA-TYPE | HD1 | HD2 | HD3 | HD4 | HD5 | HD6 | HD7 | HD8 | HD9 | HD10 | HD11 | HD12 | HD13 |
|---|---|---|---|---|---|---|---|---|---|---|---|---|---|---|
| RASSF6 | A2 | | | | | ▨ | | | | | ▨ | | | |
| DENND4C | A2 | | ▨ | | | ▨ | | | ▨ | | | | | |
| IRS2 | A2 | | | | | ▨ | ▨ | ▨ | | | | | | |
| LSP1 | A2 | | | | | | | | | | ▨ | | | |
| BARD1 | A3 | | ▨ | | | ▨ | ▨ | | | | | | | |
| PDCL | A3 | | | | | | ▨ | | | | | | | |
| RAB11FIP1 | B7 | | | | | | | | | | | | | |
| IRS2 | B7 | | | | | ▨ | | | | | ▨ | | ▨ | ▨ |
| PALLD | B7 | | | ▨ | | ▨ | | | | | | | | |
| MUC12 | B7 | | | | | ▨ | | | | | | | | |
| AHCYL2 | B7 | | | | | | | | | | | ▨ | | |
| TPX2 | B7 | | | | | | | | | | | | | |
| PDLIM2 | B7 | | | | | | | | | | | | | |
| NUMBL | B7 | | | | | | | | | | | | | |
| ZFP36L2 | B7 | ▨ | | ▨ | | ▨ | | | | | | | ▨ | ▨ |
| LISCH7 | B7 | | | | | | | | | | | | ▨ | |
| TTC22 | B7 | | | | ▨ | | | | | | | | | |
| SELH | U | | | | | ▨ | | | ▨ | | | | | |
| RNASE4 | U | | | | | ▨ | ▨ | | ▨ | | ▨ | | | |
| FILIP1L | U | | | | | | | ▨ | | | | | | |
| YT521 | U | | | | | | | | | | | | | |
| CMV | A2 | ▨ | | | | ▨ | | ▨ | | ▨ | | | | |
| EBV | A2 | | | | ▨ | ▨ | ▨ | ▨ | | | | | | |
| CMV | B7 | | | | | | ▨ | | | | | ▨ | ▨ | |
| EBV | B7 | ▨ | | ▨ | | | ▨ | | | | | ▨ | ▨ | ▨ |
| FLU | B7 | ▨ | | ▨ | | ▨ | | ▨ | | | ▨ | ▨ | ▨ | ▨ |

SFU/500 000 PBMC

FIG. 2

KEY
- 3-24 SPOTS
- 25-99 SPOTS
- 100+ SPOTS

TARGET PEPTIDES FOR COLORECTAL CANCER THERAPY AND DIAGNOSTICS

CROSS REFERENCE TO RELATED APPLICATIONS

The presently disclosed subject matter claims the benefit of U.S. Provisional Patent Application Ser. Nos. 61/697,274, filed Sep. 5, 2012; 61/712,807 filed Oct. 12, 2012; and 61/736,466, filed Dec. 12, 2012. The disclosure of each of these applications is incorporated herein by reference in its entirety.

GRANT STATEMENT

This invention was made with government support under Grant Nos. AI033993 awarded by National Institutes of Health. The government has certain rights in the invention.

REFERENCE TO SEQUENCE LISTING

The Sequence Listing associated with the instant disclosure has been electronically submitted to the United States Patent and Trademark Office as International Receiving Office as a 106 kilobyte ASCII text file created on Sep. 5, 2013 and entitled "306_2_4PCT_ST25.txt". The Sequence Listing submitted via EFS-Web is hereby incorporated by reference in its entirety.

TECHNICAL FIELD

The presently disclosed subject matter is related to the area of diagnostics and therapeutics. In particular, it relates to immunotherapies and diagnostics in the context of proliferative diseases such as cancer.

BACKGROUND

The mammalian immune system has evolved a variety of mechanisms to protect the host from cancerous cells. An important component of this response is mediated by cells referred to as T cells. Cytotoxic T lymphocytes (CTL) are specialized T cells that primarily function by recognizing and killing cancerous cells or infected cells, but they can also function by secreting soluble molecules referred to as cytokines that can mediate a variety of effects on the immune system. T helper cells primarily function by recognizing antigen on specialized antigen presenting cells, and in turn secreting cytokines that activate B cells, T cells, and macrophages. A variety of evidence suggests that immunotherapy designed to stimulate a tumor-specific CTL response would be effective in controlling cancer. For example, it has been shown that human CTL recognize sarcomas (Slovin et al., 1986), renal cell carcinomas (Schendel et al., 1993), colorectal carcinomas (Jacob et al., 1997), ovarian carcinomas (Peoples et al., 1993), pancreatic carcinomas (Peiper et al., 1997), squamous tumors of the head and neck (Yasumura et al., 1993), and squamous carcinomas of the lung (Slingluff et al., 1994; Yoshino et al., 1994). The largest number of reports of human tumor-reactive CTLs, however, has concerned melanomas (Boon et al., 1994).

The ability of tumor-specific CTL to mediate tumor regression, in both human (Parmiani et al., 2002; Weber, 2002) and animal models, suggests that methods directed at increasing CTL activity would likely have a beneficial effect with respect to tumor treatment.

Colorectal cancer (CRC), commonly also known as colon cancer or bowel cancer, is a cancer from uncontrolled cell growth in the colon or rectum (parts of the large intestine), or in the appendix. Symptoms typically include rectal bleeding and anemia which are sometimes associated with weight loss and changes in bowel habits. Most colorectal cancer occurs due to lifestyle and increasing age with only a minority of cases associated with underlying genetic disorders. It typically starts in the lining of the bowel and if left untreated, can grow into the muscle layers underneath, and then through the bowel wall. Screening is effective at decreasing the chance of dying from colorectal cancer and is recommended starting at the age of 50 and continuing until a person is 75 years old. Localized bowel cancer is usually diagnosed through sigmoidoscopy or colonoscopy. Cancers that are confined within the wall of the colon are often curable with surgery while cancer that has spread widely around the body is usually not curable and management then focuses on extending the person's life via chemotherapy and improving quality of life. Colorectal cancer is the third most commonly diagnosed cancer in the world, but it is more common in developed countries. Around 60% of cases were diagnosed in the developed world. It is estimated that worldwide in 2008, 1.23 million new cases of colorectal cancer were clinically diagnosed, and that it killed 608,000 people.

In Europe, the five year survival for colorectal cancer is less than 60%. In the developed world, about a third of people who get the disease die from it. Survival is directly related to detection and the type of cancer involved, but overall is poor for symptomatic cancers, as they are typically quite advanced. Survival rates for early stage detection are about five times that of late stage cancers. For example, patients with a tumor that has not breached the muscularis mucosa (TNM stage Tis, N0, M0) have an average 5-year survival of 100%, while those with an invasive cancer, i.e. T1 (within the submucosal layer) or T2 (within the muscular layer) cancer have an average 5-year survival of approximately 90%. Those with a more invasive tumor, yet without node involvement (T3-4, N0, M0) have an average 5-year survival of approximately 70%. Patients with positive regional lymph nodes (any T, N1-3, M0) have an average 5-year survival of approximately 40%, while those with distant metastases (any T, any N, M1) have an average 5-year survival of approximately 5%.

According to the American Cancer Society statistics in 2006, over 20% of patients present with metastatic (Stage IV) colorectal cancer at the time of diagnosis, and up to 25% of this group will have isolated liver metastasis that is potentially resectable. Lesions which undergo curative resection have demonstrated 5-year survival outcomes now exceeding 50%. Nevertheless, additional therapeutics that are safer and more effective than current therapies are in high demand.

In order for CTL to kill or secrete cytokines in response to a cancer cell, the CTL must first recognize the cancer cell (Townsend & Bodmer, 1989). This process involves the interaction of the T cell receptor, located on the surface of the CTL, with what is generically referred to as an MHC-peptide complex which is located on the surface of the cancerous cell. Major histocompatibility complex (MHC)-encoded molecules have been subdivided into two types, and are referred to as class I and class II MHC-encoded molecules. In the human immune system, MHC molecules are referred to as human leukocyte antigens (HLA). Within the MHC complex, located on chromosome six, are three different loci that encode for class I MHC molecules. MHC molecules encoded at these loci are referred to as HLA-A, HLA-B, and HLA-C. The genes that can be encoded at each of these loci are extremely polymorphic, and thus, different individuals within the population express different class I MHC molecules on the surface of their cells. HLA-A1, HLA-A2, HLA-A3, HLA-B7, HLA-B14, HLA-B27, and HLA-B44 are examples of different class I MHC molecules that can be expressed from these loci.

The peptides which associate with the MHC molecules can either be derived from proteins made within the cell, in which case they typically associate with class I MHC molecules (Rock & Goldberg, 1999); or they can be derived from proteins which are acquired from outside of the cell, in which case they typically associate with class II MHC molecules (Watts, 1997). The peptides that evoke a cancer-specific CTL response most typically associate with class I MHC molecules. The peptides themselves are typically nine amino acids in length, but can vary from a minimum length of eight amino acids to a maximum of fourteen amino acids in length. Tumor antigens may also bind to class II MHC molecules on antigen presenting cells and provoke a T helper cell response. The peptides that bind to class II MHC molecules are generally twelve to nineteen amino acids in length, but can be as short as ten amino acids and as long as thirty amino acids.

The process by which intact proteins are degraded into peptides is referred to as antigen processing. Two major pathways of antigen processing occur within cells (Rock & Goldberg, 1999). One pathway, which is largely restricted to professional antigen presenting cells such as dendritic cells, macrophages, and B cells, degrades proteins that are typically phagocytosed or endocytosed into the cell. Peptides derived from this pathway can be presented on either class I or to class II MHC molecules. A second pathway of antigen processing is present in essentially all cells of the body. This second pathway primarily degrades proteins that are made within the cells, and the peptides derived from this pathway primarily bind to class I MHC molecules. Antigen processing by this latter pathway involves polypeptide synthesis and proteolysis in the cytoplasm, followed by transport of peptides to the plasma membrane for presentation. These peptides, initially being transported into the endoplasmic reticulum of the cell, become associated with newly synthesized class I MHC molecules and the resulting complexes are then transported to the cell surface. Peptides derived from membrane and secreted proteins have also been identified. In some cases these peptides correspond to the signal sequence of the proteins which is cleaved from the protein by the signal peptidase. In other cases, it is thought that some fraction of the membrane and secreted proteins are transported from the endoplasmic reticulum into the cytoplasm where processing subsequently occurs. Once bound to the class I MHC molecule, the peptides are recognized by antigen-specific receptors on CTL. Several methods have been developed to identify the peptides recognized by CTL, each method of which relies on the ability of a CTL to recognize and kill only those cells expressing the appropriate class I MHC molecule with the peptide bound to it. Mere expression of the class I MHC molecule is insufficient to trigger the CTL to kill the target cell if the antigenic peptide is not bound to the class I MHC molecule. Such peptides can be derived from a non-self source, such as a pathogen (for example, following the infection of a cell by a bacterium or a virus) or from a self-derived protein within a cell, such as a cancerous cell. The tumor antigens from which the peptides are derived can broadly be categorized as differentiation antigens, cancer/testis antigens, mutated gene products, widely expressed proteins, viral antigens and most recently, phosphopeptides derived from dysregulated signal transduction pathways. (Zarling et al., 2006).

Immunization with cancer-derived, class I or class II MHC-encoded molecule associated peptides, or with a precursor polypeptide or protein that contains the peptide, or with a gene that encodes a polypeptide or protein containing the peptide, are forms of immunotherapy that can be employed in the treatment of colorectal cancer. Identification of the immunogens is a necessary first step in the formulation of the appropriate immunotherapeutic agent or agents. Although a large number of tumor-associated peptide antigens recognized by tumor reactive CTL have been identified, there are few examples of antigens that are derived from proteins that are selectively expressed on a broad array of tumors, as well as associated with cellular proliferation and/or transformation.

Attractive candidates for this type of antigen are peptides derived from proteins that are differentially phosphorylated on serine (Ser), threonine (Thr), and/or tyrosine (Tyr; Zarling et al., 2000). Due to the increased and dysregulated phosphorylation of cellular proteins in transformed cells as compared to normal cells, tumors are likely to present a unique subset of phosphorylated peptides on the cell surface that are available for recognition by cytotoxic T-lymphocytes (CTL). Presently, there is no way to predict which protein phosphorylation sites in a cell will be unique to tumors, survive the antigen processing pathway, and be presented to the immune system in the context of 8-14 residue phosphopeptides bound to class I MHC molecules.

Thirty-six phosphopeptides were disclosed as presented in association with HLA-A*0201 on cancer cells (see Table 1 of Zarling et al., 2006). Parent proteins for four of these peptides (β-catenin, insulin receptor substrate-2 (IRS-2), tensin-3, and Jun-C/D) are associated with cytoplasmic signaling pathways and cellular transformation.

Until the present disclosure, no studies have examined MHC class-I-bound phosphopeptide displayed on primary human tumor samples and, there is only limited evidence of a human immune response against class-I-restricted phosphopeptides.

SUMMARY

This Summary lists several embodiments of the presently disclosed subject matter, and in many cases lists variations and permutations of these embodiments. This Summary is merely exemplary of the numerous and varied embodiments. Mention of one or more representative features of a given embodiment is likewise exemplary. Such an embodiment can typically exist with or without the feature(s) mentioned; likewise, those features can be applied to other embodiments of the presently disclosed subject matter, whether listed in this Summary or not. To avoid excessive repetition, this Summary does not list or suggest all possible combinations of such features.

In some embodiments, the presently disclosed subject matter relates to compositions comprising at least or about 1, 2, 3, 4, 5, 6, 7, 8, 9, 10, or more synthetic target peptides, each of which are about or at least 8, 9, 10, 11, 12, 13, 14, or 15 amino acids long. In some embodiments, the target peptides comprise an amino acid sequence as set forth in any of SEQ ID NOs: 1-177. In some embodiments, the composition has the ability to stimulate a T cell-mediated immune response to at least one of the synthetic target peptides.

In some embodiments, at least one serine, tyrosine, and/or threonine residue in any of the peptides is phosphorylated.

In some embodiments, at least one serine residue in any of the peptides is replaced with a homoserine. In some embodiments, the composition comprises a non-hydrolyzable phosphate. In some embodiments, at least one phosphoserine residue in any of the peptides is replaced by phosphohomoserine. In some embodiments, the composition is immunologically suitable for at least 60 to 88% of colorectal cancer patients. In some embodiments, the composition comprises at least five different target peptides. In some embodiments, the composition comprises at least ten different target peptides. In some embodiments, the composition comprises at least fifteen different target peptides.

In some embodiments, the composition comprises a target peptide capable of binding to an MHC class I molecule. In some embodiments, the target peptide is capable of binding to an MHC class I molecule selected from the group consisting of HLA-A*0201, HLA-A*0101, HLA-A*0301, HLA-B*4402, HLA-B*0702, HLA-B*-2705, and HLA-B*1402. In some embodiments, the composition comprises a peptide capable of binding to an MHC class I molecule selected from the group consisting of HLA-A*0101, HLA-A*0301, HLA-B*4402, HLA-B*0702, HLA-B*-2705, and HLA-B*1402. In some embodiments, the composition comprises a peptide capable of binding to an MHC class I molecule of the HLA-A*0201, HLA-A*0101, or HLA-B*0702 alleles.

In some embodiments, the composition is capable of increasing the 5-year survival rate of colorectal cancer patients treated with the composition by at least 5%, 10%, 15%, 20%, 25%, 30%, 40%, or 50% relative to average 5-year survival rates that could have been expected without treatment with the composition. In some embodiments, the composition is capable of increasing the survival rate of colorectal cancer patients treated with the composition by at least 5%, 10%, 15%, 20%, 25%, 30%, 40%, or 50% relative to a survival rate that could have been expected without treatment with the composition. In some embodiments, the composition is capable of increasing the treatment response rate of colorectal cancer patients treated with the composition by at least 5%, 10%, 15%, 20%, 25%, 30%, 40%, or 50% relative to a treatment rate that could have been expected without treatment with the composition. In some embodiments, the composition is capable of increasing the overall median survival of patients of colorectal cancer patients treated with the composition by at least two months relative to an overall median survival that could have been expected without treatment with the composition.

In some embodiments, the composition comprises at least one peptide derived from MelanA (MART-I), gp100 (Pmel 17), tyrosinase, TRP-1, TRP-2, MAGE-1, MAGE-3, BAGE, GAGE-1, GAGE-2, p15(58), CEA, RAGE, NY-ESO (LAGE), SCP-1, Hom/Mel-40, PRAME, p53, H-Ras, HER-2/neu, BCR-ABL, E2A-PRL, H4-RET, IGH-IGK, MYL-RAR, Epstein Barr virus antigens, EBNA, human papillomavirus (HPV) antigens E6 and E7, TSP-180, MAGE-4, MAGE-5, MAGE-6, p185erbB2, p180erbB-3, c-met, nm-23H1, PSA, TAG-72-4, CA 19-9, CA 72-4, CAM 17.1, NuMa, K-ras, β-Catenin, CDK4, Mum-1, p16, TAGE, PSMA, PSCA, CT7, telomerase, 43-9F, 5T4, 791Tgp72, α-fetoprotein, β-HCG, BCA225, BTAA, CA 125, CA 15-3 (CA 27.29\BCAA), CA 195, CA 242, CA-50, CAM43, CD68\KP1, CO-029, FGF-5, G250, Ga733 (EpCAM), HTgp-175, M344, MA-50, MG7-Ag, MOV18, NB/70K, NY-CO-1, RCAS1, SDCCAG16, TA-90 (Mac-2 binding protein/cyclophilin C-associated protein), TAAL6, TAG72, TLP and TPS.

In some embodiments, the composition comprises an adjuvant. In some embodiments, the adjuvant is selected from the group consisting of montanide ISA-51 (Seppic, Inc., Fairfield, N.J., United States of America), QS-21 (Aquila Biopharmaceuticals, Inc., Lexington, Mass., United States of America), tetanus helper peptides, GM-CSF, cyclophosphamide, *bacillus* Calmette-Guérin (BCG), *Corynbacterium parvum*, levamisole, azimezone, isoprinisone, dinitrochlorobenezene (DNCB), keyhole limpet hemocyanins (KLH), Freunds adjuvant (complete and incomplete), mineral gels, aluminum hydroxide (Alum), lysolecithin, pluronic polyols, polyanions, peptides, oil emulsions, dinitrophenol, and diphtheria toxin (DT).

In some embodiments, the presently disclosed subject matter also relates to an in vitro population of dendritic cells comprising a composition comprising at least one target peptide as disclosed herein. In some embodiments, the at least one target peptide selected from the group consisting of SEQ ID NOs: 1-177.

In some embodiments, the presently disclosed subject matter also relates to an in vitro population of CD8$^+$ T cells capable of being activated upon being brought into contact with a population of dendritic cells, wherein the dendritic cells comprise a composition comprising at least one target peptide as disclosed herein. In some embodiments, the at least one target peptide selected from the group consisting of SEQ ID NOs: 1-177.

In some embodiments, the presently disclosed subject matter also relates to an antibody or antibody-like molecule that specifically binds to both a first complex of MHC class I molecule and a target peptide. In some embodiments, the at least one target peptide selected from the group consisting of SEQ ID NOs: 1-177. In some embodiments, the antibody or antibody-like molecule is a member of the immunoglobulin superfamily. In some embodiments, the antibody or antibody-like molecule comprises a binding member selected from the group consisting an Fab, Fab', F(ab')$_2$, Fv, and a single-chain antibody. In some embodiments, the antibody or antibody-like molecule comprises a therapeutic agent selected from the group consisting of an alkylating agent, an antimetabolite, a mitotic inhibitor, a taxoid, a vinca alkaloid, and an antibiotic. In some embodiments, the antibody or antibody-like molecule is a T cell receptor, which in some embodiments is optionally linked to a CD3 agonist.

In some embodiments, the presently disclosed subject matter also relates to an in vitro population of T cells transfected with an mRNA encoding a target peptide-specific T cell receptor as disclosed herein.

The presently disclosed subject matter also relates in some embodiments to methods for treating and/or preventing cancer. In some embodiments, the presently disclosed methods comprise administering to a patient in need thereof one or more doses of a composition comprising at least one target peptide as disclosed herein. In some embodiments, the at least one target peptide selected from the group consisting of SEQ ID NOs: 1-177.

In some embodiments, the presently disclosed subject matter also relates to methods for treating and/or preventing colorectal cancer. In some embodiments, the presently disclosed methods comprise administering to a patient in need thereof one or more doses of a composition comprising at least one target peptide as disclosed herein, wherein the composition in some embodiments comprises a pharmaceutically acceptable carrier, which in some embodiments is pharmaceutically acceptable for use in a human. In some embodiments, the at least one target peptide selected from the group consisting of SEQ ID NOs: 1-177.

In some embodiments, the presently disclosed subject matter also relates to methods for treating and/or preventing cancer comprising administering to a patient in need thereof a dose of a CD8+ T cell in combination with a pharmaceutically acceptable carrier, optionally a carrier that is pharmaceutically acceptable for use in a human. In some embodiments, the CD8+ T cell is capable of being activated upon being brought into contact with a population of dendritic cells, and further wherein the dendritic cells comprise a composition comprising at least one target peptide as disclosed herein.

In some embodiments, the presently disclosed subject matter also relates to methods for treating and/or preventing cancer comprising administering to a patient in need thereof the population of dendritic cells comprising a composition comprising at least one target peptide as disclosed herein. In some embodiments, the dendritic cells are administered in combination with a pharmaceutically acceptable carrier, optionally a carrier that is pharmaceutically acceptable for use in a human.

The presently disclosed subject matter also relates in some embodiments to methods for treating and/or preventing cancer comprising administering to a patient in need thereof a population T cells as disclosed herein in combination with a pharmaceutically acceptable carrier, optionally a carrier that is pharmaceutically acceptable for use in a human.

The presently disclosed subject matter also relates in some embodiments to methods for making a cancer vaccine. In some embodiments, the presently disclosed methods comprise combining a composition as disclosed herein with an adjuvant and a pharmaceutically acceptable carrier and placing the composition, adjuvant, and pharmaceutical carrier into a syringe.

The presently disclosed subject matter also relates in some embodiments to methods for screening a target peptide for inclusion in an immunotherapy composition. In some embodiments, the presently disclosed methods comprise administering the target peptide to a human; determining whether the target peptide is capable of inducing a target peptide-specific memory T cell response in the human; and selecting the target peptide for inclusion in an immunotherapy composition if the target peptide elicits a target peptide-specific memory T cell response in the human.

In some embodiments, the presently disclosed subject matter also relates to methods for determining a prognosis of a cancer patient. In some embodiments, the presently disclosed methods comprise administering a target peptide associated with the patient's cancer to the patient; determining whether the target peptide is capable of inducing a target peptide-specific memory T cell response in the patient; and determining that the patient has a better prognosis if the patient mounts a memory T cell response to the target peptide than if the patient did not mount a memory T cell response to the target peptide.

In some embodiments, the presently disclosed subject matter also relates to kits comprising at least one target peptide composition as disclosed herein, wherein the at least one target peptide composition comprises at least one target peptide and a cytokine and/or an adjuvant. In some embodiments, the kit comprises at least 2, 3, 4, 5, or more target peptide compositions as disclosed herein. In some embodiments, the cytokine is selected from the group consisting of a transforming growth factor (TGF) including but not limited to TGF-α and TGF-β; insulin-like growth factor (IGF)-I; IGF-II; erythropoietin (EPO); an osteoinductive factor; an interferon (IFN) including but not limited to IFNα, IFNβ, and IFNγ; a colony stimulating factor (CSF) including but not limited to macrophage-CSF (M-CSF); granulocyte-macrophage-CSF (GM-CSF); and granulocyte-CSF (G-CSF); an interleukin (IL) including but not limited to IL-1, IL-1α, IL-2, IL-3, IL-4, IL-5, IL-6, IL-7, IL-8, IL-9, IL-10, IL-11, IL-12; IL-13, IL-14, IL-15, IL-16, IL-17, IL-18; leukemia inhibitory factor (LIF); kit-ligand; FLT-3; angiostatin; thrombospondin; endostatin; an tumor necrosis factor (TNF) including but not limited to TNFα and TNFβ; and lymphotoxin (LT). In some embodiments, the adjuvant selected from the group consisting of montanide ISA-51 (Seppic, Inc., Fairfield, N.J., United States of America), QS-21 (Aquila Biopharmaceuticals, Inc., Lexington, Mass., United States of America), a tetanus helper peptide, GM-CSF, cyclophosphamide, *bacillus* Calmette-Guérin (BCG), *Corynbacterium parvum*, levamisole, azimezone, isoprinisone, dinitrochlorobenezene (DNCB), keyhole limpet hemocyanin (KLH), Freunds adjuvant (complete and incomplete), a mineral gel, aluminum hydroxide (Alum), lysolecithin, a pluronic polyol, a polyanion, a peptide, an oil emulsion, dinitrophenol, and diphtheria toxin (DT).

In some embodiments, the kit comprises at least one additional peptide. In some embodiments, the at least one additional peptide is a peptide derived from MelanA (MART-I), gp100 (Pmel 17), tyrosinase, TRP-1, TRP-2, MAGE-1, MAGE-3, MAGE-4, MAGE-5, MAGE-6, BAGE, GAGE-1, GAGE-2, p15(58), CEA, RAGE, NY-ESO (LAGE), SCP-1, Hom/Mel-40, PRAME, p53, H-Ras, HER-2/neu, BCR-ABL, E2A-PRL, H4-RET, IGH-IGK, MYL-RAR, an Epstein Barr virus antigen, EBNA, human papillomavirus (HPV) antigen E6, HPV antigen E7, TSP-180, p185erbB2, p180erbB-3, c-met, nm-23H1, PSA, TAG-72-4, CA 19-9, CA 72-4, CAM 17.1, NuMa, K-ras, β-Catenin, CDK4, Mum-1, p16, TAGE, PSMA, PSCA, CT7, telomerase, 43-9F, 5T4, 791Tgp72, α-fetoprotein, β-HCG, BCA225, BTAA, CA 125, CA 15-3 (CA 27.29/BCAA), CA 195, CA 242, CA-50, CAM43, CD68/KP1, CO-029, FGF-5, G250, Ga733 (EpCAM), HTgp-175, M344, MA-50, MG7-Ag, MOV18, NB/70K, NY-CO-1, RCAS1, SDCCAG16, TA-90 (Mac-2 binding protein/cyclophilin C-associated protein), TAAL6, TAG72, TLP, and TPS.

In some embodiments, the kit comprises at least one target peptide comprising an amino acid sequence as set forth in any of SEQ ID NOs: 1-177.

In some embodiments, the presently disclosed subject matter also provides methods for inducing a target peptide-specific memory T cell response in a patient having a proliferative disorder. In some embodiments, the presently disclosed methods comprise (a) administering to a patient in need thereof a composition comprising at least one target peptide and an adjuvant; and (b) inducing a memory T cell response to the at least one target peptide. In some embodiments, the memory T cell response is capable of treating the proliferative disorder. In some embodiments, the at least one target peptide is selected from SEQ ID NOs: 1-177. In some embodiments, the proliferative disorder is cancer. In some embodiments, the cancer is colorectal cancer. In some embodiments, the adjuvant is a TLR agonist. In some embodiments, the adjuvant is a Montanide ISA-51. In some embodiments, the adjuvant is a tetanus helper peptide, a modified tetanus helper peptide (including but not limited to a peptide that is at least 90% identical to a segment or fragment of a tetanus toxoid protein). In some embodiments, the composition comprises at least one peptide derived from MelanA (MART-I), gp100 (Pmel 17), tyrosinase, TRP-1, TRP-2, MAGE-1, MAGE-3, BAGE, GAGE-1, GAGE-2, p15(58), CEA, RAGE, NY-ESO (LAGE), SCP-1, Hom/ Mel-40, PRAME, p53, H-Ras, HER-2/neu, BCR-ABL, E2A-PRL, H4-RET, IGH-IGK, MYL-RAR, an Epstein Barr virus antigen, EBNA, a human papillomavirus (HPV) antigen E6 and/or E7, TSP-180, MAGE-4, MAGE-5, MAGE-6, p185erbB2, p180erbB-3, c-met, nm-23H1, PSA, TAG-72-4, CA 19-9, CA 72-4, CAM 17.1, NuMa, K-ras, β-Catenin, CDK4, Mum-1, p16, TAGE, PSMA, PSCA, CT7, telomerase, 43-9F, 5T4, 791Tgp72, α-fetoprotein, β-HCG, BCA225, BTAA, CA 125, CA 15-3 (CA 27.29\BCAA), CA 195, CA 242, CA-50, CAM43, CD68\KP1, CO-029, FGF-5, G250, Ga733 (EpCAM), HTgp-175, M344, MA-50, MG7-Ag, MOV18, NB/70K, NY-CO-1, RCAS1, SDCCAG16, TA-90 (Mac-2 binding protein/cyclophilin C-associated protein), TAAL6, TAG72, TLP, and TPS. In some embodiments, the composition is immunologically suitable for at least 60 to 88% of cancer patients. In some embodiments, the composition comprises at least 1, 2, 3, 4, or 5 different target peptides. In some embodiments, the composition comprises at least 10 different target peptides. In some embodiments, the composition comprises at least 15 different target peptides. In some embodiments, the composition comprises a peptide capable of binding to an MHC class I molecule selected from the group consisting of HLA-A*0201, HLA-A*0101, HLA-A*0301, HLA-B*4402, HLA-B*0702, HLA-B*-2705 and HLA-B*1402. In some embodiments, the composition comprises a peptide capable of binding to an MHC class I molecule selected from the group consisting of HLA-A*0101, HLA-A*0301, HLA-B*4402, HLA-B*0702, HLA-B*-2705, HLA-B*1402 and combinations thereof. In some embodiments, the composition comprises a peptide capable of binding to an MHC class I molecule of the HLA-A*0201, HLA-A*0101 or HLA-B*0702 alleles. In some embodiments, the composition comprises an agent selected from the group consisting of a CTLA-4 antagonist, vermurafenib, ipilimumab, dacarbazine, IL-2, temozolomide, imatinib, gefitinib, erlotinib, sunitinib, tyrphostins, a PD-1 agonist, and telatinib.

In some embodiments, the presently disclosed methods increase the 5-year survival rate of the patients treated with the composition by at least 20 percent relative to average 5-year survival rates that could have been expected without treatment with the composition. In some embodiments, the presently disclosed methods are capable of increasing the overall median survival of patients treated with the composition by at least two months relative to an overall median survival that could have been expected without treatment with the composition.

In some embodiments, the presently disclosed methods further comprise administering to the patient darcarbazine, carmustine, tamoxifen, or a combination thereof including but not limited to administering darcarbazine, carmustine, and tamoxifen.

In some embodiments, the presently disclosed methods further comprise administering to the patient an adjuvant selected from the group consisting of montanide ISA-51 (Seppic, Inc.), QS-21 (Aquila Pharmaceuticals, Inc.), a tetanus helper peptide, GM-CSF, cyclophosphamide, *bacillus* Calmette-Guerin (BCG), *Corynebacterium parvum*, levamisole, azimezone, isoprinisone, dinitrochlorobenezene (DNCB), keyhole limpet hemocyanins (KLH), Freunds adjuvant (complete and incomplete), mineral gels, aluminum hydroxide (Alum), lysolecithin, pluronic polyols, polyanions, peptides, oil emulsions, dinitrophenol, diphtheria toxin (DT).

In some embodiments, the presently disclosed methods further comprise determining that the T cell memory response is a T cell central memory response ($T_{CM}$).

These and other aspects and embodiments that will be apparent to those of skill in the art upon reading the specification provide the art with immunological tools and agents useful for diagnosing, prognosing, monitoring, and/or treating cancers including but not limited to human cancers.

BRIEF DESCRIPTION OF THE FIGURES

A more complete understanding of the presently disclosed subject matter can be obtained by reference to the accompanying Figures, when considered in conjunction with the subsequent Detailed Description. The embodiments illustrated in the Figures are intended to be exemplary only, and should not be construed as limiting the presently disclosed subject matter.

FIGS. 1A-1C illustrate various T cell responses to tumor specific phosphopeptides of the presently disclosed subject matter. FIG. 1A depicts the results of multiplexed intracellular cytokine staining for IL-2, IFNγ, and TNFα. FIG. 1B is a graph showing that multifunctional TILs responded to the phosphopeptides identified producing IL-2, IFNγ, and TNFα. In FIG. 1B, responses to IL-2/IFNγ/TNFα, TNFα alone, IFNγ and TNFα, IFNγ alone, IL-2 and IFNγ, IL-2 alone, and TNFα and IL-2 are depicted. The responses are also summarized in FIG. 1C. In FIG. 1C, white boxes indicate less than 0.5%, hatched boxes indicate 0.5-1.0%, light gray boxes indicate 1.0-2.0%, and dark gray boxes indicate greater than 2.0%.

FIG. 2 illustrates T cell responses in 13 healthy donors to a variety of CRC-associated phosphopeptides. In FIG. 2, a box with a diagonal line indicates that the corresponding phosphopeptide was not detected, a white box indicates that 5-24 spots were detected by ELISpot, a light gray box indicates that 25-99 spots were detected, and a dark gray box indicates that 100 or more spots were detected.

BRIEF DESCRIPTION OF TABLES 3-9

Figure 1A:
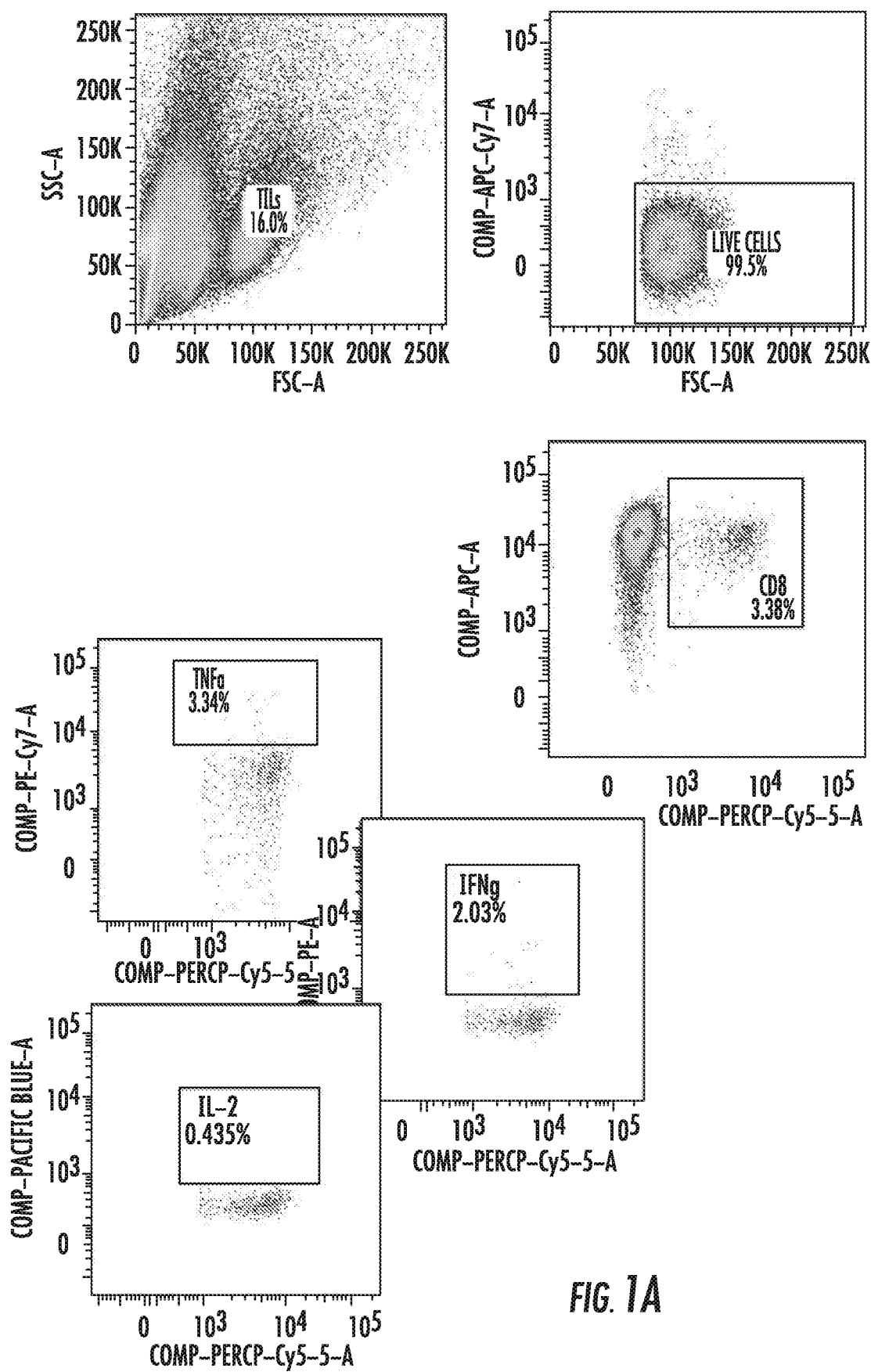

Tables 3-5 provide a listing of exemplary peptides including phosphopeptides of the presently disclosed subject matter.

Tables 3 and 4 are Table showing a list of selected CRC-associated phosphopeptides, predicted HLA type, presence in the liver in the form of a metastasis, and notes on the pathway with which the protein from which the phosphopeptide is derived is associated.

Table 5 is a Table listing various phosphopeptides associated with CRC.

Tables 6-8 list characteristics of HLA-DR-associated phosphopeptides selectively expressed by melanoma cells. Table 6 is a table derived from PCT International Patent Application Publication No. WO 2010/129537 that lists characteristics of HLA-DR-associated phosphopeptides selectively expressed by melanoma cells. Tables 7 and 8 are derived from Depontieu et al., 2009, including Depontieu et al. Supplemental Information, 10.1073 *Proc Natl Acad Sci USA* 0903852106. Table 7 lists characteristics of HLA-DR-associated phosphopeptides selectively expressed by EBV-transformed B Cells. Table 8 lists characteristics of HLA-DR-associated phosphopeptides commonly expressed by melanoma and EBV-transformed B Cells.

Table 9 lists characteristics of source proteins generating HLA-DR-restricted phosphopeptides.

DETAILED DESCRIPTION

While the following terms are believed to be well understood by one of ordinary skill in the art, the following definitions are set forth to facilitate explanation of the presently disclosed subject matter.

All technical and scientific terms used herein, unless otherwise defined below, are intended to have the same meaning as commonly understood by one of ordinary skill in the art. Mention of techniques employed herein are intended to refer to the techniques as commonly understood in the art, including variations on those techniques or substitutions of equivalent techniques that would be apparent to one of skill in the art. While the following terms are believed to be well understood by one of ordinary skill in the art, the following definitions are set forth to facilitate explanation of the presently disclosed subject matter.

Following long-standing patent law convention, the terms "a", "an", and "the" refer to "one or more" when used in this application, including the claims. Thus, in some embodiments the phrase "a peptide" refers to one or more peptides.

The term "about", as used herein to refer to a measurable value such as an amount of weight, time, dose (e.g., therapeutic dose), etc., is meant to encompass in some embodiments variations of ±20%, in some embodiments ±10%, in some embodiments ±5%, in some embodiments ±1%, in some embodiments ±0.1%, in some embodiments ±0.5%, and in some embodiments ±0.01% from the specified amount, as such variations are appropriate to perform the disclosed methods.

As used herein, the term "and/or" when used in the context of a list of entities, refers to the entities being present singly or in any possible combination or subcombination. Thus, for example, the phrase "A, B, C, and/or D" includes A, B, C, and D individually, but also includes any and all combinations and subcombinations of A, B, C, and D.

I. Target Peptides

The presently disclosed subject matter relates in some embodiments to post-translationally modified immunogenic therapeutic target peptides, e.g., phosphopeptides and optionally phosphopeptides comprising modified amino acids including, but not limited to phosphohomoserine, for use in immunotherapy and diagnostic methods of using the target peptides, as well as methods of selecting the same to make compositions for immunotherapy, e.g., in vaccines and/or in compositions useful in adaptive cell transfer.

In some embodiments, the target peptides of the presently disclosed subject matter are post-translationally modified by being provided with a phosphate group, (i.e., "phosphopeptides" including, but not limited to peptides comprising phosphoserine, phosphothreonine, phosphotyrosine, and derivatives thereof including but not limited to phosphohomoserine).

The target peptides of the presently disclosed subject matter are in some embodiments not the entire proteins from which they are derived (i.e., are fragments and/or subsequences of larger polypeptides). They are in some embodiments from 8 to 50 contiguous amino acid residues of the native human protein. In some embodiments, they can contain exactly, about, or at least 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 amino acids. The peptides of the presently disclosed subject matter can in some embodiments also have a length that falls in the ranges of 8-10, 9-12, 10-13, 11-14, 12-15, 15-20, 20-25, 25-30, 30-35, 35-40, and 45-50 amino acids. In some embodiments, exactly, about, or at least 1, 2, 3, 4, 5, 6, 7, 8, 9, 10, 11, 12, 13, 14, 15, 16, 17 or more of the amino acid residues within a recited sequence of a target peptide is phosphorylated and/or contains a modified phosphoamino acid including, but not limited to phosphohomoserine.

Target peptides can be modified and analogs (using for example, β-amino acids, L-amino acids, N-methylated amino acids, amidated amino acids, non-natural amino acids, retro inverse peptides, peptoids, PNA, halogenated amino acids) can be synthesized that retain their ability to stimulate a particular immune response but which also gain one or more beneficial features, such as those described herein below. Thus, a particular target peptide can, for example, have use for treating and vaccinating against multiple cancer types.

Substitutions can be made in the target peptides at residues known to interact with the MHC molecule. Such substitutions can have the effect of increasing the binding affinity of the target peptides for the MHC molecule and can also increase the half-life of the target peptide-MHC complex, the consequence of which is that the substituted target peptide is a more potent stimulator of an immune response than is the original target peptide.

Additionally, in some embodiments the substitutions have no effect on the immunogenicity of the target peptide per se, but rather prolong its biological half-life and/or prevent it from undergoing spontaneous alterations which might otherwise negatively impact on the immunogenicity of the peptide.

The target peptides disclosed herein can have differing levels of immunogenicity, MHC binding, and ability to elicit CTL responses against cells displaying a native target peptide (e.g., on the surface of a tumor cell).

A phosphopeptide as disclosed herein is in some embodiments modified such that its immunogenicity and/or its binding is enhanced. In some embodiments, the modified target peptide binds to an MHC class I molecule about or at least 10, 20, 30, 40, 50, 60, 70, 80, 90, 95, 100, 110, 125, 150, 175, 200, 225, 250, 275, 300, 350, 375, 400, 450, 500, 600, 700, 800, 1000% or more tightly than its native counterpart.

However, given the exquisite sensitivity of the T cell receptor, it cannot be foreseen whether such enhanced binding and/or immunogenicity will render a modified target peptide still capable of inducing an activated CTL that will cross react with the native target peptide being displayed on the surface of a tumor. Indeed, it is disclosed herein that the binding affinity of a target peptide does not predict its functional ability to elicit a T cell response.

Target peptides of the presently disclosed subject matter can in some embodiments be mixed together to form a cocktail. The target peptides can be in an admixture, or they can be linked together in a concatamer and/or in other arrangement as a single molecule. Linkers between individual target peptides can be used; these can, for example, be formed in some embodiments by any 10 to 20 amino acid residues. The linkers can be random sequences, or they can be optimized for degradation by dendritic cells.

In certain specified positions, a native amino acid residue in a native human protein can be altered to enhance its binding to an MHC class I molecule. These occur in "anchor" positions of the target peptides, often in positions 1, 2, 3, 9, or 10. Valine, alanine, lysine, leucine tyrosine, arginine, phenylalanine, proline, glutamic acid, threonine, serine, aspartic acid, tryptophan, and methionine can also be used as improved anchoring residues. Anchor residues for different HLA molecules are listed below in Table 1.

TABLE 1

Anchor Residues for HLA Molecules

| HLA Type | Residue Position | Anchor Residue(s) |
|---|---|---|
| HLA A*0201 | 2 | L, M |
|  | 9 or Last | V |
| HLA A*0301 | 2 | L, M |
|  | 9 or Last | K |
| HLA A*0101 | 2 | T, S |
|  | 3 | D, E |
|  | 9 or Last | Y |
| HLA B*2705 | 1 | R |
|  | 2 | R |
|  | 9 or Last | L, F, K, R, M |
| HLA B*0702 | 2 | P |
|  | 9 or Last | L, M, V, F |
| HLA B*4402 | 2 | E |
|  | 9 or Last | F, Y, W |

In some embodiments, the immunogenicity of a target peptide is measured using transgenic mice expressing human MHC class I genes. For example, "ADD Tg mice" express an interspecies hybrid class I MHC gene, AAD, which contains the α-1 and α-2 domains of the human HLA-A2.1 gene and the α-3 transmembrane and cytoplasmic domains of the mouse H-2Dd gene, under the transcriptional control of the human HLA-A2.1 promoter. Immunodetection of the HLA-A2.1 recombinant transgene established that expression was at equivalent levels to endogenous mouse class I molecules. The mouse α-3 domain expression enhances the immune response in this system. Compared to unmodified HLA-A2.1, the chimeric HLA-A2.1/H2-Dd MHC Class I molecule mediates efficient positive selection of mouse T cells to provide a more complete T cell repertoire capable of recognizing peptides presented by HLA-A2.1 Class I molecules.

The peptide epitopes presented and recognized by mouse T cells in the context of the HLA-A2.1/H2-Dd class I molecule are the same as those presented in HLA-A2.1+ humans. This transgenic strain enables the modeling of human T cell immune responses to HLA-A2 presented antigens, and identification of those antigens. This transgenic strain is a preclinical model for design and testing of vaccines for infectious diseases or cancer therapy involving optimal stimulation of CD8+ cytolytic T cells.

In some embodiments, the immunogenicity of a modified phosphopeptide is determined by the degree of Interferon gamma (IFNγ) and/or tumor necrosis factor-alpha (TNF-α) production of T cells from ADD Tg mice immunized with the target peptide, e.g., by immunization with target peptide pulsed bone marrow derived dendritic cells.

In some embodiments, the modified target peptides are about or at least 10, 20, 30, 40, 50, 60, 70, 80, 90, 95, 100, 110, 125, 150, 175, 200, 225, 250, 275, 300, 350, 375, 400, 450, 500, 600, 700, 800, 1000, 1500, 2000, 2500, 3000, 4000, 5000% or more immunogenic, e.g., in terms of numbers of IFNγ- and/or TNF-α-positive (i.e., "activated") T cells relative to numbers elicited by native target peptides in ADD Tg mice immunized with phosphopeptide-pulsed bone marrow derived dendritic cells (BMDCs). In some embodiments, the target peptides are modified target peptides. In some embodiments, the modified target peptides are able to elicit CD8+ T cells that are cross-reactive with the modified and the native target peptide in general and when such modified and native target peptides are complexed with MHC class I molecules in particular. In some embodiments, the CD8+ T cells that are cross-reactive with the modified and the native target peptides are able to reduce tumor size by about or at least 10%, 20%, 30%, 40%, 50%, 60%, 70%, 80%, 90%, 95%, 97% or 99% in a NOD/SCID/IL-2Ryc−/− knock out mouse relative to IL-2 treatment without such cross-reactive CD8+ T cells.

The phrase "capable of inducing a target peptide-specific memory T cell response in a patient" as used herein relates to eliciting a response from memory T cells (also referred to as "antigen-experienced T cell"), which are a subset of infection- and cancer-fighting T cells that have previously encountered and responded to their cognate antigen. Such T cells can recognize foreign invaders, such as bacteria or viruses, as well as cancer cells. Memory T cells have become "experienced" by having encountered antigen during a prior infection, having encountered cancer, or via previous vaccination. At a second encounter with the cognate antigen (e.g., by way of an initial inoculation with a target peptide of the presently disclosed subject matter), memory T cells can reproduce to mount a faster and stronger immune response than the first time the immune system responded to the invader (e.g., through the body's own consciously unperceived recognition of a target peptide being associated with diseased tissue). This behavior can be assayed in T lymphocyte proliferation assays, which can reveal exposure to specific antigens.

Memory T cells comprise two subtypes: central memory T cells ($T_{CM}$ cells) and effector memory T cells ($T_{EM}$ cells). Memory cells can be either CD4+ or CD8+. Memory T cells typically express the cell surface protein CD45RO. Central memory ($T_{CM}$) cells generally express L-selectin and CCR7, and they secrete IL-2 but not IFNγ or IL-4. Effector memory ($T_{EM}$) cells, however, generally do not express L-selectin or CCR7 but produce effector cytokines like IFNγ and IL-4.

A memory T cell response generally results in the proliferation of memory T cells and/or the upregulation or increased secretion of factors such as CD45RO, L-selectin, CCR7, IL-2, IFNγ, CD45RA, CD27, and/or IL-4. In some embodiments, the target peptides of the presently disclosed subject matter are capable of inducing a $T_{CM}$ cell response associated with L-selectin, CCR7, IL,-2 but not IFNγ or IL-4 expression and/or secretion. See e.g., Hamann et al., 1997. In some embodiments, a $T_{CM}$ cell response is associated with an at least or an about 1%, 5%, 10%, 15%, 20%, 25%, 30%, 35%, 45%, 50%, 55%, 60%, 65%, 70%, 75%, 80%, 90%, 95%, 97%, 98%, 99%, 100%, 125%, 150%, 175%, 200%, 250%, 300%, 400%, 500%, 600%, 700%, 800%, 900%, 1000%, 1500%, 2000% or more increase in T cell CD45RO/RA, L-selectin, CCR7, or IL-2 expression and/ secretion.

In some embodiments, the target peptides of the presently disclosed subject matter are capable of inducing a CD8+ $T_{CM}$ cell response in a patient the first time that patient is provided the composition including the selected target peptides. As such, the target peptides of the presently disclosed subject matter can in some embodiments be referred to as "neo-antigens." Although target peptides might be considered "self" for being derived from self-tissue, they generally are only found on the surface of cells with a dysregulated metabolism (e.g., aberrant phosphorylation), and they are likely never presented to immature T cells in the thymus. As such, these "self" antigens act are neo-antigens because they are nevertheless capable of eliciting an immune response.

In some embodiments, about or at least 1%, 5%, 10%, 15%, 20%, 25%, 30%, 35%, 45%, 50%, 55%, 60%, 65%, 70%, 75%, 80%, 90%, 95%, 97%, 98%, or 99% of T cells activated by particular target peptide in a particular patient sample are $T_{CM}$ cells.

In some embodiments, a patient sample is isolated exactly, about or at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30 or more days after an initial exposure to a particular target peptide and then assayed for target peptide-specific activated T cells and the proportion of $T_{CM}$ cells thereof.

In some embodiments, the compositions of the presently disclosed subject matter are able to elicit a CD8+ $T_{CM}$ cell response in at least or about 1%, 5%, 10%, 15%, 20%, 25%, 30%, 35%, 45%, 50%, 55%, 60%, 65%, 70%, 75%, 80%, 90%, 95%, 97%, 98%, or 99% of patients and/or healthy volunteers.

In some embodiments, the compositions of the presently disclosed subject matter are able to elicit a CD8+ $T_{CM}$ cell response in about or at least 1%, 5%, 10%, 15%, 20%, 25%, 30%, 35%, 45%, 50%, 55%, 60%, 65%, 70%, 75%, 80%, 90%, 95%, 97%, 98%, 99% of patients and/or healthy volunteers specific, and in some embodiments the CD8+ $T_{CM}$ cell response elicited is directed against all or at least or about 1, 2, 3, 4, 5, 6, 7, 8, 9, 10, or more target peptides that are present in the composition. In some embodiments, the aforementioned T cell activation tests are done by ELISpot assay.

II. Phosphopeptides

The term "phosphopeptides" includes MHC class I- and MHC class II-specific phosphopeptides. Exemplary MHC class I phosphopeptides are set forth in Table 5, for example.

In some embodiments, the phosphopeptides contain the sequences of at least one of the MHC class I-binding peptides listed in SEQ ID NO. 1-177. Moreover, in some embodiments about or at least 1, 2, 3, 4, 5, 6, 7, 8, 9, 10, 11, 12, 13, 14, 15 or more of the serine, homoserine, threonine, or tyrosine residues within the recited sequence is phosphorylated. The phosphorylation can be with a natural phosphorylation (—$CH_2$—O—$PO_3H$) or with an enzyme non-degradable, modified phosphorylation, such as but not limited to —$CH_2$—$CF_2$—$PO_3H$ or —$CH_2$—$CH_2$—$PO_3H$. Some phosphopeptides can contain more than one of the peptides listed in SEQ ID NO: 1-177, for example, if they are overlapping, adjacent, or nearby within the native protein from which they are derived.

The chemical structure of a phosphopeptide mimetic appropriate for use in the presently disclosed subject matter can in some embodiments closely approximate the natural phosphorylated residue which is mimicked, and also be chemically stable (e.g., resistant to dephosphorylation by phosphatase enzymes). This can be achieved with a synthetic molecule in which the phosphorous atom is linked to the amino acid residue, not through oxygen, but through carbon. In some embodiments, a $CF_2$ group links the amino acid to the phosphorous atom. Mimetics of several amino acids which are phosphorylated in nature can be generated by this approach. Mimetics of phosphoserine, phosphothreonine, and phosphotyrosine can be generated by placing a $CF_2$ linkage from the appropriate carbon to the phosphate moiety. The mimetic molecule L-2-amino-4(diethylphosphono)-4,4-difluorobutanoic acid (F2Pab) can substitute for phosphoserine (Otaka et al., 1995). L-2-amino-4-phosphono-4,4-difluoro-3-methylbutanoic acid (F2Pmb) can substitute for phosphothreonine, and L-2-amino-4-phosphono (difluoromethyl) phenylalanine (F2Pmp) can substitute for phosphotyrosine (Smyth et al., 1992; Akamatsu et al., 1997). Alternatively, the oxygen bridge of the natural amino acid can be replaced with a methylene group. In some embodiments, serine and threonine residues are substituted with homoserine and homothreonine residues, respectively. A phosphomimetic may also include vanadate, pyrophosphate or fluorophosphates.

IRS-2 over-expression either at the gene or protein level, is evident in many different cancer types, and has been demonstrated to cause mammary tumorigenesis and enhanced metastasis in vivo. IRS proteins are adapter proteins that link signaling from upstream activators to multiple downstream effectors to modulate normal growth, metabolism, survival and differentiation. It is disclosed herein that phosphorylated IRS-2 is broadly displayed on multiple cancer types and the resulting phosphopeptide is endogenously processed and presented at levels that allow strong immune responses to be generated against it. Phosphopeptide-specific CD8+ T cells can be generated from HLA-A2 transgenic mice upon immunization with the pIRS2 phosphopeptide and these T cells are capable of recognizing and killing human melanoma and breast tumors in vitro and controlled tumor growth in a xenograft tumor model system.

Tensin 3 (TNS3) plays a role in actin remodeling. It is involved in the dissociation of the integrin-tensin-actin complex. EGF activates TNS4 and down-regulates TNS3 which results in capping the tail of ITGB1. TN3 also seems to be involved in mammary cell migration and may be involved in cell migration and bone development. The Tensin 3 phosphopeptide (VMIGsPKKV, SEQ ID NO: 27) of the presently disclosed subject matter has been surprisingly discovered to be capable of inducing a strong phosphopeptide-specific memory T cell response in a patient. This further supports the position that peptide/MHC binding affinity does not correlate with the ability of a phosphopeptide to induce a phosphopeptide specific immune response.

III. Immunosuitablity

In some embodiments, the target peptides are combined into compositions that can be used in vaccine compositions for eliciting anti-tumor immune responses and/or in adoptive T cell therapy of colorectal cancer patients. Table 5 provides phosphopeptides presented on the surface of cancer cells.

Although individuals in the human population display hundreds of different HLA alleles, some are more prevalent than others. For example, 88% of colorectal cancer patients carry at least one of the six HLA alleles: HLA-A*0201 (51%), HLA-A*0101 (29%), HLA-A*0301 (21%), HLA-B*4402 (27%), HLA-B*0702 (30%), and HLA-B*-2705 (7%).

The presently disclosed subject matter provides in some embodiments target peptides which are immunologically suitable for each of the foregoing HLA alleles. "Immunologically suitable" means that a target peptide will bind at least one allele of an MHC class I molecule in a given patient. Compositions of the presently disclosed subject matter are in some embodiments immunologically suitable for a patient when at least one target peptide of the composition will bind at least one allele of an MHC class I molecule in a given patient. Compositions of multiple target peptides presented by each of the most prevalent alleles used in a cocktail ensures coverage of the human population and to minimize the possibility that the tumor will be able to escape immune surveillance by down-regulating expression of any one class I target peptide.

The compositions of the presently disclosed subject matter can in some embodiments comprise at least one target peptide specific for one or more of the following alleles: HLA-A*0201, HLA-A*0101, HLA-A*0301, HLA-B*4402, HLA-B*0702, HLA-B*-2705, and HLA-B*1402. The compositions of the presently disclosed subject matter can in some embodiments have at least one target peptide specific for one or more of the following alleles HLA-A*0201, HLA-A*0101, HLA-A*0301, HLA-B*4402, and HLA-B*0702. Alternatively, the compositions of the presently disclosed subject matter can in some embodiments have at least one target peptide specific for HLA-A*0201, HLA-A*0101, HLA-A*0301, HLA-B*4402, HLA-B*0702, HLA-B*-2705, HLA-B*1402, or any combination thereof. The compositions may have at least one phosphopeptide specific for about or at least 1, 2, 3, 4, 5, or all 6 of the aforementioned alleles.

As such, the compositions of the presently disclosed subject matter containing various combinations of target peptides are in some embodiments immunologically suitable for between or about 3-88%, 80-89%, 70-79%, 60-69%, 57-59%, 55-57%, 53-55% or 51-53% or 5-90%, 10-80%, 15-75%, 20-70%, 25-65%, 30-60%, 35-55% or 40-50% of the population of a particular cancer including, but not limited to colorectal cancer. In some embodiments, the compositions of the presently disclosed subject matter are able to act as vaccine compositions for eliciting anti-tumor immune responses and/or in adoptive T cell therapy of colorectal cancer patients wherein the compositions are immunologically suitable for about or at least 88, 87, 86, 85, 84, 83, 82, 81, 80, 79, 78, 77, 76, 75, 74, 73, 72, 71, 70, 69, 68, 67, 66, 65, 64, 63, 62, 61, 60, 59, 58, 57, 56, 55, 54, 53, 52, 51, 50, 49, 48, 47, 46, 45, 44, 43, 42, 41, 40, 39, 38, 37, 36, 35, 34, 33, 32, 31, 30, 29, 28, 27, 26, 25, 24, 23, 22, 20, 19, 18, 17, 16, 15, 14, 13, 12, 11, 10, 9, 8, 7, 6, 5, 4, or 3 percent of cancer such as, but not limited to colorectal cancer patients.

IV. Compositions

The phrase "target peptide compositions" as used herein refers to at least one target peptide formulated, for example, as a vaccine; or as a preparation for pulsing cells in a manner such that the pulsed cells, e.g., dendritic cells, will display the at least one target peptide in the composition on their surface, e.g., to T cells in the context of adoptive T cell therapy.

The compositions of the presently disclosed subject matter can in some embodiments include about or at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 50-55, 55-65, 65-80, 80-120, 90-150, 100-175, or 175-250 different target peptides.

The compositions of the presently disclosed subject matter in some embodiments generally include MHC class I specific target peptide(s) but can also include one or more target peptides specific for MHC class II, such as but not limited to the peptides set forth in Tables 6-9, or other peptides associated with tumors (e.g., tumor associated antigen ("TAA")).

Compositions comprising the target peptide are typically substantially free of other human proteins or peptides. They can be made synthetically or by purification from a biological source. They can be made recombinantly. Desirably they are in some embodiments at least 90% pure, in some embodiments at least 92% pure, in some embodiments at least 93% pure, in some embodiments at least 94% pure, in some embodiments at least 95% pure, in some embodiments at least 96% pure, in some embodiments at least 97% pure, in some embodiments at least 98% pure, and in some embodiments at least 99% pure. For administration to a human, they generally do not contain other components that might be harmful to a human recipient (referred to herein as "pharmaceutically acceptable for use in a human"). The compositions are typically devoid of cells, both human and recombinant producing cells. However, as noted below, in some cases, it can be desirable to load dendritic cells with a target peptide and use those loaded dendritic cells as either an immunotherapy agent themselves or as a reagent to stimulate a patient's T cells ex vivo. The stimulated T cells can be used as an immunotherapy agent.

In some cases, it can be desirable to form a complex between a target peptide and an HLA molecule of the appropriate type. Such complexes can be formed in vitro or in vivo. Such complexes are in some embodiments tetrameric with respect to an HLA-target peptide complex.

In some embodiments, the target peptide of the presently disclosed subject matter comprises an amino acid sequence that has at least 50, 60, 70, 80, 90, 95, 98, 99 or 100 percent sequence homology to an amino acid sequence as set forth in any of SEQ ID NOs: 1-177. As used herein, the phrase "sequence homology" refers to the presence of homology between two amino acid sequences. The "percentage of sequence homology" can be determined by comparing two optimally aligned sequences over a comparison window (e.g., about 5-25 contiguous amino acids or more), wherein the portion of the amino acid sequence in the comparison window can include additions or deletions (i.e., gaps) as compared to a reference sequence for optimal alignment of the two sequences. Optimal alignment of sequences for comparison can be conducted by computerized implementations of known algorithms, or by visual inspection. Readily available sequence comparison and multiple sequence alignment algorithms are, respectively, the Basic Local Alignment Search Tool (BLAST; Altschul et al., 1990; Altschul et al., 1997) and ClustalX (Chenna et al., 2003) programs, both available on the Internet. Other suitable programs include, but are not limited to, GAP, BestFit, PlotSimilarity, and FASTA, which are part of the Accelrys GCG Package available from Accelrys Software, Inc. of San Diego, Calif., United States of America.

Under certain circumstances it can be desirable to add additional proteins or peptides, for example, to make a cocktail having the ability to stimulate an immune response in a number of different HLA type hosts. Alternatively, additional proteins and/or peptides can provide an interacting function within a single host, such as but not limited to an adjuvant function or a stabilizing function. As a non-limiting example, other tumor antigens can be used in admixture with the target peptides such that multiple different immune responses are induced in a single patient.

Administration of target peptides to a mammalian recipient can be accomplished using long target peptides (e.g., longer than 15 residues), and/or using target peptide-loaded dendritic cells. See Melief, 2009. In some embodiments, an immediate goal of the administration of target peptides is to induce activation of $CD8^+$ T cells in a subject. Additional components that can be administered to the same subject, either at the same time and/or close in time (such as but not limited to within 3, 5, 7, 10, 14, 17, or 21 days of each other, or even longer) include TLR-ligand oligonucleotide CpG and related target peptides that have overlapping sequences of at least six amino acid residues. To ensure efficacy, mammalian recipients should express the appropriate human HLA molecules to bind to the target peptides. Transgenic mammals can be used as recipients, for example, if they express appropriate human HLA molecules. If a mammal's own immune system recognizes a similar target peptide then it can be used as model system directly without introducing a transgene. Useful models and recipients can be at increased risk of developing metastatic cancer, such as metastatic colorectal cancer. Other useful models and recipients can be predisposed, e.g., genetically and/or environmentally, to develop colorectal cancer or other cancer.

IV.A. Selection of Target Peptides

Disclosed herein is the finding that immune responses can be generated against phosphorylated peptides tested in healthy and diseased individuals. The T cells associated with these immune responses, when expanded in vitro, are able to recognize and kill malignant tissue (both established cells lines and primary tumor samples). Cold-target inhibition studies reveal that these target peptide-specific T cell lines kill primary tumor tissue in a target peptide-specific manner.

When selecting target peptides of the presently disclosed subject matter for inclusion in immunotherapy, e.g., in adaptive cell therapy or in the context of a vaccine, one can in some embodiments pick target peptides using one or more of the following criteria: 1) peptides associated with a particular cancer/tumor cell type; 2) a peptide derived from a gene and/or a protein associated with cell proliferation, transformation, and/or malignancy; 3) a peptide that is specific for an HLA allele carried the group of patients to be treated; and/or 4) a peptide that is capable of inducing a target peptide-specific memory T cell response in the patients to be treated upon a first exposure to a composition including the selected target peptides.

IV.B. Target Peptide Vaccines

The antigen target peptides can also be employed in a composition designed to vaccinate an individual. The antigen target peptides can in some embodiments be injected alone and can in some embodiments be administered in combination with an adjuvant and/or a pharmaceutically acceptable carrier. Vaccines are envisioned to prevent and/or treat certain diseases in general, and cancers in particular.

The target peptide-containing compositions of the presently disclosed subject matter can in some embodiments be used as a vaccine for cancer, and more specifically for melanoma, leukemia, ovarian, breast, colorectal, or lung squamous cancer, sarcoma, renal cell carcinoma, pancreatic carcinomas, squamous tumors of the head and neck, brain cancer, liver cancer, prostate cancer, ovarian cancer, and cervical cancer. The compositions can include target peptides. The vaccine compositions can in some embodiments include only the target peptides, or peptides disclosed herein, or they can include other cancer antigens that have been identified.

The vaccine compositions of the presently disclosed subject matter can be used prophylactically for the purposes of preventing, reducing the risk of, and/or delaying initiation of a cancer in an individual that does not currently have cancer. Alternatively, they can be used to treat an individual that already has cancer, so that recurrence or metastasis is delayed and/or prevented. Prevention relates to a process of prophylaxis in which the individual is immunized prior to the induction or onset of cancer. For example, in some embodiments individuals with a history of poor life style choices and at risk for developing colorectal cancer, might be immunized prior to the onset of the disease.

Alternatively, individuals that already have cancer can be immunized with the target peptide-containing compositions of the presently disclosed subject matter so as to stimulate an immune response that would be reactive against the cancer. A clinically relevant immune response would be one in which the cancer partially or completely regresses and is eliminated from the patient, and it would also include those responses in which the progression of the cancer is blocked without being eliminated. Similarly, prevention need not be total, but may result in a reduced risk, delayed onset, or delayed progression or metastasis.

The target peptide vaccines of the presently disclosed subject matter can be given to patients in some embodiments before, in some embodiments after, and/or in some embodiments during any stage of colorectal cancer. In some embodiments, they are given to patients with malignant colorectal cancer.

In some embodiments, the 5-year survival rate of patients treated with the vaccines of the presently disclosed subject matter is increased by a statistically significant amount that is, in some embodiments, by about or at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 or more percent, relative to the average 5-year survival rates described above.

In some embodiments, the target peptide vaccine composition will increase survival rates in patients with metastatic colorectal cancer by a statistically significant amount of time that is, in some embodiments, by about or at least, 0.25, 0.5, 0.75, 1.0, 1.25, 1.5, 1.75, 2.0, 2.25, 2.5, 2.75, 3.0, 3.25, 3.5, 4.0, 4.25, 4.5, 4.75, 5.0, 5.25, 5.5, 5.75, 6.0, 6.25, 6.5, 6.75, 7.0, 7.25, 7.5, 7.75, 8.0, 8.25, 8.5, 8.75, 9.0, 9.25, 9.50, 9.75, 10.0, 10.25, 10.5, 10.75, 11.0, 11.25, 11.5, 11.75 or 12 months or more compared to what could have been expected without vaccine treatment.

In some embodiments, the survival rate (e.g., the 1, 2, 3, 4, or 5-year survival rate) of patients treated with the vaccines of the presently disclosed subject matter are increased by a statistically significant amount that is, in some embodiments, by about, or at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 percent, or even greater than 100 percent, relative to the average 5-year survival rates described above.

The target peptide vaccines of the presently disclosed subject matter are in some embodiments envisioned to illicit a T cell-associated immune response such as, but not limited to generating activated $CD8^+$ T cells specific for native target peptide/MHC class I expressing cells. In some embodiments, the $CD8^+$ T cells specific for native target peptide/MHC class I expressing cells are specific for at least or about 1, 2, 3, 4, 5, 6, 7, 8, 9, 10, or more of the target peptides in the vaccine in a patient for about or at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 or more days after providing the vaccine to the patient.

In some embodiments, the treatment response rates of patients treated with the target peptide vaccines of the presently disclosed subject matter are increased by a statistically significant amount that is, in some embodiments by about or at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 150, 200, 250, 300, 350, 400, 450, or 500 or more percent, relative to treatment without the vaccine.

In some embodiments, overall median survival of patients treated with the target peptide vaccines of the presently disclosed subject matter are increased by a statistically significant amount that is, in some embodiments, by about or at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 150, 200, 250, 300, 350, 400, 450, or 500 or more percent, relative to treatment without the vaccine. Preferably, the overall median survival of colorectal cancer patients treated the target peptide vaccines is envisioned to be about or at least 10.0, 10.25, 10.5, 10.75, 11.0, 11.25, 11.5, 11.75, 12, 12.25, 12.5, 12.75, 13, 13.25, 13.5, 13.75, 14, 14.25, 14.5, 14.75, 15, 16, 17, 18, 19, 20, 21, 22, 23, 24, 25, 26, 27, 28, 29, 30, 31, 32, 33, 34, 35, 36 or more months.

In some embodiments, tumor size of patients treated with the target peptide vaccines of the presently disclosed subject matter is decreased by a statistically significant amount that is, in some embodiments, by about or at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 150, 200, 250, 300, 350, 400, 450, or 500 or more percent, relative to treatment without the vaccine.

In some embodiments, the compositions of the presently disclosed subject matter provide an clinical tumor regression by a statistically significant amount such as, but not limited to about or at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 150, 200, 250, 300, 350, 400, 450, or 500 or more percent, relative to treatment without the vaccine.

In some embodiments, the compositions of the presently disclosed subject matter provide a CTL response specific for the cancer being treated (e.g., colorectal cancer) by a statistically significant amount such as, but not limited to about or at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 percent of patients treated with the composition.

In some embodiments, the compositions of the presently disclosed subject matter provide an increase in progression free survival in the cancer being treated, such as but not limited to colorectal cancer, of about or at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 110, 120, 130, 140, 150, 160, 170, 180, 190, 200, 225, 250, 275, 300, 325, 350, 375, 400, 425, 450, 475, 500 or more weeks or months compared to the progression free survival or patients not treated with the composition.

In some embodiments, one or more of progression free survival, CTL response rates, clinical tumor regression rates, tumor size, survival rates (such as but not limited to overall survival rates), and/or response rates are determined, assessed, calculated, and/or estimated weekly, monthly, bi-monthly, quarterly, semi-annually, annually, and/or bi-annually over a period of about or at least 1, 2, 3, 4, 5, 6, 7, 8, 9, 10, 11, 12, 13, 14, 15 or more years or about or at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 110, 120, 130, 140, 150, 160, 170, 180, 190, 200, 225, 250, 275, 300, 325, 350, 375, 400, 425, 450, 475, 500 or more weeks.

IV.C. Compositions for Priming T Cells

Adoptive cell transfer (ACT) is the passive transfer of cells, in some embodiments immune-derived cells, into a recipient host with the goal of transferring the immunologic functionality and characteristics into the host. Clinically, this approach has been exploited to transfer either immune-promoting or tolerogenic cells (often lymphocytes) to patients to enhance immunity against cancer. The adoptive transfer of autologous tumor infiltrating lymphocytes (TIL) or genetically redirected peripheral blood mononuclear cells has been used to successfully treat patients with advanced solid tumors, including melanoma and colorectal carcinoma, as well as patients with CD19-expressing hematologic malignancies. In some embodiments, ACT therapies achieve T cell stimulation ex vivo by activating and expanding autologous tumor-reactive T cell populations to large numbers of cells that are then transferred back to the patient. See Gattinoni et al., 2006.

The target peptides of the presently disclosed subject matter can in some embodiments take the form of antigenic peptides formulated in a composition added to autologous dendritic cells and used to stimulate a T helper cell or CTL response in vitro. The in vitro generated T helper cells or CTL can then be infused into a patient with cancer (Yee et al., 2002), and specifically a patient with a form of cancer that expresses one or more of antigenic target peptides.

Alternatively, the target peptides can be added to dendritic cells (DCs) in vitro to produce loaded DCs, with the loaded DCs being subsequently transferred into an individual with cancer in order to stimulate an immune response. Alternatively, the loaded DCs can be used to stimulate CD8+ T cells ex vivo with subsequent reintroduction of the stimulated T cells to the patient. Although a particular target peptide might be identified on one particular cancer cell type, it might also be found on other cancer cell types.

The presently disclosed subject matter envisions treating cancer by providing a patient with cells pulsed with a composition of target peptides. The use of DCs pulsed with target peptides peptide antigens enables manipulation of the immunogen in two ways: varying the number of cells injected and varying the density of antigen presented on each cell. Exemplary non-limiting methods for DC-based based treatments can be found, for example in Mackensen et al., 2000.

IV.D. Additional Peptides Present in Target Peptide Compositions

The target peptide compositions (or target peptide composition kits comprising the same) of the presently disclosed subject matter can in some embodiments also include at least one additional peptide derived from one or more tumor-associated antigens (TAAs). Examples of TAAs include MelanA (MART-I), gp100 (Pmel 17), tyrosinase, TRP-1, TRP-2, MAGE-1, MAGE-3, BAGE, GAGE-1, GAGE-2, p15(58), CEA, RAGE, NY-ESO (LAGE), SCP-1, Hom/Mel-40, PRAME, p53, H-Ras, HER-2/neu, BCR-ABL, E2A-PRL, H4-RET, IGH-IGK, MYL-RAR, Epstein Barr virus antigens, EBNA, human papillomavirus (HPV) antigens E6 and E7, TSP-180, MAGE-4, MAGE-5, MAGE-6, p185erbB2, p180erbB-3, c-met, nm-23H1, PSA, TAG-72-4, CA 19-9, CA 72-4, CAM 17.1, NuMa, K-ras, β-Catenin, CDK4, Mum-1, p16, TAGE, PSMA, PSCA, CT7, telomerase, 43-9F, 5T4, 791Tgp72, α-fetoprotein, β-HCG, BCA225, BTAA, CA 125, CA 15-3 (CA 27.29\BCAA), CA 195, CA 242, CA-50, CAM43, CD68\KP1, CO-029, FGF-5, G250, Ga733 (EpCAM), HTgp-175, M344, MA-50, MG7-Ag, MOV18, NB/70K, NY-CO-1, RCAS1, SDCCAG16, TA-90 (Mac-2 binding protein/cyclophilin C-associated protein), TAAL6, TAG72, TLP, TPS, prostatic acid phosphatase, and the like. Exemplary, non-limiting peptides derived from TAAs that can be incorporated into target peptide compositions (or target peptide composition kits comprising the same) of the presently disclosed subject matter are presented in Table 2.

TABLE 2

Exemplary Tumor-associated Antigen Peptides

| Tumor-associated Antigen[1] | Peptide Sequence[2] |
|---|---|
| gp100$_{280-288}$ | YLEPGPVTA (SEQ ID NO: 178) |
| Tyr$_{369-377}$ | DYMDGTMSQV (SEQ ID NO: 179) |
| gp100$_{17-25}$ | ALLAVGATK (SEQ ID NO: 180) |
| Tyr$_{243-251}$ | KCDICTDEY (SEQ ID NO: 181) |
| TAG-1,2 | RLSNRLLLR (SEQ ID NO: 182) |
| — | SQNFPGSQK (SEQ ID NO: 183) |
| gp100$_{154-162}$ | KTWGQYWQV (SEQ ID NO: 184) |
| gp100$_{209-217}$ | I(T/M)DQVPFSV (SEQ ID NO: 185) |
| gp100$_{476-485}$ | VLYRYGSFSV (SEQ ID NO: 186) |
| MART-1/MelanA$_{27-35}$ | AAGIGILTV (SEQ ID NO: 187) |
| gp100 | ALNFPGSQK (SEQ ID NO: 188) |
| gp 100$_{614-622}$ | LIYRRRLMK (SEQ ID NO: 189) |
| NY-ESO-1 | AAQERRVPR (SEQ ID NO: 190) |
| NY-ESO-1$_{53-62}$ | ASGPGGGAPR (SEQ ID NO: 191) |
| NY-ESO-1 | LLGPGRPYR (SEQ ID NO: 192) |
| Tyr$_{240-251}$ | SDAEKSDICTDEY (SEQ ID NO: 193) |
| Tyr$_{146-156}$ | SSDYVIPIGTY (SEQ ID NO: 194) |
| MAGE-A1$_{161-169}$ | EADPTGHSY (SEQ ID NO: 195) |
| MAGE-A3$_{168-176}$ | EVDPIGHLY (SEQ ID NO: 196) |
| gp100$_{209-217}$ | IMDQVPFSV (SEQ ID NO: 197) |
| MAGE-A10$_{254-262}$ | GLYDGMEHL (SEQ ID NO: 198) |
| Tyr$_{56-70}$ | AQNILLSNAPLGPQFP (SEQ ID NO: 199) |
| Tyr$_{388-406}$ | FLLHHAFVDSIFEQWLQRHRP (SEQ ID NO: 200) |
| Melan-A/MART-1$_{51-73}$ | RNGYRALMDKSLHVGTQCALTRR (SEQ ID NO: 201) |
| MAGE-A3$_{281-295}$ | TSYVKVLHHMVKISG (SEQ ID NO: 202) |
| MAGE-A1,2,3,6$_{121-134}$ | LLKYRAREPVTKAF (SEQ ID NO: 203) |
| Gp100$_{44-59}$ | WNRQLYPEWTEAQRLD (SEQ ID NO: 204) |
| p2$_{830-844}$ | AQYIKANSKFIGITEL (SEQ ID NO: 205) |
| Her2/neu$_{369-377}$ | KIFGSLAFL (SEQ ID NO: 206) |
| CEA$_{571-579}$ | YLSGADLNL (SEQ ID NO: 207) |
| Her2/neu$_{754-762}$ | VLRENTSPK (SEQ ID NO: 208) |
| FBP$_{191-199}$ | EIWTHSYKV (SEQ ID NO: 209) |
| MAGE-A1$_{96-104}$ | SLFRAVITK (SEQ ID NO: 210) |
| CEA$_{27-35}$ | HLFGYSWYK (SEQ ID NO: 211) |

TABLE 2-continued

Exemplary Tumor-associated Antigen Peptides

| Tumor-associated Antigen[1] | Peptide Sequence[2] |
|---|---|
| MART-1$_{97-116}$ | APPAYEKLS (SEQ ID NO: 212) |
| MART-1$_{98-109}$ | PPAYEKLSA (SEQ ID NO: 213) |
| MART-1$_{99-110}$ | PAYEKLSAE (SEQ ID NO: 214) |
| MART-1$_{97-116}$ | VPNAPPAYEKLsAEQSPPPY (SEQ ID NO: 215) |
| MART-1$_{98-109}$ | PNAPPAYEKLsA (SEQ ID NO: 216) |
| MART-1$_{99-110}$ | NAPPAYEKLsAE (SEQ ID NO: 217) |
| MART-1$_{100-111}$ | APPAYEKLsAEQ (SEQ ID NO: 218) |
| MART-1$_{100-114}$ | APPAYEKLsAEQSPP (SEQ ID NO: 219) |
| MART-1$_{100-115}$ | APPAYEKLsAEQSPPP (SEQ ID NO: 220) |
| MART-1$_{101-112}$ | PPAYEKLsAEQS (SEQ ID NO: 221) |
| MART-1$_{102-113}$ | PAYEKLsAEQSP (SEQ ID NO: 222) |
| MART-1$_{103-114}$ | AYEKLsAEQSPP (SEQ ID NO: 223) |
| MART-1$_{104-115}$ | YEKLSAEQSPPP (SEQ ID NO: 224) |
| MART-1$_{100-115}$ | APPAYEKLSAEQSPPP (SEQ ID NO: 225) |
| MART-1$_{100-116}$ | APPAYEKLsAEQSPPPY (SEQ ID NO: 226) |

[1]the numbers listed in subscript denote the amino acid positions of the peptide sequences for each TAA.
[2]lowercase letters (s, t, or y) indicate positions of phosphorylation.

Such tumor-specific peptides (including the MHC class II phosphopeptides disclosed in Tables 6-9) can be added to the target peptide compositions in a manner, number, and in an amount as if they were an additional target peptide added to the target peptide compositions as described herein.

IV.E. Combination Therapies

In some embodiments, the target peptide compositions (or target peptide composition kits) of the presently disclosed subject matter are administered as a vaccine or in the form of pulsed cells as first, second, third, or fourth line treatment for the cancer. In some embodiments, the compositions of the presently disclosed subject matter are administered to a patient in combination with one or more therapeutic agents. Exemplary, non-limiting therapeutic agents include anti-Programmed Death-1 (PD1) or PD1-antagonists such as the anti-PD1 antibody BMS-936558 (Bristol-Myers Squibb Co., New York, N.Y., United States of America); anti-CTLA-4 or CTLA-4 antagonists; vermurafenib; ipilimumab; Dacarbazine; IL-2; Temozolomide; receptor tyrosine kinase inhibitors, including but not limited to imatinib, gefitinib, erlotinib, sunitinib, tyrphostins, telatinib; sipileucel-T; a platinum-based agent; a taxane; an alkylating agent; an antimetabolite and/or a vinca alkaloid; and combinations thereof.

In some embodiments, the cancer is sensitive to and/or refractory, relapsed, and/or resistant to one or more chemotherapeutic agents such as, but not limited to a platinum-based agent, a taxane, an alkylating agent, an anthracycline (e.g., doxorubicin including but not limited to liposomal doxorubicin), an antimetabolite, and/or a vinca alkaloid. In some embodiments, the cancer is an ovarian cancer, and the ovarian cancer is refractory, relapsed, or resistant to a platinum-based agent (e.g., carboplatin, cisplatin, oxaliplatin), a taxane (e.g., paclitaxel, docetaxel, larotaxel, cabazitaxel), and/or an anthracycline (e.g., doxorubicin including but not limited to liposomal doxorubicin). In some embodiments, the cancer is colorectal cancer, and the cancer is refractory, relapsed, or resistant to an antimetabolite (e.g., an antifolate (e.g., pemetrexed, floxuridine, raltitrexed) a pyrimidine analogue (e.g., capecitabine, cytrarabine, gemcitabine, 5FU)), and/or a platinum-based agent (e.g., carboplatin, cisplatin, irinoptecan, oxaliplatin). In some embodiments, the cancer is lung cancer, and the cancer is refractory, relapsed, or resistant to a taxane (e.g., paclitaxel, docetaxel, larotaxel, cabazitaxel), a platinum-based agent (e.g., carboplatin, cisplatin, oxaliplatin), a vinca alkaloid (e.g., vinblastine, vincristine, vindesine, vinorelbine), a vascular endothelial growth factor (VEGF) pathway inhibitor, an epidermal growth factor (EGF) pathway inhibitor) and/or an antimetabolite (e.g., an antifolate including but not limited to pemetrexed, floxuridine, or raltitrexed), and a pyrimidine analogue (e.g., capecitabine, cytrarabine, gemcitabine, 5FU). In some embodiments, the cancer is breast cancer, and the cancer is refractory, relapsed, or resistant to a taxane (e.g., paclitaxel, docetaxel, larotaxel, cabazitaxel), a VEGF pathway inhibitor, an anthracycline (e.g., daunorubicin, doxorubicin including but not limited to liposomal doxorubicin, epirubicin, valrubicin, idarubicin), a platinum-based agent (e.g., carboplatin, cisplatin, oxaliplatin), and/or an antimetabolite (e.g., an antifolate including but not limited to pemetrexed, floxuridine, or raltitrexed), and a pyrimidine analogue (e.g., capecitabine, cytrarabine, gemcitabine, 5FU). In some embodiments, the cancer is gastric cancer, and the cancer is refractory, relapsed, or resistant to an antimetabolite (e.g., an antifolate including but not limited to pemetrexed, floxuridine, raltitrexed) and a pyrimidine analogue (e.g., capecitabine, cytrarabine, gemcitabine, 5FU) and/or a platinum-based agent (e.g., carboplatin, cisplatin, oxaliplatin).

In some embodiments, the cancer is colorectal cancer. In some embodiments, chemotherapy for colorectal cancer comprises treatment with 5FU, capecitabine, irinoptecan, and/or oxaliplatin. In some embodiments, a combination of chemotherapeutics is employed. Exemplary, non-limiting chemotherapeutics that can be employed combination therapies include FOLFOX (5FU, leucovorin, and oxaliplatin); FOLFIRI (5FU, leucovorin, and irinotecan); FOLFOXIRI (leucovorin, 5FU, oxaliplatin, and irinotecan); CapeOx (capecitabine and oxaliplatin); 5FU and leucovorin; and/or capecitabine.

In some embodiments, the target peptide compositions (or target peptide composition kits comprising the same) of the presently disclosed subject matter are associated with agents that inhibit T cell apoptosis or anergy thus potentiating a T cell response (referred to herein as a "T cell potentiator"). Such agents include B7RP1 agonists, B7-H3 antagonists, B7-H4 antagonists, HVEM antagonists, HVEM antagonists, GAL9 antagonists or alternatively CD27 agonists, OX40 agonists, CD137 agonists, BTLA agonists, ICOS agonists, CD28 agonists, or soluble versions of PDLL, PDL2, CD80, CD96, B7RP1, CD137L, OX40 or CD70. See Pardoll, 2012.

In some embodiments, the T cell potentiator is a PD1 antagonist. Programmed death 1 (PD1) is a key immune checkpoint receptor expressed by activated T cells, and it mediates immunosuppression. PD1 functions primarily in peripheral tissues, where T cells can encounter the immunosuppressive PD1 ligands PD-L1 (B7-H1) and PD-L2 (B7-DC), which are expressed by tumor cells, stromal cells, or both. In some embodiments, the anti-PD1 monoclonal antibody BMS-936558 (also known as MDX-1106 and ONO-4538; Bristol-Myers Squibb) is used. In some embodiments, the T cell potentiator (e.g., PD1 antagonist) is administered as an intravenous infusion at least or about every 1, 1.5, 2, 2.5, 3, 3.5, or 4 weeks of each 4, 5, 6, 7, 8, 9, or 10-week treatment cycle of about for at least 1, 2, 3, 4, 5, 6, 7, 8, 9, 10, 11, 12, 13, 14, 15, 16, 17, 18, 19, 20, or more cycles. Exemplary, non-limiting doses of the PD1 antagonists are in some embodiments exactly, about, or at least 0.1, 0.2, 0.3, 0.4, 0.5, 0.6, 0.7, 0.8, 0.9, 1, 2, 3, 4, 5, 6, 7, 8, 9, 10, 11, 12, 13, 14, 15, 16, 17, 18, 19, 20, or more mg/kg. See Brahmer et al., 2012.

The exemplary therapeutic agents listed herein above are envisioned to be administered at a concentration of in some embodiments about 1 to 100 mg/m$^2$, in some embodiments about 10 to 80 mg/m$^2$, and in some embodiments about 40 to 60 mg/m$^2$. Further exemplary dosages include, but are not limited to about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, or more mg/m$^2$. Alternatively, an exemplary dosage range can be in some embodiments about or at least 0.001 to 100 mg/kg, in some embodiments about or at least 0.1 to 1 mg/kg, and in some embodiments about or at least 0.01 to 10 mg/kg.

The target peptide compositions (or target peptide composition kits) of the presently disclosed subject matter can in some embodiments be co-administered with cytokines such as lymphokines, monokines, growth factors, and traditional polypeptide hormones. Exemplary cytokines are growth hormones including but not limited to human growth hormone, N-methionyl human growth hormone, and bovine growth hormone; parathyroid hormone; thyroxine; insulin; proinsulin; relaxin; prorelaxin; glycoprotein hormones including but not limited to follicle stimulating hormone (FSH), thyroid stimulating hormone (TSH), and luteinizing hormone (LH); hepatic growth factor; prostaglandin, fibroblast growth factor; prolactin; placental lactogen, OB protein; TNF-α and TNF-β; mullerian-inhibiting substance; mouse gonadotropin-associated peptide; inhibin; activin; VEGF; integrin; thrombopoietin (TPO); nerve growth factors including but not limited to NGF-β; platelet-growth factor; transforming growth factors (TGFs) including but not limited to TGF-α and TGF-β; insulin-like growth factor (IGF)-I and IGF-II; erythropoietin (EPO); osteoinductive factors; interferons (IFN) including but not limited to IFNα, IFNβ, and IFNγ; colony stimulating factors (CSFs) including but not limited to macrophage-CSF (M-CSF), granulocyte-macrophage-CSF (GM-CSF), and granulocyte-CSF (G-CSF); interleukins (ILs) including but not limited to IL-1, IL-1α, IL-2, IL-3, IL-4, IL-5, IL-6, IL-7, IL-8, IL-9, IL-10, IL-11, IL-12; IL-13, IL-14, IL-15, IL-16, IL-17, and IL-18; leukemia inhibitory factor (LIF), kit-ligand; FLT-3; angiostatin; thrombospondin; endostatin; and lymphotoxin (LT). As used herein, the term cytokine includes proteins from natural sources and/or from recombinant cell culture and biologically active equivalents thereof.

The target peptide compositions of the presently disclosed subject matter can in some embodiments be provided with administration of cytokines around the time of (including but not limited to about or at least 1, 2, 3, or 4 weeks or days before and/or after) the initial dose of a target peptide composition.

Exemplary non-limiting doses of the cytokine are in some embodiments about or at least 1-100, 10-80, 20-70, 30-60, 40-50, or 1, 2, 3, 4, 5, 6, 7, 8, 9 or 10 Mu/m$^2$/day over about or at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, or 70 days. The cytokine can in some embodiments be delivered at least or about once every 1, 2, 3, 4, 5, 6, 7, 8, 9, 10, 11, 12, 13, 14, 15, 16, 17, 18, 19, 20, 21, 22, 23, or 24 hours. Cytokine treatment can be provided in at least or about 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 cycles of at least or about 1, 2, 3, 4, 5, 6, 7, 8, 9, 10, or more weeks, wherein each cycle has at least or about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, or more cytokine doses. Cytokine treatment can in some embodiments be on the same schedule as administration of the target peptide compositions or in some embodiments on a different schedule, which differing schedule can in some embodiments be an overlapping schedule.

In some embodiments, the cytokine is IL-2 and is dosed in an amount about or at least 100,000 to 1,000,000; 200,000-900,000; 300,000-800,000; 450,000-750,000; 600,000-800,000; or 700,000-800,000 (in some embodiments. 720,000) units (IU)/kg administered, e.g., as a bolus, every 1, 2, 3, 4, 5, 6, 7, 8, 9, 10, 11, 12, 13, 14, 15, 16, 17, 18, 19, or 20 hours for 1, 2, 3, 4, 5, 6, 7, 8, 9, 10, 11, 12, 13, 14, or more days, in a cycle, for example.

V. Types of Proliferative Diseases

In some embodiments, the compositions of the presently disclosed subject matter are envisioned to be useful in the treatment of benign and/or malignant proliferative diseases. Excessive proliferation of cells and turnover of cellular matrix contribute significantly to the pathogenesis of several diseases including but not limited to cancer, atherosclerosis, rheumatoid arthritis, psoriasis, idiopathic pulmonary fibrosis, scleroderma and cirrhosis of the liver, ductal hyperplasia, lobular hyperplasia, papillomas, and others.

In some embodiments, the proliferative disease is cancer, including but not limited to breast cancer, colorectal cancer, squamous carcinoma of the lung, sarcoma, renal cell carcinoma, pancreatic carcinomas, squamous tumors of the head and neck, leukemia, brain cancer, liver cancer, prostate cancer, ovarian cancer, and cervical cancer. In some embodiments, the presently disclosed compositions and methods are used to treat colorectal cancer, acute myelogenous leukemia (AML), acute lyphocytic leukemia (ALL), chronic lymphocytic lymphoma (CLL), chronic myelogenous leukemia (CML), breast cancer, renal cancer, pancreatic cancer, and/or ovarian cancer.

In some embodiments, the target peptide compositions of the presently disclosed subject matter can be used to treat colorectal cancer. Colorectal cancer is typically staged in five stages: Stage 0-IV, with several substages. When metastatic (i.e., Stage IV), the colorectal cancer has in some embodiments spread to the lung, bone, liver, and/or brain.

In some embodiments, the cancer is a cancer described herein. For example, the cancer can be a cancer of the bladder (including but not limited to accelerated and metastatic bladder cancer), breast (including but not limited to estrogen receptor positive breast cancer, estrogen receptor negative breast cancer, HER-2 positive breast cancer, HER-2 negative breast cancer, triple negative breast cancer, and inflammatory breast cancer), colon (including but not limited to colorectal cancer), kidney (including but not limited to renal cell carcinoma), liver, lung (including but not limited to small cell lung cancer and non-small cell lung cancer such as but not limited to adenocarcinoma, squamous cell carcinoma, bronchoalveolar carcinoma and large cell carcinoma), genitourinary tract cancer, including but not limited to ovary (such as but not limited to fallopian, endometrial, and peritoneal cancers), cervix, prostate, and testes, lymphatic system, rectum, larynx, pancreas (including but not limited to exocrine pancreatic carcinoma), stomach (including but not limited to gastroesophageal, upper gastric, and lower gastric cancers), gastrointestinal cancer (including but not limited to anal cancer), gall bladder, thyroid, lymphoma (including but not limited to Burkitt's, Hodgkin's, and non-Hodgkin's lymphoma), leukemia (including but not limited to acute myeloid leukemia), Ewing's sarcoma, nasoesophageal cancer, nasopharyngeal cancer, neural and glial cell cancers (including but not limited to glioblastoma multiforme), and head and neck cancers. Exemplary non-limiting cancers also include melanoma, breast cancer (including but not limited to metastatic or locally advanced breast cancer), prostate cancer (including but not limited to hormone refractory prostate cancer), renal cell carcinoma, lung cancer (including but not limited to small cell lung cancer and non-small cell lung cancer (including adenocarcinoma, squamous cell carcinoma, bronchoalveolar carcinoma, and large cell carcinoma), pancreatic cancer, gastric cancer (including but not limited to gastroesophageal, upper gastric, and/or lower gastric cancer), colorectal cancer, squamous cell cancer of the head and neck, ovarian cancer (including but not limited to advanced ovarian cancer, platinum-based agent-resistant, and/or relapsed ovarian cancer), lymphoma (including but not limited to Burkitt's, Hodgkin's, or non-Hodgkin's lymphoma), leukemia (including but not limited to acute myeloid leukemia), and gastrointestinal cancer.

VI. Administration of Vaccine Compositions

VI.A. Routes of Administration

The target peptide compositions of the presently disclosed subject matter can be administered parenterally, systemically, topically, or any combination thereof. By way of example and not limitation, composition injections can be performed by intravenous (i.v.) injection, subcutaneous (s.c.) injection, intradermal (i.d.) injection, intraperitoneal (i.p.) injection, and/or intramuscular (i.m.) injection. One or more such routes can be employed. Parenteral administration can be, for example, by bolus injection or by gradual perfusion over time. Alternatively or in addition, administration can be by the oral route.

In some embodiments, an injection is an intradermal (i.d.) injection. The target peptide compositions are in some embodiments suitable for administration of the peptides by any acceptable route such as but not limited to oral (enteral), nasal, ophthal, and transdermal. In some embodiments, the administration is subcutaneous, and in some embodiments the subcutaneous administration is by an infusion pump.

VI.B. Formulations

Pharmaceutical carriers, diluents, and excipients are generally added to the target peptide compositions or (target peptide compositions kits) that are compatible with the active ingredients and acceptable for pharmaceutical use. Examples of such carriers include but are not limited to water, saline solutions, dextrose, and/or glycerol. Combinations of carriers can also be used.

The vaccine compositions of the presently disclosed subject matter can further incorporate additional substances to stabilize pH and/or to function as adjuvants, wetting agents, and/or emulsifying agents, which can serve to improve the effectiveness of the vaccine.

The target peptide compositions can in some embodiments include one or more adjuvants such as for example: montanide ISA-51 (Seppic Inc., Fairfield, N.J. United States of America); QS-21 (Aquila Biopharmaceuticals, Inc., Framingham, Mass., United States of America); Arlacel A; oeleic acid; tetanus helper peptides (such as but not limited to QYIKANSKFIGITEL (SEQ ID NO: 368) or AQYIKANSKFIGITEL (SEQ ID NO: 205)); GM-CSF; cyclophosamide; bacillus Calmette-Guérin (BCG); Corynbacterium parvum; levamisole, azimezone; isoprinisone; dinitrochlorobenezene (DNCB); keyhole limpet hemocyanin (KLH); Freunds adjuvant (complete and incomplete); mineral gels; aluminum hydroxide (Alum); lysolecithin; pluronic polyols; polyanions; peptides; oil emulsions; nucleic acids (such as but not limited to double-stranded RNAs; dsRNA) dinitrophenol; diphtheria toxin (DT); toll-like receptor (TLR; such as but not limited to TLR3, TLR4, TLR7, TLR8, and/or TLR9) agonists (including but not limited to endotoxins such as lipopolysaccharide (LPS); monophosphoryl lipid A (MPL); and/or polyinosinic-polycytidylic acid (poly-ICLC/HILTONOL®; Oncovir, Inc., Washington, D.C., United States of America); IMO-2055; glucopyranosyl lipid A (GLA); QS-21 (a saponin extracted from the bark of the Quillaja saponaria tree, also known as the soap bark tree or Soapbark); resiquimod (a TLR7/8 agonist); CDX-1401 (a fusion protein consisting of a fully human monoclonal antibody with specificity for the dendritic cell receptor DEC-205 linked to the NY-ESO-1 tumor antigen); Juvaris' Cationic Lipid-DNA Complex; Vaxfectin; and combinations thereof.

In some embodiments, the tetanus peptide can be about or at least 10, 11, 12, 13, 14, 15, 16, 17, 18, 19, 20, 21, 22, 23, 24, 25, (in some embodiments 10-25) natural or non-natural amino acids in length. In some embodiments, the tetanus peptide is a segment or fragment of a tetanus toxoid protein. In some embodiments the tetanus toxoid peptide used herein is at least or about 70%, 75%, 80%, 85%, 90%, 95%, 98%, 99%, or 100% identical to a 10, 11, 12, 13, 14, 15, 16, 17, 18, 19, 20, 21, 22, 23, 24, or 25 amino acids segment of the wild type tetanus toxoid protein. In some embodiments the tetanus toxoid peptide used herein is at least or about 70%, 75%, 80%, 85%, 90%, 95%, 98%, 99%, or 100% identical to SEQ ID NOs: 205 or 368. In some embodiments, the tetanus peptide binds to one or more MHC Class II molecules. In some embodiments, the tetanus peptide is modified so as to prevent formation of tetanus peptide secondary structures. In some embodiments, a nucleic acid (e.g., DNA or RNA) is provided that encodes a tetanus peptide. In some embodiments, the tetanus peptide belongs to the 830 to 844 amino acid sequence of the tetanus toxin Tc (see Demotz et al., 1989; El Kasmi et al., 2000).

Polyinosinic-Polycytidylic acid (Poly IC) is a double-stranded RNA (dsRNA) that acts as a TLR3 agonist. To increase half-life, it has been stabilized with polylysine and carboxymethylcellulose as poly-ICLC. It has been used to induce interferon in cancer patients, with intravenous doses up to 300 μg/kg. Like poly-IC, poly-ICLC is a TLR3 agonist. TLR3 is expressed in the early endosome of myeloid DC; thus poly-ICLC preferentially activates myeloid dendritic cells, thus favoring a Th1 cytotoxic T cell response. Poly-ICLC activates natural killer (NK) cells, induces cytolytic potential, and induces IFNγ from myeloid DC.

In some embodiments, an adjuvant is provided at about or at least 10, 20, 30, 40, 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, 900, 910, 920, 930, 940, 950, 960, 970, 980, 990, or 1000 µg per dose or per kg in each dose. In some embodiments, the adjuvant is provided in a dosage of at least or about 0.1, 0.2, 0.3, 0.40, 0.50, 0.60, 0.70, 0.80, 0.90, 0.100, 1.10, 1.20, 1.30, 1.40, 1.50, 1.60, 1.70, 1.80, 1.90, 2.00, 2.10, 2.20, 2.30, 2.40, 2.50, 2.60, 2.70, 2.80, 2.90, 3.00, 3.10, 3.20, 3.30, 3.40, 3.50, 3.60, 3.70, 3.80, 3.90, 4.00, 4.10, 4.20, 4.30, 4.40, 4.50, 4.60, 4.70, 4.80, 4.90, 5.00, 5.10, 5.20, 5.30, 5.40, 5.50, 5.60, 5.70, 5.80, 5.90, 6.00, 6.10, 6.20, 6.30, 6.40, 6.50, 6.60, 6.70, 6.80, 6.90, 7.00, 7.10, 7.20, 7.30, 7.40, 7.50, 7.60, 7.70, 7.80, 7.90, 8.00, 8.10, 8.20, 8.30, 8.40, 8.50, 8.60, 8.70, 8.80, 8.90, 9.00, 9.10, 9.20, 9.30, 9.40, 9.50, 9.60, 9.70, 9.80, 9.90, or 10.00 grams per dose or per kg in each dose. In some embodiments, the adjuvant is given at about or at least 10, 15, 20, 25, 50, 75, 100, 125, 150, 175, 150, 175, 200, 225, 250, 275, 300, 325, 350, 375, 400, 425, 450, 500, 525, 550, 575, 600, 625, 675, 700, 725, 750, 775, 800, 900, 1000, 1100, 1200, 1300, 1400, 1500, 1600, 1700, 1800, 1900 or 2000 endotoxin units ("EU") per dose.

The target peptide compositions of the presently disclosed subject matter can in some embodiments be provided with an administration of cyclophosamide around the time (such as but not limited to about or at least 1, 2, 3, or 4 weeks or days before or after) of the initial dose of a target peptide composition. Exemplary non-limiting dose of cyclophosamide are in some embodiments about or at least 100, 200, 300, 400, 500, 600, 700, 800, 900 or 1000 Mg/m$^2$/day over about or at least 1, 2, 3, 4, 5, 6, 7, 8, 9 or 10 days.

The compositions may comprise the target peptides in the free form and/or in the form of a pharmaceutically acceptable salt. As used herein, "a pharmaceutically acceptable salt" refers to a derivative of a disclosed target peptide wherein the target peptide is modified by making acid or base salts of the agent. For example, acid salts are prepared from the free base (typically wherein the neutral form of the drug has a neutral —NH$_2$ group) involving reaction with a suitable acid. Suitable acids for preparing acid salts include both organic acids such as but not limited to acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluenesulfonic acid, salicylic acid, and the like, as well as inorganic acids such as but not limited to hydrochloric acid, hydrobromic acid, sulfuric acid, nitric acid phosphoric acid, and the like. Conversely, basic salts of acid moieties that can be present on a target peptide are in some embodiments prepared using a pharmaceutically acceptable base such as but not limited to sodium hydroxide, potassium hydroxide, ammonium hydroxide, calcium hydroxide, trimethylamine, and the like. By way of example and not limitation, the compositions can comprise target peptides as salts of acetic acid (acetates), ammonium, or hydrochloric acid (chlorides).

In some embodiments, a composition can include one or more sugars, sugar alcohols, amino acids such but not limited to glycine, arginine, glutamic acid, and/or others as framework formers. The sugars can be mono-, di-, or trisaccharides. These sugars can be used alone and/or in combination with sugar alcohols. Exemplary sugars include glucose, mannose, galactose, fructose, or sorbose as monosaccharides; sucrose, lactose, maltose, and trehalose as disaccharides; and raffinose as a trisaccharide. A sugar alcohol can be, for example, mannitose. In some embodiments, the composition comprises sucrose, lactose, maltose, trehalose, mannitol, and/or sorbitol. In some embodiments, the composition comprises mannitol.

Furthermore, in some embodiments compositions can include physiological well-tolerated excipients (see *Handbook of Pharmaceutical Excipients*, 5$^{th}$ ed., edited by Raymond Rowe, Paul Sheskey and Sian Owen, Pharmaceutical Press (2006)) such as antioxidants like ascorbic acid or glutathione; preserving agents such as phenol, m-cresol, methyl- or propylparaben, chlorobutanol, thiomersal/thimerosal, and/or benzalkoniumchloride; stabilizers, framework formers such as sucrose, lactose, maltose, trehalose, mannitose, mannitol, and/or sorbitol; mannitol and/or lactose and solubilizers such as polyethylene glycols (PEG; e.g., PEG 3000, 3350, 4000, or 6000), cyclodextrins (e.g., hydroxypropyl-β-cyclodextrin, sulfobutylethyl-β-cyclodextrin, or γ-cyclodextrin), dextrans, or poloxamers (e.g., poloxamer 407 or poloxamer 188); or TWEEN® 20 or TWEEN® 80. In some embodiments, one or more well-tolerated excipients can be included, optionally selected from the group consisting of antioxidants, framework formers, and stabilizers.

In some embodiments, the pH for intravenous and/or intramuscular administration is selected from pH 2 to pH 12. In some embodiments, the pH for subcutaneous administration is selected from pH 2.7 to pH 9.0 as the rate of in vivo dilution is reduced resulting in more potential for irradiation at the injection site (Strickley, 2004).

VI.C. Dosage

It is understood that a suitable dosage of a target peptide composition vaccine immunogen cam depend upon the age, sex, health, and/or weight of the recipient, the kind of concurrent treatment, if any, the frequency of treatment, and the nature of the effect desired. However, it is understood that dosages can be tailored to the individual subject, as determined by the researcher or clinician. The total dose required for any given treatment will in some embodiments be determined with respect to a standard reference dose based on the experience of the researcher or clinician, such dose being administered either in a single treatment or in a series of doses, the success of which will depend on the production of a desired immunological result (such as but not limited to successful production of a T helper cell and/or CTL-mediated response to the target peptide immunogen composition, which response gives rise to the prevention and/or treatment desired).

Thus, in some embodiments the overall administration schedule is considered in determining the success of a course of treatment and not whether a single dose, given in isolation, would or would not produce the desired immunologically therapeutic result or effect.

Thus, the therapeutically effective amount (i.e., in some embodiments that amount that produces a desired T helper cell and/or CTL-mediated response) can depend on the antigenic composition of the vaccine used, the nature of the disease condition, the severity of the disease condition, the extent of any need to prevent such a condition where it has not already been detected, the manner of administration dictated by the situation requiring such administration, the weight and state of health of the individual receiving such administration, and/or the sound judgment of the clinician or researcher. In some embodiments, the efficacy of administering additional doses and/or of increasing or decreasing the interval can be continually re-evaluated in view of the recipient's immunocompetence (including but not limited to the level of T helper cell and/or CTL activity with respect to tumor-associated or tumor-specific antigens).

The concentration of the T helper or CTL stimulatory target peptides of the presently disclosed subject matter in pharmaceutical formulations can be subject to wide variation, including anywhere from less than 0.01% by weight to as much as 50% or more. Factors such as volume and viscosity of the resulting composition can in some embodiments also be considered. The solvents or diluents used for such compositions can include water, phosphate buffered saline (PBS), and/or saline, or any other possible carriers or excipients.

The immunogens of the presently disclosed subject matter can in some embodiments also be contained in artificially created structures such as liposomes, which structures in some embodiments can contain additional molecules such as but not limited to proteins or polysaccharides, inserted in the outer membranes of said structures and having the effect of targeting the liposomes to particular areas of the body and/or to particular cells within a given organ or tissue. Such targeting molecules can in some embodiments comprise an immunoglobulin. Antibodies can work particularly well for targeting of liposomes and/or other scaffolds to tumor cells.

Single i.d., i.m., s.c., i.p., and/or i.v. doses of in some embodiments about 1 to 50 µg, in some embodiments about 1 to 100 µg, in some embodiments about 1 to 500 µg, in some embodiments about 1 to 1000 µg, in some embodiments about 1 to 50 mg, in some embodiments about 1 to 100 mg, in some embodiments about 1 to 500 mg, or in some embodiments about 1 to 1000 mg of target peptide composition can be given and can depend from the respective compositions of target peptides with respect to total amount for all target peptides in the composition or alternatively for each individual target peptide in the composition. A single dose of a target peptide vaccine composition of the presently disclosed subject matter can in some embodiments have a target peptide amount (e.g., total amount for all target peptides in the composition or alternatively for each individual target peptide in the composition) of about or at least 1, 5, 10, 15, 20, 25, 30, 35, 40, 45, 50, 55, 60, 65, 70, 75, 80, 85, 90, 95, 100, 125, 150, 175, 200, 225, 250, 275, 300, 325, 350, 375, 400, 425, 450, 475, 500, 525, 550, 575, 600, 625, 650, 675, 700, 725, 750, 775, 800, 825, 850, 875, 900, or 950 µg. In some embodiments, a single dose of a target peptide composition of the presently disclosed subject matter can have a total target peptide amount (e.g., total amount for all target peptides in the composition or alternatively for each individual target peptide in the composition) of about or at least 1, 5, 10, 15, 20, 25, 30, 35, 40, 45, 50, 55, 60, 65, 70, 75, 80, 85, 90, 95, 100, 125, 150, 175, 200, 225, 250, 275, 300, 325, 350, 375, 400, 425, 450, 475, 500, 525, 550, 575, 600, 625, 650, 675, 700, 725, 750, 775, 800, 825, 850, 875, 900, or 950 mg. In some embodiments, the target peptides of a composition of the presently disclosed subject matter are present in equal amounts of about 100 micrograms per dose in combination with an adjuvant peptide present in an amount of about 200 micrograms per dose.

In a single dose of the target peptide composition of the presently disclosed subject matter, the amount of each target peptide in the composition is in some embodiments equal or substantially equal. Alternatively, a ratio of the target peptides present in the least amount relative to the target peptide present in the greatest amount is about or at least 1:1.25, 1:1.5, 1:1.75, 1:2.0, 1:2.25, 1:2.5, 1:2.75, 1:3, 1:4, 1:5, 1:6, 1:7, 1:8, 1:9, 1:10, 1:20, 1:30; 1:40, 1:50, 1:100, 1:200, 1:500, 1:1000, 1:5000; 1:10,000; or 1:100,000. Alternatively, a ratio of the target peptides present in the least amount relative to the target peptide present in the greatest amount is about or at least 1 or 2 to 25; 1 or 2 to 20; 1 or 2 to 15; 1 or 2 to 10; 1 to 3; 1 to 4; 1 to 5; 1 to 6; 1 to 7; 1 to 10; 2 to 3; 2 to 4; 2 to 5; 2 to 6; 2 to 7; 2 to 10; 3 to 4; 3 to 5; 3 to 6; 3 to 7; 3 to 10; 5 to 10; 10 to 15; 15 to 20; 20 to 25; 1 to 40; 1 to 30; 1 to 20; 1 to 15; 10 to 40; 10 to 30; 10 to 20; 10 to 15; 20 to 40; 20 to 30; or 20 to 25; 1 to 100; 25 to 100; 50 to 100; 75 to 100; 25 to 75, 25 to 50, or 50 to 75; 25 to 40; 25 to 50; 30 to 50; 30 to 40; or 30 to 75.

Single dosages can be given to a patient about or at least 1, 2, 3, 4, or 5 times per day. Single dosages can be given to a patient about or at least 1, 2, 3, 4, 5, 6, 7, 8, 9, 10, 11, 12, 13, 14, 15, 16, 18, 19, 20, 21, 22, 23, 24, 36, 48, 60, or 72 hours subsequent to a previous dose.

Single dosages can be given to a patient about or at least 1, 2, 3, 4, 5, 6, or 7 times per week, or every other, third, fourth, or fifth day. Single doses can also be given every week, every other week, or only during 1, 2, or 3 weeks per month. A course of treatment can in some embodiments last about or at least 1, 2, 3, 4, 5, 6, 7, 8, 9, 10, 11. or 12 months.

In some embodiments, the single dosages of the compositions of the presently disclosed subject matter can be provided to a patient in at least two phases: e.g., during an initial phase and then during a subsequent phase. An initial phase can be about or at least 1, 2, 3, 4, 5, or 6 weeks in length. The subsequent phase can last at least or about 1, 2, 3, 4, 5, 6, 7, or 8 times as long as the initial phase. The initial phase can be separated from the subsequent phase by about or at least 1, 2, 3, 4, 5, 6, 7, 8, 9, 10, 11, or 12 weeks or months.

The target peptide composition dosage during the subsequent phase can be at least 1, 2, 3, 4, 5, 6, 7, 8, 9, 10, 15, 20, 30, 40, 50, 60, 70, 80, 90, 100, 200, 300, 400, 500, 600, 700, 800, 900, or 1000 times greater than during the initial phase.

The target peptide composition dosage during the subsequent phase can be at least 1, 2, 3, 4, 5, 6, 7, 8, 9, 10, 15, 20, 30, 40, 50, 60, 70, 80, 90, 100, 200, 300, 400, 500, 600, 700, 800, 900, or 1000 times less than during the initial phase.

In some embodiments, the initial phase is about three weeks and the second phase is about 9 weeks. The target peptide compositions can be administered to the patient on or about days 1, 8, 15, 36, 57, and 78.

VI.D. Kits and Storage

In some embodiments, a kit is disclosed comprising (a) a container that contains at least one target peptide composition as described herein, in solution or in lyophilized form; (b) optionally, a second container containing a diluent or reconstituting solution for the lyophilized formulation; and (c) optionally, instructions for (i) use of the solution or (ii) reconstitution and/or use of the lyophilized formulation. The kit may further comprise one or more of (iii) a buffer, (iv) a diluent, (v) a filter, (vi) a needle, or (v) a syringe. In some embodiments, the container is selected from the group consisting of: a bottle, a vial, a syringe, a test tube, or a multi-use container. In some embodiments, the target peptide composition is lyophilized.

The kits can contain exactly, about, or at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 45, 46, 47, 48, 49, 50, 51, or more target peptide-containing compositions. Each composition in the kit can be administered at the same time and/or at different times.

In some embodiments, the kits can comprise a lyophilized formulation of the presently disclosed compositions and/or vaccines in a suitable container and instructions for its reconstitution and/or use. Suitable containers include, for example, bottles, vials (e.g., dual chamber vials), syringes (such as dual chamber syringes), and test tubes. The container can be formed from a variety of materials such as glass or plastic. In some embodiments, the kit and/or the container contain(s) instructions on or associated therewith that indicate(s) directions for reconstitution and/or use of a lyophilized formulation. For example, the label can indicate that the lyophilized formulation is to be reconstituted to target peptide concentrations as described herein. The label can further indicate that the formulation is useful or intended for subcutaneous administration. Lyophilized and liquid formulations are typically stored at −20° C. to −80° C.

The container holding the target peptide composition(s) can be a multi-use vial, which in some embodiments allows for repeat administrations (e.g., from 2-6 or more administrations) of the reconstituted formulation. The kit can further comprise a second container comprising a suitable diluent (e.g., sodium bicarbonate solution).

In some embodiments, upon mixing of the diluent and the lyophilized formulation, the final peptide concentration in the reconstituted formulation is at least or about 0.15, 0.20, 0.25, 0.5, 0.75, 1.0, 1.25, 1.5, 1.75, 2.0, 2.25, 2.5, 2.75, 3.0, 3.25, 3.50, 3.75, 4.0, 4.25, 4.5, 4.75, 5.0, 6.0, 7.0, 8.0, 9.0, or 10 mg/mL/target peptide. In some embodiments, upon mixing of the diluent and the lyophilized formulation, the final peptide concentration in the reconstituted formulation is at least or about 0.15, 0.20, 0.25, 0.5, 0.75, 1.0, 1.25, 1.5, 1.75, 2.0, 2.25, 2.5, 2.75, 3.0, 3.25, 3.50, 3.75, 4.0, 4.25, 4.5, 4.75, 5.0, 6.0, 7.0, 8.0, 9.0, or 10 μg/mL/target peptide.

The kit can further include other materials desirable from a commercial and/or user standpoint, including other buffers, diluents, filters, needles, syringes, and package inserts with or without instructions for use.

The kits can have a single container that contains the formulation of the target peptide compositions with or without other components (e.g., other compounds or compositions of these other compounds) or can have a distinct container for each component.

Additionally, the kits can include a formulation of the presently disclosed target peptide compositions and/or vaccines packaged for use in combination with the co-administration of a second compound such as an adjuvant including but not limited to imiquimod, a chemotherapeutic agent, a natural product, a hormone or antagonist, an anti-angiogenesis agent or inhibitor, an apoptosis-inducing agent or a chelator) or a composition thereof. One or more of the components of the kit can be pre-complexed or one or more components can be in a separate distinct container prior to administration to a patient. One or more of the components of the kit can be provided in one or more liquid solutions. In some embodiments, the liquid solution is an aqueous solution. In some embodiments, the liquid solution is a sterile aqueous solution. One or more of the components of the kit can also be provided as solids, which in some embodiments can be converted into liquids by addition of suitable solvents, which in some embodiments can be provided in another distinct container.

The container of a therapeutic kit can be a vial, a test tube, a flask, a bottle, a syringe, or any other structure suitable for enclosing a solid or liquid. Typically, when there is more than one component, the kit contains a second vial or other container that allows for separate dosing. The kit can also contain another container for a pharmaceutically acceptable liquid. In some embodiments, a therapeutic kit contains an apparatus (e.g., one or more needles, syringes, eye droppers, pipette, etc.), which enables administration of the agents of the disclosure that are components of the kit.

VI.E. Markers for Efficacy

When administered to a patient, the vaccine compositions of the presently disclosed subject matter are in some embodiments envisioned to have certain physiological effects including but not limited to the induction of a T cell mediated immune response.

VI.E.1. Immunohistochemistry, Immunofluorescence, Western Blots, and Flow Cytometry Validation and testing of antibodies for characterization of cellular and molecular features of lymphoid neogenesis has been performed. Commercially available antibodies for use in immunohistochemistry (IHC), immunofluorescence (IF), flow cytometry (FC), and/or western blotting (WB) can be used. In some embodiments, such techniques can be employed to assay patient samples including but not limited to formalin-fixed, paraffin-embedded tissue samples for the presence or absence of and/or for a level of expression of one or more of CD1a, S100, CD83, DC-LAMP, CD3, CD4, CD8, CD20, CD45, CD79a, PNAd, TNFα, LIGHT, CCL19, CCL21, CXCL12, TLR4, TLR7, FoxP3, PD-1, and Ki67 gene products. In some embodiments, flow cytometry is used to determine an expression level for one or more of CD3, CD4, CD8, CD13, CD14, CD16, CD19, CD45RA, CD45RO, CD56, CD62L, CD27, CD28, CCR7, FoxP3 (intracellular), and MHC-peptide tetramers for class I MHC associated (phospho)-peptides. In some embodiments, a positive control is employed, which in some embodiments can comprise a tissue sample comprising normal human peripheral blood lymphocytes (PBL), PBL activated with CD3/CD28 beads (activated PBL), human lymph node tissue from non-colorectal cancer patients (LN), and/or inflamed human tissue from a surgical specimen of Crohn's disease (Crohn's), although any other positive control cell and/or tissue can be employed.

VI.E.2. ELISpot Assay

In some embodiments, vaccination site infiltrating lymphocytes and lymphocytes from the sentinel immunized node (SIN) and vaccine site can be evaluated by ELISpot. ELISpot permits the direct counting of T cells reacting to antigen by production of IFNγ. Peripheral blood lymphocytes can be evaluated by ELISpot assay for the number of peptide-reactive T cells. Vaccine site infiltrating lymphocytes and SIN lymphocytes can be compared to those in peripheral blood. It is envisioned that positive results of the ELISpot assay correlates with increased patient progression free survival. Progression free survival is defined as the time from start of treatment until death from any cause or date of last follow up.

VI.E.3. Tetramer Assay

Peripheral blood lymphocytes and lymphocytes from the SIN and vaccine site can be evaluated by flow cytometry after incubation with MHC-peptide tetramers for the number of peptide-reactive T cells.

VI.E.4. Proliferation Assay and Cytokine Analysis

Peripheral blood mononuclear cells (PBMC), vaccine-site inflammatory cells, and/or lymphocytes from the SIN isolated from subjects can be evaluated for $CD4^+$ T cell reactivity to, e.g., tetanus helper peptide mixture, using a $^3$H-thymidine uptake assay. Additionally, Th1 (IL-2, IFNγ, TNFα), Th2 (IL-4, IL-5, IL-10), Th17 (IL-17, and IL23), and T-reg (TGF-β) cytokines in media from 48 hours in that proliferation assay can be used to determine if the microenvironment supports generation of Th1, Th2, Th17, and/or T-reg responses. In some embodiments, one or both of the following peptides are used as negative controls: a tetanus peptide and the PADRE peptide (AK(X)VAAWTLKAA; SEQ ID NO: 367.

VI.E.5. Evaluation of Tumors

In some embodiments, tumor tissue collected prior to treatment or at the time of progression can be evaluated by routine histology and immunohistochemistry. Alternatively or in addition, in vitro evaluations of tumor tissue and tumor infiltrating lymphocytes can be performed.

VI.E.6. Studies of Homing Receptor Expression

Patient samples can be studied for T cell homing receptors induced by vaccination with the compositions of the presently disclosed subject matter. These include but are not limited to integrins (including but not limited to αEβ7, α1β1, α4β1), chemokine receptors (including but not limited to CXCR3), and selectin ligands (including but not limited to CLA and PSL) on lymphocytes, and their ligands in the vaccine sites and SIN. In some embodiments, these can be assayed by immunohistochemistry, flow cytometry, and/or any other appropriate technique(s).

VI.E.7. Studies of Gene and Protein Expression

Differences in gene expression and/or differences in protein expression profiles can be determined by high-throughput screening assays (e.g., nucleic acid chips, protein arrays, etc.) of samples isolated from vaccine sites and/or SIN.

VII. Antibodies and Antibody-Like Molecules

Antibodies and antibody-like molecules (including but not limited to T cell receptors) specific for target peptides and/or target peptide/MHC complexes are in some embodiments useful for analyzing biological samples. In some embodiments, an analysis can comprise determining the pathological nature of tumor margins.

Antibodies and antibody-like molecules can also be used as therapeutics. In some embodiments, such molecules can be used as therapeutics that target cells, including but not limited to tumor cells, which display target peptides on their surfaces. In some embodiments, antibodies and antibody-like molecules bind to phosphorylated target peptides and/or target peptide-MHC complex specifically and do not substantially cross react with the corresponding non-phosphorylated native peptides.

As used herein, the terms "antibody", "antibody peptide(s)", and "antibody-like molecule(s)" refer to an intact antibody, a binding fragment thereof (i.e., a fragment of an antibody that comprises a paratope), or a polypeptide that can specifically recognize an antigen or epitope and bind to the same in a fashion that mimics antibody binding. In some embodiments, antibodies, antibody peptides, and antibody-like molecules compete with intact antibodies for specific binding to an antigen or epitope.

In some embodiments, antibody fragments can be produced by recombinant DNA techniques and/or by enzymatic and/or chemical cleavage of intact antibodies. Antibody fragments thus include but are not limited to Fab fragments, Fab' fragments, F(ab')$_2$ fragments, Fv, and single-chain antibodies including but not limited to single-chain fragment variable (scFv) antibodies. An antibody is said to be "monospecific" if each of its paratopes is identical and/or binds to the same epitope. Similarly, "bispecific" or "bifunctional" antibodies comprise paratopes that bind to different antigens and/or epitopes. In some embodiments, an antibody substantially inhibits adhesion of a receptor to a counterreceptor when an excess of antibody reduces the quantity of receptor bound to counterreceptor by at least about 20%, 40%, 60%, 80%, 85%, 90%, 95%, or more as measured by, for example, an in vitro competitive binding assay.

The term "MHC" as used herein refers to the Major Histocompatibility Complex, which is defined as a set of gene loci specifying major histocompatibility antigens. The term "HLA" as used herein will be understood to refer to Human Leukocyte Antigens, which is defined as the histocompatibility antigens found in humans. As used herein, "HLA" is the human form of "MHC". IN murine species, the MHC is referred to as the "H-2" complex.

The terms "MHC light chain" and "MHC heavy chain" as used herein refer to particular portions of a MHC molecule. Structurally, class I molecules are heterodimers comprised of two noncovalently bound polypeptide chains, a larger "heavy" chain (α) and a smaller "light" chain (β2-microglobulin or β2m). The polymorphic, polygenic heavy chain (45 kDa), encoded within the MHC on chromosome human 6 is subdivided into three extracellular domains (designated 1, 2, and 3), one intracellular domain, and one transmembrane domain. The two outermost extracellular domains, 1 and 2, together form the groove that binds to antigenic peptides and/or other epitopes. Thus, interaction with the TCR occurs at this region of the protein. Domain 3 of the molecule contains the recognition site for the CD8 protein on the CTL. This interaction serves to stabilize the contact between the T cell and an antigen-presenting cell (APC). The invariant light chain (12 kDa), encoded on human chromosome 15, consists of a single, extracellular polypeptide. The terms "MHC light chain", "β2-microglobulin", and "β2m" are used interchangeably herein.

The term "epitope" includes any protein determinant capable of specific binding to an antibody, antibody peptide, and/or antibody-like molecule (including but not limited to a T cell receptor) as defined herein. Epitopic determinants typically consist of chemically active surface groups of molecules such as amino acids or sugar side chains and generally have specific three dimensional structural characteristics as well as specific charge characteristics. An antibody or antibody-like molecule is said to "specifically" bind an antigen when the dissociation constant ($K_d$) is in some embodiments less than about 1 μM, in some embodiments less that about 100 nM, and in some embodiments less than about 10 nM. Interactions between antibodies and antibody-like molecules and an epitope can also be characterized by an affinity constant ($K_a$). In some embodiments, a $K_a$ of less than about $10^7$/M is considered "high affinity".

The term "antibody" is used in the broadest sense, and covers monoclonal antibodies (including full length monoclonal antibodies), polyclonal antibodies, multispecific antibodies (e.g., bispecific and/or trispecific antibodies), and antibody fragments (including but not limited to Fab, F(ab')$_2$ and Fv fragments) as well as antibody-like molecules provided that they exhibit the desired biological activity (e.g., antigen binding). Antibodies (Abs) and immunoglobulins (Igs) are glycoproteins that in some embodiments have the same structural characteristics. The term is also meant to encompass "antibody like molecules" and other members of the immunoglobulin superfamily including, but not limited to T cell receptors, MHC molecules, and other polypeptides that contain one or more antigen-binding regions and/or variable regions including, but not limited to complementary determining regions (CDRs) that specifically bind the target peptides disclosed herein.

In some embodiments, antibodies and antibody-like molecules bind to the target peptides disclosed herein but do not substantially and/or specifically crossreact with the same peptide in a modified form. See e.g., U.S. Patent Application Publication No. 2009/0226474, which is incorporated by reference.

The presently disclosed subject matter includes in some embodiments antibodies that recognize target peptides associated with a tumorigenic or disease state, wherein the peptides are displayed in the context of HLA molecules. These antibodies can mimic the specificity of a T cell receptor (TCR) but can have higher binding affinities such that the molecules can be employed as therapeutic, diagnostic, and/or research reagents. Methods of producing a T cell receptor mimic of the presently disclosed subject matter in some embodiments comprise identifying a target peptide of interest, generating and isolating CD8+ T cells specific for the target peptide, and cloning gene sequences that encode the target peptide-specific TCR.

In some embodiments an immunogen comprising at least one target peptide/MHC complex is formed. An effective amount of the immunogen is in some embodiments administered to a host to elicit an immune response in the host, and serum collected from the host can assayed to determine if antibodies that recognize a three-dimensional presentation of the target peptide in the binding groove of the MHC molecule have been produced. The desired antibodies can in some embodiments differentiate the target peptide/MHC complex from the MHC molecule alone, the target peptide alone, and/or a complex of MHC and an irrelevant peptide (in some embodiments, a peptide having the same amino acid composition as a target peptide but wherein the amino acids are in a different order that in the target peptide). Finally, in some embodiments the desired antibodies can be isolated.

The term "antibody" also encompasses soluble T cell receptor (TCR) cytoplasmic domains that are stable at low concentrations and which can recognize MHC-peptide complexes. See e.g., U.S. Patent Application Publication No. 2002/0119149, which is incorporated by reference. Such soluble TCRs can in some embodiments be conjugated to immunostimulatory peptides and/or proteins, and/or moieties such as but not limited to CD3 agonists (e.g., anti-CD3 antibodies). The CD3 antigen is present on mature human T cells, thymocytes, and a subset of natural killer cells. It is associated with the TCR and is involved in signal transduction of the TCR. Antibodies specific for the human CD3 antigen are well known. One such antibody is the murine monoclonal antibody OKT3 which was the first monoclonal antibody approved by the FDA. OKT3 is reported to be a potent T cell mitogen (Van Wauve, 1980; U.S. Pat. No. 4,361,539) and a potent T cell killer (Wong, 1990). Other antibodies specific for the CD3 antigen have also been reported (see PCT International Patent Application Publication No. WO 2004/106380; U.S. Patent Application Publication No. 2004/0202657; U.S. Pat. No. 6,750,325; U.S. Pat. No. 6,706,265; United Kingdom Patent GB 2249310A; Clark et al., 1989; U.S. Pat. No. 5,968,509; and U.S. Patent Application Publication No. 2009/0117102). Immune mobilizing mTCR Against Cancer (ImmTAC; Immunocore Limited, Milton Park, Abington, Oxon, United Kingdom) are bifunctional proteins that combine high-affinity monoclonal T cell receptor (mTCR) targeting with a therapeutic mechanism of action (i.e., an anti-CD3 scFv).

Native antibodies and immunoglobulins are generally heterotetrameric glycoproteins of about 150,000 daltons (Da) composed of two identical light (L) chains and two identical heavy (H) chains. Each light chain is linked to a heavy chain by a covalent disulfide bond. Disulfide bonds also link the heavy chains of intact antibodies, although the number of disulfide bonds between the heavy chains of different immunoglobulin isotypes can vary. Each heavy and light chain also has regularly spaced intrachain disulfide bridges. Each heavy chain has at one end a variable domain ($V_H$) followed by a number of constant domains. Each light chain has a variable domain at one end ($V_L$) and a constant domain at its other end. The constant domain of the light chain is aligned with the first constant domain of the heavy chain, and the light chain variable domain is aligned with the variable domain of the heavy chain. Particular amino acid residues are believed to form an interface between the light and heavy chain variable domains (Clothia et al., 1985; Novotny & Haber, 1985).

An "isolated" antibody is one which has been identified and/or separated and/or recovered from a component of the environment in which it was produced or otherwise present. Contaminant components of its production environment are materials that in some embodiments interfere with diagnostic and/or therapeutic uses for the antibody, and in some embodiments can include enzymes, hormones, and other proteinaceous or nonproteinaceous solutes. In some embodiments, an antibody can be purified as measurable by one or more of the following methods: 1) to greater than 50%, 75%, 80%, 85%, 90%, 95%, 96%, 97%, 98%, or 99% by weight of antibody as determined by the Lowry method; 2) to a degree sufficient to obtain at least 10 or 15 residues of N-terminal or internal amino acid sequence by use of a spinning cup sequenator; or 3) to homogeneity by SDS-PAGE under reducing or non-reducing conditions using Coomassie blue or, in some embodiments, silver stain. Isolated antibodies include an antibody in situ within recombinant cells since at least one component of the antibody's natural environment will not be present. Ordinarily, however, isolated antibodies will be prepared by a method that comprises at least one purification step.

The terms "antibody mutant" and "antibody variant" refer to antibodies that relative to a reference antibody comprise one or more amino acid sequence differences, wherein one or more of the amino acid residues have been modified such as but not limited to substitution and/or deletion. Such mutants and/or variants comprise in some embodiments less than 100%, 99%, 98%, 97%, 96%, 95%, 90%, 85%, 80%, or 75% sequence identity and/or similarity to the amino acid sequence of either the heavy or light chain variable domain amino acid sequence of the reference antibody.

The term "variable" in the context of variable domain of antibodies, refers to the fact that certain portions of the variable domains differ extensively in sequence among antibodies and are used in the binding and specificity of each particular antibody for its particular antigen. However, sequence variability is generally not evenly distributed throughout the variable domains of antibodies. Typically, sequence variability is concentrated in three segments called complementarity determining regions (CDRs; also known as hypervariable regions) both in the light chain and heavy chain variable domains.

There are at least two techniques for determining CDRs: (1) an approach based on cross-species sequence variability (i.e., Kabat et al., 1991); and (2) an approach based on crystallographic studies of antigen-antibody complexes (Chothia et al., 1989). The more highly conserved portions of variable domains are called the framework (FR). The variable domains of native heavy and light chains each comprise four FR regions, largely adopting a β-sheet configuration, connected by three CDRs, which form loops connecting, and in some cases forming part of, the β-sheet structure. The CDRs in each chain are held together in close proximity by the FR regions and, with the CDRs from the other chain, contribute to the formation of the antigen binding site of antibodies (see Kabat et al., 1991) The constant domains are generally not involved directly in binding between antibody and antigen, but exhibit various effector functions such as but not limited to participation of the antibody in antibody-dependent cellular toxicity.

The term "antibody fragment" refers to a portion of a full-length antibody, generally the antigen binding or variable region. Examples of antibody fragments include Fab, Fab', F(ab')$_2$, and Fv fragments. Papain digestion of antibodies produces two identical antigen binding fragments, called the Fab fragment, each with a single antigen binding site, and a residual "Fc" fragment, so-called for its ability to crystallize readily. Pepsin treatment yields an F(ab')$_2$ fragment that has two antigen binding fragments which are capable of cross-linking antigen, and a residual other fragment (which is termed pFc'). As used herein, the phrase "functional fragment" with respect to antibodies refers in some embodiments to a fragment that contains at least one antigen-binding domain (referred to as a "paratope"), and thus includes, but is not limited to Fv, F(ab) and F(ab')$_2$ fragments.

An "Fv" fragment is the minimum antibody fragment which contains a complete antigen recognition and binding site. This region consists of a heterodimer of one heavy and one light chain variable domain in a tight, non-covalent or covalent association ($V_H$-$V_L$ dimer). It is in this configuration that the three CDRs of each variable domain interact to define an antigen binding site (paratope) on the surface of the $V_H$-$V_L$ dimer. Collectively, the six CDRs confer antigen binding specificity to the antibody. However, in some embodiments even a single variable domain (or half of an Fv comprising only three CDRs specific for an antigen) has the ability to recognize and bind antigen, although at a lower affinity than the entire binding site.

The Fab or F(ab) fragment also contains the constant domain of the light chain and the first constant domain (CH1) of the heavy chain. Fab' fragments differ from Fab fragments by the addition of a few residues at the carboxyl terminus of the heavy chain CH1 domain including one or more cysteines from the antibody hinge region. Fab'-SH is the designation herein for Fab' in which the cysteine residue(s) of the constant domains have a free thiol group. F(ab') fragments are produced by cleavage of the disulfide bond at the hinge cysteines of the F(ab')$_2$ pepsin digestion product. Additional chemical couplings of antibody fragments are known to those of ordinary skill in the art.

The light chains of antibodies (immunoglobulin) from any vertebrate species can be assigned to one of two clearly distinct types, called kappa (κ) and lambda (λ), based on the amino sequences of the corresponding constant domain.

Depending on the amino acid sequences of the constant domain of their heavy chains, immunoglobulins can be assigned to different classes. There are at least five (5) major classes of immunoglobulins: IgA, IgD, IgE, IgG and IgM, and several of these may be further divided into subclasses or isotypes (e.g., IgG$_1$, IgG$_2$, IgG$_3$, IgG$_4$, IgA$_1$, IgA$_2$, etc.). The heavy chains constant domains that correspond to the different classes of immunoglobulins are called alpha (α), delta (Δ), epsilon (δ), gamma (γ), and mu (μ), respectively. The subunit structures and three-dimensional configurations of different classes of immunoglobulins are well known.

The term "monoclonal antibody" as used herein refers to an antibody obtained from a population of substantially homogeneous antibodies, i.e., the individual antibodies comprising the population are identical except for possible naturally occurring mutations that can be present in minor amounts. Monoclonal antibodies are highly specific, being directed against a single antigenic site. Furthermore, in contrast to conventional (polyclonal) antibody preparations, which typically include different antibodies directed against different determinants (epitopes), each monoclonal antibody is directed against a single determinant on the antigen. In additional to their specificity, monoclonal antibodies can be advantageous in that they are typically synthesized from hybridomas and thus can be isolated in a form that is uncontaminated by other immunoglobulins. Methods for generating hybridomas are known in the art. The modifier "monoclonal" indicates the character of the antibody as being obtained from a substantially homogeneous population of antibodies, and is not to be construed as requiring production of the antibody by any particular method. By way of example and not limitation, monoclonal antibodies to be used in accordance with the presently disclosed subject matter can be made by the hybridoma method first described by Kohler & Milstein, 1975, or can be made by recombinant methods (see e.g., U.S. Pat. No. 4,816,567; Harlow & Lane, 1988). In some embodiments, the monoclonal antibodies for use with the presently disclosed subject matter can be isolated from phage antibody libraries using the techniques described in Clackson et al., 1991 and/or Marks et al., 1991.

Utilization of the monoclonal antibodies of the presently disclosed subject matter can in some embodiments comprise administering one or more monoclonal antibodies to a subject, such as but not limited to a human subject. However, when the monoclonal antibodies are produced in a non-human animal, such as a rodent, administration of such antibodies to a human patient can elicit an immune response, wherein the immune response is directed towards the administered antibodies themselves. Such reactions can limit the duration and effectiveness of such a therapy. In order to overcome such a problem, the monoclonal antibodies of the presently disclosed subject matter can in some embodiments be "humanized", that is, the antibodies are engineered such that antigenic portions thereof are removed and like portions of a human antibody are substituted therefor, while the antibodies' affinity for specific peptide/MHC complexes is retained. This engineering can involve a few amino acids, or can include the entire framework regions of the antibody, leaving only the complementarity determining regions of the parent antibody intact. Several methods of humanizing antibodies are known in the art and are disclosed in U.S. Pat. Nos. 6,180,370; 6,054,927; 5,869,619; 5,861,155; 5,712,120; and 4,816,567, the entire disclosure of each of which is hereby expressly incorporated herein by reference in its entirety.

Humanized forms of antibodies are thus chimeric immunoglobulins, immunoglobulin chains, or fragments thereof (such as Fv, Fab, Fab', F(ab')$_2$ or other antigen-binding subsequences of antibodies) that are principally comprised of the sequence of a human immunoglobulin, but that contain at least some subsequences derived from a non-human immunoglobulin. Humanization can be performed following the method of Winter and co-workers by substituting rodent CDRs or CDR sequences for the corresponding sequences of a human antibody (Jones et al., 1986; Riechmann et al., 1988; Verhoeyen et al., 1988; see also U.S. Pat. No. 5,225,539). In some embodiments, F$_v$ framework residues of a human immunoglobulin are replaced with corresponding non-human residues from an antibody of interest. Humanized antibodies can also comprise residues which are found neither in the recipient antibody nor in the imported CDR or framework sequences. In general, the humanized antibody comprises substantially all of at least one, and typically two, variable domains, in which all or substantially all of the CDR regions correspond to those of a non-human immunoglobulin and all or substantially all of the framework regions are those of a human immunoglobulin consensus sequence. The humanized antibody optimally can also comprise at least a portion of an immunoglobulin constant region (Fc), typically that of a human immunoglobulin (Jones et al., 1986; Riechmann et al., 1988; and Presta, 1992).

Exemplary publications relating to the generation and/or use of humanized antibodies include Sandborn et al., 2001; Mihara et al., 2001; Yenari et al., 2001; Morales et al., 2000; Richards et al., 1999; Yenari et al., 1998; and Shinkura et al., 1998; each of which is expressly incorporated by reference herein in its entirety. For example, a treatment protocol that can be utilized in such a method includes a single dose, generally administered intravenously, of 10-20 mg of humanized mAb per kg (see e.g., Sandborn et al., 2001). In some cases, alternative dosing patterns can be appropriate, such as the use of three infusions, administered once every two weeks, of 800-1600 mg or even higher amounts of humanized mAb (see e.g., Richards et al., 1999). However, it is to be understood that the presently disclosed subject matter is not limited to the treatment protocols described herein, and further that other treatment protocols that are known to one of ordinary skill in the art can be employed in the methods of the presently disclosed subject matter.

In some embodiments, the presently disclosed subject matter further relates to fully human monoclonal antibodies against specific target peptide/MHC complexes. Fully human antibodies essentially relate to antibody molecules in which the entire sequence of both the light chain and the heavy chain, including the CDRs, arise from human genes. Such antibodies are referred to herein as "human antibodies" or "fully human antibodies".

Human monoclonal antibodies can be prepared by the trioma technique (see U.S. Pat. No. 4,714,681; PCT International Patent Application Publication No. WO 1999/047929); the human B-cell hybridoma technique (see Kozbor et al., 1983), and/or the EBV hybridoma technique (see Cole et al., 1985). In some embodiments, human monoclonal antibodies can be utilized in the practice of the presently disclosed subject matter and can be produced by using human hybridomas (see Cote et al., 1983) or by transforming human B-cells with Epstein Barr Virus in vitro (see Cole et al., 1985). In addition, human antibodies can also be produced using additional techniques, such as but not limited to phage display libraries (Hoogenboom et al., 1991; Marks et al., 1991). Similarly, human antibodies can be made by introducing human immunoglobulin loci into transgenic animals, e.g., mice in which the endogenous immunoglobulin genes have been partially or completely inactivated. Upon challenge, human antibody production is observed, which closely resembles that seen in humans in all respects, including gene rearrangement, assembly, and antibody repertoire. This approach is described, for example, in U.S. Pat. Nos. 5,545,807; 5,545,806; 5,569,825; 5,625,126; 5,633,425; 5,661,016, and in Marks et al., 1992; Lonberg et al., 1994; Fishwild et al., 1996; Neuberger, 1996; and Lonberg & Huszar, 1995.

Human antibodies can additionally be produced using transgenic non-human animals that have been modified to produce fully human antibodies in addition to or rather than the non-human animal's endogenous antibodies in response to challenge by an antigen. See PCT International Patent Application Publication No. WO 1994/02602. In some embodiments, endogenous genes encoding the heavy and light immunoglobulin chains present in the non-human animal have been deleted or otherwise inactivated, and nucleic acids encoding human heavy and light chain immunoglobulins have been inserted into the host's genome. The human genes are incorporated, for example, using yeast artificial chromosomes containing the requisite human DNA segments. An animal that provides all the desired modifications is then obtained as progeny by crossbreeding intermediate transgenic animals containing fewer than the full complement of the modifications.

One embodiment of such a non-human animal is a mouse termed the XENOMOUSE™, which is described in PCT International Patent Application Publication Nos. WO 1996/33735 and WO 1996/34096. The XENOMOUSE™ produces B cells that secrete fully human immunoglobulins. The antibodies can be obtained directly from the animal after immunization with an immunogen of interest, as, for example, a preparation of polyclonal antibodies, or alternatively from immortalized B cells derived from an immunized animal, such as hybridomas producing monoclonal antibodies. Additionally, the genes encoding the immunoglobulins with human variable regions can be recovered and expressed to obtain the antibodies directly and/or can be further modified to obtain analogs of antibodies such as, for example, single chain Fv molecules.

An example of a method for producing a non-human animal such as but not limited to a mouse that lacks expression of an endogenous immunoglobulin heavy chain is disclosed in U.S. Pat. No. 5,939,598, incorporated herein by reference. Such a non-human animal can be obtained by a method that comprises deleting the J segment genes from at least one endogenous heavy chain locus in an embryonic stem cell, thereby preventing rearrangement of the locus and formation of an RNA encoding a rearranged immunoglobulin heavy chain locus. In some embodiments, the deletion can be effected by a targeting vector that contains a selectable marker, Thereafter, a transgenic animal (e.g., a mouse) having somatic and germ cells containing the gene encoding the selectable marker can be produced from the embryonic stem cell. The transgenic animal would be expected to be unable to rearrange its endogenous immunoglobulin heavy chain locus, and thus would be expected to be unable to produce endogenous immunoglobulins.

A method for producing an antibody of interest, such as a human antibody, is also disclosed in U.S. Pat. No. 5,916,771, incorporated herein by reference. It includes introducing a first expression vector that contains a nucleotide sequence encoding a heavy chain into one mammalian host cell in culture, introducing a second expression vector containing a nucleotide sequence encoding a light chain into another mammalian host cell, and fusing the two cells to form a hybrid cell. The hybrid cell can express thus an antibody made up of a heavy chain and a light chain encoded by the first and second expression vectors.

Target peptides disclosed herein are in some embodiments expressed on a variety of cancer cell types. Thus, in some embodiments antibodies and antibody-like molecules can be used in treating, diagnosing, vaccinating, preventing, retarding, and attenuating a cancer such as but not limited to melanoma, ovarian cancer, breast cancer, colorectal cancer, squamous carcinoma of the lung, sarcoma, renal cell carcinoma, pancreatic carcinomas, squamous tumors of the head and neck, leukemia, brain cancer, liver cancer, prostate cancer, ovarian cancer, and cervical cancer.

Antibodies generated with specificity for a target peptide as disclosed herein can be used to detect the corresponding target peptides in a biological sample. The biological sample is in some embodiments isolated from an individual who is suspected of having cancer, and thus detection could serve to diagnose the cancer. Alternatively, the biological sample could be isolated from an individual known to have cancer, and detection of a target peptide therein can serve as an indicator of disease prognosis, cancer characterization, treatment efficacy, disease progression, or any combination thereof. Immunoassays that can be employed for these purposes are known in the art and include, but are not limited to, immunohistochemistry, flow cytometry, radioimmunoassay, western blotting, and ELISA. Biological samples suitable for such testing include, but are not limited to, cells, tissue biopsy specimens, whole blood, plasma, serum, sputum, cerebrospinal fluid, pleural fluid, and urine.

Antigens recognized by T cells, whether helper T lymphocytes or CTL, are not recognized as intact proteins, but rather as small peptides that associate with class I or class II MHC proteins on the surface of cells. During the course of a naturally occurring immune response, antigens that are recognized in association with class II MHC molecules on antigen presenting cells (APCs) are acquired from outside the cell, internalized, and processed into small peptides that associate with the class II MHC molecules.

Antigens that give rise to proteins that are recognized in association with class I MHC molecules are generally proteins that are produced within the cells, and these antigens are processed and associate with class I MHC molecules. It is now understood that the peptides that associate with given class I or class II MHC molecules are characterized as having a common binding motif, and the binding motifs for a large number of different class I and II MHC molecules have been determined. Synthetic peptides can also be synthesized that correspond to the amino acid sequence of a given antigen and that contain a binding motif for a given class I or II MHC molecule. These peptides can then be added to appropriate APCs, and the APCs can be used to stimulate a T helper cell or CTL response either in vitro or in vivo. The binding motifs, methods for synthesizing the peptides, and methods for stimulating a T helper cell or CTL response are all known and readily available to one of ordinary skill in the art.

Kits can be prepared to assist in diagnosis, monitoring, and/or prognosis of diseases. In some embodiments, the kits facilitate the detection and/or measurement of cancer-specific phosphopeptides and/or phosphoproteins. Such kits can contain, in a single or divided container, a molecule comprising an antigen-binding region. In some embodiments, such molecules are antibodies or antibody-like molecules. Additional components that can be included in the kit include one or more of solid supports, detection reagents, secondary antibodies, instructions for use, vessels for running assays, gels, control samples, and the like. In some embodiments, an antibody or antibody-like molecules can optionally be directly or indirectly labeled.

Alternatively, the antibody or antibody-like molecules specific for phosphopeptides and/or phosphopeptide/MHC complexes can be conjugated to therapeutic agents. Exemplary therapeutic agents include, but are not limited to the following:

Alkylating Agents.

Alkylating agents are drugs that directly interact with genomic DNA to prevent cells from proliferating. This category of chemotherapeutic drugs represents agents that affect all phases of the cell cycle (i.e., they are not cell cycle phase-specific). Alkylating agents include, but are not limited to nitrogen mustards, ethylenimenes, methylmelamines, alkyl sulfonates, nitrosoureas, and triazines. Particularly exemplary alkylating agents include but are not limited to busulfan, chlorambucil, cisplatin, cyclophosphamide (cytoxan), dacarbazine, ifosfamide, mechlorethamine (mustargen), and melphalan.

Antimetabolites.

Antimetabolites disrupt DNA and RNA synthesis. Unlike alkylating agents, they specifically influence the cell cycle during S phase. Antimetabolites can be differentiated into various categories, such as folic acid analogs, pyrimidine analogs, purine analogs, and related inhibitory compounds. Antimetabolites include but are not limited to 5-fluorouracil (5-FU), cytarabine (Ara-C), fludarabine, gemcitabine, and methotrexate.

Natural Products.

Natural products generally refer to compounds originally isolated from a natural source and identified as having a desirable pharmacological activity. Such compounds, including analogs and derivatives thereof, can be isolated from a natural source, chemically synthesized, and/or recombinantly produced by any technique known to those of skill in the art. Natural products include such categories as mitotic inhibitors, antitumor antibiotics, enzymes, and biological response modifiers.

Mitotic inhibitors include plant alkaloids and other natural agents that can in some embodiments inhibit protein synthesis required for cell division and in some embodiments inhibit mitosis. They typically operate during a specific phase of the cell cycle. Mitotic inhibitors include, for example, docetaxel, etoposide (VP16), teniposide, paclitaxel, taxol, vinblastine, vincristine, and vinorelbine, among others.

Taxoids are a class of related compounds isolated from the bark of the ash tree, *Taxus brevifolia*. Taxoids include but are not limited to compounds such as docetaxel and paclitaxel. Paclitaxel binds to tubulin (at a site distinct from that used by the vinca alkaloids) and promotes the assembly of microtubules.

Vinca alkaloids are a type of plant alkaloid identified to have pharmaceutical activity. Exemplary vinca alkaloids include vinblastine (VLB) and vincristine.

Antibiotics.

Certain antibiotics have both antimicrobial and/or cytotoxic activity. These drugs also interfere with DNA by chemically inhibiting enzymes and mitosis or altering cellular membranes. These agents are typically not cell cycle phase-specific. Examples of cytotoxic antibiotics include but are not limited to bleomycin, dactinomycin, daunorubicin, doxorubicin (Adriamycin), plicamycin (mithramycin), and idarubicin.

Miscellaneous Agents.

Miscellaneous cytotoxic agents that do not fall into the previous categories include but are not limited to platinum coordination complexes, anthracenediones, substituted ureas, methyl hydrazine derivatives, amsacrine, L-asparaginase, and tretinoin. Platinum coordination complexes include such compounds as carboplatin and cisplatin (cis-DDP). An exemplary anthracenedione is mitoxantrone. An exemplary substituted urea is hydroxyurea. An exemplary methyl hydrazine derivative is procarbazine (N-methylhydrazine, MIH). These examples are non-limiting and it is contemplated that any known cytotoxic, cytostatic, and/or cytocidal agent can be attached to a targeting peptide of the presently disclosed subject matter and administered to a targeted organ, tissue, and/or cell type.

Chemotherapeutic (cytotoxic) agents including, but are not limited to, 5-fluorouracil, bleomycin, busulfan, camptothecin, carboplatin, chlorambucil, cisplatin (CDDP), cyclophosphamide, dactinomycin, daunorubicin, doxorubicin, estrogen receptor binding agents, etoposide (VP16), farnesyl-protein transferase inhibitors, gemcitabine, ifosfamide, mechlorethamine, melphalan, mitomycin, navelbine, nitrosurea, plicomycin, procarbazine, raioxifene, tamoxifen, taxol, temazolomide (an aqueous form of DTIC), transplatinum, vinblastine, methotrexate, vincristine, and any analogs and/or derivatives or variants of the foregoing. Most chemotherapeutic agents fall into the categories of alkylating agents, antimetabolites, antitumor antibiotics, corticosteroid hormones, mitotic inhibitors, and nitrosoureas, hormone agents, miscellaneous agents, and any analog, derivative, or variant thereof.

The peptides identified and tested thus far in peptide-based vaccine approaches have generally fallen into one of three categories: 1) mutated on individual tumors, and thus not displayed on a broad cross-section of tumors from different patients; 2) derived from unmutated tissue-specific proteins, and thus compromised by mechanisms of self-tolerance; and 3) expressed in subsets of cancer cells and normal testes.

Antigens linked to transformation or oncogenic processes are of primary interest for immunotherapeutic development based on the hypothesis that tumor escape through mutation of these proteins could be more difficult without compromising tumor growth or metastatic potential The target peptides of the presently disclosed subject matter are in some embodiments unique in that the identified target peptides are modified by intracellular modification. This modification is of particular relevance because it is associated with a variety of cellular control processes, some of which are dysregulated in cancer cells. For example, the source proteins for class I MHC-associated phosphopeptides are often known phosphoproteins, supporting the idea that the phosphopeptides are processed from folded proteins participating in signaling pathways.

Although not wishing to be bound by any particular theory, it is envisioned that in some embodiments the target peptides of the presently disclosed subject matter are unexpectedly superior than known tumor-associated antigen-derived peptides for use in immunotherapy because: 1) they only displayed on the surface of cells in which intracellular phosphorylation is dysregulated (i.e., cancer cells) and not normal thymus cells, and thus they are not compromised by self-tolerance (as opposed to TAAs generally, which are associated with overexpression or otherwise expressed on non-mutated cells); and/or 2) they identify a cell displaying them on their surface as having dysregulated phosphorylation. Thus, post-translationally modified phosphopeptides that are differentially displayed on cancer cells and derived from source proteins objectively linked to cellular transformation and metastasis allow for more extensive anti-tumor responses to be elicited following vaccination. Target peptides are, therefore, better immunogens in peptide-based vaccines, as target peptides are derived from proteins involved with cellular growth control, survival, and/or metastasis, and alterations in these proteins as a mechanism of immune escape might interfere with the malignant phenotype of tumors.

As such, the presently disclosed subject matter also includes in some embodiments methods of identifying target peptides for use in immunotherapy which are displayed on transformed cells but are not substantially expressed on normal tissue in general or in the thymus in particular. In some embodiments, such target peptides bind the MHC class I molecule more tightly than their non-phosphorylated native counterparts. Moreover, such target peptides might have additional binding strength by having amino acid substitutions at certain anchor positions. In some embodiments, such modified target peptides will remain cross-reactive with TCRs specific for native target peptide MHC complexes.

Additionally, it is envisioned that the target peptides associated with proteins involved in intracellular signaling cascades or cycle regulation are of particular interest for use in immunotherapy. In some cases, the TCR might specifically react with the phosphate groups on the target peptide being displayed on an MHC class I molecule.

In some embodiments, a method for screening target peptides for use in immunotherapy (e.g., in adaptive cell therapy or in a vaccine) involves determining whether the candidate target peptides are capable of inducing a memory T cell response. The contemplated screening methods can include providing target peptides (including but not limited to those disclosed herein or those to be identified in the future) to a healthy volunteer and determining the extent to which a target peptide-specific T cell response is observed. In some embodiments, the extent to which the T cell response is a memory T cell response is also determined. In some embodiments, the extent to which a $T_{CM}$ response is elicited, such as but not limited to the extent to which a $T_{CM}$ response is elicited relative to other T cell types, is determined. In some embodiments, those target peptides that are capable of inducing a memory T cell response in healthy and/or diseased patients are selected for inclusion in the therapeutic compositions of the presently disclosed subject matter.

In some embodiments, the presently disclosed subject matter also provides methods for inducing a target peptide-specific memory T cell (e.g., $T_{CM}$) response in a patient by providing the patient with a composition comprising the target peptides disclosed herein. In some embodiments, the compositions are provided in a dosing regimen as disclosed herein.

In some embodiments, the presently disclosed subject matter also relates to methods for determining a cancer disease prognosis. These methods can involve providing a patient with target peptide compositions and determining the extent to which the patient is able to mount a target peptide-specific T cell response. In some embodiments, the target peptide composition comprises target peptides selected in substantially the same manner that one would select target peptides for inclusion in a therapeutic composition. If a patient is able to mount a significant target peptide specific T cell response, then the patient is likely to have a better prognosis than a patient with the similar disease and therapeutic regimen who is not able to mount a target peptide specific T cell response. In some embodiments, the methods involve determining whether the target peptide specific T cell response is a $T_{CM}$ response. In some embodiments, the presence of a target peptide-specific T cell response as a result of the contemplated diagnostic method correlates with an at least or about 5, 10, 15, 20, 25, 30, 35, 40, 45, 50, 55, 60, 65, 70, 75, 80, 85, 90, 95, 100, 125, 150, 175, 200, 250, 300, 400, 500 or more percent increase in progression free survival over standard of care.

The above disclosure generally describes the presently disclosed subject matter. A more complete understanding can be obtained by reference to the following specific examples which are provided herein for purposes of illustration only, and are not intended to limit the scope of the presently disclosed subject matter.

EXAMPLES

The following Examples provide further illustrative embodiments. In light of the present disclosure and the general level of skill in the art, those of skill will appreciate that the following EXAMPLES are intended to be exemplary only and that numerous changes, modifications, and alterations can be employed without departing from the scope of the presently disclosed subject matter.

Example 1

MHC Class-I-Associated Phosphopeptides Associated with CRC

Disclosed herein are MHC class-I-associated phosphopeptides associated with colorectal cancer (CRC). CRC tumors and matched normal tissues were lysed, the MHC class-I complexes affinity-purified, and bound peptides eluted. Phosphopeptides were enriched using immobilized metal affinity chromatography and characterized using mass spectrometry. Phosphopeptides were considered tumor specific if their levels in tumor were at least double that of the matched normal tissue.

21 tumor-specific CRC-associated MHC class I phosphopeptides were identified from a liver metastasis. A selection of these phosphopeptides was also found on primary tumors and CRC cell lines. These phosphopeptides derive from proteins that contribute to key CRC-associated oncogenic pathways, including the MAP kinase, interleukin, and p53 signaling pathways.

Figure 1C:
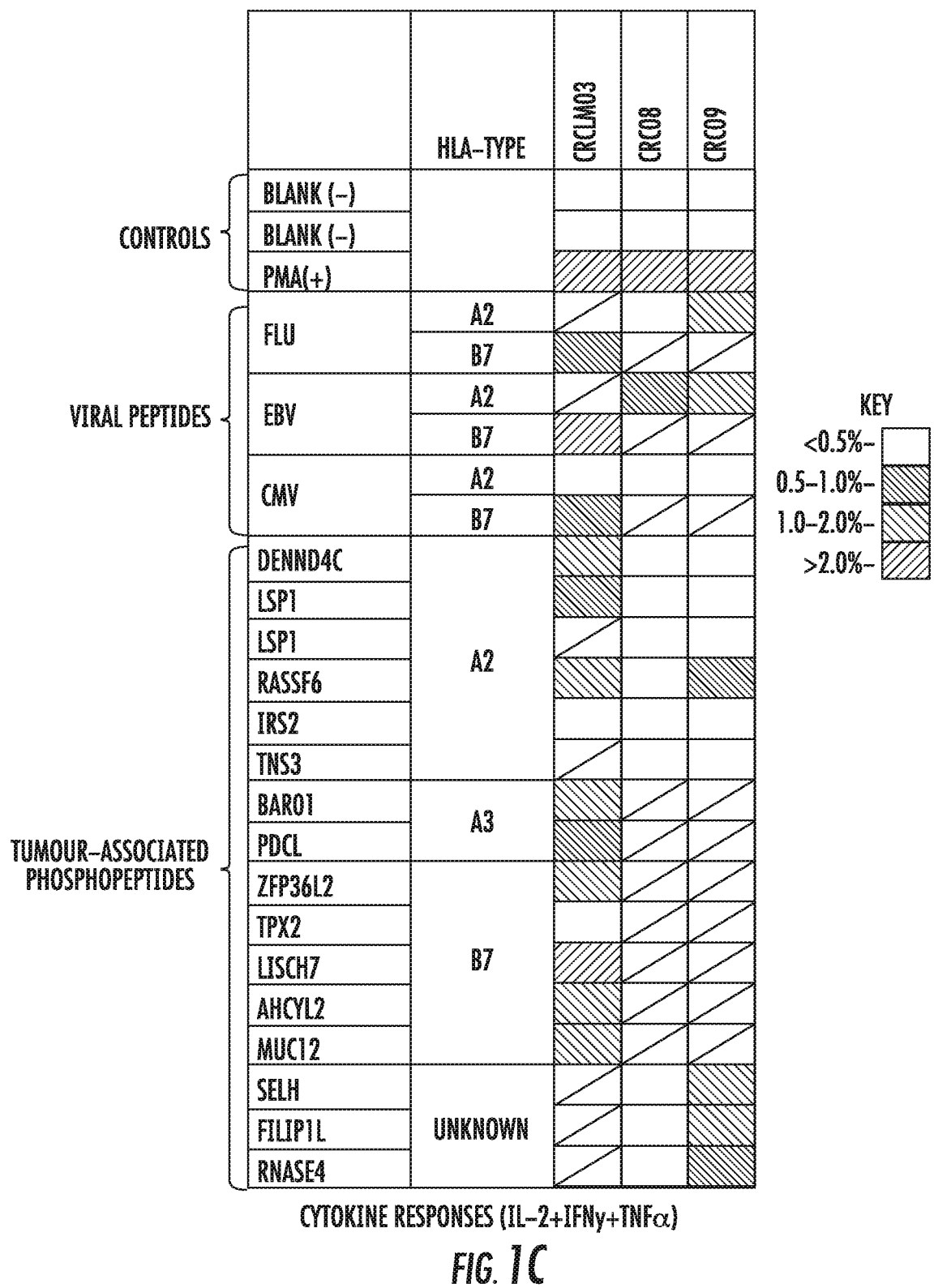

Tumor infiltrating lymphocytes ("TILs") from the same tumors, were extracted and expanded, and their responses to the phosphopeptides assessed using multiplexed intracellular cytokine staining for IL-2, IFNγ, and TNFα as depicted in FIG. 1A. Multifunctional TILs were found that responded to the phosphopeptides identified producing IL-2, IFNγ, and TNFα (see FIG. 1B). These responses are summarized in FIG. 1C.

The TILs from the tumor from which the phosphopeptides were identified responded to many more of the phosphopeptides than TILs from other tumors. In particular, there was a significant response (~2% of TILs, equivalent to the EBV peptide response) to the HLA-B7-associated phosphopeptide from LISCH7, which was also the most abundant phosphopeptide found on the tumor. There were, however, TIL responses from other tumors to some of the tumor-specific phosphopeptides, particularly those MHC class-I-associated phosphopeptides whose HLA specificity is unknown. These phosphopeptides have been found on many tumors from patients of differing HLA-types. Additionally, responses were seen to the phosphopeptide from RASSF6, a key oncoprotein involved in MAPK signaling, suggesting that these oncogenic proteins may be good targets for tumor immunotherapeutics.

Example 2

Healthy Donor PBMC Responses to Exemplary CRC Tumor-Specific Phosphopeptides Assessed by ELISpot Healthy donor PBMC responses to the CRC tumor-specific phosphopeptides were assessed using a cultured IFNγ ELISpot on day 7. Heterogeneous responses were seen to many of the phosphopeptides from different HLA-matched healthy donors (see FIG. 2). This indicates that these phosphopeptides are good vaccine candidates. In particular, many responses were seen to the RNASE4 phosphopeptide, of unknown HLA-specificity, the HLA-B7 phosphopeptide from ZPF36L2 and strong responses were often seen to the two IRS2 phosphopeptides.

Example 3

Establishment of Phosphopeptide-Specific T Cell Lines and Assays for Ability to Kill CRC Cell Line SW620

Figure 3:
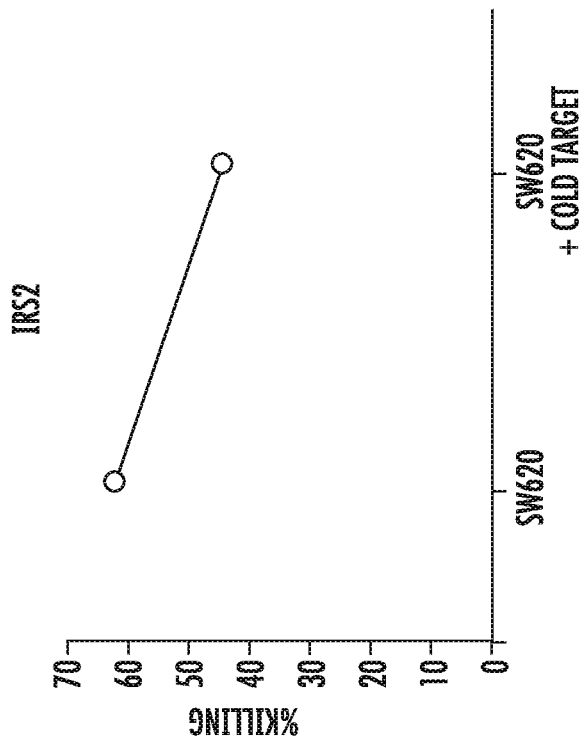
FIG. 3 is a series of graphs illustrating that T cells lines established against phosphopeptide targets IRS2 (HLA-A2; bottom panel) and ZPF36L2 (HLA-B7; top panel) were able to specifically kill the CRC cell line SW620 (ATCC® CCL-227™; American Type Culture Collection, Manassas, Va., United States of America).
Figure 3:
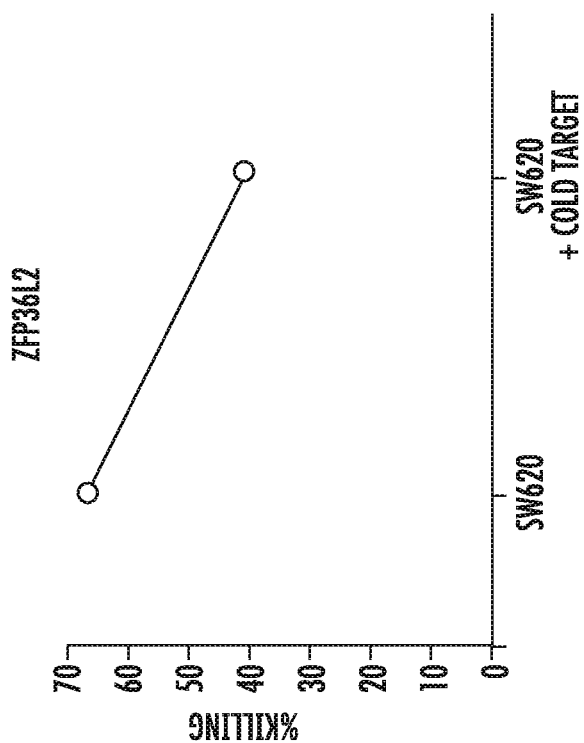

T cells lines were established against some of these key phosphopeptide targets. Both the IRS2 (A2) and ZPF36L2 (B7) phosphopeptide-specific cell lines were shown to specifically kill the CRC cell line SW620 (see FIG. 3).

The phosphopeptides disclosed herein are involved in key CRC oncogenic pathways. TILs from the same tumor as that which the phosphopeptides were identified in, respond to a subset of the phosphopeptides. TILs from other tumors also respond to some of these phosphopeptides. The phosphopeptides are also immunogenic in healthy donors, producing heterogeneous responses and are thus good vaccine candidates. Phosphopeptide-specific T cell lines from healthy donors can kill a CRC cell line.

Example 4

T Cell Recognition and Memory Response Assays

Generally, quantification of T cell IFNγ production in response to peptides was performed by ELISpot as per manufacturer's instructions. In brief, ELISpotPRO wells, pre-coated with IFNγ monoclonal antibody mAb 1-D1K (MabTech, product code: 3420-2APW-2), were washed four times with sterile PBS and blocked for 30 minutes with 200 μl 10% RPMI 1640 after which the blocking medium was removed.

Figure 4:
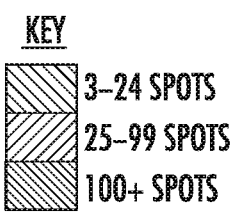
FIG. 4 is a Table summarizing the results of a Day 7 ELISpot experiment that demonstrated that healthy humans have an immunological recall response to certain colorectal class I phosphopeptides. Importantly, this response comes from central memory T cells and is comparable to the recall response that the same individuals have to viral peptides presented as a result of flu, EBV, etc. The left column lists various synthetic samples of CRC phosphopeptides. They were tested on 8 healthy B7/A3 donors and memory T cell responses were observed for several of the peptides. "KPE" is KPEsRRSSLL (SEQ ID NO: 54); "AVR" is AVRPTRLsL (SEQ ID NO 93); "RPD" is RPDsAHKML (SEQ ID NO 67); "SPR" is SPRsPDRTL (SEQ ID NO: 87); "RPT" is RPTKIGRRsL (SEQ ID NO: 81); "QPQ" is QPQRRsLRL (SEQ ID NO: 63); "RPG" is RPGsRQAGL (SEQ ID NO: 71); "SPF" is SPFKRQLsL (SEQ ID NO 84); "APD": is APDsPRAFL (SEQ ID NO 49); "LPI" is LPIFSRLsI (SEQ ID NO 60); "RPR" is RPRARsVDAL (SEQ ID NO 75); "RLS" is RLSsPISKR (SEQ ID NO 39); "SVR" is SVRRs-VLMK (SEQ ID NO 45); "RTM" is RTMsEAALVRK (SEQ ID NO 40); "RPF" is RPFHGISTVsL (SEQ ID NO 69); "RQAv" is RQAsIELPSMAV (SEQ ID NO 18); "RRG" is RRGsFEVTL (SEQ ID NO: 132); "RTH" is RTHsLLLLL (SEQ ID NO: 176); "NLV" and "TPR" are cytomegalovirus (CMV) peptides, "GLC" and "RPP" are Epstein-Barr Virus (EBV) peptides; "FLU" and "ADENO" are influenza and adenoviral peptides respectively. Phosphopeptide sequences; pSer, pThr, and pTyr are specified by lowercase s, t, and y, respectively.

For ELISpot analysis, PBMCs and CD8+ T cells were isolated fresh from healthy donors and patients. 1×10$^6$ PBMCs were isolated from both disease patients and healthy donors and re-suspended in AIM-V media (10% human AB serum) in a 96 well plate. Peptide or phosphopeptides were added individually at 10 μg/ml and placed at 37° C. in $CO_2$ incubator for 7 days. Cells were then harvested, washed four times, and re-challenged with either phosphopeptides, peptides, anti CD3 (OKT3, 100 ng/ml, Mabtech) as per manufacturer's instructions. Individual cytokine-producing cells were identified as dark spots after a 15 minute reaction with 5-bromo-4-chloro-3-indolyl phosphate and NBT by means of an alkaline phosphatase conjugate substrate (Mabtech). Spots were counted using an automated reader, (AID-Diagnostika), and results displayed as number of spot-forming cells (SFC) per 10$^6$ PBMCs (see FIGS. 2 and 4).

It is envisioned that the T cell activated by the peptides disclosed herein express increased levels of CD45RA and/or CD27 in accordance with the target peptides' ability to stimulate central memory ($T_{CM}$) T cells.

Example 5

Figure 5:
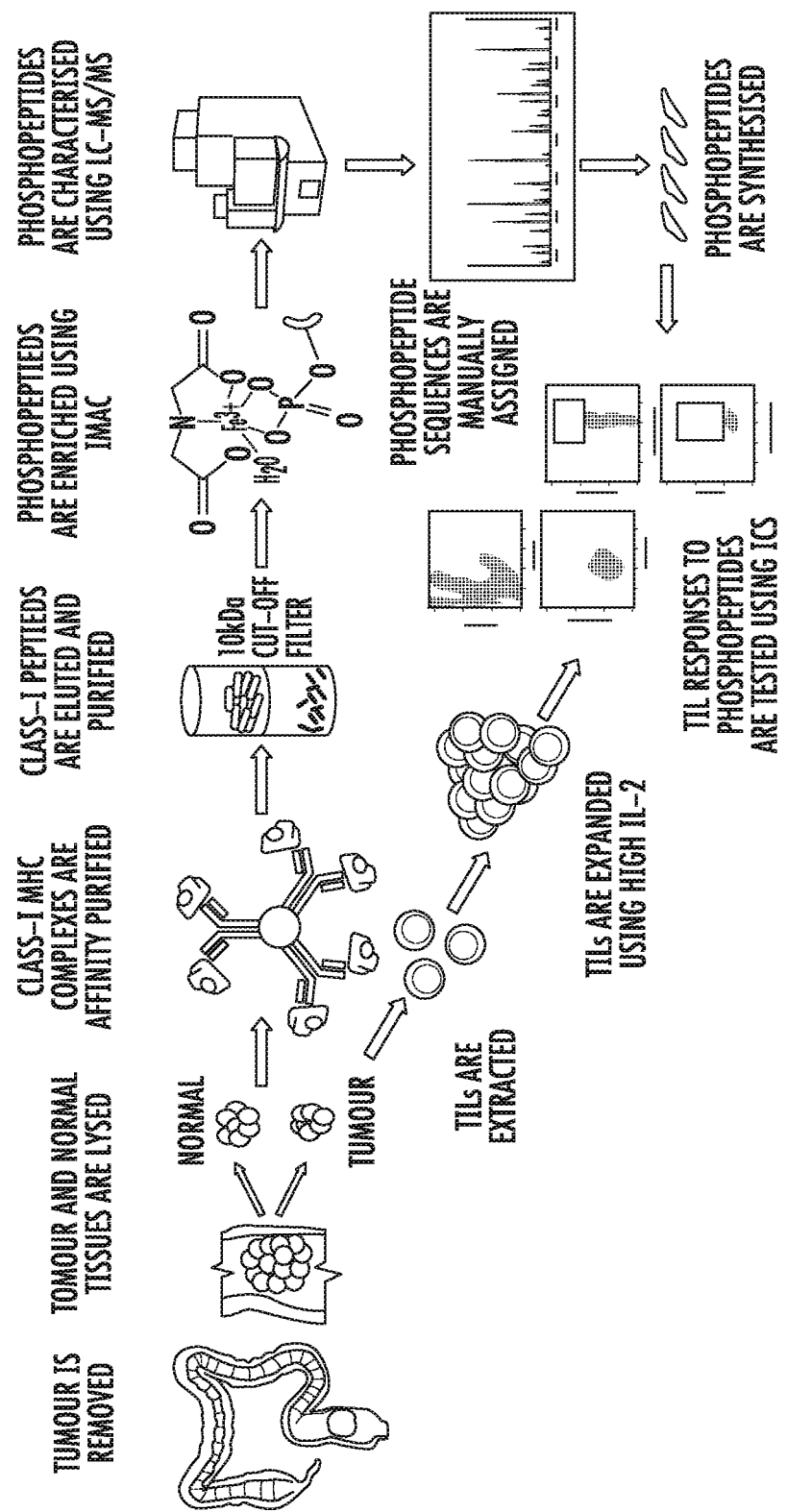
FIG. 5 is a schematic diagram of the isolating and characterization of phosphopeptides present in CRC tumor samples.

TIL Responses to Tumor-Specific, MHC Class-I Associated Phosphopeptide Discovered in Patient Samples An exemplary scheme for isolating and characterizing phosphopeptides from CRC tumor samples is depicted in FIG. 5. Summarily, tumor and normal tissue were taken from the same patient at resection. These were each lysed and the MHC Class I complexes affinity purified using pan Class I antibody, W6/32. The MHC Class I-associated peptides were eluted in acid and phosphopeptides enriched using immobilized metal affinity chromatography (IMAC). These phosphopeptides were characterized using CAD and ETD LC-MS/MS and the sequences manually assigned. The phosphopeptides were then synthesized and verified.

Figure 6:
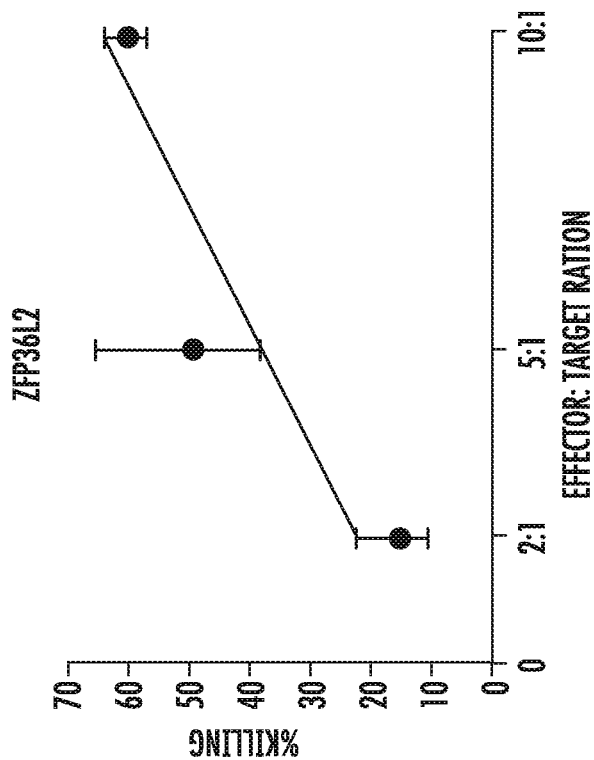
FIG. 6 is two graphs showing TIL responses to phosphopeptides derived from IRS2 (left panel) and ZFP36L2 (SEQ ID NO: 60; right panel).
Figure 6:
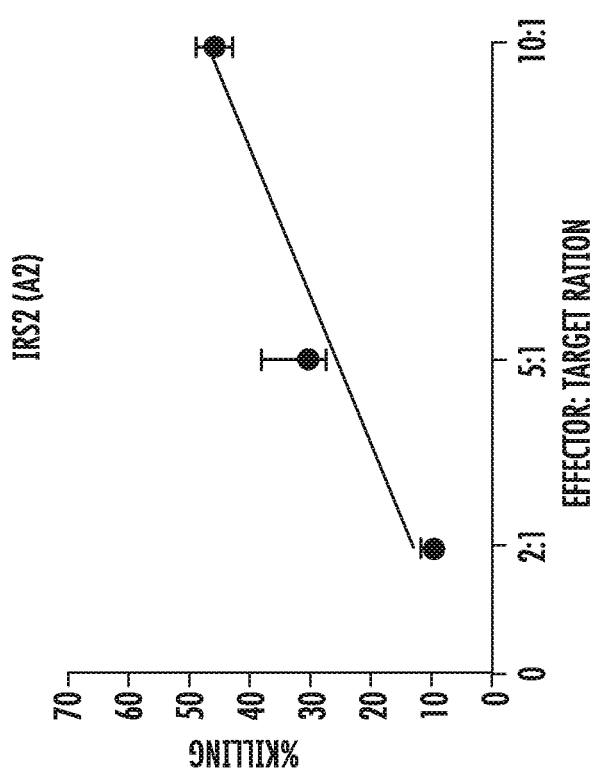

Tumor infiltrating lymphocytes (TILs) were also taken from the patient tumors at resection and expanded, using high-dose IL-2 (6000 IU/ml). TIL responses to the phosphopeptides were then tested using ICS. TILs were stimulated with phosphopeptide and cultured for 7 days before being re-stimulated in an intracellular cytokine staining assay assessing production of tumor necrosis factor alpha (TNFα), interferon gamma (IFNγ) and interleukin-2 (IL-2). The results are depicted in FIG. 6.

REFERENCES

All references listed in the instant disclosure, including but not limited to all patents, patent applications and publications thereof, scientific journal articles, and database entries (including but not limited to Uniprot and GEN-BANK® database entries and including all annotations available therein) are incorporated herein by reference in their entireties to the extent that they supplement, explain, provide a background for, and/or teach methodology, techniques, and/or compositions employed herein. The discussion of the references is intended merely to summarize the assertions made by their authors. No admission is made that any reference (or a portion of any reference) is relevant prior art. Applicants reserve the right to challenge the accuracy and pertinence of any cited reference.

Akamatsu et al. (1997) *Bioorg Med Chem* 5:157-163.
Altman et al. (1996) Phenotypic analysis of antigen-specific T lymphocytes. *Science* 274:94-96 [published erratum appears in *Science* 1998 Jun. 19; 280(5371):1821].
Altschul et al. (1990) Basic local alignment search tool. *J Mol Biol* 215:403-10.
Altschul et al. (1997) Gapped BLAST and PSI-BLAST: a new generation of protein database search programs. *Nucleic Acids Res* 25:3389-3402.
Arentz-Hansen et al. (2000) The intestinal T cell response to alpha-gliadin in adult celiac disease is focused on a single deamidated glutamine targeted by tissue transglutaminase. *J Exp Med* 191:603-612.
Arozarena et al. (2011) In melanoma, beta-catenin is a suppressor of invasion. *Oncogene* 30(45):4531-4543.
Bachmann et al. (2005) Importance of P-cadherin, beta-catenin, and Wnt5a/frizzled for progression of melanocytic tumors and prognosis in cutaneous melanoma. *Clin Cancer Res* 11:8606-8614.
Baron et al. (2005) Graft-versus-tumor effects after allogeneic hematopoietic cell transplantation with nonmyeloablative conditioning. *J Clin Oncol* 23:1993-2003.
Bertoletti et al. (1994) Natural variants of cytotoxic epitopes are T cell receptor antagonists for antiviral cytotoxic T cells. *Nature* 369:407-410.
Berzofsky et al. (1988) Antigen processing for presentation to T lymphocytes: function, mechanisms, and implications for the T cell repertoire. *Immunol Rev* 106:5-31.
Boon et al. (1994) *Annu Rev Immunol* 12:337-365.
Bullock et al. (2000) The density of peptides displayed by dendritic cells affects immune responses to human tyrosinase and gp100 in HLA-A2 transgenic mice. *J Immunol* 164:2354-2361.
Chenna et al. (2003) Multiple sequence alignment with the Clustal series of programs. *Nucleic Acids Res* 31:3497-3500.
Chi (2011) Cancer research: Promise of protection. *Nature* 471:537-538.
Chien et al. (2009) Activated Wnt/beta-catenin signaling in melanoma is associated with decreased proliferation in patient tumors and a murine melanoma model. *Proc Natl Acad Sci USA* 106:1193-1198.
Chothia et al. (1989) *Nature* 342:877-883.
Clackson et al. (1991) *Nature* 352: 624-628.
Clark et al. (1989) *Eur J Immunol* 19:381-388.
Clothia et al. (1985) *J Mol Biol* 186:651-666.
Cobbold et al. (2005) Adoptive transfer of cytomegalovirus-specific CTL to stem cell transplant patients after selection by HLA-peptide tetramers. *J Exp Med* 202:379-386.
Cole et al. (1985) *Proc Natl Acad Sci USA* 82:859.
Cote et al. (1983) *Proc Natl Acad Sci USA* 80:2026.
Crawford et al. (1999) The metalloproteinase matrilysin is a target of beta-catenin transactivation in intestinal tumors. *Oncogene* 18:2883-2891.
Demotz et al. (1989) Delineation of several DR-restricted tetanus toxin T cell epitopes. *J Immunol* 142:394-402.
Demunter et al. (2002) Loss of membranous expression of beta-catenin is associated with tumor progression in cutaneous melanoma and rarely caused by exon 3 mutations. *Modern Pathol* 15:454-461.
Dephoure et al. (2008) A quantitative atlas of mitotic phosphorylation. *Proc Natl Acad Sci USA* 105:10762-10767.
Depontieu et al. (2009) Identification of tumor-associated, MHC class II-restricted phosphopeptides as targets for immunotherapy. *Proc Natl Acad Sci USA* 106:12073-12078.
Depontieu et al. Supplemental Information, 10.1073 *Proc Natl Acad Sci USA* 0903852106.
Dudley et al. (2008) Adoptive cell therapy for patients with metastatic melanoma: evaluation of intensive myeloablative chemoradiation preparative regimens. *J Clin Oncol* 26:5233-5239.
DuPage et al. (2012) Expression of tumour-specific antigens underlies cancer immunoediting. *Nature* 482:405-409.
El Kasmi et al. (2000) Neutralization of measles virus wild-type isolates after immunization with a synthetic peptide vaccine which is not recognized by neutralizing passive antibodies. *J Gen Virol* 81:729.
Finn (2003) Premalignant lesions as targets for cancer vaccines. *J Exp Med* 198:1623-1626.
Fiol et al. (1988) Phosphoserine as a recognition determinant for glycogen synthase kinase-3: phosphorylation of a synthetic peptide based on the G-component of protein phosphatase-1. *Arch Biochem Biophys* 267:797-802.
Fiol et al. (1990) Ordered multisite protein phosphorylation. Analysis of glycogen synthase kinase 3 action using model peptide substrates. *J Biol Chem* 265:6061-6065.
Fischbein et al. (2000) CD40 signaling replaces CD4[+] lymphocytes and its blocking prevents chronic rejection of heart transplants. *J Immunol* 165:7316-7322.
Fishwild et al. (1996) *Nature Biotechnol* 14:845.
Gale et al. (1994) Identical-twin bone marrow transplants for leukemia. *Ann Intern Med* 120:646-652.
Gattinoni et al. (2006) *Nat Rev Immunol* 6: 383-93.
Gerdes et al. (1999) Analysis of beta-catenin gene mutations in pancreatic tumors. *Digestion* 60:544-548.
Girbal-Neuhauser et al. (1999) The epitopes targeted by the rheumatoid arthritis-associated antifilaggrin autoantibodies are posttranslationally generated on various sites of (pro)filaggrin by deimination of arginine residues. *J Immunol* 162:585-594.

Goldman & DeFrancesco (2009) The cancer vaccine roller coaster, *Nat Biotech* 27:129-139 (Corrected online: 7 Jun. 2010|doi:10.1038/nbt0209-129).

Hall et al. (2010) Comprehensive analysis of phosphorylation sites in Tensin1 reveals regulation by p38MAPK. *Mol Cellul Proteom* 9:2853-2863.

Haluska et al. (2006) Genetic alterations in signaling pathways in melanoma. *Clin Cancer Res* 12:2301s-2307s.

Hamann et al. (1997) Phenotypic and functional separation of memory and effector human CD8+ T cells. *J Exp Med* 186:1407-1418.

He et al. (1998) Identification of c-MYC as a target of the APC pathway. *Science* 281:1509-1512.

Hirohashi et al. (2009) The functioning antigens: beyond just as the immunological targets. *Cancer Sci* 100:798-806.

Ho et al. (2006) In vitro methods for generating CD8+ T cell clones for immunotherapy from the naive repertoire. *J Immunol Meth* 310:40-52.

Hoek et al. (2006) Metastatic potential of melanomas defined by specific gene expression profiles with no BRAF signature. *Pigment Cell Res* 19:290-302.

Hogan et al. (1998) The peptide recognized by HLA-A68.2-restricted, squamous cell carcinoma of the lung-specific cytotoxic T lymphocytes is derived from a mutated elongation factor 2 gene. *Cancer Res* 58:5144-5150.

Homfray et al. (1998) Defects in mismatch repair occur after APC mutations in the pathogenesis of sporadic colorectal tumours. *Human Mutation* 11:114-120.

Hoogenboom et al. (1991) *Nucleic Acids Res* 19:4133.

Horowitz et al. (1990) Graft-versus-leukemia reactions after bone marrow transplantation. *Blood* 75:555-562.

Hulsken et al. (1994) E-cadherin and APC compete for the interaction with beta-catenin and the cytoskeleton. *J Cell Biol* 127:2061-2069.

Ilyas et al. (1997) Beta-catenin mutations in cell lines established from human colorectal cancers. *Proc Natl Acad Sci USA* 94:10330-10334.

Isakoff et al. (2005) Breast cancer-associated PIK3CA mutations are oncogenic in mammary epithelial cells. *Cancer Res* 65:10992-11000.

Jacob et al. (1997) *Int J Cancer* 71:325-332.

Jimbow et al. (1975) Mitotic activity in non-neoplastic melanocytes in vivo as determined by histochemical, autoradiographic, and electron microscope studies. *J Cell Biol* 66:663-670.

Jones et al. (1986) *Nature* 321:522-525.

Jones et al. (2008) Core signaling pathways in human pancreatic cancers revealed by global genomic analyses. *Science* 321:1801-1806.

Kabat et al., (1991) *Sequences of Proteins of Immunological Interest, Fifth Edition*, NIH Publication No. 91-3242, National Institute of Health, Bethesda, Md., United States of America.

Kageshita et al. (2001) Loss of beta-catenin expression associated with disease progression in malignant melanoma. *Br J Dermatol* 145:210-216.

Kantoff et al. (2010) Sipuleucel-T immunotherapy for castration-resistant prostate cancer. *N Engl J Med* 363:411-422.

Kielhorn et al. (2003) Tissue microarray-based analysis shows phospho-beta-catenin expression in malignant melanoma is associated with poor outcome. *Int J Cancer* 103:652-656.

Kim et al. (2000) beta-catenin expression and mutational analysis in renal cell carcinomas. *Pathol Intl* 50:725-730.

Kimelman & Xu (2006) beta-catenin destruction complex: insights and questions from a structural perspective. *Oncogene* 25:7482-7491.

Klenerman et al. (1994) Cytotoxic T cell activity antagonized by naturally occurring HIV-1 Gag variants. *Nature* 369:403-407.

Kohler & Milstein (1975) *Nature* 256:495.

Kolb (2008) Graft-versus-leukemia effects of transplantation and donor lymphocytes. *Blood* 112:4371-4383.

Kolb et al. (1990) Donor leukocyte transfusions for treatment of recurrent chronic myelogenous leukemia in marrow transplant patients. *Blood* 76:2462-2465.

Kozbor et al. (1983) *Hybridoma* 2:7.

Krengel et al. (2004) Cadherin expression pattern in melanocytic tumors more likely depends on the melanocyte environment than on tumor cell progression. *J Cutaneous Pathol* 31:1-7.

Kroger et al. (2005) Stem cell transplantation from identical twins in patients with myelodysplastic syndromes. *Bone Marrow Transplant* 35:37-43.

Ley et al. (2008) DNA sequencing of a cytogenetically normal acute myeloid leukaemia genome. *Nature* 456:66-72.

Liu et al. (2002) Control of beta-catenin phosphorylation/degradation by a dual-kinase mechanism. *Cell* 108:837-847.

Lonberg & Huszar (1995) *Int Rev Immunol* 13:65.

Lonberg et al. (1994) *Nature* 368:856.

Lucas & Coulie (2008) About human tumor antigens to be used in immunotherapy. *Seminars Immunol* 20:301-307.

Mackensen et al. (2000) *Int J Cancer* 86, 385-392.

Maelandsmo et al. (2003) Reduced beta-catenin expression in the cytoplasm of advanced-stage superficial spreading malignant melanoma. *Clin Cancer Res* 9:3383-3388.

Mamula et al. (1999) Isoaspartyl post-translational modification triggers autoimmune responses to self-proteins. *J Biol Chem* 274:22321-22327.

Marafioti et al. (2004) Leukocyte-specific phosphoprotein-1 and PU.1: two useful markers for distinguishing T cell-rich B-cell lymphoma from lymphocyte-predominant Hodgkin's disease. *Haematologica* 89:957-964.

Marks et al. (1991) *J Mol Biol* 222:581-597.

Marks et al. (1992) *J Biol Chem* 267:16007.

Matsushita et al. (2012) Cancer exome analysis reveals a T cell-dependent mechanism of cancer immunoediting. *Nature* 482:400-404.

Meyer et al. (2009) Identification of natural MHC class II presented phosphopeptides and tumor-derived MHC class I phospholigands. *J Proteome Res* 8:3666-3674.

Mihara et al. (2001) *Clin Immunol* 98:319.

Miyake et al. (2001) Absence of mutations in the beta-catenin and adenomatous polyposis coli genes in papillary and follicular thyroid carcinomas. *Pathol Intl* 51:680-685.

Mohammed et al. (2008) Phosphorylation-dependent interaction between antigenic peptides and MHC class I: a molecular basis for the presentation of transformed self. *Nat Immunol* 9:1236-1243.

Molina et al. (2007) Global proteomic profiling of phosphopeptides using electron transfer dissociation tandem mass spectrometry. *Proc Natl Acad Sci USA* 104: 2199-2204.

Morales et al. (2000) *Nucl Med Biol* 27:199.

Morin et al. (1997) Activation of beta-catenin-Tcf signaling in colon cancer by mutations in beta-catenin or APC. *Science* 275:1787-1790.

Neuberger (1996) *Nat Biotechnol* 14:826.

Newberg et al. (1992) Species specificity in the interaction of CD8 with the α3 domain of MHC class I molecules. *J Immunol* 149:136-142.

Niedermann et al. (1995) Contribution of proteasome-mediated proteolysis to the hierarchy of epitopes presented by major histocompatibility complex class I molecules. *Immunity* 2:289-299.

Novotny & Haber (1985) *Proc Natl Acad Sci USA* 82:4592-4596.

Nunes et al. (2011) A novel tumor antigen derived from enhanced degradation of bax protein in human cancers. *Cancer Res* 71:5435-5444.

Offringa (2009) Antigen choice in adoptive T cell therapy of cancer. *Curr Opin Immunol* 21:190-199.

Ogasawara et al. (2006) Mutations and nuclear accumulation of beta-catenin correlate with intestinal phenotypic expression in human gastric cancer. *Histopathology* 49:612-621.

Ohgaki et al. (2004) APC mutations are infrequent but present in human lung cancer. *Cancer Lett* 207:197-203.

Oliva et al. (2006) High frequency of beta-catenin mutations in borderline endometrioid tumours of the ovary. *J Pathol* 208:708-713.

Olmeda et al. (2003) Beta-catenin regulation during the cell cycle: implications in G2/M and apoptosis. *Mol Biol Cell* 14:2844-2860.

Omholt et al. (2001) Cytoplasmic and nuclear accumulation of beta-catenin is rarely caused by CTNNB1 exon 3 mutations in cutaneous malignant melanoma. *Intl J Cancer* 92:839-842.

Otaka et al. (1995) *Tetrahedron Lett* 36:927-930.

Pardoll (2012) The blockade of immune checkpoints in cancer immunotherapy. *Nature Reviews Cancer* 12:252-264.

Parmiani et al. (2002) *J Natl Cancer Inst* 94:805-818.

Parsons et al. (2011) The Genetic Landscape of the Childhood Cancer Medulloblastoma. *Science* 331:435-439.

Pavletic et al. (2007) Genetically identical twin transplantation for chronic lymphocytic leukemia. *Leukemia* 21:2452-2455.

PCT International Patent Application Publication Nos. WO 1994/02602; WO 1996/033735; WO 1996/034096; WO 2004/106380; WO 2004/106380; 2010/129537; WO 2011/149909.

Pecina-Slaus et al. (2007) E-cadherin and beta-catenin expression patterns in malignant melanoma assessed by image analysis. *J Cutaneous Pathol* 34:239-246.

Peiper et al. (1997) *Eur J Immunol* 27:1115-1123.

Peoples et al. (1993) *Surgery* 114:227-234.

Petersen et al. (2009) Phosphorylated self-peptides alter human leukocyte antigen class I-restricted antigen presentation and generate tumor-specific epitopes. *Proc Natl Acad Sci USA* 106:2776-2781.

Pollock & Hayward (2002) Mutations in exon 3 of the beta-catenin gene are rare in melanoma cell lines. *Melanoma Res* 12:183-186.

Presta (1992) *Proc Natl Acad Sci US A* 89:4285-4289.

Preudhomme et al. (2010) Imatinib plus peginterferon alfa-2a in chronic myeloid leukemia. *N Engl J Med* 363:2511-2521

Rappsilber et al. (2007) Protocol for micro-purification, enrichment, pre-fractionation and storage of peptides for proteomics using StageTips. *Nat Protocols* 2:1896-1906.

Restifo et al. (1993) Identification of human cancers deficient in antigen processing. *J Exper Med* 177:265-272.

Richards et al. (1999) *Cancer Res* 59:2096.

Riechmann et al. (1988) *Nature* 332:323-327.

Rimm et al. (1999) Frequent nuclear/cytoplasmic localization of beta-catenin without exon 3 mutations in malignant melanoma. *Am J Pathol* 154:325-329.

Robila et al. (2008) MHC class II presentation of gp100 epitopes in melanoma cells requires the function of conventional endosomes and is influenced by melanosomes. *J Immunol* 181:7843-7852.

Rock & Goldberg (1999) *Annu Rev Immunol* 17:739-779.

Rosenberg & Dudley (2009) Adoptive cell therapy for the treatment of patients with metastatic melanoma. *Curr Opin Immunol* 21:233-240.

Rosenberg et al. (1986) A new approach to the adoptive immunotherapy of cancer with tumor-infiltrating lymphocytes. *Science* 233:1318-1321.

Rosenberg et al. (2004) Cancer immunotherapy: moving beyond current vaccines. *Nat Med* 10:909-915.

Ruppert et al. (1993) Prominent role of secondary anchor residues in peptide binding to A2.1 molecules. *Cell* 74:929-937.

Sadot et al. (2002) Regulation of S33/S37 phosphorylated beta-catenin in normal and transformed cells. *J Cell Sci* 115:2771-2780.

Sandborn et al. (2001) *Gastroenterology,* 120:1330-1338.

Sanders et al. (1999) Alterations in cadherin and catenin expression during the biological progression of melanocytic tumours. *Mol Pathol* 52:151-157.

Schendel et al. (1993) *J Immunol* 151:4209-4220.

Schreiber et al. (2011) Cancer immunoediting: integrating immunity's roles in cancer suppression and promotion. *Science* 331:1565-1570.

Seidensticker & Behrens (2000) Biochemical interactions in the wnt pathway. *Biochim Biophys Acta* 1495:168-182.

Sette et al. (1994) The relationship between class I binding affinity and immunogenicity of potential cytotoxic T cell epitopes. *J Immunol* 153:5586-5592.

Shinkura et al. (1998) *Anticancer Res* 18:1217.

Slawson et al. (2005) Perturbations in O-linked β-N-acetylglucosamine proteim modification cause severe defects in mitotic progression and cytokinesis. *J Biol Chem,* 280:32944-32956.

Slawson et al. (2008) A mitotic GlcN Acylation/phosphorylation signaling complex alters the posttranslational state of the cytoskeletal proteim vimentin. *Mol Biol Cell* 19:4130-4140.

Slingluff et al. (1994) *Cancer Res* 54:2731-2737.

Slingluff et al. (2000) Melanomas with concordant loss of multiple melanocytic differentiation proteins: immune escape that may be overcome by targeting unique or undefined antigens. *Cancer Immunol Immunother* 48:661-672.

Slovin et al. (1986) *J Immunol* 137:3042-3048.

Smyth et al. (1992) *Tetrahedron Lett* 33:4137-4140.

Strickley (2004) Solubilizing excipients in oral and injectable formulations. *Pharm Res* 21:201-230.

Sun et al. (2005) Infrequent mutation of APC, AXIN1, and GSK3B in human pituitary adenomas with abnormal accumulation of CTNNB1. *J Neuro-Oncol* 73:131-134.

Takahashi et al. (2002) Identification of membrane-type matrix metalloproteinase-1 as a target of the beta-catenin/Tcf4 complex in human colorectal cancers. *Oncogene* 21:5861-5867.

Takemaru et al. (2008) An oncogenic hub: β-catenin as a molecular target for cancer therapeutics. *Handb Exp Pharmacol* 186:261-284.

Talpaz et al. (1986) Hematologic remission and cytogenetic improvement induced by recombinant human interferon alpha A in chronic myelogenous leukemia. *N Engl J Med* 314:1065-1069.

Tetsu & McCormick (1999) Beta-catenin regulates expression of cyclin D1 in colon carcinoma cells. *Nature* 398: 422-426.

Townsend & Bodmer (1989) *Ann Rev Immunol* 7:601-624.

United Kingdom Patent GB 2249310A.

United States Patent Application Publication Nos. 2002/0119149; 2004/0202657; 2005/0277161; 2009/0117102; 2009/0226474.

U.S. Pat. Nos. 4,361,539; 4,816,567; 5,225,539; 5,545,806; 5,545,807; 5,569,825; 5,625,126; 5,633,425; 5,661,016; 5,712,120; 5,861,155; 5,869,619; 5,916,771; 5,939,598; 5,968,509; 6,054,927; 6,180,370; 6,706,265; 6,750,325.

U.S. Provisional Patent Application Ser. Nos. 61/695,776.

Utz et al. (1997) Proteins phosphorylated during stress-induced apoptosis are common targets for autoantibody production in patients with systemic lupus erythematosus. *J Exp Med* 185:843-854.

van Doorn et al. (2005) Epigenetic profiling of cutaneous T cell lymphoma: promoter hypermethylation of multiple tumor suppressor genes including BCL7a, PTPRG, and p73. *J Clin Oncol* 23:3886-3896.

van Wauve (1980) *J Immunol* 124:2708-18.

Verhoeyen et al. (1988) *Science* 239:1534-1536.

Wang et al. (2007) Dynamic interplay between O-linked N-acetylglucosaminylation and glycon synthase kinase-3-dependent phosphorylation. *Mol Cell Proteomics* 6:1365-1379.

Wang et al. (2010) Extensive Crosstalk Between O-GlcNAcylation and Phosphorylation Regulates Cytokinesis, *Sci Signal* 3(104):ra2, including Supplemental Materials.

Watts (1997) *Annu Rev Immunol* 15:821-850.

Waun Ki Hong et al. *Holland-Frei Cancer Medicine* 10 A.D. McGraw-Hill Medical. Ref Type: Edited Book Weber (2002) *Cancer Invest* 20:208-221.

Wong (1990) *Transplantation* 50:683-689.

Worm et al. (2004) Genetic and epigenetic alterations of the APC gene in malignant melanoma. *Oncogene* 23:5215-5226.

Wuttge et al. (1999) T cell recognition of lipid peroxidation products breaks tolerance to self proteins. *Immunol* 98:273-279.

Yasumura et al. (1993) *Cancer Res* 53:1461-1468.

Yee et al. (2002) *Proc Natl Acad Sci USA* 99:16168-16173.

Yenari et al. (1998) *Exp Neurol* 153:223.

Yenari et al. (2001) *Neurol Res* 23:72.

Yewdell (2002) To DRiP or not to DRiP: generating peptide ligands for MHC class I molecules from biosynthesized proteins. *Mol Immunol* 39:139-146.

Yoshino et al. (1994) *Cancer Res* 54:3387-3390.

Yost et al. (1996) The axis-inducing activity, stability, and subcellular distribution of beta-catenin is regulated in *Xenopus* embryos by glycogen synthase kinase 3. *Genes Dev* 10:1443-1454.

Zarling et al. (2000) Phosphorylated peptides are naturally processed and presented by MHC class I molecules in vivo. *J Exp Med* 192:1755-1762.

Zarling et al. (2006) Identification of class I MHC associated phosphopeptides as targets for cancer immunotherapy. *Proc Natl Acad Sci USA* 103:14889-14894.

It will be understood that various details of the presently disclosed subject matter may be changed without departing from the scope of the presently disclosed subject matter. Furthermore, the foregoing description is for the purpose of illustration only, and not for the purpose of limitation.

TABLE 3

Annotation for Protein Sources of Class I MHC Phosphopeptides Presented on Colorectal Cancer

| Source Protein | Predicted HLA Type | Liver Metastasis | Primary | Cell Line | CRC Pathway |
|---|---|---|---|---|---|
| RASSF6 | A2 | + | | | MPAK signaling |
| DENND4C | B7 | ++ | | | |
| IRS2 | A2 | | | | Insulin signaling |
| LSP1 | A2 | | | | |
| BARD1 | A3 | ++ | | | DNA damage signaling |
| PDCL | A3 | + | | | |
| Rab11FIP1 | B7 | ++ | | | |
| IRS2 | A2 | +++ | | | Insulin signaling |
| PALLD | B7 | ++ | | | |
| MUC12 | B7 | +++ | | | TGFβ signaling |
| AHCYL2 | B7 | ++ | | | Methionine metabolism |
| TPX2 | B7 | ++ | | | p53 signaling |
| PDLIM2 | B7 | ++ | | | IL-12 signaling |
| NUMBL | B7 | +++ | ++ | | Notch signaling |
| Unidentified | B7 | ++ | | | |
| ZFP36L2 | B7 | ++ | ++ | | |
| LISCH7 | B7 | ++++ | | | |
| YT521 | Unknown | ++ | | | |
| RNASE4 | Unknown | +++ | | ++ | |
| FILIP1L | Unknown | +++ | ++ | | |
| SELH | Unknown | +++ | ++ | | |

TABLE 4

Exemplary MHC Class I Phosphopeptides Associated with Colorectal Cancer

| Source Protein | MHC Class I Subtype | Peptide Sequence | SEQ ID NO. |
|---|---|---|---|
| RASSF6 | A*0301 | RTMsEAALVRK | 40 |
| DENND4C | B*0702 | RPFHGISTVsL | 69 |
| IRS2 | A*0201 | RVAsPTSGV | 23 |
| LSP1 | A*0201 | RQAsIELPSMAV | 18 |
| BARD1 | A*0301 | RLSsPISKR | 39 |
| PDCL | A*0301 | SVRRsVLMK | 45 |
| Rab11-FIP1 | B*0702 | KPEsRRSSLL | 54 |
| IRS2 | A*0201 | AVRPTRLsL | 93 |
| PALLD | B*0702 | RPDsAHKML | 67 |
| MUC12 | B*0702 | SPRsPDRTL | 87 |
| AHCYL2 | B*0702 | RPTKIGRRsL | 81 |
| TPX2 | B*0702 | QPQRRsLRL | 63 |
| PDZ-LIM2 | B*0702 | RPGsRQAGL | 71 |
| NUMB | B*0702 | SPFKRQLsL | 84 |
| ZFP36L2 | B*0702 | LPIFSRLsI | 60 |
| LISCH7 | B*0702 | RPRARsVDAL | 75 |
| TTC22 | B*0702 | APRDRRAVsF | 50 |

TABLE 4-continued

Exemplary MHC Class I Phosphopeptides Associated with Colorectal Cancer

| Source Protein | MHC Class I Subtype | Peptide Sequence | SEQ ID NO. |
|---|---|---|---|
| SELH | B*2705 | RRGsFEVTL | 132 |
| RNASE4 | unknown | RTHsLLLLL | 176 |
| FILIP1L | B*2705 | RRIsDPQVF | 135 |
| YT521 | unknown | RARGIsPIVF | 64 |

TABLE 5

Exemplary Phosphopeptides Associated with Colorectal Cancer (CRC)

| SEQ ID NO. | Sequence | Accession[a] | Amino Acids[b] | Source Protein |
|---|---|---|---|---|
| 1 | ISSsMHSLY | P50616 | 222-230 | Protein Tob1 |
| 2 | ITQGtPLKY | Q9Y618 | 1459-1467 | Nuclear receptor corepressor 2 |
| 3 | LTDPSsPTISSY | Q8IX90 | 341-352 | Spindle and kinetochore-associated protein 3 |
| 4 | TMAsPGKDNY | O60684 | 3-12 | Importin subunit alpha-7 |
| 5 | AIsDLQQL | O15302 | 152-159 | CaM kinase II isoform |
| 6 | DLKRRsMSI | Q96N67 | 175-183 | Dedicator of cytokinesis protein 7 |
| 7 | FLDtPIAKV | Q969G9 | 320-238 | Protein naked cuticle homolog 1 |
| 8 | KAFsPVRSV | Q02363 | 2-10 | DNA-binding protein inhibitor ID-2 |
| 9 | KLAsPELERL | P05412 | 70-79 | Transcription factor AP-1 |
| 10 | KLFPDtPLAL | Q12906 | 587-596 | Interleukin enhancer-binding factor 3 |
| 11 | KLIDRTEsL | P33241 | 197-205 | Lymphocyte-specific protein 1 |
| 12 | KLIDVsSQKV | O14757 | 461-471 | Serine; threonine-protein kinase Chk1 |
| 13 | KVQsLRRAL | Q969G5 | 185-193 | PRKCDBP; Protein kinase C delta-binding protein |
| 14 | LLLsEEVEL | Q8IY92 | 489-497 | Structure-specific endonuclease subunit SLX4 |
| 15 | RLAsYLDRV | P05783 | 90-98 | Keratin, type I, cytoskeletal 18 |
| 16 | RLSsPLHFV | Q8NC44 | 400-408 | Protein FAM134A |
| 17 | RQAsIELPSM | P33241 | 249-258 | Lymphocyte-specific protein 1 |
| 18 | RQAsIELPSMAV | P33241 | 249-260 | Lymphocyte-specific protein 1 |
| 19 | RQDsTPGKVFL | P13056 | 61-71 | Nuclear receptor subfamily 2 group C member 1 |
| 20 | RQDStPGKVFL | P13056 | 61-71 | Nuclear receptor subfamily 2 group C member 1 |
| 21 | RQIsQDVKL | Q01433 | 165-173 | AMP deaminase 2 |
| 22 | RTLsPEIITV | Q9H4A3 | 1802-1812 | Serine; threonine-protein kinase WNK1 |
| 23 | RVAsPTSGV | Q9Y4H2 | 1097-1105 | Insulin receptor substrate 2; IRS2 |
| 24 | RVLHsPPAV | Q9Y4B5 | 1510-1518 | SOGA2; coiled-coil domain-containing protein 165 |
| 25 | SMTRsPPRV | Q9BRL6 | 248-256 | Serine; arginine-rich splicing factor 8 |
| 26 | SVKPRRTsL | P15822 | 766-774 | Zinc finger protein 40 |
| 27 | VMIGsPKKV | Q68CZ2 | 1437-1445 | Tensin-3 |
| 28 | RADsPVHM | O95402 | 444-451 | Mediator of RNA polymerase II transcription subunit 26 |
| 29 | RAHSsPASL | P46937 | 124-132 | Yorkie homolog; 65 kDa Yes-associated protein; YAP65 |
| 30 | RIsHELDS | P10451 | 301-308 | Osteopontin |

TABLE 5-continued

Exemplary Phosphopeptides Associated with Colorectal Cancer (CRC)

| SEQ ID NO. | Sequence | Accession[a] | Amino Acids[b] | Source Protein |
|---|---|---|---|---|
| 31 | RSHSsPASL | Q9GZV5 | 86-94 | WW domain-containing transcription regulator protein 1 |
| 32 | YAVPRRGsL | O95425 | 993-1001 | Supervillin |
| 33 | GIMsPLAKK | Q03989 | 253-262 | AT-rich interactive domain-containing protein 5A |
| 34 | KLPsPAPARK | Q8IY33 | 140-149 | MICALL2; MICAL-like protein 2 |
| 35 | RAKsPISLK | Q9BXL7 | 509-517 | Caspase recruitment domain-containing protein 11; CARD-containing MAGUK protein 1; CARMA1 |
| 36 | RILsGVVTK | P62280 | 71-79 | 40S ribosomal protein S11 |
| 37 | RIYQyIQSR | Q9Y463 | 269-277 | Dual specificity tyrosine-phosphorylation-regulated kinase 1B |
| 38 | RIYQyIQSRF | Q9Y463 | 269-278 | Dual specificity tyrosine-phosphorylation-regulated kinase 1B |
| 39 | RLSsPISKR | Q99728 | 327-335 | BARD1; BRCA1-associated RING domain protein 1 |
| 40 | RTMsEAALVRK | Q6ZTQ3 | 184-194 | RASSF6; RASF6; Ras association domain-containing protein 6 |
| 41 | RTRsLSSLREK | O94915 | 1975-1985 | FRYU; FRYL; Protein furry homolog-like |
| 42 | RVAsPTSGVK | Q9Y4H2 | 1097-1106 | Insulin receptor substrate 2; IRS2 |
| 43 | RVLsPLIIK | Q8NCN4 | 400-408 | E3 Ubiquitin-protein ligase RNF169 |
| 44 | RVYsPYNHR | Q9NS56 | 582-590 | E3 Ubiquitin-protein ligase Topers |
| 45 | SVRRsVLMK | Q9H2J4 | 223-231 | PDCL3; Phosducin-like protein 3 |
| 46 | KRAsVFVKL | P50502 | 153-161 | Hsc70-interacting protein |
| 47 | SVKsPVTVK | Q9HCS4 | 329-337 | Transcription factor 7-like 1 |
| 48 | INKERRSsL | Q5JTZ5 | 81-89 | Uncharacterized protein C9orf152 |
| 49 | APDsPRAFL | — | — | No data base hit |
| 50 | APRDRRAVsF | Q5TAA0 | 560-569 | TTC22, Tetratricopeptide repeat protein 22 |
| 51 | APRRYsSSL | Q68EM7 | 697-705 | ARHGAP17; RGH17; Rho GTPase-activating protein 17 |
| 52 | GPRsPKAPP | Q6PJ34 | 313-321 | ARHGAP4 protein |
| 53 | KPAsPKFIVTL | Q6PJT7 | 512-522 | Zinc finger CCCH domain-containing protein 14 |
| 54 | KPEsRRSSLL | Q6WKZ4 | 428-437 | RABI1-FIP1; Rab11 family-interacting protein 1 |
| 55 | KPRPPPLsP | Q15642; XP_005259738 | 328-336 | Cdc42-interacting protein 4; CIP4 |
| 56 | KPRsPFSKI | Q9BXF6 | 185-193 | RAB11-FIP5; RFIP5; Rab11 family-interacting protein 5 |
| 57 | KPRsPPRAL | Q86TG8; P07288; NP_001035242 | 249-257 | Retrotransposon-derived protein PEG10 isoform 2 |
| 58 | KPRsPVVEL | P25098 | 667-675 | Beta-Adrenergic receptor kinase 1 |
| 59 | LPAsPRARL | Q3KQU3 | 443-451 | Map 7 domain-containing protein 1 |
| 60 | LPIFSRLsI | P47974 | 483-491 | ZFP36L2; Zinc finger protein 36, C3H1 type-like 2 |
| 61 | LPVsPRLQL | P40199 | 185-193 | Carcinoembryonic antigen-related cell adhesion molecule 6 |
| 62 | MPRQPsATRL | Q6P582 | 134-143 | Mitotic-spindle organizing protein 2A |
| 63 | QPQRRsLRL | Q9ULW0 | 116-124 | TPX2; Targeting protein for Xklp2 |
| 64 | RARGIsPIVF | Q96MU7 | 303-312 | YTHDC1; YTDC1; YTH domain-containing protein 1; YT521 |

TABLE 5-continued

Exemplary Phosphopeptides Associated with Colorectal Cancer (CRC)

| SEQ ID NO. | Sequence | Accession[a] | Amino Acids[b] | Source Protein |
|---|---|---|---|---|
| 65 | RPAsAGAML | Q14814 | 198-206 | Monocyte-specific enhancer factor 20 |
| 66 | RPAsPQRAQL | — | — | No data base hit |
| 67 | RPDsAHKML | B7ZMM5 | 969-977 | PALLD; Palladin protein |
| 68 | RPDVAKRLsL | O75815 | 282-291 | BCAR3; Breast cancer anti-estrogen resistance protein 3 |
| 69 | RPFHGISTVsL | Q5VZ89 | 1417-1427 | DENND4C; DENN domain-containing protein 4C |
| 70 | RPFsPREAL | Q86V48 | 742-750 | Leucine zipper protein 1 |
| 71 | RPGsRQAGL | Q96JY6 | 175-183 | PDZ-LIM2; PDZ and LIM domain protein 2 |
| 72 | RPKsPLSKM | Q9HCD6 | 1576-1584 | TANC2; Tetratricopeptide repeat |
| 73 | RPKsVDFDSL | Q9Y5K6 | 455-464 | CD2AP; CD2-associated protein |
| 74 | RPQRATsNVF | P19105 | 13-22 | Myosin regulatory light chain 12A |
| 75 | RPRARsVDAL | Q9BT33; Q86X29 | 426-435 | LSR Protein; Lipolysis-stimulated lipoprotein receptor; LISCH7 |
| 76 | RPRGsQSLL | P21860 | 1040-1047 | Receptor tyrosine-protein kinase erbB-3 |
| 77 | RPRPVsPSSL | P57059 | 430-439 | Serine/threonine-protein kinase SIK1 |
| 78 | RPRsAVLL | Q12802 | 1873-1880 | A-kinase anchor protein 13; AKAP-13 |
| 79 | RPRsPNMQDL | Q6T310 | 214-223 | RASL-11A; Ras-like protein family member 11A |
| 80 | RPRsPRQNSI | Q99700 | 689-698 | Ataxin-2 |
| 81 | RPTKIGRRsL | Q96HN2 | 135-144 | AHCYL2; SAHH3; Putative adenosylhomocysteinase 3 |
| 82 | RPTsRLNRL | Q15788 | 860-868 | NCoA1; Nuclear receptor coactivator 1 |
| 83 | RPVtPVSDL | Q13118 | 63-71 | KLF10; Krueppel-like factor 10 |
| 84 | SPFKRQLsL | P49757 | 288-296 | NUMB; Numb protein homolog |
| 85 | SPRAPVsPLKF | Q9UBS0 | 417-427 | RPS6KB2; Ribosomal protein S6 kinase beta-2 |
| 86 | SPRRsRSISL | Q16629 | 159-168 | Serine/arginine-rich splicing factor 7 |
| 87 | SPRsPDRTL | Q9UKN1 | 286-294 | MUC 12; Mucin-12 |
| 88 | SPRSPsTTYL | Q13111 | 772-781 | Chromatin assembly factor 1 subunit A |
| 89 | SPRsPSTTYL | Q13111 | 772-781 | Chromatin assembly factor 1 subunit A |
| 90 | TPRsPPLGL | Q16584 | 755-763 | Mitogen-activated protein kinase kinase kinase 11 |
| 91 | VPRPERRsL | Q6UWJ1 | 668-677 | TMCO3; Transmembrane and coiled-coil domain-containing protein 3 |
| 92 | APRKGsFSAL | Q13619 | 5-14 | Cullin-4A |
| 93 | AVRPTRLsL | Q9Y4H2 | 887-895 | Insulin receptor substrate 2; IRS2 |
| 94 | KPRPLsMDL | Q9BY89 | 279-287 | Uncharacterized protein KIAA1671 |
| 95 | KPRRFsRsL | Q7L4I2 | 209-217 | Arginine/serine-rich coiled-coil protein 2 |
| 96 | LPRtPRPEL | Q8N1W2 | 174-182 | Zinc finger protein 710 |
| 97 | RPAsPAAKL | Q9P2N6 | 512-520 | KIAA1310; KAT8 regulatory NSL complex subunit 3 |
| 98 | RPDsPTRPTL | Q7RTP6 | 1646-1655 | Protein-methionine sulfoxide oxidase MICAL3 |
| 99 | RPIsPRIGAL | Q9Y6I3; NP_001123543 | 93-102 | Epsin-1 |

TABLE 5-continued

Exemplary Phosphopeptides Associated with Colorectal Cancer (CRC)

| SEQ ID NO. | Sequence | Accession[a] | Amino Acids[b] | Source Protein |
|---|---|---|---|---|
| 100 | RPRAAtW | P10644 | 333-340 | cAMP-dependent protein kinase type 1-alpha regulatory subunit |
| 101 | RPRAAtWA | P10644 | 333-341 | cAMP-dependent protein kinase type 1-alpha regulatory subunit |
| 102 | RPRANsGGVDL | Q92766 | 1162-1172 | Ras-responsive element-binding protein 1 |
| 103 | RPRsAVEQL | Q9HAU0 | 882-890 | Pleckstrin homology domain-containing family A member 5 |
| 104 | RPRsMTVSA | O43312 | 457-465 | Metastasis suppressor protein 1 |
| 105 | RPRsPPGGP | Q86UZ6 | 573-581 | Zinc finger and BTB domain-containing protein 46 |
| 106 | RPRsPTGPSNSF | Q9HAU0 | 882-890 | Pleckstrin homology domain-containing family A member 5 |
| 107 | SPKsPGLKA | B7ZKW8; XP_005245662 | 75-83 | CapZ-interacting protein isoform X1 |
| 108 | YPGGRRsSL | P22897 | 1037-1045 | Macrophage mannose receptor 1 |
| 109 | KYIsGPHEL | P49454 | 1270-1279 | Centromere protein F |
| 110 | RYQtQPVTL | O95425 | 849-857 | Supervillin |
| 111 | FRRsPTKSSL | Q96PK6 | 624-633 | RNA-binding protein 14 |
| 112 | FRRsPTKSSLDY | Q96PK6 | 624-635 | RNA-binding protein 14 |
| 113 | GRKsPPPSF | B4DLE8; NP_705833 | 713-721 | Beta gamma crystallin domain-containing protein 3 |
| 114 | GRLsPAYSL | Q86UU1 | 536-544 | Pleckstrin homology-like domain family B member 1 |
| 115 | GRLsPVPVPR | Q9UKM9 | 132-141 | RNA-binding protein Raly |
| 116 | HRLsPVKGEF | Q9Y2L9 | 367-376 | Leucine-rich repeat and calponin homology domain-containing protein 1 |
| 117 | HRNsMKVFL | Q9NPR2 | 735-743 | Semaphorin-4B |
| 118 | KRFsFKKSF | P29966 | 156-164 | Myristoylated alanine-rich C-kinase substrate |
| 119 | KRFsFKKsF | P29966 | 156-164 | Myristoylated alanine-rich C-kinase substrate |
| 120 | KRFsGTVRL | P62906 | 47-55 | RPL10N 60S ribosomal protein L10a; NEDD-6 |
| 121 | KRLsPAPQL | Q9UH99 | 51-59 | SUN domain-containing protein 2 |
| 122 | KRLsVERIY | P11388 | 26-34 | DNA Topoisomerase 2-alpha; TOP2A |
| 123 | KRMsPKPEL | P41208 | 17-25 | Centrin-2 |
| 124 | KRYsGNMEY | O95835 | 275-283 | Serine/threonine-protein kinase LATS1 |
| 125 | RRAsLSEIGF | Q00537 | 177-186 | Cyclin-dependent kinase 17 |
| 126 | RRAsQEANL | Q6PJG2 | 458-466 | Uncharacterized protein C14orf43; LM2 and SANT domain-containing protein 1 |
| 127 | RRDsIVAEL | O14579 | 96-104 | Coatomer subunit epsilon |
| 128 | RRDsLQKPGL | Q9NRM7 | 376-386 | Serine/threonine-protein kinase LATS2 |
| 129 | RRFsGTAVY | Q6AHZ1 | 652-660 | ZNF518N Zinc finger protein 518A |
| 130 | RRFsPPRRM | Q15287 | 248-256 | RNA-binding protein with serine-rich domain 1 |
| 131 | RRFsRLENRY | O43293 | 411-420 | Death-associated protein kinase 3 |
| 132 | RRGsFEVTL | Q8IZQ5; NP_734467 | 75-83 | Protein C11orf31; selenoprotein H; SELH |
| 133 | RRIDIsPSTF | Q9Y2W1 | 677-686 | Thyroid hormone receptor-associated protein 3 |

TABLE 5-continued

Exemplary Phosphopeptides Associated with Colorectal Cancer (CRC)

| SEQ ID NO. | Sequence | Accession[a] | Amino Acids[b] | Source Protein |
|---|---|---|---|---|
| 134 | RRIDIsPSTLR | Q9NYF8 | 653-663 | Bcl-2-associated transcription factor 1 |
| 135 | RRIsDPQVF | Q4L180 | 788-796 | FILIP1L; Filamin A-interacting protein 1-like |
| 136 | RRIsGVDRY | O15239 | 52-60 | NADH dehydrogenase [ubiquinone] 1 alpha subcomplex subunit 1 |
| 137 | RRIsGVDRYY | O15239 | 52-61 | NADH dehydrogenase [ubiquinone) 1 alpha subcomplex subunit 1 |
| 138 | RRKsQVAEL | Q9BYG3 | 244-252 | MKI67 FHA domain-interacting nucleolar phosphoprotein |
| 139 | RRLsADIRL | O60307 | 744-752 | Microtubule-associated serine/threonine-protein kinase 3 |
| 140 | RRLsDSPVF | P47974 | 435-443 | Zinc finger protein 36, C3H1 type-like 2 |
| 141 | RRLsESSAL | Q96S55 | 72-80 | ATPase WRNIP1 |
| 142 | RRLsGPLHTL | Q86Y91 | 610-619 | Kinesin-like protein KIF18B |
| 143 | RRLsLFLNV | Q99836 | 31-39 | Myeloid differentiation primary response protein MyD88 |
| 144 | RRMsFQKP | Q8N573 | 88-95 | Oxidation resistance protein 1 |
| 145 | RRMsLLSVV | Q9ULI2 | 314-322 | Beta-citryl-glutamate synthase B |
| 146 | RRNsAPVSV | Q2M1Z3 | 1175-1183 | Rho GTPase-activating protein 31 |
| 147 | RRNsINRNF | O00160 | 731-739 | Unconventional myosin-1f |
| 148 | RRPsLLSEF | O75376 | 67-75 | Nuclear receptor corepressor 1 |
| 149 | RRQsKVEAL | Q03169 | 120-128 | TNFAIP2; tumor necrosis factor alpha-Induced protein 2 |
| 150 | RRLsELLRY | P08238 | 449-457 | Heat shock Protein HSP 90-beta |
| 151 | RRLsFLVSY | P47897 | 67-75 | Glutamine-tRNA ligase |
| 152 | RRSsFLQVF | Q15436 | 585-593 | Protein transport protein Sec23A |
| 153 | RRSsIQSTF | Q92542 | 232-240 | Nicastrin |
| 154 | RRsSIQSTF | Q92542 | 232-240 | Nicastrin |
| 155 | RRSsSVAQV | O15205 | 107-115 | Ubiquitin D |
| 156 | RRYsPPIQ | AAP97290; AF419855 | 592-599 | Ser/Arg repetitive nuclear matrix protein 1 |
| 157 | VRAsKDLAQ | O60563 | 164-172 | CCNT1; Cyclin-T1 |
| 158 | KRLEKsPSF | Q92625 | 656-664 | Ankyrin repeat and SAM domain-containing protein 1A |
| 159 | KRLEKSPsF | Q92625 | 656-664 | Ankyrin repeat and SAM domain-containing protein 1A |
| 160 | KRWQsPVTK | XP_005245779 | 518-526 | Serine/arginine repetitive matrix protein 1 isoform X6 |
| 161 | RRFsIATLR | Q16696 | 128-136 | Cytochrome P450 2A13 |
| 162 | RRFsLTTLR | P10632 | 124-132 | Cytochrome P450 2C8 |
| 163 | RRFsRsPIR | P18583 | 2026-2034 | Protein SON isoformB |
| 164 | RRFsVSTLR | P10635 | 132-140 | Cytochrome P450 2D6 |
| 165 | RRFsVTTMR | P20813 | 125-133 | Cytochrome P450 2B6 |
| 166 | RRVVQRSsL | Q04637 | 1098-1105 | Eukaryotic translation initiation factor 4 gamma 1 isoform 2 |
| 167 | RRYsPPIER | Q8IYB3 | 594-602 | Serine/arginine repetitive matrix protein 1 |
| 168 | RRYsPPIQR | Q8IYB3 | 594-602 | Serine/arginine repetitive matrix protein 1 |
| 169 | AENsPTRQQF | Q86XP3 | 93-102 | ATP-dependent RNA helicase DDX42 |

TABLE 5-continued

Exemplary Phosphopeptides Associated with Colorectal Cancer (CRC)

| SEQ ID NO. | Sequence | Accession[a] | Amino Acids[b] | Source Protein |
|---|---|---|---|---|
| 170 | EELsPTKAF | Q99612 | 117-125 | Krueppel-like factor 6 |
| 171 | KEMsPTRQL | Q4G0N7 | 36-44 | UPF0731 protein C6orf225; protein FAM229B |
| 172 | RFKtQPVTF | Q7Z7L8 | 365-373 | Uncharacterized protein C11orf96 |
| 173 | EERRsPPAP | P15408 | 196-204 | Fos-related antigen 2 |
| 174 | FEDDDsNEKL | O43719 | 697-706 | HIV Tat-specific factor 1 |
| 175 | KsLVRLLLL | P07998 | 5-13 | Ribonuclease pancreatic |
| 176 | RTHsLLLLL | P34096 | 5-13 | RNASE4; Ribonuclease 4 |
| 177 | RTSSFtFQN | P27540 | 440-448 | Aryl hydrocarbon receptor nuclear translocator; ARNT |

[a] Refers to the Uniprot and/or GENBANK® biosequence database accession number(s).
[b] Refers to the amino acid positions for the peptide in the corresponding Uniprot and/or GENBANK® biosequence database accession(s).

TABLE 6

Characteristics of HLA-DR-associated Phosphopeptides Selectively Expressed by Melanoma Cells

| Source Protein | Phosphopeptide | SEQ ID NO |
|---|---|---|
| 1363-mel and 2048-mel Melanoma antigen recognized by T cells- 1/MART-1 | $_{100}$APPAYEKLsAEQ$_{111}$<br>$_{100}$APPAYEKLsAEQSPP$_{114}$<br>$_{100}$APPAYEKLsAEQSPPP$_{115}$<br>$_{100}$APPAYEKLsAEQSPPPY$_{116}$ | 218<br>219<br>220<br>226 |
| Tensin-3 | $_{1434}$VSKVMIGsPKKV$_{1445}$<br>$_{1437}$VMIGsPKKV$_{1445}$ | 227<br>228 |
| 1363-mel alone Matrix-remodeling-Associated protein 7 | $_{142}$KYsPGKLRGN$_{151}$ | 229 |
| 2048-mel alone Amino-terminal enhancer of split | $_{176}$SKEDKNGHDGDTHQEDDGEKsD$_{197}$ | 230 |
| Ankyrin repeat domain-containing protein-54 | $_{43}$GSALGGGGAGLSGRASGGAQsPLRYLHV$_{71}$<br>$_{46}$LGGGGAGLSGRASGGAQsPLRYLHV$_{71}$<br>$_{58}$SGGAQsPLRYLHVL$_{72}$ | 231<br>232<br>233 |
| Anoctamin-8 | $_{638}$EEGsPTMVEKGLEPGVPTL$_{656}$<br>$_{639}$EGsPTMVEKGLEPGVFTL$_{656}$<br>$_{640}$GsPTMVEKGLEPGVFTL$_{656}$ | 234<br>235<br>236 |
| AP-3 complex subunit-Δ-1 | $_{779}$EEMPENALPsDEDDKDPNDPYRAL$_{802}$ | 237 |
| Casein kinase II subunit-β | $_{202}$QAASNFKsPVKTIR$_{215}$<br>$_{203}$AASNFKsPVKTIR$_{215}$<br>$_{205}$SNFKsPVKTIR$_{215}$<br>$_{206}$NFKsPVKTIR$_{215}$<br>$_{207}$FKsPVKTIR$_{215}$ | 238<br>239<br>240<br>241<br>242 |
| Claudin-11 | $_{191}$YYTAGSSsPTHAKSAHV$_{207}$<br>$_{196}$SSsPTHAKSAHV$_{207}$ | 243<br>244 |
| Emerin | $_{117}$VRQsVTSFPDADAFHHQ$_{133}$ | 245 |
| FLJ20689 | $_{471}$FKMPQEKsPGYS$_{482}$ | 246 |
| Insulin receptor Substrate 2 | $_{1097}$RVAsPTSGVKR$_{1107}$ | 247 |

TABLE 6-continued

Characteristics of HLA-DR-associated Phosphopeptides
Selectively Expressed by Melanoma Cells

| Source Protein | Phosphopeptide | SEQ ID NO |
|---|---|---|
| Interleukin 1 receptor accessory protein | $_{543}$QVAMPVKKSPRRSsSDEQGLSYSSLKNV$_{570}$ | 248 |
|  | $_{544}$VAMPVKKSPRRSsSDEQGLSYSSLKNV$_{570}$ | 249 |
| LUC7-like isoform b | $_{353}$SSNGKMASRRsEEKEAG$_{369}$ | 250 |
|  | $_{353}$SSNGKMASRRsEEKEAGEI$_{371}$ | 251 |
| Membrane-associated progesterone receptor component 1 | $_{172}$KEGEEPTVYsDEEEPKDESARKND$_{195}$ | 252 |
|  | $_{173}$EGEEPTVYsDEEEPKDESARKND$_{195}$ | 253 |
| NF-κB inhibitor-interacting Ras-like protein 2 | $_{165}$ASKMTQPQSKSAFPLSRKNKGsGsLDG$_{191}$ | 254 |
| Probable fibrosin-1 long transcript protein isoform 2 | $_{348}$APPPLVPAPRPSsPPRGPGPARADR$_{372}$ | 255 |
| Small acidic protein | $_{2}$SAARESHPHGVKRSAsPDDDLG$_{23}$ | 256 |
|  | $_{2}$(AcS)AARESHPHGVKRSAsPDDDLG$_{23}$ | 257 |
| Synaptojanin-170 | $_{1561}$ASKAsPTLDFTER$_{1573}$ | 258 |
| Tetraspanin-10 | $_{4}$GERsPLLSQETAGQKP$_{19}$ | 259 |
|  | $_{4}$GERsPLLSQETAGQKPL$_{20}$ | 260 |
|  | $_{5}$ERsPLLSQETAGQKP$_{19}$ | 261 |
|  | $_{5}$ERsPLLSQETAGQKPL$_{20}$ | 262 |
| Transmembrane protein 184 | $_{424}$TIGEKKEPsDKSVDS$_{438}$ | 263 |

TABLE 7

Characteristics of HLA-DR-associated Phosphopeptides
Selectively Expressed by EBV-transformed B Cells

| Source Protein | Phosphopeptide | SEQ ID NO. |
|---|---|---|
| B lymphocyte antigen CD20 | $_{25}$SGPKPLFRRMsSLVGPTQ$_{42}$ | 264 |
|  | $_{26}$GPKPLFRRMsS$_{36}$ | 265 |
|  | $_{26}$GPKPLFRRMsSL$_{37}$ | 266 |
|  | $_{26}$GPKPLFRRMsSLV$_{38}$ | 267 |
|  | $_{26}$GPKPLFRRMsSLVG$_{39}$ | 268 |
|  | $_{26}$GPKPLFRRMsSLVGP$_{40}$ | 269 |
|  | $_{26}$GPKPLFRRMsSLVGPT$_{41}$ | 270 |
|  | $_{26}$GPKPLFRRMsSLVGPTQ$_{42}$ | 271 |
|  | $_{26}$GPKPLFRRMsSLVGPTQS$_{43}$ | 272 |
| Lymphoid-restricted membrane protein | $_{130}$AsPTIEAQGTSPAHDN$_{145}$ | 273 |
|  | $_{130}$AsPTIEAQGTSPAHDNI$_{146}$ | 274 |
|  | $_{130}$AsPTIEAQGTSPAHDNIA$_{147}$ | 275 |
|  | $_{402}$SSsWRILGSKQSEHRP$_{417}$ | 276 |
| 1363-EBV alone | | |
| ADAM 8 | $_{758}$sPPFPVPVYTRQAPKQVIK$_{776}$ | 277 |
| B lymphocyte antigen CD19 | $_{328}$DPTRRFFKVtPPPGSGPQ$_{345}$ | 278 |
| Germinal center B cell-Expressed transcript 2 protein | $_{142}/_{76}$RsPEDEYELLMPHRISSH$_{159}/_{93}$ | 279 |
|  | $_{143}/_{77}$sPEDEYELLMPHRISSH$_{159}/_{93}$ | 280 |
|  | $_{143}/_{77}$sPEDEYELLMPHRIsSH$_{159}/_{93}$ | 281 |
|  | $_{149}/_{83}$ELLMPHRIsSHF$_{160}/_{94}$ | 282 |
|  | $_{149}/_{83}$ELLMPHRIsSHFL$_{161}/_{95}$ | 283 |
| Interleukin-2 receptor subunit-β | $_{282}$TPDPSKFFSQLsSEHGGDV$_{300}$ | 284 |
|  | $_{282}$tPDPSKFFSQLSSEHGGDVQ$_{301}$ | 285 |
| Optineurin | $_{473}$SDFHAERAAREK$_{484}$ | 286 |
| Phosphoglycerate kinase 1 | $_{203}$sPERPFLAILGGAKVADK$_{220}$ | 287 |
|  | $_{203}$sPERPFLAILGGAKVADKIQ$_{222}$ | 288 |
| Solute carrier family 12, member 6, isoform a | $_{1050}$TKDKYMASRGQKAKsMEG$_{1067}$ | 289 |

TABLE 7-continued

Characteristics of HLA-DR-associated Phosphopeptides
Selectively Expressed by EBV-transformed B Cells

| Source Protein | Phosphopeptide | SEQ ID NO. |
|---|---|---|
| TNFAIP3-interacting protein 1 | $_{559}$VPHHGFEDWsQIR$_{571}$ | 290 |
| Tumor necrosis factor receptor superfamily member 8 | $_{513/50}$KIEKIyIMKADTVIVG$_{528/65}$ | 291 |
|  | $_{514/51}$IEKIyIMKADTVIVG$_{528/65}$ | 292 |
| UPF050 1 protein KIAA1430 | $_{136}$EESsDDGKKY$_{145}$ | 293 |
| Xenotropic and polytropic retrovirus receptor 1 | $_{657}$KNRsWKYN$_{664}$ | 294 |
|  | $_{657}$KNRsWKYNQ$_{665}$ | 295 |
|  | $_{657}$KNRsWKYNQSISLR$_{670}$ | 296 |
|  | $_{657}$KNRsWKYNQSISLRRP$_{672}$ | 297 |
|  | $_{658}$NRsWKYNQSISLR$_{670}$ | 298 |
|  | $_{658}$NRsWKYNQSISLRRP$_{672}$ | 299 |
|  | $_{659}$RsWKYNQSISLRRP$_{672}$ | 300 |

2048-EBV alone

| Source Protein | Phosphopeptide | SEQ ID NO. |
|---|---|---|
| BCL2-associated transcription factor 1 | $_{653}$RRIDIsPSTLR$_{663}$ | 134 |
| Caspase recruitment domain-containing protein 11 | $_{653}$RRIDIsPSTLRK$_{664}$ | 301 |
| Chromatin-modifying protein 1a | $_{509}$RAKsPISLK$_{517}$ | 35 |
|  | $_{49/177}$ESsVRSQEDQLSR$_{61/189}$ | 302 |
|  | $_{49/177}$ESsVRSQEDQLSRR$_{62/190}$ | 303 |
| Interleukin-10 receptor-5 chain | $_{293}$DKLsVIAEDSESGKQ$_{307}$ | 304 |
|  | $_{293}$DKLsVIAEDSESGKQN$_{308}$ | 305 |
|  | $_{293}$DKLsVIAEDSESGKQNP$_{309}$ | 306 |
|  | $_{293}$DKLsVIAEDSESGKQNPG$_{310}$ | 307 |
|  | $_{293}$DKLsVIAEDSESGKQNPGDS$_{312}$ | 308 |
|  | $_{294}$KLsVIAEDSESGKQN$_{308}$ | 309 |
|  | $_{294}$KLsVIAEDSESGKQNP$_{309}$ | 310 |
|  | $_{294}$KLsVIAEDSESGKQNPG$_{310}$ | 311 |
| NADH-ubiquinone oxidoreductase flavoprotein 3 | $_{88}$NLELSKFRMPQPSSGREsPRH$_{108}$ | 312 |
|  | $_{91}$LSKFRMPQPSSGREsPRH$_{108}$ | 313 |
| Protein FAM40A | $_{318}$PPLPEDSIKVIRNMRAAsPPA$_{338}$ | 314 |
| Ras association domain containing protein 6 | $_{184/152/140}$RTMsEAALVRK$_{194/162/150}$ | 40 |
| SH2 domain containing 3C isoform 1 | $_{80}$MPRPsIKKAQNSQAARQ$_{96}$ | 315 |
| Tax1-binding protein 1, isoform 1 or 2 | $_{106}$THKGEIRGASTPFQFRAssP$_{125}$ | 316 |
|  | $_{107}$HKGEIRGASTPFQFRAssP$_{125}$ | 317 |
| UPF0492 protein C20orf94 | $_{391}$STIQNsPTKK$_{400}$ | 318 |

TABLE 8

Characteristics of HLA-DR-associated Phosphopeptides
Commonly Expressed by Melanoma and EBV-B Cells

| Source Protein | Phosphopeptide | SEQ ID NO |
|---|---|---|
| Elongin A | $_{122}$RSYsPDHRQK$_{131}$ | 319 |
| Ferritin heavy chain | $_{171}$FDKHTLGDsDNES$_{183}$ | 320 |
| Frizzled-6 | $_{617}$EPAsPAAsISRLSGEQVDGKG$_{637}$ | 321 |
|  | $_{620}$SPAASISRLsGEQVDGKG$_{637}$ | 322 |
|  | $_{623}$ASISRLsGEQVDGKG$_{637}$ | 323 |
|  | $_{623}$AsISRLSGEQVDGKG$_{637}$ | 324 |
|  | $_{623}$AsISRLsGEQVDGKG$_{637}$ | 325 |
| Insulin like growth factor 2 receptor | $_{2392}$TTKsVKALSSLHG$_{2404}$ | 326 |
|  | $_{2392}$TTKsVKALSSLHGDD$_{2406}$ | 327 |
|  | $_{2392}$TTKsVKALSSLHGDDQ$_{2407}$ | 328 |
|  | $_{2392}$TTKsVKALSSLHGDDQD$_{2408}$ | 329 |
|  | $_{2392}$TTKsVKALSSLHGDDQDS$_{2409}$ | 330 |
|  | $_{2393}$TKsVKALSSLHGDD$_{2406}$ | 331 |
|  | $_{2393}$TKsVKALSSLHGDDQ$_{2407}$ | 332 |
|  | $_{2393}$TKsVKALSSLHGDDQD$_{2408}$ | 333 |
|  | $_{2394}$KsVKALSSLHGDDQ$_{2407}$ | 334 |
|  | $_{2394}$KsVKALSSLHGDDQD$_{2408}$ | 335 |
|  | $_{2392}$TTKSVKALSSLHGDDQDsED$_{2411}$ | 336 |
|  | $_{2392}$TTKSVKALSSLHGDDQDsEDE$_{2412}$ | 337 |
|  | $_{2394}$KSVKALSSLHGDDQDsEDE$_{2412}$ | 338 |
|  | $_{2476}$KLVSFHDDsDEDL$_{2488}$ | 339 |

TABLE 8-continued

Characteristics of HLA-DR-associated Phosphopeptides
Commonly Expressed by Melanoma and EBV-B Cells

| Source Protein | Phosphopeptide | SEQ ID NO |
|---|---|---|
| Lipolysis-stimulated lipoprotein receptor | $_{324}/_{287}/_{305}$APSTYAHLsPAK$_{335}/_{398}/_{316}$ | 340 |
| | $_{324}/_{287}/_{305}$APSTYAHLsPAKTPPPP$_{340}/_{303}/_{321}$ | 341 |
| Plakophilin-4 | $_{206}$NRAMRRVsSVPSR$_{218}$ | 342 |
| | $_{206}$NRAMRRVsSVPSRAQ$_{220}$ | 343 |
| | $_{278}$RPAsPtAIRRIGSVTSRQT$_{296}$ | 344 |
| Sequestosome-1 | $_{332}$sGGDDDWTHLSSKEVDPST$_{350}$ | 345 |
| | $_{332}$sGGDDDWTHLSSKEVDPSTG$_{351}$ | 346 |
| | $_{332}$sGGDDDWTHLSSKEVDPSTGE$_{352}$ | 347 |
| | $_{332}$sGGDDDWTHLSSKEVDPSTGEL$_{353}$ | 348 |
| | $_{332}$sGGDDDWTHLSSKEVDPSTGELQ$_{354}$ | 349 |
| | $_{333}$GGDDDWTHLsSKEVDPS$_{349}$ | 350 |
| | $_{333}$GGDDDWTHLsSKEVDPSTG$_{351}$ | 351 |
| | $_{334}$GDDDWTHLsSKEVD$_{347}$ | 352 |
| | $_{334}$GDDDWTHLsSKEVDP$_{348}$ | 353 |
| | $_{334}$GDDDWTHLsSKEVDPS$_{349}$ | 354 |
| | $_{334}$GDDDWTHLsSKEVDPSTG$_{351}$ | 355 |
| | $_{335}$DDDWTHLsSKEVDPS$_{349}$ | 356 |
| | $_{335}$DDDWTHLsSKEVDPSTG$_{351}$ | 357 |
| | $_{336}$DDWTHLsSKEVDPS$_{349}$ | 358 |
| | $_{337}$DWTHLsSKEVDPS$_{349}$ | 359 |
| | $_{337}$DWTHLsSKEVDPSTG$_{351}$ | 360 |
| | $_{338}$WTHLsSKEVDPS$_{349}$ | 361 |
| | $_{338}$WTHLsSKEVDPSTG$_{351}$ | 362 |
| Sorting nexin-17 | $_{402}$GtLRRSDSQQAVK$_{414}$ | 363 |
| | $_{402}$GtLRRSDSQQAVKS$_{415}$ | 364 |
| | $_{402}$GtLRRSDSQQAVKSPP$_{417}$ | 365 |
| UPF0555 protein KIAA0776 | $_{783}$VLKSRKssVTEE$_{794}$ | 366 |

TABLE 9

Characteristics of Source Proteins Generating HLA-DR-restricted Phosphopeptides

| Source protein | GENBANK® Accession No. | Known Phosphoprotein? | Function | Other Names |
|---|---|---|---|---|
| ADAM 8 | P78325 | N | Cellular trafficking | A disintegrin and metalloproteinase domain 8, Cell surface antigen MS2, CD 156a |
| Amino-terminal enhancer of split | Q08117 | N | Transcriptional regulation | GRG protein, Protein ESP1, Gp130-associated protein GAM |
| Ankyrin repeat domain-containing protein 54 | Q6NXT1 | Y | Unknown | N/A |
| Anoctamin-8 | Q9HCE9 | N | Ion transport | Transmembrane protein 16H |
| AP-3 complex subunit-A-1 | O14617 | Y | Trafficking | Adapter-related protein complex 3 subunit-A-1, AP-3 complex subunit-Δ, Δ-adaptin |
| BCL2-associated transcription factor 1 | A2RU75 | N | Transcription factor | N/A |
| B lymphocyte antigen CD19 | P15391 | Y | Receptor/signal transduction | Differentiation antigen CD19, B lymphocyte surface antigen B4, Leu-12 |
| B lymphocyte antigen CD20 | P11836 | Y | Receptor/signal transduction | Membrane-spanning 4-domains subfamily A member 1, B lymphocyte surface antigen 81, Leu-16, Bp35 |
| Casein kinase II subunit-ll | P67870 | Y | Signal transduction | Phosvitin, G5a |
| Caspase recruitment domain-containing protein 11 | Q9BXL7 | N | Signal transduction | CARD-containing MAGUK protein 3, Carma 1 |
| Chromatin-modifying protein 1a | Q9HD42 | N | Cell cycle/protein trafficking | Chromatin-modifying protein 1a, Vacuolar protein sorting-associated protein 46-1 |
| Claudin-11 | O75508 | N | Cell adhesion | Oligodendrocyte-specific protein |
| Elongin A | Q14241 | Y | Transcriptional regulation | Transcription elongation factor B polypeptide 3, RNA polymerase II transcription factor SIII subunit A 1, SIII p110, Elongin 110-kDa subunit |
| Emerin | P50402 | Y | Protein binding | N/A |
| Ferritin heavy chain | P02794 | Y | Ion storage | Cell proliferation-inducing gene 15 protein |
| FU20689 | Q9H3M3 | N | Unknown | N/A |
| Frizzled-6 | O60353 | Y | Receptor/Signal transduction | N/A |

TABLE 9-continued

Characteristics of Source Proteins Generating HLA-DR-restricted Phosphopeptides

| Source protein | GENBANK® Accession No. | Known Phosphoprotein? | Function | Other Names |
|---|---|---|---|---|
| Germinal center B-cell-expressed transcript 2 protein | Q8N6F7 | Y | Signal transduction• | Germinal center-associated lymphoma protein |
| Insulin-like growth factor 2 receptor | P11717 | Y | Metabolism | Cation-independent mannose-6-phosphate receptor, M6P/IGF2 receptor, 300 kDa mannose 6-phosphate receptor, CD222 |
| Insulin receptor substrate 2 | Q9Y4H2 | Y | Receptor/signal transduction | N/A |
| Interleukin 1 receptor accessory protein | Q9NPH3 | N | Receptor/signal transduction | N/A |
| Interleukin-2 receptor subunit-ll | P14784 | Y | Receptor/signal transduction | High-affinity ll-2 receptor subunit-β, P70-75, CD122 |
| Interleukin-10 receptor-β chain | Q08334 | N | Receptor/signal transduction | ll-10R2, Cytokine receptor family 2 member 4, CDw210b |
| Lipolysis-stimulated lipoprotein receptor | Q86X29 | Y | Receptor/metabolism | N/A |
| LUC7-like isoform b | Q53G47 | Y | Unknown | N/A |
| Lymphoid-restricted membrane protein | Q12912 | N | Metabolism | Protein Jaw1 |
| Matrix-remodeling-associated protein 7 | P84157 | N | Unknown | Transmembrane anchor protein 1 |
| Melanoma antigen recognized by T cells 1 | Q16655 | N | Unknown | MART-1, Melan-A, Antigen SK29-AA, Antigen LB39-AA |
| Membrane-associated progesterone receptor component 1 | O00264 | Y | Receptor | N/A |
| NADH-ubiquinone oxidoreductase flavoprotein 3 | P56181 | N | Metabolism | NADH-ubiquinone oxidoreductase 9-kDa subunit, Complex 1-9 kD, Renal carcinoma antigen NY-REN-4 |
| Nf-KB inhibitor-interacting Ras-like protein 2 | Q9NYR9 | N | Signal regulation | IκB-interacting Ras-like protein 2 |
| Optineurin | Q96CV9 | Y | Signal transduction/ protein trafficking | Optic neuropathy-inducing protein, E3-14.7K-interacting protein, FIP-2, Huntingtin-interacting protein L, Huntingtin yeast partner L, NEMO-related protein, Transcription factor IIIA-interacting protein |
| Phosphoglycerate kinase 1 | P005658 | Y | Metabolism | Primer recognition protein 2, Cell migration-inducing gene 10 protein |
| Plakophilin-4 | Q99569 | Y | Cell adhesion | p0071 |
| Probable fibrosin-1 long-transcript protein isoform 2 | Q9HAH7 | Y | Unknown | N/A |
| Protein FAM40A | QSVSL9 | Y | Unknown | N/A |
| Ras association domain-containing protein 6 | Q6ZTQ3 | N | Signal transduction | N/A |
| Sequestosome-1 | Q13501 | Y | Signal transduction | Phosphotyrosine-independent ligand for the Lck SH2 domain of 62 kDa, Ubiquitin-binding protein p62, EBI3-associated protein of 60 kDa |
| SH2 domain containing 3C isoform 1 | QBN5H7 | Y | Signal transduction | Novel SH2-containing protein 3 |
| Small acidic protein | O00193 | Y | Unknown | N/A |
| Solute carrier family 12, member 6, isoform a | Q9UHW9 | Y | Ion transport | Electroneutral potassium chloride cotransporter 3, KCl cotransporter 3 |
| Sorting nexin-17 | Q15036 | Y | Trafficking* | N/A |
| Synaptojanin-170 | O43426 | Y | Metabolism | Synaptic inositol-1,4,5-trisphosphate 5-phosphatase 1 |
| Tax1-binding protein 1, isoform 1 or 2 | Q86VP1 | N | Signal transduction | TRAF6-binding protein |
| Tensin-3 | Q68CZ2 | Y | Cellular structure | Tumor endothelial marker 6, Tensin-like SH2 domain-containing protein 1 |
| Tetrasporin-10 | Q9H1Z9 | N | Unknown | Oculospanin |
| TNFAIP3 interacting protein 1 | Q15025 | Y | Signal transduction | Nef-associated factor 1, HIV-1 Net-interacting protein, Virion-associated nuclear shuttling protein, Nip40-1 |
| Transmembrane protein 184C | Q9NVA4 | N | Unknown | Transmembrane protein 34 |
| Tumor necrosis factor receptor superfamily member 8 | P28908 | N | Receptor/signal transduction | CD30L receptor, Lymphocyte activation antigen CD30, K1-1 antigen, CD30 |
| UPF0492 protein C20orf94 | Q5VYV7 | N | Unknown | N/A |
| UPF0501 protein KIAA1430 | Q9P2B7 | Y | Unknown | N/A |

TABLE 9-continued

Characteristics of Source Proteins Generating HLA-DR-restricted Phosphopeptides

| Source protein | GENBANK® Accession No. | Known Phosphoprotein? | Function | Other Names |
|---|---|---|---|---|
| UPF0555 protein KIAA0776 | O94874 | Y | Unknown | N/A |
| Xenotropic and polytropic retrovirus receptor 1 | Q9UBH6 | Y | Receptor/signal transduction | Protein SYG 1 homolog, Xenotropic and polytropic murine leukemia virus receptor X3 |

What is claimed is:

1. A composition comprising:
(a) at least one synthetic target peptide, wherein each synthetic target peptide:
   (i) is 8 to 50 amino acids long; and
   (ii) comprises an amino acid sequence selected from the group consisting of:
   SEQ ID NO: 3, wherein the serine at the sixth position is phosphorylated or replaced with a mimetic of phosphoserine;
   SEQ ID NO: 5, wherein the serine at the third position is phosphorylated or replaced with a mimetic of phosphoserine;
   SEQ ID NO: 6, wherein the serine at the sixth position is phosphorylated or replaced with a mimetic of phosphoserine;
   SEQ ID NO: 7, wherein the threonine at the fourth position is phosphorylated or replaced with a mimetic of phosphothreonine;
   SEQ ID NO: 12, wherein the serine at the sixth position is phosphorylated or replaced with a mimetic of phosphoserine;
   SEQ ID NO: 13, wherein the serine at the fourth position is phosphorylated or replaced with a mimetic of phosphoserine;
   SEQ ID NO: 14, wherein the serine at the fourth position is phosphorylated or replaced with a mimetic of phosphoserine;
   SEQ ID NO: 15, wherein the serine at the fourth position is phosphorylated or replaced with a mimetic of phosphoserine;
   SEQ ID NO: 20, wherein the threonine at the fifth position is phosphorylated or replaced with a mimetic of phosphothreonine;
   SEQ ID NO: 22, wherein the serine at the fourth position is phosphorylated or replaced with a mimetic of phosphoserine;
   SEQ ID NO: 24, wherein the serine at the fifth position is phosphorylated or replaced with a mimetic of phosphoserine;
   SEQ ID NO: 26, wherein the serine at the eighth position is phosphorylated or replaced with a mimetic of phosphoserine;
   SEQ ID NO: 28, wherein the serine at the fourth position is phosphorylated or replaced with a mimetic of phosphoserine;
   SEQ ID NO: 29, wherein the serine at the fifth position is phosphorylated or replaced with a mimetic of phosphoserine;
   SEQ ID NO: 30, wherein the serine at the third position is phosphorylated or replaced with a mimetic of phosphoserine;
   SEQ ID NO: 31, wherein the serine at the fifth position is phosphorylated or replaced with a mimetic of phosphoserine;
   SEQ ID NO: 32, wherein the serine at the eighth position is phosphorylated or replaced with a mimetic of phosphoserine;
   SEQ ID NO: 33, wherein the serine at the fourth position is phosphorylated or replaced with a mimetic of phosphoserine;
   SEQ ID NO: 34, wherein the serine at the fourth position is phosphorylated or replaced with a mimetic of phosphoserine;
   SEQ ID NO: 43, wherein the serine at the fourth position is phosphorylated or replaced with a mimetic of phosphoserine;
   SEQ ID NO: 48, wherein the serine at the eighth position is phosphorylated or replaced with a mimetic of phosphoserine;
   SEQ ID NO: 49, wherein the serine at the fourth position is phosphorylated or replaced with a mimetic of phosphoserine;
   SEQ ID NO: 50, wherein the serine at the ninth position is phosphorylated or replaced with a mimetic of phosphoserine;
   SEQ ID NO: 52, wherein the serine at the fourth position is phosphorylated or replaced with a mimetic of phosphoserine;
   SEQ ID NO: 54, wherein the serine at the fourth position is phosphorylated or replaced with a mimetic of phosphoserine;
   SEQ ID NO: 56, wherein the serine at the fourth position is phosphorylated or replaced with a mimetic of phosphoserine;
   SEQ ID NO: 61, wherein the serine at the fourth position is phosphorylated or replaced with a mimetic of phosphoserine;
   SEQ ID NO: 63, wherein the serine at the sixth position is phosphorylated or replaced with a mimetic of phosphoserine;
   SEQ ID NO: 67, wherein the serine at the fourth position is phosphorylated or replaced with a mimetic of phosphoserine;
   SEQ ID NO: 68, wherein the serine at the ninth position is phosphorylated or replaced with a mimetic of phosphoserine;
   SEQ ID NO: 71, wherein the serine at the fourth position is phosphorylated or replaced with a mimetic of phosphoserine;
   SEQ ID NO: 72, wherein the serine at the fourth position is phosphorylated or replaced with a mimetic of phosphoserine;
   SEQ ID NO: 73, wherein the serine at the fourth position is phosphorylated or replaced with a mimetic of phosphoserine;
   SEQ ID NO: 81, wherein the serine at the ninth position is phosphorylated or replaced with a mimetic of phosphoserine;
   SEQ ID NO: 85, wherein the serine at the seventh position of is phosphorylated or replaced with a mimetic of phosphoserine;
   SEQ ID NO: 87, wherein the serine at the fourth position is phosphorylated or replaced with a mimetic of phosphoserine;
   SEQ ID NO: 91, wherein the serine at the eighth position is phosphorylated or replaced with a mimetic of phosphoserine;
   SEQ ID NO: 93, wherein the serine at the eighth position is phosphorylated or replaced with a mimetic of phosphoserine;
   SEQ ID NO: 94, wherein the serine at the sixth position is phosphorylated or replaced with a mimetic of phosphoserine;
   SEQ ID NO: 95, wherein the serine at the sixth position is phosphorylated or replaced with a mimetic of phosphoserine, the serine at the eighth position is phosphorylated or replaced with a mimetic of phosphoserine, or any combination thereof;
   SEQ ID NO: 96, wherein the threonine at the fourth position is phosphorylated or replaced with a mimetic of phosphothreonine;

SEQ ID NO: 99, wherein the serine at the fourth position is phosphorylated or replaced with a mimetic of phosphoserine;
SEQ ID NO: 100, wherein the threonine at the sixth position is phosphorylated or replaced with a mimetic of phosphothreonine;
SEQ ID NO: 101, wherein the threonine at the sixth position is phosphorylated or replaced with a mimetic of phosphothreonine;
SEQ ID NO: 103, wherein the serine at the fourth position is phosphorylated or replaced with a mimetic of phosphoserine;
SEQ ID NO: 104, wherein the serine at the fourth position is phosphorylated or replaced with a mimetic of phosphoserine;
SEQ ID NO: 105, wherein the serine at the fourth position is phosphorylated or replaced with a mimetic of phosphoserine;
SEQ ID NO: 106, wherein the serine at the fourth position is phosphorylated or replaced with a mimetic of phosphoserine;
SEQ ID NO: 108, wherein the serine at the seventh position is phosphorylated or replaced with a mimetic of phosphoserine;
SEQ ID NO: 109, wherein the serine at the fourth position is phosphorylated or replaced with a mimetic of phosphoserine;
SEQ ID NO: 110, wherein the threonine at the fourth position is phosphorylated or replaced with a mimetic of phosphothreonine;
SEQ ID NO: 114, wherein the serine at the fourth position is phosphorylated or replaced with a mimetic of phosphoserine;
SEQ ID NO: 117, wherein the serine at the fourth position is phosphorylated or replaced with a mimetic of phosphoserine;
SEQ ID NO: 119, wherein the serine at the fourth position is phosphorylated or replaced with a mimetic of phosphoserine and the serine at the eighth position is phosphorylated or replaced with a mimetic of phosphoserine;
SEQ ID NO: 123, wherein the serine at the fourth position is phosphorylated or replaced with a mimetic of phosphoserine;
SEQ ID NO: 126, wherein the serine at the fourth position is phosphorylated or replaced with a mimetic of phosphoserine;
SEQ ID NO: 128, wherein the serine at the fourth position is phosphorylated or replaced with a mimetic of phosphoserine;
SEQ ID NO: 129, wherein the serine at the fourth position is phosphorylated or replaced with a mimetic of phosphoserine;
SEQ ID NO: 131, wherein the serine at the fourth position is phosphorylated or replaced with a mimetic of phosphoserine;
SEQ ID NO: 132, wherein the serine at the fourth position is phosphorylated or replaced with a mimetic of phosphoserine;
SEQ ID NO: 135, wherein the serine at the fourth position is phosphorylated or replaced with a mimetic of phosphoserine;
SEQ ID NO: 140, wherein the serine at the fourth position is phosphorylated or replaced with a mimetic of phosphoserine;
SEQ ID NO: 141, wherein the serine at the fourth position is phosphorylated or replaced with a mimetic of phosphoserine;
SEQ ID NO: 143, wherein the serine at the fourth position is phosphorylated or replaced with a mimetic of phosphoserine;
SEQ ID NO: 144, wherein the serine at the fourth position is phosphorylated or replaced with a mimetic of phosphoserine;
SEQ ID NO: 146, wherein the serine at the fourth position is phosphorylated or replaced with a mimetic of phosphoserine;
SEQ ID NO: 147, wherein the serine at the fourth position is phosphorylated or replaced with a mimetic of phosphoserine;
SEQ ID NO: 148, wherein the serine at the fourth position is phosphorylated or replaced with a mimetic of phosphoserine;
SEQ ID NO: 149, wherein the serine at the fourth position is phosphorylated or replaced with a mimetic of phosphoserine;
SEQ ID NO: 150, wherein the serine at the fourth position is phosphorylated or replaced with a mimetic of phosphoserine;
SEQ ID NO: 154, wherein the serine at the third position is phosphorylated or replaced with a mimetic of phosphoserine;
SEQ ID NO: 155, wherein the serine at the fourth position is phosphorylated or replaced with a mimetic of phosphoserine;
SEQ ID NO: 157, wherein the serine at the fourth position of is phosphorylated or replaced with a mimetic of phosphoserine;
SEQ ID NO: 158, wherein the serine at the sixth position is phosphorylated or replaced with a mimetic of phosphoserine;
SEQ ID NO: 159, wherein the serine at the eighth position is phosphorylated or replaced with a mimetic of phosphoserine;
SEQ ID NO: 160, wherein the serine at the fifth position is phosphorylated or replaced with a mimetic of phosphoserine;
SEQ ID NO: 161, wherein the serine at the fourth position is phosphorylated or replaced with a mimetic of phosphoserine;
SEQ ID NO: 162, wherein the serine at the fourth position is phosphorylated or replaced with a mimetic of phosphoserine;
SEQ ID NO: 164, wherein the serine at the fourth position is phosphorylated or replaced with a mimetic of phosphoserine;
SEQ ID NO: 165, wherein the serine at the fourth position is phosphorylated or replaced with a mimetic of phosphoserine;
SEQ ID NO: 167, wherein the serine at the fourth position is phosphorylated or replaced with a mimetic of phosphoserine;
SEQ ID NO: 170, wherein the serine at the fourth position is phosphorylated or replaced with a mimetic of phosphoserine;
SEQ ID NO: 172, wherein the threonine at the fourth position is phosphorylated or replaced with a mimetic of phosphothreonine;
SEQ ID NO: 173, wherein the serine at the fifth position is phosphorylated or replaced with a mimetic of phosphoserine;

SEQ ID NO: 174, wherein the serine at the sixth position is phosphorylated or replaced with a mimetic of phosphoserine;

SEQ ID NO: 176, wherein the serine at the fourth position is phosphorylated or replaced with a mimetic of phosphoserine; and SEQ ID NO: 177, wherein the threonine at the sixth position is phosphorylated or replaced with a mimetic of phosphothreonine, and (b) a therapeutically effective amount of an adjuvant.

2. The composition of claim 1, wherein at least one serine residue in at least one of the synthetic target peptides is replaced with a homoserine.

3. The composition of claim 1, wherein the composition comprises at least 5 different synthetic target peptides.

4. The composition of claim 1, wherein the composition comprises at least 10 different synthetic target peptides.

5. The composition of claim 1, wherein the composition comprises at least 15 different synthetic target peptides.

6. The composition of claim 1, wherein the composition further comprises at least one peptide derived from MelanA (MART-I), gp100 (Pmel 17), tyrosinase, TRP-1, TRP-2, MAGE-1, MAGE-3, BAGE, GAGE-1, GAGE-2, p15(58), CEA, RAGE, NY-ESO (LAGE), SCP-1, Hom/Mel-40, PRAME, p53, H-Ras, HER-2/neu, BCR-ABL, E2A-PRL, H4-RET, IGH-IGK, MYL-RAR, Epstein Barr virus antigens, EBNA, human papillomavirus (HPV) antigens E6 and E7, TSP-180, MAGE-4, MAGE-5, MAGE-6, p185erbB2, p180erbB-3, c-met, nm-23H1, PSA, TAG-72-4, CA 19-9, CA 72-4, CAM 17.1, NuMa, K-ras, β-Catenin, CDK4, Mum-1, p16, TAGE, PSMA, PSCA, CT7, telomerase, 43-9F, 5T4, 791Tgp72, α-fetoprotein, β-HCG, BCA225, BTAA, CA 125, CA 15-3 (CA 27.29\BCAA), CA 195, CA 242, CA-50, CAM43, CD68\KP1, CO-029, FGF-5, G250, Ga733 (EpCAM), HTgp-175, M344, MA-50, MG7-Ag, MOV18, NB/70K, NY-CO-1, RCAS1, SDCCAG16, TA-90 (Mac-2 binding protein\cyclophilin C-associated protein), TAAL6, TAG72, TLP and TPS.

7. A method for treating colorectal cancer comprising administering to a patient in need thereof a dose of a composition of claim 1 in combination with a pharmaceutically acceptable carrier.

8. A method for making the composition of claim 1, the method comprising combining at least one synthetic target peptide set forth in claim 1 with an adjuvant selected from the group consisting of montanide ISA-51, QS-21, tetanus helper peptides, granulocyte-macrophage colony stimulating factor (GM-CSF), cyclophosphamide, *bacillus* Calmette-Guérin (BCG), *Corynbacterium parvum*, levamisole, azimezone, isoprinisone, dinitrochlorobenezene (DNCB), keyhole limpet hemocyanins (KLH), Freunds adjuvant (complete and incomplete), mineral gels, aluminum hydroxide (Alum), lysolecithin, pluronic polyols, polyanions, peptides, oil emulsions, dinitrophenol, diphtheria toxin (DT) and a pharmaceutically acceptable carrier.

9. The composition of claim 1, wherein the mimetic of phosphoserine or phosphothreonine is a synthetic molecule in which a phosphorous atom is linked to a serine or a threonine amino acid residue, respectively, through a carbon atom.

10. The composition of claim 1, wherein the adjuvant is selected from the group consisting of montanide ISA-51, QS-21, tetanus helper peptides, granulocyte-macrophage colony stimulating factor (GM-CSF), cyclophosphamide, *bacillus* Calmette-Guerin (BCG), *Corynbacterium parvum*, levamisole, azimezone, isoprinisone, dinitrochlorobenezene (DNCB), keyhole limpet hemocyanins (KLH), incomplete Freunds adjuvant, complete Freunds adjuvant, mineral gels, aluminum hydroxide (Alum), lysolecithin, pluronic polyols, polyanions, peptides, oil emulsions, dinitrophenol, and diphtheria toxin (DT).

11. The composition of claim 1, wherein composition has the ability to stimulate a T cell mediated immune response to at least one of the synthetic target peptides.

12. A composition comprising a synthetic target peptide, wherein the synthetic target peptide:
is 8 to 50 amino acids long; and
(ii) comprises an amino acid sequence selected from the group consisting of:
SEQ ID NO: 3, wherein the serine at the sixth position is replaced with a mimetic of phosphoserine;
SEQ ID NO: 5, wherein the serine at the third position is replaced with a mimetic of phosphoserine;
SEQ ID NO: 6, wherein the serine at the sixth position is replaced with a mimetic of phosphoserine;
SEQ ID NO: 7, wherein the threonine at the fourth position is replaced with a mimetic of phosphothreonine;
SEQ ID NO: 12, wherein the serine at the sixth position is replaced with a mimetic of phosphoserine;
SEQ ID NO: 13, wherein the serine at the fourth position is replaced with a mimetic of phosphoserine;
SEQ ID NO: 14, wherein the serine at the fourth position is replaced with a mimetic of phosphoserine;
SEQ ID NO: 15, wherein the serine at the fourth position is replaced with a mimetic of phosphoserine;
SEQ ID NO: 20, wherein the threonine at the fifth position is replaced with a mimetic of phosphothreonine;
SEQ ID NO: 22, wherein the serine at the fourth position is replaced with a mimetic of phosphoserine;
SEQ ID NO: 24, wherein the serine at the fifth position is replaced with a mimetic of phosphoserine;
SEQ ID NO: 26, wherein the serine at the eighth position is replaced with a mimetic of phosphoserine;
SEQ ID NO: 28, wherein the serine at the fourth position is replaced with a mimetic of phosphoserine;
SEQ ID NO: 29, wherein the serine at the fifth position is replaced with a mimetic of phosphoserine;
SEQ ID NO: 30, wherein the serine at the third position is replaced with a mimetic of phosphoserine;
SEQ ID NO: 31, wherein the serine at the fifth position is replaced with a mimetic of phosphoserine;
SEQ ID NO: 32, wherein the serine at the eighth position is replaced with a mimetic of phosphoserine;
SEQ ID NO: 33, wherein the serine at the fourth position is replaced with a mimetic of phosphoserine;
SEQ ID NO: 34, wherein the serine at the fourth position is replaced with a mimetic of phosphoserine;
SEQ ID NO: 43, wherein the serine at the fourth position is replaced with a mimetic of phosphoserine;
SEQ ID NO: 48, wherein the serine at the eighth position is replaced with a mimetic of phosphoserine;
SEQ ID NO: 49, wherein the serine at the fourth position is replaced with a mimetic of phosphoserine;
SEQ ID NO: 50, wherein the serine at the ninth position is replaced with a mimetic of phosphoserine;
SEQ ID NO: 52, wherein the serine at the fourth position is replaced with a mimetic of phosphoserine;
SEQ ID NO: 54, wherein the serine at the fourth position is replaced with a mimetic of phosphoserine;
SEQ ID NO: 56, wherein the serine at the fourth position is replaced with a mimetic of phosphoserine;
SEQ ID NO: 61, wherein the serine at the fourth position is replaced with a mimetic of phosphoserine;

SEQ ID NO: 63, wherein the serine at the sixth position is replaced with a mimetic of phosphoserine;
SEQ ID NO: 67, wherein the serine at the fourth position is replaced with a mimetic of phosphoserine;
SEQ ID NO: 68, wherein the serine at the ninth position is replaced with a mimetic of phosphoserine;
SEQ ID NO: 71, wherein the serine at the fourth position is replaced with a mimetic of phosphoserine;
SEQ ID NO: 72, wherein the serine at the fourth position is replaced with a mimetic of phosphoserine;
SEQ ID NO: 73, wherein the serine at the fourth position is replaced with a mimetic of phosphoserine;
SEQ ID NO: 81, wherein the serine at the ninth position is replaced with a mimetic of phosphoserine;
SEQ ID NO: 85, wherein the serine at the seventh position of is replaced with a mimetic of phosphoserine;
SEQ ID NO: 87, wherein the serine at the fourth position is replaced with a mimetic of phosphoserine;
SEQ ID NO: 91, wherein the serine at the eighth position is replaced with a mimetic of phosphoserine;
SEQ ID NO: 93, wherein the serine at the eighth position is replaced with a mimetic of phosphoserine;
SEQ ID NO: 94, wherein the serine at the sixth position is replaced with a mimetic of phosphoserine;
SEQ ID NO: 95, wherein the serine at the sixth position is replaced with a mimetic of phosphoserine, the serine at the eighth position is replaced with a mimetic of phosphoserine, or any combination thereof;
SEQ ID NO: 96, wherein the threonine at the fourth position is replaced with a mimetic of phosphothreonine;
SEQ ID NO: 99, wherein the serine at the fourth position is replaced with a mimetic of phosphoserine;
SEQ ID NO: 100, wherein the threonine at the sixth position is replaced with a mimetic of phosphothreonine;
SEQ ID NO: 101, wherein the threonine at the sixth position is replaced with a mimetic of phosphothreonine;
SEQ ID NO: 103, wherein the serine at the fourth position is replaced with a mimetic of phosphoserine;
SEQ ID NO: 104, wherein the serine at the fourth position is replaced with a mimetic of phosphoserine;
SEQ ID NO: 105, wherein the serine at the fourth position is replaced with a mimetic of phosphoserine;
SEQ ID NO: 106, wherein the serine at the fourth position is replaced with a mimetic of phosphoserine;
SEQ ID NO: 108, wherein the serine at the seventh position is replaced with a mimetic of phosphoserine;
SEQ ID NO: 109, wherein the serine at the fourth position is replaced with a mimetic of phosphoserine;
SEQ ID NO: 110, wherein the threonine at the fourth position is replaced with a mimetic of phosphothreonine;
SEQ ID NO: 114, wherein the serine at the fourth position is replaced with a mimetic of phosphoserine;
SEQ ID NO: 117, wherein the serine at the fourth position is replaced with a mimetic of phosphoserine;
SEQ ID NO: 119, wherein the serine at the fourth position is replaced with a mimetic of phosphoserine and the serine at the eighth position is replaced with a mimetic of phosphoserine;
SEQ ID NO: 123, wherein the serine at the fourth position is replaced with a mimetic of phosphoserine;
SEQ ID NO: 126, wherein the serine at the fourth position is replaced with a mimetic of phosphoserine;
SEQ ID NO: 128, wherein the serine at the fourth position is replaced with a mimetic of phosphoserine;
SEQ ID NO: 129, wherein the serine at the fourth position is replaced with a mimetic of phosphoserine;
SEQ ID NO: 131, wherein the serine at the fourth position is replaced with a mimetic of phosphoserine;
SEQ ID NO: 132, wherein the serine at the fourth position is replaced with a mimetic of phosphoserine;
SEQ ID NO: 135, wherein the serine at the fourth position is replaced with a mimetic of phosphoserine;
SEQ ID NO: 140, wherein the serine at the fourth position is replaced with a mimetic of phosphoserine;
SEQ ID NO: 141, wherein the serine at the fourth position is replaced with a mimetic of phosphoserine;
SEQ ID NO: 143, wherein the serine at the fourth position is replaced with a mimetic of phosphoserine;
SEQ ID NO: 144, wherein the serine at the fourth position is replaced with a mimetic of phosphoserine;
SEQ ID NO: 146, wherein the serine at the fourth position is replaced with a mimetic of phosphoserine;
SEQ ID NO: 147, wherein the serine at the fourth position is replaced with a mimetic of phosphoserine;
SEQ ID NO: 148, wherein the serine at the fourth position is replaced with a mimetic of phosphoserine;
SEQ ID NO: 149, wherein the serine at the fourth position is replaced with a mimetic of phosphoserine;
SEQ ID NO: 150, wherein the serine at the fourth position is replaced with a mimetic of phosphoserine;
SEQ ID NO: 154, wherein the serine at the third position is replaced with a mimetic of phosphoserine;
SEQ ID NO: 155, wherein the serine at the fourth position is replaced with a mimetic of phosphoserine;
SEQ ID NO: 157, wherein the serine at the fourth position of is replaced with a mimetic of phosphoserine;
SEQ ID NO: 158, wherein the serine at the sixth position is replaced with a mimetic of phosphoserine;
SEQ ID NO: 159, wherein the serine at the eighth position is replaced with a mimetic of phosphoserine;
SEQ ID NO: 160, wherein the serine at the fifth position is replaced with a mimetic of phosphoserine;
SEQ ID NO: 161, wherein the serine at the fourth position is replaced with a mimetic of phosphoserine;
SEQ ID NO: 162, wherein the serine at the fourth position is replaced with a mimetic of phosphoserine;
SEQ ID NO: 164, wherein the serine at the fourth position is replaced with a mimetic of phosphoserine;
SEQ ID NO: 165, wherein the serine at the fourth position is replaced with a mimetic of phosphoserine;
SEQ ID NO: 167, wherein the serine at the fourth position is replaced with a mimetic of phosphoserine;
SEQ ID NO: 170, wherein the serine at the fourth position is replaced with a mimetic of phosphoserine;
SEQ ID NO: 172, wherein the threonine at the fourth position is replaced with a mimetic of phosphothreonine;
SEQ ID NO: 173, wherein the serine at the fifth position is replaced with a mimetic of phosphoserine;
SEQ ID NO: 174, wherein the serine at the sixth position is replaced with a mimetic of phosphoserine;
SEQ ID NO: 176, wherein the serine at the fourth position is replaced with a mimetic of phosphoserine; and
SEQ ID NO: 177, wherein the threonine at the sixth position is replaced with a mimetic of phosphothreonine.

13. The composition of claim 12, wherein the mimetic of phosphoserine or phosphothreonine is a synthetic molecule in which a phosphorous atom is linked to a serine or a threonine amino acid residue, respectively, through a carbon atom.

14. The composition of claim 1, wherein the adjuvant comprises QS-21.

15. The composition of claim 1, wherein the at least one synthetic target peptide comprises the amino acid sequence as set forth in SEQ ID NO: 3, wherein the serine at the sixth position is phosphorylated or replaced with a mimetic of phosphoserine.

16. The composition of claim 1, wherein the at least one synthetic target peptide comprises the amino acid sequence as set forth in SEQ ID NO: 5, wherein the serine at the third position is phosphorylated or replaced with a mimetic of phosphoserine.

17. The composition of claim 1, wherein the at least one synthetic target peptide comprises the amino acid sequence as set forth in SEQ ID NO: 6, wherein the serine at the sixth position is phosphorylated or replaced with a mimetic of phosphoserine.

18. The composition of claim 1, wherein the at least one synthetic target peptide comprises the amino acid sequence as set forth in SEQ ID NO: 7, wherein the threonine at the fourth position is phosphorylated or replaced with a mimetic of phosphothreonine.

19. The composition of claim 1, wherein the at least one synthetic target peptide comprises the amino acid sequence as set forth in SEQ ID NO: 12, wherein the serine at the sixth position is phosphorylated or replaced with a mimetic of phosphoserine.

20. The composition of claim 1, wherein the at least one synthetic target peptide comprises the amino acid sequence as set forth in SEQ ID NO: 13, wherein the serine at the fourth position is phosphorylated or replaced with a mimetic of phosphoserine.

21. The composition of claim 1, wherein the at least one synthetic target peptide comprises the amino acid sequence as set forth in SEQ ID NO: 14, wherein the serine at the fourth position is phosphorylated or replaced with a mimetic of phosphoserine.

22. The composition of claim 1, wherein the at least one synthetic target peptide comprises the amino acid sequence as set forth in SEQ ID NO: 15, wherein the serine at the fourth position is phosphorylated or replaced with a mimetic of phosphoserine.

23. The composition of claim 1, wherein the at least one synthetic target peptide comprises the amino acid sequence as set forth in SEQ ID NO: 20, wherein the threonine at the fifth position is phosphorylated or replaced with a mimetic of phosphothreonine.

24. The composition of claim 1, wherein the at least one synthetic target peptide comprises the amino acid sequence as set forth in SEQ ID NO: 22, wherein the serine at the fourth position is phosphorylated or replaced with a mimetic of phosphoserine.

25. The composition of claim 1, wherein the at least one synthetic target peptide comprises the amino acid sequence as set forth in SEQ ID NO: 24, wherein the serine at the fifth position is phosphorylated or replaced with a mimetic of phosphoserine.

26. The composition of claim 1, wherein the at least one synthetic target peptide comprises the amino acid sequence as set forth in SEQ ID NO: 26, wherein the serine at the eighth position is phosphorylated or replaced with a mimetic of phosphoserine.

27. The composition of claim 1, wherein the at least one synthetic target peptide comprises the amino acid sequence as set forth in SEQ ID NO: 28, wherein the serine at the fourth position is phosphorylated or replaced with a mimetic of phosphoserine.

28. The composition of claim 1, wherein the at least one synthetic target peptide comprises the amino acid sequence as set forth in SEQ ID NO: 29, wherein the serine at the fifth position is phosphorylated or replaced with a mimetic of phosphoserine.

29. The composition of claim 1, wherein the at least one synthetic target peptide comprises the amino acid sequence as set forth in SEQ ID NO: 30, wherein the serine at the third position is phosphorylated or replaced with a mimetic of phosphoserine.

30. The composition of claim 1, wherein the at least one synthetic target peptide comprises the amino acid sequence as set forth in SEQ ID NO: 31, wherein the serine at the fifth position is phosphorylated or replaced with a mimetic of phosphoserine.

31. The composition of claim 1, wherein the at least one synthetic target peptide comprises the amino acid sequence as set forth in SEQ ID NO: 32, wherein the serine at the eighth position is phosphorylated or replaced with a mimetic of phosphoserine.

32. The composition of claim 1, wherein the at least one synthetic target peptide comprises the amino acid sequence as set forth in SEQ ID NO: 33, wherein the serine at the fourth position is phosphorylated or replaced with a mimetic of phosphoserine.

33. The composition of claim 1, wherein the at least one synthetic target peptide comprises the amino acid sequence as set forth in SEQ ID NO: 34, wherein the serine at the fourth position is phosphorylated or replaced with a mimetic of phosphoserine.

34. The composition of claim 1, wherein the at least one synthetic target peptide comprises the amino acid sequence as set forth in SEQ ID NO: 43, wherein the serine at the fourth position is phosphorylated or replaced with a mimetic of phosphoserine.

35. The composition of claim 1, wherein the at least one synthetic target peptide comprises the amino acid sequence as set forth in SEQ ID NO: 48, wherein the serine at the eighth position is phosphorylated or replaced with a mimetic of phosphoserine.

36. The composition of claim 1, wherein the at least one synthetic target peptide comprises the amino acid sequence as set forth in SEQ ID NO: 49, wherein the serine at the fourth position is phosphorylated or replaced with a mimetic of phosphoserine.

37. The composition of claim 1, wherein the at least one synthetic target peptide comprises the amino acid sequence as set forth in SEQ ID NO: 50, wherein the serine at the ninth position is phosphorylated or replaced with a mimetic of phosphoserine.

38. The composition of claim 1, wherein the at least one synthetic target peptide comprises the amino acid sequence as set forth in SEQ ID NO: 52, wherein the serine at the fourth position is phosphorylated or replaced with a mimetic of phosphoserine.

39. The composition of claim 1, wherein the at least one synthetic target peptide comprises the amino acid sequence as set forth in SEQ ID NO: 54, wherein the serine at the fourth position is phosphorylated or replaced with a mimetic of phosphoserine.

40. The composition of claim 1, wherein the at least one synthetic target peptide comprises the amino acid sequence as set forth in SEQ ID NO: 56, wherein the serine at the fourth position is phosphorylated or replaced with a mimetic of phosphoserine.

41. The composition of claim 1, wherein the at least one synthetic target peptide comprises the amino acid sequence as set forth in SEQ ID NO: 61, wherein the serine at the fourth position is phosphorylated or replaced with a mimetic of phosphoserine.

42. The composition of claim 1, wherein the at least one synthetic target peptide comprises the amino acid sequence as set forth in SEQ ID NO: 63, wherein the serine at the sixth position is phosphorylated or replaced with a mimetic of phosphoserine.

43. The composition of claim 1, wherein the at least one synthetic target peptide comprises the amino acid sequence as set forth in SEQ ID NO: 67, wherein the serine at the fourth position is phosphorylated or replaced with a mimetic of phosphoserine.

44. The composition of claim 1, wherein the at least one synthetic target peptide comprises the amino acid sequence as set forth in SEQ ID NO: 68, wherein the serine at the ninth position is phosphorylated or replaced with a mimetic of phosphoserine.

45. The composition of claim 1, wherein the at least one synthetic target peptide comprises the amino acid sequence as set forth in SEQ ID NO: 71, wherein the serine at the fourth position is phosphorylated or replaced with a mimetic of phosphoserine.

46. The composition of claim 1, wherein the at least one synthetic target peptide comprises the amino acid sequence as set forth in SEQ ID NO: 72, wherein the serine at the fourth position is phosphorylated or replaced with a mimetic of phosphoserine.

47. The composition of claim 1, wherein the at least one synthetic target peptide comprises the amino acid sequence as set forth in SEQ ID NO: 73, wherein the serine at the fourth position is phosphorylated or replaced with a mimetic of phosphoserine.

48. The composition of claim 1, wherein the at least one synthetic target peptide comprises the amino acid sequence as set forth in SEQ ID NO: 81, wherein the serine at the ninth position is phosphorylated or replaced with a mimetic of phosphoserine.

49. The composition of claim 1, wherein the at least one synthetic target peptide comprises the amino acid sequence as set forth in SEQ ID NO: 85, wherein the serine at the seventh position of is phosphorylated or replaced with a mimetic of phosphoserine.

50. The composition of claim 1, wherein the at least one synthetic target peptide comprises the amino acid sequence as set forth in SEQ ID NO: 87, wherein the serine at the fourth position is phosphorylated or replaced with a mimetic of phosphoserine.

51. The composition of claim 1, wherein the at least one synthetic target peptide comprises the amino acid sequence as set forth in SEQ ID NO: 91, wherein the serine at the eighth position is phosphorylated or replaced with a mimetic of phosphoserine.

52. The composition of claim 1, wherein the at least one synthetic target peptide comprises the amino acid sequence as set forth in SEQ ID NO: 93, wherein the serine at the eighth position is phosphorylated or replaced with a mimetic of phosphoserine.

53. The composition of claim 1, wherein the at least one synthetic target peptide comprises the amino acid sequence as set forth in SEQ ID NO: 94, wherein the serine at the sixth position is phosphorylated or replaced with a mimetic of phosphoserine.

54. The composition of claim 1, wherein the at least one synthetic target peptide comprises the amino acid sequence as set forth in SEQ ID NO: 95, wherein the serine at the sixth position is phosphorylated or replaced with a mimetic of phosphoserine, the serine at the eighth position is phosphorylated or replaced with a mimetic of phosphoserine, or any combination thereof.

55. The composition of claim 1, wherein the at least one synthetic target peptide comprises the amino acid sequence as set forth in SEQ ID NO: 96, wherein the threonine at the fourth position is phosphorylated or replaced with a mimetic of phosphothreonine.

56. The composition of claim 1, wherein the at least one synthetic target peptide comprises the amino acid sequence as set forth in SEQ ID NO: 99, wherein the serine at the fourth position is phosphorylated or replaced with a mimetic of phosphoserine.

57. The composition of claim 1, wherein the at least one synthetic target peptide comprises the amino acid sequence as set forth in SEQ ID NO: 100, wherein the threonine at the sixth position is phosphorylated or replaced with a mimetic of phosphothreonine.

58. The composition of claim 1, wherein the at least one synthetic target peptide comprises the amino acid sequence as set forth in SEQ ID NO: 101, wherein the threonine at the sixth position is phosphorylated or replaced with a mimetic of phosphothreonine.

59. The composition of claim 1, wherein the at least one synthetic target peptide comprises the amino acid sequence as set forth in SEQ ID NO: 103, wherein the serine at the fourth position is phosphorylated or replaced with a mimetic of phosphoserine.

60. The composition of claim 1, wherein the at least one synthetic target peptide comprises the amino acid sequence as set forth in SEQ ID NO: 104, wherein the serine at the fourth position is phosphorylated or replaced with a mimetic of phosphoserine.

61. The composition of claim 1, wherein the at least one synthetic target peptide comprises the amino acid sequence as set forth in SEQ ID NO: 105, wherein the serine at the fourth position is phosphorylated or replaced with a mimetic of phosphoserine.

62. The composition of claim 1, wherein the at least one synthetic target peptide comprises the amino acid sequence as set forth in SEQ ID NO: 106, wherein the serine at the fourth position is phosphorylated or replaced with a mimetic of phosphoserine.

63. The composition of claim 1, wherein the at least one synthetic target peptide comprises the amino acid sequence as set forth in SEQ ID NO: 108, wherein the serine at the seventh position is phosphorylated or replaced with a mimetic of phosphoserine.

64. The composition of claim 1, wherein the at least one synthetic target peptide comprises the amino acid sequence as set forth in SEQ ID NO: 109, wherein the serine at the fourth position is phosphorylated or replaced with a mimetic of phosphoserine.

65. The composition of claim 1, wherein the at least one synthetic target peptide comprises the amino acid sequence as set forth in SEQ ID NO: 110, wherein the threonine at the fourth position is phosphorylated or replaced with a mimetic of phosphothreonine.

66. The composition of claim 1, wherein the at least one synthetic target peptide comprises the amino acid sequence as set forth in SEQ ID NO: 114, wherein the serine at the fourth position is phosphorylated or replaced with a mimetic of phosphoserine.

67. The composition of claim 1, wherein the at least one synthetic target peptide comprises the amino acid sequence as set forth in SEQ ID NO: 117, wherein the serine at the fourth position is phosphorylated or replaced with a mimetic of phosphoserine.

68. The composition of claim 1, wherein the at least one synthetic target peptide comprises the amino acid sequence as set forth in SEQ ID NO: 119, wherein the serine at the fourth position is phosphorylated or replaced with a mimetic of phosphoserine and the serine at the eighth position is phosphorylated or replaced with a mimetic of phosphoserine.

69. The composition of claim 1, wherein the at least one synthetic target peptide comprises the amino acid sequence as set forth in SEQ ID NO: 123, wherein the serine at the fourth position is phosphorylated or replaced with a mimetic of phosphoserine.

70. The composition of claim 1, wherein the at least one synthetic target peptide comprises the amino acid sequence as set forth in SEQ ID NO: 126, wherein the serine at the fourth position is phosphorylated or replaced with a mimetic of phosphoserine.

71. The composition of claim 1, wherein the at least one synthetic target peptide comprises the amino acid sequence as set forth in SEQ ID NO: 128, wherein the serine at the fourth position is phosphorylated or replaced with a mimetic of phosphoserine.

72. The composition of claim 1, wherein the at least one synthetic target peptide comprises the amino acid sequence as set forth in SEQ ID NO: 129, wherein the serine at the fourth position is phosphorylated or replaced with a mimetic of phosphoserine.

73. The composition of claim 1, wherein the at least one synthetic target peptide comprises the amino acid sequence as set forth in SEQ ID NO: 131, wherein the serine at the fourth position is phosphorylated or replaced with a mimetic of phosphoserine.

74. The composition of claim 1, wherein the at least one synthetic target peptide comprises the amino acid sequence as set forth in SEQ ID NO: 132, wherein the serine at the fourth position is phosphorylated or replaced with a mimetic of phosphoserine.

75. The composition of claim 1, wherein the at least one synthetic target peptide comprises the amino acid sequence as set forth in SEQ ID NO: 135, wherein the serine at the fourth position is phosphorylated or replaced with a mimetic of phosphoserine.

76. The composition of claim 1, wherein the at least one synthetic target peptide comprises the amino acid sequence as set forth in SEQ ID NO: 140, wherein the serine at the fourth position is phosphorylated or replaced with a mimetic of phosphoserine.

77. The composition of claim 1, wherein the at least one synthetic target peptide comprises the amino acid sequence as set forth in SEQ ID NO: 141, wherein the serine at the fourth position is phosphorylated or replaced with a mimetic of phosphoserine.

78. The composition of claim 1, wherein the at least one synthetic target peptide comprises the amino acid sequence as set forth in SEQ ID NO: 143, wherein the serine at the fourth position is phosphorylated or replaced with a mimetic of phosphoserine.

79. The composition of claim 1, wherein the at least one synthetic target peptide comprises the amino acid sequence as set forth in SEQ ID NO: 144, wherein the serine at the fourth position is phosphorylated or replaced with a mimetic of phosphoserine.

80. The composition of claim 1, wherein the at least one synthetic target peptide comprises the amino acid sequence as set forth in SEQ ID NO: 146, wherein the serine at the fourth position is phosphorylated or replaced with a mimetic of phosphoserine.

81. The composition of claim 1, wherein the at least one synthetic target peptide comprises the amino acid sequence as set forth in SEQ ID NO: 147, wherein the serine at the fourth position is phosphorylated or replaced with a mimetic of phosphoserine.

82. The composition of claim 1, wherein the at least one synthetic target peptide comprises the amino acid sequence as set forth in SEQ ID NO: 148, wherein the serine at the fourth position is phosphorylated or replaced with a mimetic of phosphoserine.

83. The composition of claim 1, wherein the at least one synthetic target peptide comprises the amino acid sequence as set forth in SEQ ID NO: 149, wherein the serine at the fourth position is phosphorylated or replaced with a mimetic of phosphoserine.

84. The composition of claim 1, wherein the at least one synthetic target peptide comprises the amino acid sequence as set forth in SEQ ID NO: 150, wherein the serine at the fourth position is phosphorylated or replaced with a mimetic of phosphoserine.

85. The composition of claim 1, wherein the at least one synthetic target peptide comprises the amino acid sequence as set forth in SEQ ID NO: 154, wherein the serine at the third position is phosphorylated or replaced with a mimetic of phosphoserine.

86. The composition of claim 1, wherein the at least one synthetic target peptide comprises the amino acid sequence as set forth in SEQ ID NO: 155, wherein the serine at the fourth position is phosphorylated or replaced with a mimetic of phosphoserine.

87. The composition of claim 1, wherein the at least one synthetic target peptide comprises the amino acid sequence as set forth in SEQ ID NO: 157, wherein the serine at the fourth position of is phosphorylated or replaced with a mimetic of phosphoserine.

88. The composition of claim 1, wherein the at least one synthetic target peptide comprises the amino acid sequence as set forth in SEQ ID NO: 158, wherein the serine at the sixth position is phosphorylated or replaced with a mimetic of phosphoserine.

89. The composition of claim 1, wherein the at least one synthetic target peptide comprises the amino acid sequence as set forth in SEQ ID NO: 159, wherein the serine at the eighth position is phosphorylated or replaced with a mimetic of phosphoserine.

90. The composition of claim 1, wherein the at least one synthetic target peptide comprises the amino acid sequence as set forth in SEQ ID NO: 160, wherein the serine at the fifth position is phosphorylated or replaced with a mimetic of phosphoserine.

91. The composition of claim 1, wherein the at least one synthetic target peptide comprises the amino acid sequence as set forth in SEQ ID NO: 161, wherein the serine at the fourth position is phosphorylated or replaced with a mimetic of phosphoserine.

92. The composition of claim 1, wherein the at least one synthetic target peptide comprises the amino acid sequence 93. The composition of claim 1, wherein the at least one synthetic target peptide comprises the amino acid sequence as set forth in SEQ ID NO: 162, wherein the serine at the fourth position is phosphorylated or replaced with a mimetic of phosphoserine.

93. The composition of claim 1, wherein the at least one synthetic target peptide comprises the amino acid sequence as set forth in SEQ ID NO: 164, wherein the serine at the fourth position is phosphorylated or replaced with a mimetic of phosphoserine.

94. The composition of claim 1, wherein the at least one synthetic target peptide comprises the amino acid sequence as set forth in SEQ ID NO: 165, wherein the serine at the fourth position is phosphorylated or replaced with a mimetic of phosphoserine.

95. The composition of claim 1, wherein the at least one synthetic target peptide comprises the amino acid sequence as set forth in SEQ ID NO: 167, wherein the serine at the fourth position is phosphorylated or replaced with a mimetic of phosphoserine.

96. The composition of claim 1, wherein the at least one synthetic target peptide comprises the amino acid sequence as set forth in SEQ ID NO: 170, wherein the serine at the fourth position is phosphorylated or replaced with a mimetic of phosphoserine.

97. The composition of claim 1, wherein the at least one synthetic target peptide comprises the amino acid sequence as set forth in SEQ ID NO: 172, wherein the threonine at the fourth position is phosphorylated or replaced with a mimetic of phosphothreonine.

98. The composition of claim 1, wherein the at least one synthetic target peptide comprises the amino acid sequence as set forth in SEQ ID NO: 173, wherein the serine at the fifth position is phosphorylated or replaced with a mimetic of phosphoserine.

99. The composition of claim 1, wherein the at least one synthetic target peptide comprises the amino acid sequence as set forth in SEQ ID NO: 174, wherein the serine at the sixth position is phosphorylated or replaced with a mimetic of phosphoserine.

100. The composition of claim 1, wherein the at least one synthetic target peptide comprises the amino acid sequence as set forth in SEQ ID NO: 176, wherein the serine at the fourth position is phosphorylated or replaced with a mimetic of phosphoserine.

101. The composition of claim 1, wherein the at least one synthetic target peptide comprises the amino acid sequence as set forth in SEQ ID NO: 177, wherein the threonine at the sixth position is phosphorylated or replaced with a mimetic of phosphothreonine.

\* \* \* \* \*

SEQUENCE LISTING

```
<160> NUMBER OF SEQ ID NOS: 368

<210> SEQ ID NO 1
<211> LENGTH: 9
<212> TYPE: PRT
<213> ORGANISM: Homo sapiens
<220> FEATURE:
<221> NAME/KEY: MISC_FEATURE
<222> LOCATION: (4)..(4)
<223> OTHER INFORMATION: The amino acid at the noted position is
      optionally phosphorylated

<400> SEQUENCE: 1

Ile Ser Ser Ser Met His Ser Leu Tyr
1               5

<210> SEQ ID NO 2
<211> LENGTH: 9
<212> TYPE: PRT
<213> ORGANISM: Homo sapiens
<220> FEATURE:
<221> NAME/KEY: MISC_FEATURE
<222> LOCATION: (5)..(5)
<223> OTHER INFORMATION: The amino acid at the noted position is
      optionally phosphorylated

<400> SEQUENCE: 2

Ile Thr Gln Gly Thr Pro Leu Lys Tyr
1               5

<210> SEQ ID NO 3
<211> LENGTH: 12
<212> TYPE: PRT
<213> ORGANISM: Homo sapiens
<220> FEATURE:
<221> NAME/KEY: MISC_FEATURE
<222> LOCATION: (6)..(6)
<223> OTHER INFORMATION: The amino acid at the noted position is
      optionally phosphorylated

<400> SEQUENCE: 3

Leu Thr Asp Pro Ser Ser Pro Thr Ile Ser Ser Tyr
1               5                   10

<210> SEQ ID NO 4
<211> LENGTH: 10
<212> TYPE: PRT
<213> ORGANISM: Homo sapiens
<220> FEATURE:
<221> NAME/KEY: MISC_FEATURE
<222> LOCATION: (4)..(4)
<223> OTHER INFORMATION: The amino acid at the noted position is
      optionally phosphorylated

<400> SEQUENCE: 4
```

```
Thr Met Ala Ser Pro Gly Lys Asp Asn Tyr
1               5                   10
```

<210> SEQ ID NO 5
<211> LENGTH: 8
<212> TYPE: PRT
<213> ORGANISM: Homo sapiens
<220> FEATURE:
<221> NAME/KEY: MISC_FEATURE
<222> LOCATION: (3)..(3)
<223> OTHER INFORMATION: The amino acid at the noted position is
      optionally phosphorylated

<400> SEQUENCE: 5

```
Ala Ile Ser Asp Leu Gln Gln Leu
1               5
```

<210> SEQ ID NO 6
<211> LENGTH: 9
<212> TYPE: PRT
<213> ORGANISM: Homo sapiens
<220> FEATURE:
<221> NAME/KEY: MISC_FEATURE
<222> LOCATION: (6)..(6)
<223> OTHER INFORMATION: The amino acid at the noted position is
      optionally phosphorylated

<400> SEQUENCE: 6

```
Asp Leu Lys Arg Arg Ser Met Ser Ile
1               5
```

<210> SEQ ID NO 7
<211> LENGTH: 9
<212> TYPE: PRT
<213> ORGANISM: Homo sapiens
<220> FEATURE:
<221> NAME/KEY: MISC_FEATURE
<222> LOCATION: (4)..(4)
<223> OTHER INFORMATION: The amino acid at the noted position is
      optionally phosphorylated

<400> SEQUENCE: 7

```
Phe Leu Asp Thr Pro Ile Ala Lys Val
1               5
```

<210> SEQ ID NO 8
<211> LENGTH: 9
<212> TYPE: PRT
<213> ORGANISM: Homo sapiens
<220> FEATURE:
<221> NAME/KEY: MISC_FEATURE
<222> LOCATION: (4)..(4)
<223> OTHER INFORMATION: The amino acid at the noted position is
      optionally phosphorylated

<400> SEQUENCE: 8

```
Lys Ala Phe Ser Pro Val Arg Ser Val
1               5
```

<210> SEQ ID NO 9
<211> LENGTH: 10
<212> TYPE: PRT
<213> ORGANISM: Homo sapiens
<220> FEATURE:
<221> NAME/KEY: MISC_FEATURE
<222> LOCATION: (4)..(4)
<223> OTHER INFORMATION: The amino acid at the noted position is
      optionally phosphorylated

<400> SEQUENCE: 9

Lys Leu Ala Ser Pro Glu Leu Glu Arg Leu
1               5                   10

<210> SEQ ID NO 10
<211> LENGTH: 10
<212> TYPE: PRT
<213> ORGANISM: Homo sapiens
<220> FEATURE:
<221> NAME/KEY: MISC_FEATURE
<222> LOCATION: (6)..(6)
<223> OTHER INFORMATION: The amino acid at the noted position is
      optionally phosphorylated

<400> SEQUENCE: 10

Lys Leu Phe Pro Asp Thr Pro Leu Ala Leu
1               5                   10

<210> SEQ ID NO 11
<211> LENGTH: 9
<212> TYPE: PRT
<213> ORGANISM: Homo sapiens
<220> FEATURE:
<221> NAME/KEY: MISC_FEATURE
<222> LOCATION: (8)..(8)
<223> OTHER INFORMATION: The amino acid at the noted position is
      optionally phosphorylated

<400> SEQUENCE: 11

Lys Leu Ile Asp Arg Thr Glu Ser Leu
1               5

<210> SEQ ID NO 12
<211> LENGTH: 10
<212> TYPE: PRT
<213> ORGANISM: Homo sapiens
<220> FEATURE:
<221> NAME/KEY: MISC_FEATURE
<222> LOCATION: (6)..(6)
<223> OTHER INFORMATION: The amino acid at the noted position is
      optionally phosphorylated

<400> SEQUENCE: 12

Lys Leu Ile Asp Val Ser Ser Gln Lys Val
1               5                   10

<210> SEQ ID NO 13
<211> LENGTH: 9
<212> TYPE: PRT
<213> ORGANISM: Homo sapiens
<220> FEATURE:
<221> NAME/KEY: MISC_FEATURE
<222> LOCATION: (4)..(4)
<223> OTHER INFORMATION: The amino acid at the noted position is
      optionally phosphorylated

<400> SEQUENCE: 13

Lys Val Gln Ser Leu Arg Arg Ala Leu
1               5

<210> SEQ ID NO 14
<211> LENGTH: 9
<212> TYPE: PRT
<213> ORGANISM: Homo sapiens
<220> FEATURE:
<221> NAME/KEY: MISC_FEATURE
<222> LOCATION: (4)..(4)
<223> OTHER INFORMATION: The amino acid at the noted position is
      optionally phosphorylated

```
<400> SEQUENCE: 14

Leu Leu Leu Ser Glu Glu Val Glu Leu
1               5

<210> SEQ ID NO 15
<211> LENGTH: 9
<212> TYPE: PRT
<213> ORGANISM: Homo sapiens
<220> FEATURE:
<221> NAME/KEY: MISC_FEATURE
<222> LOCATION: (4)..(4)
<223> OTHER INFORMATION: The amino acid at the noted position is
      optionally phosphorylated

<400> SEQUENCE: 15

Arg Leu Ala Ser Tyr Leu Asp Arg Val
1               5

<210> SEQ ID NO 16
<211> LENGTH: 9
<212> TYPE: PRT
<213> ORGANISM: Homo sapiens
<220> FEATURE:
<221> NAME/KEY: MISC_FEATURE
<222> LOCATION: (4)..(4)
<223> OTHER INFORMATION: The amino acid at the noted position is
      optionally phosphorylated

<400> SEQUENCE: 16

Arg Leu Ser Ser Pro Leu His Phe Val
1               5

<210> SEQ ID NO 17
<211> LENGTH: 10
<212> TYPE: PRT
<213> ORGANISM: Homo sapiens
<220> FEATURE:
<221> NAME/KEY: MISC_FEATURE
<222> LOCATION: (4)..(4)
<223> OTHER INFORMATION: The amino acid at the noted position is
      optionally phosphorylated

<400> SEQUENCE: 17

Arg Gln Ala Ser Ile Glu Leu Pro Ser Met
1               5                   10

<210> SEQ ID NO 18
<211> LENGTH: 12
<212> TYPE: PRT
<213> ORGANISM: Homo sapiens
<220> FEATURE:
<221> NAME/KEY: MISC_FEATURE
<222> LOCATION: (4)..(4)
<223> OTHER INFORMATION: The amino acid at the noted position is
      optionally phosphorylated

<400> SEQUENCE: 18

Arg Gln Ala Ser Ile Glu Leu Pro Ser Met Ala Val
1               5                   10

<210> SEQ ID NO 19
<211> LENGTH: 11
<212> TYPE: PRT
<213> ORGANISM: Homo sapiens
<220> FEATURE:
<221> NAME/KEY: MISC_FEATURE
<222> LOCATION: (4)..(4)
<223> OTHER INFORMATION: The amino acid at the noted position is
      optionally phosphorylated
```

<400> SEQUENCE: 19

Arg Gln Asp Ser Thr Pro Gly Lys Val Phe Leu
1               5                   10

<210> SEQ ID NO 20
<211> LENGTH: 11
<212> TYPE: PRT
<213> ORGANISM: Homo sapiens
<220> FEATURE:
<221> NAME/KEY: MISC_FEATURE
<222> LOCATION: (5)..(5)
<223> OTHER INFORMATION: The amino acid at the noted position is
      optionally phosphorylated

<400> SEQUENCE: 20

Arg Gln Asp Ser Thr Pro Gly Lys Val Phe Leu
1               5                   10

<210> SEQ ID NO 21
<211> LENGTH: 9
<212> TYPE: PRT
<213> ORGANISM: Homo sapiens
<220> FEATURE:
<221> NAME/KEY: MISC_FEATURE
<222> LOCATION: (4)..(4)
<223> OTHER INFORMATION: The amino acid at the noted position is
      optionally phosphorylated

<400> SEQUENCE: 21

Arg Gln Ile Ser Gln Asp Val Lys Leu
1               5

<210> SEQ ID NO 22
<211> LENGTH: 10
<212> TYPE: PRT
<213> ORGANISM: Homo sapiens
<220> FEATURE:
<221> NAME/KEY: MISC_FEATURE
<222> LOCATION: (4)..(4)
<223> OTHER INFORMATION: The amino acid at the noted position is
      optionally phosphorylated

<400> SEQUENCE: 22

Arg Thr Leu Ser Pro Glu Ile Ile Thr Val
1               5                   10

<210> SEQ ID NO 23
<211> LENGTH: 9
<212> TYPE: PRT
<213> ORGANISM: Homo sapiens
<220> FEATURE:
<221> NAME/KEY: MISC_FEATURE
<222> LOCATION: (4)..(4)
<223> OTHER INFORMATION: The amino acid at the noted position is
      optionally phosphorylated

<400> SEQUENCE: 23

Arg Val Ala Ser Pro Thr Ser Gly Val
1               5

<210> SEQ ID NO 24
<211> LENGTH: 9
<212> TYPE: PRT
<213> ORGANISM: Homo sapiens
<220> FEATURE:
<221> NAME/KEY: MISC_FEATURE
<222> LOCATION: (5)..(5)
<223> OTHER INFORMATION: The amino acid at the noted position is

```
      optionally phosphorylated

<400> SEQUENCE: 24

Arg Val Leu His Ser Pro Pro Ala Val
1               5

<210> SEQ ID NO 25
<211> LENGTH: 9
<212> TYPE: PRT
<213> ORGANISM: Homo sapiens
<220> FEATURE:
<221> NAME/KEY: MISC_FEATURE
<222> LOCATION: (5)..(5)
<223> OTHER INFORMATION: The amino acid at the noted position is
      optionally phosphorylated

<400> SEQUENCE: 25

Ser Met Thr Arg Ser Pro Pro Arg Val
1               5

<210> SEQ ID NO 26
<211> LENGTH: 9
<212> TYPE: PRT
<213> ORGANISM: Homo sapiens
<220> FEATURE:
<221> NAME/KEY: MISC_FEATURE
<222> LOCATION: (8)..(8)
<223> OTHER INFORMATION: The amino acid at the noted position is
      optionally phosphorylated

<400> SEQUENCE: 26

Ser Val Lys Pro Arg Arg Thr Ser Leu
1               5

<210> SEQ ID NO 27
<211> LENGTH: 9
<212> TYPE: PRT
<213> ORGANISM: Homo sapiens
<220> FEATURE:
<221> NAME/KEY: MISC_FEATURE
<222> LOCATION: (5)..(5)
<223> OTHER INFORMATION: The amino acid at the noted position is
      optionally phosphorylated

<400> SEQUENCE: 27

Val Met Ile Gly Ser Pro Lys Lys Val
1               5

<210> SEQ ID NO 28
<211> LENGTH: 8
<212> TYPE: PRT
<213> ORGANISM: Homo sapiens
<220> FEATURE:
<221> NAME/KEY: MISC_FEATURE
<222> LOCATION: (4)..(4)
<223> OTHER INFORMATION: The amino acid at the noted position is
      optionally phosphorylated

<400> SEQUENCE: 28

Arg Ala Asp Ser Pro Val His Met
1               5

<210> SEQ ID NO 29
<211> LENGTH: 9
<212> TYPE: PRT
<213> ORGANISM: Homo sapiens
<220> FEATURE:
<221> NAME/KEY: MISC_FEATURE
<222> LOCATION: (5)..(5)
```

```
<223> OTHER INFORMATION: The amino acid at the noted position is
      optionally phosphorylated

<400> SEQUENCE: 29

Arg Ala His Ser Ser Pro Ala Ser Leu
1               5

<210> SEQ ID NO 30
<211> LENGTH: 8
<212> TYPE: PRT
<213> ORGANISM: Homo sapiens
<220> FEATURE:
<221> NAME/KEY: MISC_FEATURE
<222> LOCATION: (3)..(3)
<223> OTHER INFORMATION: The amino acid at the noted position is
      optionally phosphorylated

<400> SEQUENCE: 30

Arg Ile Ser His Glu Leu Asp Ser
1               5

<210> SEQ ID NO 31
<211> LENGTH: 9
<212> TYPE: PRT
<213> ORGANISM: Homo sapiens
<220> FEATURE:
<221> NAME/KEY: MISC_FEATURE
<222> LOCATION: (5)..(5)
<223> OTHER INFORMATION: The amino acid at the noted position is
      optionally phosphorylated

<400> SEQUENCE: 31

Arg Ser His Ser Ser Pro Ala Ser Leu
1               5

<210> SEQ ID NO 32
<211> LENGTH: 9
<212> TYPE: PRT
<213> ORGANISM: Homo sapiens
<220> FEATURE:
<221> NAME/KEY: MISC_FEATURE
<222> LOCATION: (8)..(8)
<223> OTHER INFORMATION: The amino acid at the noted position is
      optionally phosphorylated

<400> SEQUENCE: 32

Tyr Ala Val Pro Arg Arg Gly Ser Leu
1               5

<210> SEQ ID NO 33
<211> LENGTH: 9
<212> TYPE: PRT
<213> ORGANISM: Homo sapiens
<220> FEATURE:
<221> NAME/KEY: MISC_FEATURE
<222> LOCATION: (4)..(4)
<223> OTHER INFORMATION: The amino acid at the noted position is
      optionally phosphorylated

<400> SEQUENCE: 33

Gly Ile Met Ser Pro Leu Ala Lys Lys
1               5

<210> SEQ ID NO 34
<211> LENGTH: 10
<212> TYPE: PRT
<213> ORGANISM: Homo sapiens
<220> FEATURE:
<221> NAME/KEY: MISC_FEATURE
```

```
<222> LOCATION: (4)..(4)
<223> OTHER INFORMATION: The amino acid at the noted position is
      optionally phosphorylated

<400> SEQUENCE: 34

Lys Leu Pro Ser Pro Ala Pro Ala Arg Lys
1               5                   10

<210> SEQ ID NO 35
<211> LENGTH: 9
<212> TYPE: PRT
<213> ORGANISM: Homo sapiens
<220> FEATURE:
<221> NAME/KEY: MISC_FEATURE
<222> LOCATION: (4)..(4)
<223> OTHER INFORMATION: The amino acid at the noted position is
      optionally phosphorylated

<400> SEQUENCE: 35

Arg Ala Lys Ser Pro Ile Ser Leu Lys
1               5

<210> SEQ ID NO 36
<211> LENGTH: 9
<212> TYPE: PRT
<213> ORGANISM: Homo sapiens
<220> FEATURE:
<221> NAME/KEY: MISC_FEATURE
<222> LOCATION: (4)..(4)
<223> OTHER INFORMATION: The amino acid at the noted position is
      optionally phosphorylated

<400> SEQUENCE: 36

Arg Ile Leu Ser Gly Val Val Thr Lys
1               5

<210> SEQ ID NO 37
<211> LENGTH: 9
<212> TYPE: PRT
<213> ORGANISM: Homo sapiens
<220> FEATURE:
<221> NAME/KEY: MISC_FEATURE
<222> LOCATION: (5)..(5)
<223> OTHER INFORMATION: The amino acid at the noted position is
      optionally phosphorylated

<400> SEQUENCE: 37

Arg Ile Tyr Gln Tyr Ile Gln Ser Arg
1               5

<210> SEQ ID NO 38
<211> LENGTH: 10
<212> TYPE: PRT
<213> ORGANISM: Homo sapiens
<220> FEATURE:
<221> NAME/KEY: MISC_FEATURE
<222> LOCATION: (5)..(5)
<223> OTHER INFORMATION: The amino acid at the noted position is
      optionally phosphorylated

<400> SEQUENCE: 38

Arg Ile Tyr Gln Tyr Ile Gln Ser Arg Phe
1               5                   10

<210> SEQ ID NO 39
<211> LENGTH: 9
<212> TYPE: PRT
<213> ORGANISM: Homo sapiens
<220> FEATURE:
```

```
<221> NAME/KEY: MISC_FEATURE
<222> LOCATION: (4)..(4)
<223> OTHER INFORMATION: The amino acid at the noted position is
      optionally phosphorylated

<400> SEQUENCE: 39

Arg Leu Ser Ser Pro Ile Ser Lys Arg
1               5

<210> SEQ ID NO 40
<211> LENGTH: 11
<212> TYPE: PRT
<213> ORGANISM: Homo sapiens
<220> FEATURE:
<221> NAME/KEY: MISC_FEATURE
<222> LOCATION: (4)..(4)
<223> OTHER INFORMATION: The amino acid at the noted position is
      optionally phosphorylated

<400> SEQUENCE: 40

Arg Thr Met Ser Glu Ala Ala Leu Val Arg Lys
1               5                   10

<210> SEQ ID NO 41
<211> LENGTH: 11
<212> TYPE: PRT
<213> ORGANISM: Homo sapiens
<220> FEATURE:
<221> NAME/KEY: MISC_FEATURE
<222> LOCATION: (4)..(4)
<223> OTHER INFORMATION: The amino acid at the noted position is
      optionally phosphorylated

<400> SEQUENCE: 41

Arg Thr Arg Ser Leu Ser Ser Leu Arg Glu Lys
1               5                   10

<210> SEQ ID NO 42
<211> LENGTH: 10
<212> TYPE: PRT
<213> ORGANISM: Homo sapiens
<220> FEATURE:
<221> NAME/KEY: MISC_FEATURE
<222> LOCATION: (4)..(4)
<223> OTHER INFORMATION: The amino acid at the noted position is
      optionally phosphorylated

<400> SEQUENCE: 42

Arg Val Ala Ser Pro Thr Ser Gly Val Lys
1               5                   10

<210> SEQ ID NO 43
<211> LENGTH: 9
<212> TYPE: PRT
<213> ORGANISM: Homo sapiens
<220> FEATURE:
<221> NAME/KEY: MISC_FEATURE
<222> LOCATION: (4)..(4)
<223> OTHER INFORMATION: The amino acid at the noted position is
      optionally phosphorylated

<400> SEQUENCE: 43

Arg Val Leu Ser Pro Leu Ile Ile Lys
1               5

<210> SEQ ID NO 44
<211> LENGTH: 9
<212> TYPE: PRT
<213> ORGANISM: Homo sapiens
```

```
<220> FEATURE:
<221> NAME/KEY: MISC_FEATURE
<222> LOCATION: (4)..(4)
<223> OTHER INFORMATION: The amino acid at the noted position is
      optionally phosphorylated

<400> SEQUENCE: 44

Arg Val Tyr Ser Pro Tyr Asn His Arg
1               5

<210> SEQ ID NO 45
<211> LENGTH: 9
<212> TYPE: PRT
<213> ORGANISM: Homo sapiens
<220> FEATURE:
<221> NAME/KEY: MISC_FEATURE
<222> LOCATION: (5)..(5)
<223> OTHER INFORMATION: The amino acid at the noted position is
      optionally phosphorylated

<400> SEQUENCE: 45

Ser Val Arg Arg Ser Val Leu Met Lys
1               5

<210> SEQ ID NO 46
<211> LENGTH: 9
<212> TYPE: PRT
<213> ORGANISM: Homo sapiens
<220> FEATURE:
<221> NAME/KEY: MISC_FEATURE
<222> LOCATION: (4)..(4)
<223> OTHER INFORMATION: The amino acid at the noted position is
      optionally phosphorylated

<400> SEQUENCE: 46

Lys Arg Ala Ser Val Phe Val Lys Leu
1               5

<210> SEQ ID NO 47
<211> LENGTH: 9
<212> TYPE: PRT
<213> ORGANISM: Homo sapiens
<220> FEATURE:
<221> NAME/KEY: MISC_FEATURE
<222> LOCATION: (4)..(4)
<223> OTHER INFORMATION: The amino acid at the noted position is
      optionally phosphorylated

<400> SEQUENCE: 47

Ser Val Lys Ser Pro Val Thr Val Lys
1               5

<210> SEQ ID NO 48
<211> LENGTH: 9
<212> TYPE: PRT
<213> ORGANISM: Homo sapiens
<220> FEATURE:
<221> NAME/KEY: MISC_FEATURE
<222> LOCATION: (8)..(8)
<223> OTHER INFORMATION: The amino acid at the noted position is
      optionally phosphorylated

<400> SEQUENCE: 48

Ile Asn Lys Glu Arg Arg Ser Ser Leu
1               5

<210> SEQ ID NO 49
<211> LENGTH: 9
<212> TYPE: PRT
```

```
<213> ORGANISM: Homo sapiens
<220> FEATURE:
<221> NAME/KEY: MISC_FEATURE
<222> LOCATION: (4)..(4)
<223> OTHER INFORMATION: The amino acid at the noted position is
      optionally phosphorylated

<400> SEQUENCE: 49

Ala Pro Asp Ser Pro Arg Ala Phe Leu
1               5

<210> SEQ ID NO 50
<211> LENGTH: 10
<212> TYPE: PRT
<213> ORGANISM: Homo sapiens
<220> FEATURE:
<221> NAME/KEY: MISC_FEATURE
<222> LOCATION: (9)..(9)
<223> OTHER INFORMATION: The amino acid at the noted position is
      optionally phosphorylated

<400> SEQUENCE: 50

Ala Pro Arg Asp Arg Arg Ala Val Ser Phe
1               5                   10

<210> SEQ ID NO 51
<211> LENGTH: 9
<212> TYPE: PRT
<213> ORGANISM: Homo sapiens
<220> FEATURE:
<221> NAME/KEY: MISC_FEATURE
<222> LOCATION: (6)..(6)
<223> OTHER INFORMATION: The amino acid at the noted position is
      optionally phosphorylated

<400> SEQUENCE: 51

Ala Pro Arg Arg Tyr Ser Ser Ser Leu
1               5

<210> SEQ ID NO 52
<211> LENGTH: 9
<212> TYPE: PRT
<213> ORGANISM: Homo sapiens
<220> FEATURE:
<221> NAME/KEY: MISC_FEATURE
<222> LOCATION: (4)..(4)
<223> OTHER INFORMATION: The amino acid at the noted position is
      optionally phosphorylated

<400> SEQUENCE: 52

Gly Pro Arg Ser Pro Lys Ala Pro Pro
1               5

<210> SEQ ID NO 53
<211> LENGTH: 11
<212> TYPE: PRT
<213> ORGANISM: Homo sapiens
<220> FEATURE:
<221> NAME/KEY: MISC_FEATURE
<222> LOCATION: (4)..(4)
<223> OTHER INFORMATION: The amino acid at the noted position is
      optionally phosphorylated

<400> SEQUENCE: 53

Lys Pro Ala Ser Pro Lys Phe Ile Val Thr Leu
1               5                   10

<210> SEQ ID NO 54
<211> LENGTH: 10
```

```
<212> TYPE: PRT
<213> ORGANISM: Homo sapiens
<220> FEATURE:
<221> NAME/KEY: MISC_FEATURE
<222> LOCATION: (4)..(4)
<223> OTHER INFORMATION: The amino acid at the noted position is
      optionally phosphorylated

<400> SEQUENCE: 54

Lys Pro Glu Ser Arg Arg Ser Ser Leu Leu
1               5                   10

<210> SEQ ID NO 55
<211> LENGTH: 9
<212> TYPE: PRT
<213> ORGANISM: Homo sapiens
<220> FEATURE:
<221> NAME/KEY: MISC_FEATURE
<222> LOCATION: (8)..(8)
<223> OTHER INFORMATION: The amino acid at the noted position is
      optionally phosphorylated

<400> SEQUENCE: 55

Lys Pro Arg Pro Pro Pro Leu Ser Pro
1               5

<210> SEQ ID NO 56
<211> LENGTH: 9
<212> TYPE: PRT
<213> ORGANISM: Homo sapiens
<220> FEATURE:
<221> NAME/KEY: MISC_FEATURE
<222> LOCATION: (4)..(4)
<223> OTHER INFORMATION: The amino acid at the noted position is
      optionally phosphorylated

<400> SEQUENCE: 56

Lys Pro Arg Ser Pro Phe Ser Lys Ile
1               5

<210> SEQ ID NO 57
<211> LENGTH: 9
<212> TYPE: PRT
<213> ORGANISM: Homo sapiens
<220> FEATURE:
<221> NAME/KEY: MISC_FEATURE
<222> LOCATION: (4)..(4)
<223> OTHER INFORMATION: The amino acid at the noted position is
      optionally phosphorylated

<400> SEQUENCE: 57

Lys Pro Arg Ser Pro Pro Arg Ala Leu
1               5

<210> SEQ ID NO 58
<211> LENGTH: 9
<212> TYPE: PRT
<213> ORGANISM: Homo sapiens
<220> FEATURE:
<221> NAME/KEY: MISC_FEATURE
<222> LOCATION: (4)..(4)
<223> OTHER INFORMATION: The amino acid at the noted position is
      optionally phosphorylated

<400> SEQUENCE: 58

Lys Pro Arg Ser Pro Val Val Glu Leu
1               5

<210> SEQ ID NO 59
```

```
<211> LENGTH: 9
<212> TYPE: PRT
<213> ORGANISM: Homo sapiens
<220> FEATURE:
<221> NAME/KEY: MISC_FEATURE
<222> LOCATION: (4)..(4)
<223> OTHER INFORMATION: The amino acid at the noted position is
      optionally phosphorylated

<400> SEQUENCE: 59

Leu Pro Ala Ser Pro Arg Ala Arg Leu
1               5

<210> SEQ ID NO 60
<211> LENGTH: 9
<212> TYPE: PRT
<213> ORGANISM: Homo sapiens
<220> FEATURE:
<221> NAME/KEY: MISC_FEATURE
<222> LOCATION: (8)..(8)
<223> OTHER INFORMATION: The amino acid at the noted position is
      optionally phosphorylated

<400> SEQUENCE: 60

Leu Pro Ile Phe Ser Arg Leu Ser Ile
1               5

<210> SEQ ID NO 61
<211> LENGTH: 9
<212> TYPE: PRT
<213> ORGANISM: Homo sapiens
<220> FEATURE:
<221> NAME/KEY: MISC_FEATURE
<222> LOCATION: (4)..(4)
<223> OTHER INFORMATION: The amino acid at the noted position is
      optionally phosphorylated

<400> SEQUENCE: 61

Leu Pro Val Ser Pro Arg Leu Gln Leu
1               5

<210> SEQ ID NO 62
<211> LENGTH: 10
<212> TYPE: PRT
<213> ORGANISM: Homo sapiens
<220> FEATURE:
<221> NAME/KEY: MISC_FEATURE
<222> LOCATION: (6)..(6)
<223> OTHER INFORMATION: The amino acid at the noted position is
      optionally phosphorylated

<400> SEQUENCE: 62

Met Pro Arg Gln Pro Ser Ala Thr Arg Leu
1               5                   10

<210> SEQ ID NO 63
<211> LENGTH: 9
<212> TYPE: PRT
<213> ORGANISM: Homo sapiens
<220> FEATURE:
<221> NAME/KEY: MISC_FEATURE
<222> LOCATION: (6)..(6)
<223> OTHER INFORMATION: The amino acid at the noted position is
      optionally phosphorylated

<400> SEQUENCE: 63

Gln Pro Gln Arg Arg Ser Leu Arg Leu
1               5
```

```
<210> SEQ ID NO 64
<211> LENGTH: 10
<212> TYPE: PRT
<213> ORGANISM: Homo sapiens
<220> FEATURE:
<221> NAME/KEY: MISC_FEATURE
<222> LOCATION: (6)..(6)
<223> OTHER INFORMATION: The amino acid at the noted position is
      optionally phosphorylated

<400> SEQUENCE: 64

Arg Ala Arg Gly Ile Ser Pro Ile Val Phe
1               5                   10

<210> SEQ ID NO 65
<211> LENGTH: 9
<212> TYPE: PRT
<213> ORGANISM: Homo sapiens
<220> FEATURE:
<221> NAME/KEY: MISC_FEATURE
<222> LOCATION: (4)..(4)
<223> OTHER INFORMATION: The amino acid at the noted position is
      optionally phosphorylated

<400> SEQUENCE: 65

Arg Pro Ala Ser Ala Gly Ala Met Leu
1               5

<210> SEQ ID NO 66
<211> LENGTH: 10
<212> TYPE: PRT
<213> ORGANISM: Homo sapiens
<220> FEATURE:
<221> NAME/KEY: MISC_FEATURE
<222> LOCATION: (4)..(4)
<223> OTHER INFORMATION: The amino acid at the noted position is
      optionally phosphorylated

<400> SEQUENCE: 66

Arg Pro Ala Ser Pro Gln Arg Ala Gln Leu
1               5                   10

<210> SEQ ID NO 67
<211> LENGTH: 9
<212> TYPE: PRT
<213> ORGANISM: Homo sapiens
<220> FEATURE:
<221> NAME/KEY: MISC_FEATURE
<222> LOCATION: (4)..(4)
<223> OTHER INFORMATION: The amino acid at the noted position is
      optionally phosphorylated

<400> SEQUENCE: 67

Arg Pro Asp Ser Ala His Lys Met Leu
1               5

<210> SEQ ID NO 68
<211> LENGTH: 10
<212> TYPE: PRT
<213> ORGANISM: Homo sapiens
<220> FEATURE:
<221> NAME/KEY: MISC_FEATURE
<222> LOCATION: (9)..(9)
<223> OTHER INFORMATION: The amino acid at the noted position is
      optionally phosphorylated

<400> SEQUENCE: 68

Arg Pro Asp Val Ala Lys Arg Leu Ser Leu
1               5                   10
```

```
<210> SEQ ID NO 69
<211> LENGTH: 11
<212> TYPE: PRT
<213> ORGANISM: Homo sapiens
<220> FEATURE:
<221> NAME/KEY: MISC_FEATURE
<222> LOCATION: (10)..(10)
<223> OTHER INFORMATION: The amino acid at the noted position is
      optionally phosphorylated

<400> SEQUENCE: 69

Arg Pro Phe His Gly Ile Ser Thr Val Ser Leu
1               5                   10

<210> SEQ ID NO 70
<211> LENGTH: 9
<212> TYPE: PRT
<213> ORGANISM: Homo sapiens
<220> FEATURE:
<221> NAME/KEY: MISC_FEATURE
<222> LOCATION: (4)..(4)
<223> OTHER INFORMATION: The amino acid at the noted position is
      optionally phosphorylated

<400> SEQUENCE: 70

Arg Pro Phe Ser Pro Arg Glu Ala Leu
1               5

<210> SEQ ID NO 71
<211> LENGTH: 9
<212> TYPE: PRT
<213> ORGANISM: Homo sapiens
<220> FEATURE:
<221> NAME/KEY: MISC_FEATURE
<222> LOCATION: (4)..(4)
<223> OTHER INFORMATION: The amino acid at the noted position is
      optionally phosphorylated

<400> SEQUENCE: 71

Arg Pro Gly Ser Arg Gln Ala Gly Leu
1               5

<210> SEQ ID NO 72
<211> LENGTH: 9
<212> TYPE: PRT
<213> ORGANISM: Homo sapiens
<220> FEATURE:
<221> NAME/KEY: MISC_FEATURE
<222> LOCATION: (4)..(4)
<223> OTHER INFORMATION: The amino acid at the noted position is
      optionally phosphorylated

<400> SEQUENCE: 72

Arg Pro Lys Ser Pro Leu Ser Lys Met
1               5

<210> SEQ ID NO 73
<211> LENGTH: 10
<212> TYPE: PRT
<213> ORGANISM: Homo sapiens
<220> FEATURE:
<221> NAME/KEY: MISC_FEATURE
<222> LOCATION: (4)..(4)
<223> OTHER INFORMATION: The amino acid at the noted position is
      optionally phosphorylated

<400> SEQUENCE: 73

Arg Pro Lys Ser Val Asp Phe Asp Ser Leu
1               5                   10
```

```
<210> SEQ ID NO 74
<211> LENGTH: 10
<212> TYPE: PRT
<213> ORGANISM: Homo sapiens
<220> FEATURE:
<221> NAME/KEY: MISC_FEATURE
<222> LOCATION: (7)..(7)
<223> OTHER INFORMATION: The amino acid at the noted position is
      optionally phosphorylated

<400> SEQUENCE: 74

Arg Pro Gln Arg Ala Thr Ser Asn Val Phe
1               5                   10

<210> SEQ ID NO 75
<211> LENGTH: 10
<212> TYPE: PRT
<213> ORGANISM: Homo sapiens
<220> FEATURE:
<221> NAME/KEY: MISC_FEATURE
<222> LOCATION: (6)..(6)
<223> OTHER INFORMATION: The amino acid at the noted position is
      optionally phosphorylated

<400> SEQUENCE: 75

Arg Pro Arg Ala Arg Ser Val Asp Ala Leu
1               5                   10

<210> SEQ ID NO 76
<211> LENGTH: 9
<212> TYPE: PRT
<213> ORGANISM: Homo sapiens
<220> FEATURE:
<221> NAME/KEY: MISC_FEATURE
<222> LOCATION: (5)..(5)
<223> OTHER INFORMATION: The amino acid at the noted position is
      optionally phosphorylated

<400> SEQUENCE: 76

Arg Pro Arg Gly Ser Gln Ser Leu Leu
1               5

<210> SEQ ID NO 77
<211> LENGTH: 10
<212> TYPE: PRT
<213> ORGANISM: Homo sapiens
<220> FEATURE:
<221> NAME/KEY: MISC_FEATURE
<222> LOCATION: (6)..(6)
<223> OTHER INFORMATION: The amino acid at the noted position is
      optionally phosphorylated

<400> SEQUENCE: 77

Arg Pro Arg Pro Val Ser Pro Ser Ser Leu
1               5                   10

<210> SEQ ID NO 78
<211> LENGTH: 8
<212> TYPE: PRT
<213> ORGANISM: Homo sapiens
<220> FEATURE:
<221> NAME/KEY: MISC_FEATURE
<222> LOCATION: (4)..(4)
<223> OTHER INFORMATION: The amino acid at the noted position is
      optionally phosphorylated

<400> SEQUENCE: 78

Arg Pro Arg Ser Ala Val Leu Leu
```

<210> SEQ ID NO 79
<211> LENGTH: 10
<212> TYPE: PRT
<213> ORGANISM: Homo sapiens
<220> FEATURE:
<221> NAME/KEY: MISC_FEATURE
<222> LOCATION: (4)..(4)
<223> OTHER INFORMATION: The amino acid at the noted position is
      optionally phosphorylated

<400> SEQUENCE: 79

Arg Pro Arg Ser Pro Asn Met Gln Asp Leu
1               5                   10

<210> SEQ ID NO 80
<211> LENGTH: 10
<212> TYPE: PRT
<213> ORGANISM: Homo sapiens
<220> FEATURE:
<221> NAME/KEY: MISC_FEATURE
<222> LOCATION: (4)..(4)
<223> OTHER INFORMATION: The amino acid at the noted position is
      optionally phosphorylated

<400> SEQUENCE: 80

Arg Pro Arg Ser Pro Arg Gln Asn Ser Ile
1               5                   10

<210> SEQ ID NO 81
<211> LENGTH: 10
<212> TYPE: PRT
<213> ORGANISM: Homo sapiens
<220> FEATURE:
<221> NAME/KEY: MISC_FEATURE
<222> LOCATION: (9)..(9)
<223> OTHER INFORMATION: The amino acid at the noted position is
      optionally phosphorylated

<400> SEQUENCE: 81

Arg Pro Thr Lys Ile Gly Arg Arg Ser Leu
1               5                   10

<210> SEQ ID NO 82
<211> LENGTH: 9
<212> TYPE: PRT
<213> ORGANISM: Homo sapiens
<220> FEATURE:
<221> NAME/KEY: MISC_FEATURE
<222> LOCATION: (4)..(4)
<223> OTHER INFORMATION: The amino acid at the noted position is
      optionally phosphorylated

<400> SEQUENCE: 82

Arg Pro Thr Ser Arg Leu Asn Arg Leu
1               5

<210> SEQ ID NO 83
<211> LENGTH: 9
<212> TYPE: PRT
<213> ORGANISM: Homo sapiens
<220> FEATURE:
<221> NAME/KEY: MISC_FEATURE
<222> LOCATION: (4)..(4)
<223> OTHER INFORMATION: The amino acid at the noted position is
      optionally phosphorylated

<400> SEQUENCE: 83

```
Arg Pro Val Thr Pro Val Ser Asp Leu
1               5

<210> SEQ ID NO 84
<211> LENGTH: 9
<212> TYPE: PRT
<213> ORGANISM: Homo sapiens
<220> FEATURE:
<221> NAME/KEY: MISC_FEATURE
<222> LOCATION: (8)..(8)
<223> OTHER INFORMATION: The amino acid at the noted position is
      optionally phosphorylated

<400> SEQUENCE: 84

Ser Pro Phe Lys Arg Gln Leu Ser Leu
1               5

<210> SEQ ID NO 85
<211> LENGTH: 11
<212> TYPE: PRT
<213> ORGANISM: Homo sapiens
<220> FEATURE:
<221> NAME/KEY: MISC_FEATURE
<222> LOCATION: (7)..(7)
<223> OTHER INFORMATION: The amino acid at the noted position is
      optionally phosphorylated

<400> SEQUENCE: 85

Ser Pro Arg Ala Pro Val Ser Pro Leu Lys Phe
1               5                   10

<210> SEQ ID NO 86
<211> LENGTH: 10
<212> TYPE: PRT
<213> ORGANISM: Homo sapiens
<220> FEATURE:
<221> NAME/KEY: MISC_FEATURE
<222> LOCATION: (5)..(5)
<223> OTHER INFORMATION: The amino acid at the noted position is
      optionally phosphorylated

<400> SEQUENCE: 86

Ser Pro Arg Arg Ser Arg Ser Ile Ser Leu
1               5                   10

<210> SEQ ID NO 87
<211> LENGTH: 9
<212> TYPE: PRT
<213> ORGANISM: Homo sapiens
<220> FEATURE:
<221> NAME/KEY: MISC_FEATURE
<222> LOCATION: (4)..(4)
<223> OTHER INFORMATION: The amino acid at the noted position is
      optionally phosphorylated

<400> SEQUENCE: 87

Ser Pro Arg Ser Pro Asp Arg Thr Leu
1               5

<210> SEQ ID NO 88
<211> LENGTH: 10
<212> TYPE: PRT
<213> ORGANISM: Homo sapiens
<220> FEATURE:
<221> NAME/KEY: MISC_FEATURE
<222> LOCATION: (6)..(6)
<223> OTHER INFORMATION: The amino acid at the noted position is
      optionally phosphorylated

<400> SEQUENCE: 88
```

```
Ser Pro Arg Ser Pro Ser Thr Thr Tyr Leu
1               5                   10

<210> SEQ ID NO 89
<211> LENGTH: 10
<212> TYPE: PRT
<213> ORGANISM: Homo sapiens
<220> FEATURE:
<221> NAME/KEY: MISC_FEATURE
<222> LOCATION: (4)..(4)
<223> OTHER INFORMATION: The amino acid at the noted position is
      optionally phosphorylated

<400> SEQUENCE: 89

Ser Pro Arg Ser Pro Ser Thr Thr Tyr Leu
1               5                   10

<210> SEQ ID NO 90
<211> LENGTH: 9
<212> TYPE: PRT
<213> ORGANISM: Homo sapiens
<220> FEATURE:
<221> NAME/KEY: MISC_FEATURE
<222> LOCATION: (4)..(4)
<223> OTHER INFORMATION: The amino acid at the noted position is
      optionally phosphorylated

<400> SEQUENCE: 90

Thr Pro Arg Ser Pro Pro Leu Gly Leu
1               5

<210> SEQ ID NO 91
<211> LENGTH: 10
<212> TYPE: PRT
<213> ORGANISM: Homo sapiens
<220> FEATURE:
<221> NAME/KEY: MISC_FEATURE
<222> LOCATION: (8)..(8)
<223> OTHER INFORMATION: The amino acid at the noted position is
      optionally phosphorylated

<400> SEQUENCE: 91

Val Pro Arg Pro Glu Arg Arg Ser Ser Leu
1               5                   10

<210> SEQ ID NO 92
<211> LENGTH: 10
<212> TYPE: PRT
<213> ORGANISM: Homo sapiens
<220> FEATURE:
<221> NAME/KEY: MISC_FEATURE
<222> LOCATION: (6)..(6)
<223> OTHER INFORMATION: The amino acid at the noted position is
      optionally phosphorylated

<400> SEQUENCE: 92

Ala Pro Arg Lys Gly Ser Phe Ser Ala Leu
1               5                   10

<210> SEQ ID NO 93
<211> LENGTH: 9
<212> TYPE: PRT
<213> ORGANISM: Homo sapiens
<220> FEATURE:
<221> NAME/KEY: MISC_FEATURE
<222> LOCATION: (8)..(8)
<223> OTHER INFORMATION: The amino acid at the noted position is
      optionally phosphorylated
```

```
<400> SEQUENCE: 93

Ala Val Arg Pro Thr Arg Leu Ser Leu
1               5

<210> SEQ ID NO 94
<211> LENGTH: 9
<212> TYPE: PRT
<213> ORGANISM: Homo sapiens
<220> FEATURE:
<221> NAME/KEY: MISC_FEATURE
<222> LOCATION: (6)..(6)
<223> OTHER INFORMATION: The amino acid at the noted position is
      optionally phosphorylated

<400> SEQUENCE: 94

Lys Pro Arg Pro Leu Ser Met Asp Leu
1               5

<210> SEQ ID NO 95
<211> LENGTH: 9
<212> TYPE: PRT
<213> ORGANISM: Homo sapiens
<220> FEATURE:
<221> NAME/KEY: MISC_FEATURE
<222> LOCATION: (6)..(6)
<223> OTHER INFORMATION: The amino acid at the noted position is
      optionally phosphorylated

<400> SEQUENCE: 95

Lys Pro Arg Arg Phe Ser Arg Ser Leu
1               5

<210> SEQ ID NO 96
<211> LENGTH: 9
<212> TYPE: PRT
<213> ORGANISM: Homo sapiens
<220> FEATURE:
<221> NAME/KEY: MISC_FEATURE
<222> LOCATION: (4)..(4)
<223> OTHER INFORMATION: The amino acid at the noted position is
      optionally phosphorylated

<400> SEQUENCE: 96

Leu Pro Arg Thr Pro Arg Pro Glu Leu
1               5

<210> SEQ ID NO 97
<211> LENGTH: 9
<212> TYPE: PRT
<213> ORGANISM: Homo sapiens
<220> FEATURE:
<221> NAME/KEY: MISC_FEATURE
<222> LOCATION: (4)..(4)
<223> OTHER INFORMATION: The amino acid at the noted position is
      optionally phosphorylated

<400> SEQUENCE: 97

Arg Pro Ala Ser Pro Ala Ala Lys Leu
1               5

<210> SEQ ID NO 98
<211> LENGTH: 10
<212> TYPE: PRT
<213> ORGANISM: Homo sapiens
<220> FEATURE:
<221> NAME/KEY: MISC_FEATURE
<222> LOCATION: (4)..(4)
<223> OTHER INFORMATION: The amino acid at the noted position is
      optionally phosphorylated
```

<400> SEQUENCE: 98

Arg Pro Asp Ser Pro Thr Arg Pro Thr Leu
1               5                   10

<210> SEQ ID NO 99
<211> LENGTH: 10
<212> TYPE: PRT
<213> ORGANISM: Homo sapiens
<220> FEATURE:
<221> NAME/KEY: MISC_FEATURE
<222> LOCATION: (4)..(4)
<223> OTHER INFORMATION: The amino acid at the noted position is
      optionally phosphorylated

<400> SEQUENCE: 99

Arg Pro Ile Ser Pro Arg Ile Gly Ala Leu
1               5                   10

<210> SEQ ID NO 100
<211> LENGTH: 8
<212> TYPE: PRT
<213> ORGANISM: Homo sapiens
<220> FEATURE:
<221> NAME/KEY: MISC_FEATURE
<222> LOCATION: (6)..(6)
<223> OTHER INFORMATION: The amino acid at the noted position is
      optionally phosphorylated

<400> SEQUENCE: 100

Arg Pro Arg Ala Ala Thr Val Val
1               5

<210> SEQ ID NO 101
<211> LENGTH: 9
<212> TYPE: PRT
<213> ORGANISM: Homo sapiens
<220> FEATURE:
<221> NAME/KEY: MISC_FEATURE
<222> LOCATION: (6)..(6)
<223> OTHER INFORMATION: The amino acid at the noted position is
      optionally phosphorylated

<400> SEQUENCE: 101

Arg Pro Arg Ala Ala Thr Val Val Ala
1               5

<210> SEQ ID NO 102
<211> LENGTH: 11
<212> TYPE: PRT
<213> ORGANISM: Homo sapiens
<220> FEATURE:
<221> NAME/KEY: MISC_FEATURE
<222> LOCATION: (6)..(6)
<223> OTHER INFORMATION: The amino acid at the noted position is
      optionally phosphorylated

<400> SEQUENCE: 102

Arg Pro Arg Ala Asn Ser Gly Gly Val Asp Leu
1               5                   10

<210> SEQ ID NO 103
<211> LENGTH: 9
<212> TYPE: PRT
<213> ORGANISM: Homo sapiens
<220> FEATURE:
<221> NAME/KEY: MISC_FEATURE
<222> LOCATION: (4)..(4)
<223> OTHER INFORMATION: The amino acid at the noted position is

```
      optionally phosphorylated

<400> SEQUENCE: 103

Arg Pro Arg Ser Ala Val Glu Gln Leu
1               5

<210> SEQ ID NO 104
<211> LENGTH: 9
<212> TYPE: PRT
<213> ORGANISM: Homo sapiens
<220> FEATURE:
<221> NAME/KEY: MISC_FEATURE
<222> LOCATION: (4)..(4)
<223> OTHER INFORMATION: The amino acid at the noted position is
      optionally phosphorylated

<400> SEQUENCE: 104

Arg Pro Arg Ser Met Thr Val Ser Ala
1               5

<210> SEQ ID NO 105
<211> LENGTH: 9
<212> TYPE: PRT
<213> ORGANISM: Homo sapiens
<220> FEATURE:
<221> NAME/KEY: MISC_FEATURE
<222> LOCATION: (4)..(4)
<223> OTHER INFORMATION: The amino acid at the noted position is
      optionally phosphorylated

<400> SEQUENCE: 105

Arg Pro Arg Ser Pro Pro Gly Gly Pro
1               5

<210> SEQ ID NO 106
<211> LENGTH: 12
<212> TYPE: PRT
<213> ORGANISM: Homo sapiens
<220> FEATURE:
<221> NAME/KEY: MISC_FEATURE
<222> LOCATION: (4)..(4)
<223> OTHER INFORMATION: The amino acid at the noted position is
      optionally phosphorylated

<400> SEQUENCE: 106

Arg Pro Arg Ser Pro Thr Gly Pro Ser Asn Ser Phe
1               5                   10

<210> SEQ ID NO 107
<211> LENGTH: 9
<212> TYPE: PRT
<213> ORGANISM: Homo sapiens
<220> FEATURE:
<221> NAME/KEY: MISC_FEATURE
<222> LOCATION: (4)..(4)
<223> OTHER INFORMATION: The amino acid at the noted position is
      optionally phosphorylated

<400> SEQUENCE: 107

Ser Pro Lys Ser Pro Gly Leu Lys Ala
1               5

<210> SEQ ID NO 108
<211> LENGTH: 9
<212> TYPE: PRT
<213> ORGANISM: Homo sapiens
<220> FEATURE:
<221> NAME/KEY: MISC_FEATURE
<222> LOCATION: (7)..(7)
```

```
<223> OTHER INFORMATION: The amino acid at the noted position is
      optionally phosphorylated

<400> SEQUENCE: 108

Tyr Pro Gly Gly Arg Arg Ser Ser Leu
1               5

<210> SEQ ID NO 109
<211> LENGTH: 9
<212> TYPE: PRT
<213> ORGANISM: Homo sapiens
<220> FEATURE:
<221> NAME/KEY: MISC_FEATURE
<222> LOCATION: (4)..(4)
<223> OTHER INFORMATION: The amino acid at the noted position is
      optionally phosphorylated

<400> SEQUENCE: 109

Lys Tyr Ile Ser Gly Pro His Glu Leu
1               5

<210> SEQ ID NO 110
<211> LENGTH: 9
<212> TYPE: PRT
<213> ORGANISM: Homo sapiens
<220> FEATURE:
<221> NAME/KEY: MISC_FEATURE
<222> LOCATION: (4)..(4)
<223> OTHER INFORMATION: The amino acid at the noted position is
      optionally phosphorylated

<400> SEQUENCE: 110

Arg Tyr Gln Thr Gln Pro Val Thr Leu
1               5

<210> SEQ ID NO 111
<211> LENGTH: 10
<212> TYPE: PRT
<213> ORGANISM: Homo sapiens
<220> FEATURE:
<221> NAME/KEY: MISC_FEATURE
<222> LOCATION: (4)..(4)
<223> OTHER INFORMATION: The amino acid at the noted position is
      optionally phosphorylated

<400> SEQUENCE: 111

Phe Arg Arg Ser Pro Thr Lys Ser Ser Leu
1               5                   10

<210> SEQ ID NO 112
<211> LENGTH: 12
<212> TYPE: PRT
<213> ORGANISM: Homo sapiens
<220> FEATURE:
<221> NAME/KEY: MISC_FEATURE
<222> LOCATION: (4)..(4)
<223> OTHER INFORMATION: The amino acid at the noted position is
      optionally phosphorylated

<400> SEQUENCE: 112

Phe Arg Arg Ser Pro Thr Lys Ser Ser Leu Asp Tyr
1               5                   10

<210> SEQ ID NO 113
<211> LENGTH: 9
<212> TYPE: PRT
<213> ORGANISM: Homo sapiens
<220> FEATURE:
<221> NAME/KEY: MISC_FEATURE
```

```
<222> LOCATION: (4)..(4)
<223> OTHER INFORMATION: The amino acid at the noted position is
      optionally phosphorylated

<400> SEQUENCE: 113

Gly Arg Lys Ser Pro Pro Pro Ser Phe
1               5

<210> SEQ ID NO 114
<211> LENGTH: 9
<212> TYPE: PRT
<213> ORGANISM: Homo sapiens
<220> FEATURE:
<221> NAME/KEY: MISC_FEATURE
<222> LOCATION: (4)..(4)
<223> OTHER INFORMATION: The amino acid at the noted position is
      optionally phosphorylated

<400> SEQUENCE: 114

Gly Arg Leu Ser Pro Ala Tyr Ser Leu
1               5

<210> SEQ ID NO 115
<211> LENGTH: 10
<212> TYPE: PRT
<213> ORGANISM: Homo sapiens
<220> FEATURE:
<221> NAME/KEY: MISC_FEATURE
<222> LOCATION: (4)..(4)
<223> OTHER INFORMATION: The amino acid at the noted position is
      optionally phosphorylated

<400> SEQUENCE: 115

Gly Arg Leu Ser Pro Val Pro Val Pro Arg
1               5                   10

<210> SEQ ID NO 116
<211> LENGTH: 10
<212> TYPE: PRT
<213> ORGANISM: Homo sapiens
<220> FEATURE:
<221> NAME/KEY: MISC_FEATURE
<222> LOCATION: (4)..(4)
<223> OTHER INFORMATION: The amino acid at the noted position is
      optionally phosphorylated

<400> SEQUENCE: 116

His Arg Leu Ser Pro Val Lys Gly Glu Phe
1               5                   10

<210> SEQ ID NO 117
<211> LENGTH: 9
<212> TYPE: PRT
<213> ORGANISM: Homo sapiens
<220> FEATURE:
<221> NAME/KEY: MISC_FEATURE
<222> LOCATION: (4)..(4)
<223> OTHER INFORMATION: The amino acid at the noted position is
      optionally phosphorylated

<400> SEQUENCE: 117

His Arg Asn Ser Met Lys Val Phe Leu
1               5

<210> SEQ ID NO 118
<211> LENGTH: 9
<212> TYPE: PRT
<213> ORGANISM: Homo sapiens
<220> FEATURE:
```

```
<221> NAME/KEY: MISC_FEATURE
<222> LOCATION: (4)..(4)
<223> OTHER INFORMATION: The amino acid at the noted position is
      optionally phosphorylated

<400> SEQUENCE: 118

Lys Arg Phe Ser Phe Lys Lys Ser Phe
1               5

<210> SEQ ID NO 119
<211> LENGTH: 9
<212> TYPE: PRT
<213> ORGANISM: Homo sapiens
<220> FEATURE:
<221> NAME/KEY: MISC_FEATURE
<222> LOCATION: (4)..(4)
<223> OTHER INFORMATION: The amino acid at the noted position is
      optionally phosphorylated

<400> SEQUENCE: 119

Lys Arg Phe Ser Phe Lys Lys Ser Phe
1               5

<210> SEQ ID NO 120
<211> LENGTH: 9
<212> TYPE: PRT
<213> ORGANISM: Homo sapiens
<220> FEATURE:
<221> NAME/KEY: MISC_FEATURE
<222> LOCATION: (4)..(4)
<223> OTHER INFORMATION: The amino acid at the noted position is
      optionally phosphorylated

<400> SEQUENCE: 120

Lys Arg Phe Ser Gly Thr Val Arg Leu
1               5

<210> SEQ ID NO 121
<211> LENGTH: 9
<212> TYPE: PRT
<213> ORGANISM: Homo sapiens
<220> FEATURE:
<221> NAME/KEY: MISC_FEATURE
<222> LOCATION: (4)..(4)
<223> OTHER INFORMATION: The amino acid at the noted position is
      optionally phosphorylated

<400> SEQUENCE: 121

Lys Arg Leu Ser Pro Ala Pro Gln Leu
1               5

<210> SEQ ID NO 122
<211> LENGTH: 9
<212> TYPE: PRT
<213> ORGANISM: Homo sapiens
<220> FEATURE:
<221> NAME/KEY: MISC_FEATURE
<222> LOCATION: (4)..(4)
<223> OTHER INFORMATION: The amino acid at the noted position is
      optionally phosphorylated

<400> SEQUENCE: 122

Lys Arg Leu Ser Val Glu Arg Ile Tyr
1               5

<210> SEQ ID NO 123
<211> LENGTH: 9
<212> TYPE: PRT
<213> ORGANISM: Homo sapiens
```

```
<220> FEATURE:
<221> NAME/KEY: MISC_FEATURE
<222> LOCATION: (4)..(4)
<223> OTHER INFORMATION: The amino acid at the noted position is
      optionally phosphorylated

<400> SEQUENCE: 123

Lys Arg Met Ser Pro Lys Pro Glu Leu
1               5

<210> SEQ ID NO 124
<211> LENGTH: 9
<212> TYPE: PRT
<213> ORGANISM: Homo sapiens
<220> FEATURE:
<221> NAME/KEY: MISC_FEATURE
<222> LOCATION: (4)..(4)
<223> OTHER INFORMATION: The amino acid at the noted position is
      optionally phosphorylated

<400> SEQUENCE: 124

Lys Arg Tyr Ser Gly Asn Met Glu Tyr
1               5

<210> SEQ ID NO 125
<211> LENGTH: 10
<212> TYPE: PRT
<213> ORGANISM: Homo sapiens
<220> FEATURE:
<221> NAME/KEY: MISC_FEATURE
<222> LOCATION: (4)..(4)
<223> OTHER INFORMATION: The amino acid at the noted position is
      optionally phosphorylated

<400> SEQUENCE: 125

Arg Arg Ala Ser Leu Ser Glu Ile Gly Phe
1               5                   10

<210> SEQ ID NO 126
<211> LENGTH: 9
<212> TYPE: PRT
<213> ORGANISM: Homo sapiens
<220> FEATURE:
<221> NAME/KEY: MISC_FEATURE
<222> LOCATION: (4)..(4)
<223> OTHER INFORMATION: The amino acid at the noted position is
      optionally phosphorylated

<400> SEQUENCE: 126

Arg Arg Ala Ser Gln Glu Ala Asn Leu
1               5

<210> SEQ ID NO 127
<211> LENGTH: 9
<212> TYPE: PRT
<213> ORGANISM: Homo sapiens
<220> FEATURE:
<221> NAME/KEY: MISC_FEATURE
<222> LOCATION: (4)..(4)
<223> OTHER INFORMATION: The amino acid at the noted position is
      optionally phosphorylated

<400> SEQUENCE: 127

Arg Arg Asp Ser Ile Val Ala Glu Leu
1               5

<210> SEQ ID NO 128
<211> LENGTH: 10
<212> TYPE: PRT
```

```
<213> ORGANISM: Homo sapiens
<220> FEATURE:
<221> NAME/KEY: MISC_FEATURE
<222> LOCATION: (4)..(4)
<223> OTHER INFORMATION: The amino acid at the noted position is
      optionally phosphorylated

<400> SEQUENCE: 128

Arg Arg Asp Ser Leu Gln Lys Pro Gly Leu
1               5                   10

<210> SEQ ID NO 129
<211> LENGTH: 9
<212> TYPE: PRT
<213> ORGANISM: Homo sapiens
<220> FEATURE:
<221> NAME/KEY: MISC_FEATURE
<222> LOCATION: (4)..(4)
<223> OTHER INFORMATION: The amino acid at the noted position is
      optionally phosphorylated

<400> SEQUENCE: 129

Arg Arg Phe Ser Gly Thr Ala Val Tyr
1               5

<210> SEQ ID NO 130
<211> LENGTH: 9
<212> TYPE: PRT
<213> ORGANISM: Homo sapiens
<220> FEATURE:
<221> NAME/KEY: MISC_FEATURE
<222> LOCATION: (4)..(4)
<223> OTHER INFORMATION: The amino acid at the noted position is
      optionally phosphorylated

<400> SEQUENCE: 130

Arg Arg Phe Ser Pro Pro Arg Arg Met
1               5

<210> SEQ ID NO 131
<211> LENGTH: 10
<212> TYPE: PRT
<213> ORGANISM: Homo sapiens
<220> FEATURE:
<221> NAME/KEY: MISC_FEATURE
<222> LOCATION: (4)..(4)
<223> OTHER INFORMATION: The amino acid at the noted position is
      optionally phosphorylated

<400> SEQUENCE: 131

Arg Arg Phe Ser Arg Leu Glu Asn Arg Tyr
1               5                   10

<210> SEQ ID NO 132
<211> LENGTH: 9
<212> TYPE: PRT
<213> ORGANISM: Homo sapiens
<220> FEATURE:
<221> NAME/KEY: MISC_FEATURE
<222> LOCATION: (4)..(4)
<223> OTHER INFORMATION: The amino acid at the noted position is
      optionally phosphorylated

<400> SEQUENCE: 132

Arg Arg Gly Ser Phe Glu Val Thr Leu
1               5

<210> SEQ ID NO 133
<211> LENGTH: 10
```

```
<212> TYPE: PRT
<213> ORGANISM: Homo sapiens
<220> FEATURE:
<221> NAME/KEY: MISC_FEATURE
<222> LOCATION: (6)..(6)
<223> OTHER INFORMATION: The amino acid at the noted position is
      optionally phosphorylated

<400> SEQUENCE: 133

Arg Arg Ile Asp Ile Ser Pro Ser Thr Phe
1               5                   10

<210> SEQ ID NO 134
<211> LENGTH: 11
<212> TYPE: PRT
<213> ORGANISM: Homo sapiens
<220> FEATURE:
<221> NAME/KEY: MISC_FEATURE
<222> LOCATION: (6)..(6)
<223> OTHER INFORMATION: The amino acid at the noted position is
      optionally phosphorylated

<400> SEQUENCE: 134

Arg Arg Ile Asp Ile Ser Pro Ser Thr Leu Arg
1               5                   10

<210> SEQ ID NO 135
<211> LENGTH: 9
<212> TYPE: PRT
<213> ORGANISM: Homo sapiens
<220> FEATURE:
<221> NAME/KEY: MISC_FEATURE
<222> LOCATION: (4)..(4)
<223> OTHER INFORMATION: The amino acid at the noted position is
      optionally phosphorylated

<400> SEQUENCE: 135

Arg Arg Ile Ser Asp Pro Gln Val Phe
1               5

<210> SEQ ID NO 136
<211> LENGTH: 9
<212> TYPE: PRT
<213> ORGANISM: Homo sapiens
<220> FEATURE:
<221> NAME/KEY: MISC_FEATURE
<222> LOCATION: (4)..(4)
<223> OTHER INFORMATION: The amino acid at the noted position is
      optionally phosphorylated

<400> SEQUENCE: 136

Arg Arg Ile Ser Gly Val Asp Arg Tyr
1               5

<210> SEQ ID NO 137
<211> LENGTH: 10
<212> TYPE: PRT
<213> ORGANISM: Homo sapiens
<220> FEATURE:
<221> NAME/KEY: MISC_FEATURE
<222> LOCATION: (4)..(4)
<223> OTHER INFORMATION: The amino acid at the noted position is
      optionally phosphorylated

<400> SEQUENCE: 137

Arg Arg Ile Ser Gly Val Asp Arg Tyr Tyr
1               5                   10

<210> SEQ ID NO 138
```

```
<211> LENGTH: 9
<212> TYPE: PRT
<213> ORGANISM: Homo sapiens
<220> FEATURE:
<221> NAME/KEY: MISC_FEATURE
<222> LOCATION: (4)..(4)
<223> OTHER INFORMATION: The amino acid at the noted position is
      optionally phosphorylated

<400> SEQUENCE: 138

Arg Arg Lys Ser Gln Val Ala Glu Leu
1               5

<210> SEQ ID NO 139
<211> LENGTH: 9
<212> TYPE: PRT
<213> ORGANISM: Homo sapiens
<220> FEATURE:
<221> NAME/KEY: MISC_FEATURE
<222> LOCATION: (4)..(4)
<223> OTHER INFORMATION: The amino acid at the noted position is
      optionally phosphorylated

<400> SEQUENCE: 139

Arg Arg Leu Ser Ala Asp Ile Arg Leu
1               5

<210> SEQ ID NO 140
<211> LENGTH: 9
<212> TYPE: PRT
<213> ORGANISM: Homo sapiens
<220> FEATURE:
<221> NAME/KEY: MISC_FEATURE
<222> LOCATION: (4)..(4)
<223> OTHER INFORMATION: The amino acid at the noted position is
      optionally phosphorylated

<400> SEQUENCE: 140

Arg Arg Leu Ser Asp Ser Pro Val Phe
1               5

<210> SEQ ID NO 141
<211> LENGTH: 9
<212> TYPE: PRT
<213> ORGANISM: Homo sapiens
<220> FEATURE:
<221> NAME/KEY: MISC_FEATURE
<222> LOCATION: (4)..(4)
<223> OTHER INFORMATION: The amino acid at the noted position is
      optionally phosphorylated

<400> SEQUENCE: 141

Arg Arg Leu Ser Glu Ser Ser Ala Leu
1               5

<210> SEQ ID NO 142
<211> LENGTH: 10
<212> TYPE: PRT
<213> ORGANISM: Homo sapiens
<220> FEATURE:
<221> NAME/KEY: MISC_FEATURE
<222> LOCATION: (4)..(4)
<223> OTHER INFORMATION: The amino acid at the noted position is
      optionally phosphorylated

<400> SEQUENCE: 142

Arg Arg Leu Ser Gly Pro Leu His Thr Leu
1               5                   10
```

```
<210> SEQ ID NO 143
<211> LENGTH: 9
<212> TYPE: PRT
<213> ORGANISM: Homo sapiens
<220> FEATURE:
<221> NAME/KEY: MISC_FEATURE
<222> LOCATION: (4)..(4)
<223> OTHER INFORMATION: The amino acid at the noted position is
      optionally phosphorylated

<400> SEQUENCE: 143

Arg Arg Leu Ser Leu Phe Leu Asn Val
1               5

<210> SEQ ID NO 144
<211> LENGTH: 8
<212> TYPE: PRT
<213> ORGANISM: Homo sapiens
<220> FEATURE:
<221> NAME/KEY: MISC_FEATURE
<222> LOCATION: (4)..(4)
<223> OTHER INFORMATION: The amino acid at the noted position is
      optionally phosphorylated

<400> SEQUENCE: 144

Arg Arg Met Ser Phe Gln Lys Pro
1               5

<210> SEQ ID NO 145
<211> LENGTH: 9
<212> TYPE: PRT
<213> ORGANISM: Homo sapiens
<220> FEATURE:
<221> NAME/KEY: MISC_FEATURE
<222> LOCATION: (4)..(4)
<223> OTHER INFORMATION: The amino acid at the noted position is
      optionally phosphorylated

<400> SEQUENCE: 145

Arg Arg Met Ser Leu Leu Ser Val Val
1               5

<210> SEQ ID NO 146
<211> LENGTH: 9
<212> TYPE: PRT
<213> ORGANISM: Homo sapiens
<220> FEATURE:
<221> NAME/KEY: MISC_FEATURE
<222> LOCATION: (4)..(4)
<223> OTHER INFORMATION: The amino acid at the noted position is
      optionally phosphorylated

<400> SEQUENCE: 146

Arg Arg Asn Ser Ala Pro Val Ser Val
1               5

<210> SEQ ID NO 147
<211> LENGTH: 9
<212> TYPE: PRT
<213> ORGANISM: Homo sapiens
<220> FEATURE:
<221> NAME/KEY: MISC_FEATURE
<222> LOCATION: (4)..(4)
<223> OTHER INFORMATION: The amino acid at the noted position is
      optionally phosphorylated

<400> SEQUENCE: 147

Arg Arg Asn Ser Ile Asn Arg Asn Phe
1               5
```

<210> SEQ ID NO 148
<211> LENGTH: 9
<212> TYPE: PRT
<213> ORGANISM: Homo sapiens
<220> FEATURE:
<221> NAME/KEY: MISC_FEATURE
<222> LOCATION: (4)..(4)
<223> OTHER INFORMATION: The amino acid at the noted position is
      optionally phosphorylated

<400> SEQUENCE: 148

Arg Arg Pro Ser Leu Leu Ser Glu Phe
1               5

<210> SEQ ID NO 149
<211> LENGTH: 9
<212> TYPE: PRT
<213> ORGANISM: Homo sapiens
<220> FEATURE:
<221> NAME/KEY: MISC_FEATURE
<222> LOCATION: (4)..(4)
<223> OTHER INFORMATION: The amino acid at the noted position is
      optionally phosphorylated

<400> SEQUENCE: 149

Arg Arg Gln Ser Lys Val Glu Ala Leu
1               5

<210> SEQ ID NO 150
<211> LENGTH: 9
<212> TYPE: PRT
<213> ORGANISM: Homo sapiens
<220> FEATURE:
<221> NAME/KEY: MISC_FEATURE
<222> LOCATION: (4)..(4)
<223> OTHER INFORMATION: The amino acid at the noted position is
      optionally phosphorylated

<400> SEQUENCE: 150

Arg Arg Leu Ser Glu Leu Leu Arg Tyr
1               5

<210> SEQ ID NO 151
<211> LENGTH: 9
<212> TYPE: PRT
<213> ORGANISM: Homo sapiens
<220> FEATURE:
<221> NAME/KEY: MISC_FEATURE
<222> LOCATION: (4)..(4)
<223> OTHER INFORMATION: The amino acid at the noted position is
      optionally phosphorylated

<400> SEQUENCE: 151

Arg Arg Leu Ser Phe Leu Val Ser Tyr
1               5

<210> SEQ ID NO 152
<211> LENGTH: 9
<212> TYPE: PRT
<213> ORGANISM: Homo sapiens
<220> FEATURE:
<221> NAME/KEY: MISC_FEATURE
<222> LOCATION: (4)..(4)
<223> OTHER INFORMATION: The amino acid at the noted position is
      optionally phosphorylated

<400> SEQUENCE: 152

Arg Arg Ser Ser Phe Leu Gln Val Phe
1               5

```
<210> SEQ ID NO 153
<211> LENGTH: 9
<212> TYPE: PRT
<213> ORGANISM: Homo sapiens
<220> FEATURE:
<221> NAME/KEY: MISC_FEATURE
<222> LOCATION: (4)..(4)
<223> OTHER INFORMATION: The amino acid at the noted position is
      optionally phosphorylated

<400> SEQUENCE: 153

Arg Arg Ser Ser Ile Gln Ser Thr Phe
1               5

<210> SEQ ID NO 154
<211> LENGTH: 9
<212> TYPE: PRT
<213> ORGANISM: Homo sapiens
<220> FEATURE:
<221> NAME/KEY: MISC_FEATURE
<222> LOCATION: (3)..(3)
<223> OTHER INFORMATION: The amino acid at the noted position is
      optionally phosphorylated

<400> SEQUENCE: 154

Arg Arg Ser Ser Ile Gln Ser Thr Phe
1               5

<210> SEQ ID NO 155
<211> LENGTH: 9
<212> TYPE: PRT
<213> ORGANISM: Homo sapiens
<220> FEATURE:
<221> NAME/KEY: MISC_FEATURE
<222> LOCATION: (4)..(4)
<223> OTHER INFORMATION: The amino acid at the noted position is
      optionally phosphorylated

<400> SEQUENCE: 155

Arg Arg Ser Ser Ser Val Ala Gln Val
1               5

<210> SEQ ID NO 156
<211> LENGTH: 8
<212> TYPE: PRT
<213> ORGANISM: Homo sapiens
<220> FEATURE:
<221> NAME/KEY: MISC_FEATURE
<222> LOCATION: (4)..(4)
<223> OTHER INFORMATION: The amino acid at the noted position is
      optionally phosphorylated

<400> SEQUENCE: 156

Arg Arg Tyr Ser Pro Pro Ile Gln
1               5

<210> SEQ ID NO 157
<211> LENGTH: 9
<212> TYPE: PRT
<213> ORGANISM: Homo sapiens
<220> FEATURE:
<221> NAME/KEY: MISC_FEATURE
<222> LOCATION: (4)..(4)
<223> OTHER INFORMATION: The amino acid at the noted position is
      optionally phosphorylated

<400> SEQUENCE: 157

Val Arg Ala Ser Lys Asp Leu Ala Gln
```

<210> SEQ ID NO 158
<211> LENGTH: 9
<212> TYPE: PRT
<213> ORGANISM: Homo sapiens
<220> FEATURE:
<221> NAME/KEY: MISC_FEATURE
<222> LOCATION: (6)..(6)
<223> OTHER INFORMATION: The amino acid at the noted position is
      optionally phosphorylated

<400> SEQUENCE: 158

Lys Arg Leu Glu Lys Ser Pro Ser Phe
1               5

<210> SEQ ID NO 159
<211> LENGTH: 9
<212> TYPE: PRT
<213> ORGANISM: Homo sapiens
<220> FEATURE:
<221> NAME/KEY: MISC_FEATURE
<222> LOCATION: (8)..(8)
<223> OTHER INFORMATION: The amino acid at the noted position is
      optionally phosphorylated

<400> SEQUENCE: 159

Lys Arg Leu Glu Lys Ser Pro Ser Phe
1               5

<210> SEQ ID NO 160
<211> LENGTH: 9
<212> TYPE: PRT
<213> ORGANISM: Homo sapiens
<220> FEATURE:
<221> NAME/KEY: MISC_FEATURE
<222> LOCATION: (5)..(5)
<223> OTHER INFORMATION: The amino acid at the noted position is
      optionally phosphorylated

<400> SEQUENCE: 160

Lys Arg Trp Gln Ser Pro Val Thr Lys
1               5

<210> SEQ ID NO 161
<211> LENGTH: 9
<212> TYPE: PRT
<213> ORGANISM: Homo sapiens
<220> FEATURE:
<221> NAME/KEY: MISC_FEATURE
<222> LOCATION: (4)..(4)
<223> OTHER INFORMATION: The amino acid at the noted position is
      optionally phosphorylated

<400> SEQUENCE: 161

Arg Arg Phe Ser Ile Ala Thr Leu Arg
1               5

<210> SEQ ID NO 162
<211> LENGTH: 9
<212> TYPE: PRT
<213> ORGANISM: Homo sapiens
<220> FEATURE:
<221> NAME/KEY: MISC_FEATURE
<222> LOCATION: (4)..(4)
<223> OTHER INFORMATION: The amino acid at the noted position is
      optionally phosphorylated

<400> SEQUENCE: 162

```
Arg Arg Phe Ser Leu Thr Thr Leu Arg
1               5
```

<210> SEQ ID NO 163
<211> LENGTH: 9
<212> TYPE: PRT
<213> ORGANISM: Homo sapiens
<220> FEATURE:
<221> NAME/KEY: MISC_FEATURE
<222> LOCATION: (4)..(4)
<223> OTHER INFORMATION: The amino acid at the noted position is
      optionally phosphorylated

<400> SEQUENCE: 163

```
Arg Arg Phe Ser Arg Ser Pro Ile Arg
1               5
```

<210> SEQ ID NO 164
<211> LENGTH: 9
<212> TYPE: PRT
<213> ORGANISM: Homo sapiens
<220> FEATURE:
<221> NAME/KEY: MISC_FEATURE
<222> LOCATION: (4)..(4)
<223> OTHER INFORMATION: The amino acid at the noted position is
      optionally phosphorylated

<400> SEQUENCE: 164

```
Arg Arg Phe Ser Val Ser Thr Leu Arg
1               5
```

<210> SEQ ID NO 165
<211> LENGTH: 9
<212> TYPE: PRT
<213> ORGANISM: Homo sapiens
<220> FEATURE:
<221> NAME/KEY: MISC_FEATURE
<222> LOCATION: (4)..(4)
<223> OTHER INFORMATION: The amino acid at the noted position is
      optionally phosphorylated

<400> SEQUENCE: 165

```
Arg Arg Phe Ser Val Thr Thr Met Arg
1               5
```

<210> SEQ ID NO 166
<211> LENGTH: 9
<212> TYPE: PRT
<213> ORGANISM: Homo sapiens
<220> FEATURE:
<221> NAME/KEY: MISC_FEATURE
<222> LOCATION: (8)..(8)
<223> OTHER INFORMATION: The amino acid at the noted position is
      optionally phosphorylated

<400> SEQUENCE: 166

```
Arg Arg Val Val Gln Arg Ser Ser Leu
1               5
```

<210> SEQ ID NO 167
<211> LENGTH: 9
<212> TYPE: PRT
<213> ORGANISM: Artificial Sequence
<220> FEATURE:
<223> OTHER INFORMATION: Artificially synthesized peptide
<220> FEATURE:
<221> NAME/KEY: MISC_FEATURE
<222> LOCATION: (4)..(4)
<223> OTHER INFORMATION: The amino acid at the noted position is
      optionally phosphorylated

```
<400> SEQUENCE: 167

Arg Arg Tyr Ser Pro Pro Ile Glu Arg
1               5

<210> SEQ ID NO 168
<211> LENGTH: 9
<212> TYPE: PRT
<213> ORGANISM: Homo sapiens
<220> FEATURE:
<221> NAME/KEY: MISC_FEATURE
<222> LOCATION: (4)..(4)
<223> OTHER INFORMATION: The amino acid at the noted position is
      optionally phosphorylated

<400> SEQUENCE: 168

Arg Arg Tyr Ser Pro Pro Ile Gln Arg
1               5

<210> SEQ ID NO 169
<211> LENGTH: 10
<212> TYPE: PRT
<213> ORGANISM: Homo sapiens
<220> FEATURE:
<221> NAME/KEY: MISC_FEATURE
<222> LOCATION: (4)..(4)
<223> OTHER INFORMATION: The amino acid at the noted position is
      optionally phosphorylated

<400> SEQUENCE: 169

Ala Glu Asn Ser Pro Thr Arg Gln Gln Phe
1               5                   10

<210> SEQ ID NO 170
<211> LENGTH: 9
<212> TYPE: PRT
<213> ORGANISM: Homo sapiens
<220> FEATURE:
<221> NAME/KEY: MISC_FEATURE
<222> LOCATION: (4)..(4)
<223> OTHER INFORMATION: The amino acid at the noted position is
      optionally phosphorylated

<400> SEQUENCE: 170

Glu Glu Leu Ser Pro Thr Lys Ala Phe
1               5

<210> SEQ ID NO 171
<211> LENGTH: 9
<212> TYPE: PRT
<213> ORGANISM: Homo sapiens
<220> FEATURE:
<221> NAME/KEY: MISC_FEATURE
<222> LOCATION: (4)..(4)
<223> OTHER INFORMATION: The amino acid at the noted position is
      optionally phosphorylated

<400> SEQUENCE: 171

Lys Glu Met Ser Pro Thr Arg Gln Leu
1               5

<210> SEQ ID NO 172
<211> LENGTH: 9
<212> TYPE: PRT
<213> ORGANISM: Homo sapiens
<220> FEATURE:
<221> NAME/KEY: MISC_FEATURE
<222> LOCATION: (4)..(4)
<223> OTHER INFORMATION: The amino acid at the noted position is
```

```
      optionally phosphorylated

<400> SEQUENCE: 172

Arg Phe Lys Thr Gln Pro Val Thr Phe
1               5

<210> SEQ ID NO 173
<211> LENGTH: 9
<212> TYPE: PRT
<213> ORGANISM: Homo sapiens
<220> FEATURE:
<221> NAME/KEY: MISC_FEATURE
<222> LOCATION: (5)..(5)
<223> OTHER INFORMATION: The amino acid at the noted position is
      optionally phosphorylated

<400> SEQUENCE: 173

Glu Glu Arg Arg Ser Pro Pro Ala Pro
1               5

<210> SEQ ID NO 174
<211> LENGTH: 10
<212> TYPE: PRT
<213> ORGANISM: Homo sapiens
<220> FEATURE:
<221> NAME/KEY: MISC_FEATURE
<222> LOCATION: (6)..(6)
<223> OTHER INFORMATION: The amino acid at the noted position is
      optionally phosphorylated

<400> SEQUENCE: 174

Phe Glu Asp Asp Asp Ser Asn Glu Lys Leu
1               5                   10

<210> SEQ ID NO 175
<211> LENGTH: 9
<212> TYPE: PRT
<213> ORGANISM: Homo sapiens
<220> FEATURE:
<221> NAME/KEY: MISC_FEATURE
<222> LOCATION: (2)..(2)
<223> OTHER INFORMATION: The amino acid at the noted position is
      optionally phosphorylated

<400> SEQUENCE: 175

Lys Ser Leu Val Arg Leu Leu Leu Leu
1               5

<210> SEQ ID NO 176
<211> LENGTH: 9
<212> TYPE: PRT
<213> ORGANISM: Homo sapiens
<220> FEATURE:
<221> NAME/KEY: MISC_FEATURE
<222> LOCATION: (4)..(4)
<223> OTHER INFORMATION: The amino acid at the noted position is
      optionally phosphorylated

<400> SEQUENCE: 176

Arg Thr His Ser Leu Leu Leu Leu Leu
1               5

<210> SEQ ID NO 177
<211> LENGTH: 9
<212> TYPE: PRT
<213> ORGANISM: Homo sapiens
<220> FEATURE:
<221> NAME/KEY: MISC_FEATURE
<222> LOCATION: (6)..(6)
```

<223> OTHER INFORMATION: The amino acid at the noted position is
      optionally phosphorylated

<400> SEQUENCE: 177

Arg Thr Ser Ser Phe Thr Phe Gln Asn
1               5

<210> SEQ ID NO 178
<211> LENGTH: 9
<212> TYPE: PRT
<213> ORGANISM: Homo sapiens

<400> SEQUENCE: 178

Tyr Leu Glu Pro Gly Pro Val Thr Ala
1               5

<210> SEQ ID NO 179
<211> LENGTH: 10
<212> TYPE: PRT
<213> ORGANISM: Homo sapiens

<400> SEQUENCE: 179

Asp Tyr Met Asp Gly Thr Met Ser Gln Val
1               5                   10

<210> SEQ ID NO 180
<211> LENGTH: 9
<212> TYPE: PRT
<213> ORGANISM: Homo sapiens

<400> SEQUENCE: 180

Ala Leu Leu Ala Val Gly Ala Thr Lys
1               5

<210> SEQ ID NO 181
<211> LENGTH: 9
<212> TYPE: PRT
<213> ORGANISM: Homo sapiens

<400> SEQUENCE: 181

Lys Cys Asp Ile Cys Thr Asp Glu Tyr
1               5

<210> SEQ ID NO 182
<211> LENGTH: 9
<212> TYPE: PRT
<213> ORGANISM: Homo sapiens

<400> SEQUENCE: 182

Arg Leu Ser Asn Arg Leu Leu Leu Arg
1               5

<210> SEQ ID NO 183
<211> LENGTH: 9
<212> TYPE: PRT
<213> ORGANISM: Homo sapiens

<400> SEQUENCE: 183

Ser Gln Asn Phe Pro Gly Ser Gln Lys
1               5

<210> SEQ ID NO 184
<211> LENGTH: 9
<212> TYPE: PRT
<213> ORGANISM: Homo sapiens

<400> SEQUENCE: 184

Lys Thr Trp Gly Gln Tyr Trp Gln Val
1               5

<210> SEQ ID NO 185
<211> LENGTH: 9
<212> TYPE: PRT
<213> ORGANISM: Homo sapiens
<220> FEATURE:
<221> NAME/KEY: MISC_FEATURE
<222> LOCATION: (2)..(2)
<223> OTHER INFORMATION: Xaa can be Thr or Met

<400> SEQUENCE: 185

Ile Xaa Asp Gln Val Pro Phe Ser Val
1               5

<210> SEQ ID NO 186
<211> LENGTH: 10
<212> TYPE: PRT
<213> ORGANISM: Homo sapiens

<400> SEQUENCE: 186

Val Leu Tyr Arg Tyr Gly Ser Phe Ser Val
1               5                   10

<210> SEQ ID NO 187
<211> LENGTH: 9
<212> TYPE: PRT
<213> ORGANISM: Homo sapiens

<400> SEQUENCE: 187

Ala Ala Gly Ile Gly Ile Leu Thr Val
1               5

<210> SEQ ID NO 188
<211> LENGTH: 9
<212> TYPE: PRT
<213> ORGANISM: Homo sapiens

<400> SEQUENCE: 188

Ala Leu Asn Phe Pro Gly Ser Gln Lys
1               5

<210> SEQ ID NO 189
<211> LENGTH: 9
<212> TYPE: PRT
<213> ORGANISM: Homo sapiens

<400> SEQUENCE: 189

Leu Ile Tyr Arg Arg Arg Leu Met Lys
1               5

<210> SEQ ID NO 190
<211> LENGTH: 9
<212> TYPE: PRT
<213> ORGANISM: Homo sapiens

<400> SEQUENCE: 190

Ala Ala Gln Glu Arg Arg Val Pro Arg
1               5

<210> SEQ ID NO 191
<211> LENGTH: 10

<212> TYPE: PRT
<213> ORGANISM: Homo sapiens

<400> SEQUENCE: 191

Ala Ser Gly Pro Gly Gly Gly Ala Pro Arg
1               5                   10

<210> SEQ ID NO 192
<211> LENGTH: 9
<212> TYPE: PRT
<213> ORGANISM: Homo sapiens

<400> SEQUENCE: 192

Leu Leu Gly Pro Gly Arg Pro Tyr Arg
1               5

<210> SEQ ID NO 193
<211> LENGTH: 13
<212> TYPE: PRT
<213> ORGANISM: Homo sapiens

<400> SEQUENCE: 193

Ser Asp Ala Glu Lys Ser Asp Ile Cys Thr Asp Glu Tyr
1               5                   10

<210> SEQ ID NO 194
<211> LENGTH: 11
<212> TYPE: PRT
<213> ORGANISM: Homo sapiens

<400> SEQUENCE: 194

Ser Ser Asp Tyr Val Ile Pro Ile Gly Thr Tyr
1               5                   10

<210> SEQ ID NO 195
<211> LENGTH: 9
<212> TYPE: PRT
<213> ORGANISM: Homo sapiens

<400> SEQUENCE: 195

Glu Ala Asp Pro Thr Gly His Ser Tyr
1               5

<210> SEQ ID NO 196
<211> LENGTH: 9
<212> TYPE: PRT
<213> ORGANISM: Homo sapiens

<400> SEQUENCE: 196

Glu Val Asp Pro Ile Gly His Leu Tyr
1               5

<210> SEQ ID NO 197
<211> LENGTH: 9
<212> TYPE: PRT
<213> ORGANISM: Homo sapiens

<400> SEQUENCE: 197

Ile Met Asp Gln Val Pro Phe Ser Val
1               5

<210> SEQ ID NO 198
<211> LENGTH: 9
<212> TYPE: PRT
<213> ORGANISM: Homo sapiens

```
<400> SEQUENCE: 198

Gly Leu Tyr Asp Gly Met Glu His Leu
1               5

<210> SEQ ID NO 199
<211> LENGTH: 16
<212> TYPE: PRT
<213> ORGANISM: Homo sapiens

<400> SEQUENCE: 199

Ala Gln Asn Ile Leu Leu Ser Asn Ala Pro Leu Gly Pro Gln Phe Pro
1               5                   10                  15

<210> SEQ ID NO 200
<211> LENGTH: 21
<212> TYPE: PRT
<213> ORGANISM: Homo sapiens

<400> SEQUENCE: 200

Phe Leu Leu His His Ala Phe Val Asp Ser Ile Phe Glu Gln Trp Leu
1               5                   10                  15

Gln Arg His Arg Pro
            20

<210> SEQ ID NO 201
<211> LENGTH: 23
<212> TYPE: PRT
<213> ORGANISM: Homo sapiens

<400> SEQUENCE: 201

Arg Asn Gly Tyr Arg Ala Leu Met Asp Lys Ser Leu His Val Gly Thr
1               5                   10                  15

Gln Cys Ala Leu Thr Arg Arg
            20

<210> SEQ ID NO 202
<211> LENGTH: 15
<212> TYPE: PRT
<213> ORGANISM: Homo sapiens

<400> SEQUENCE: 202

Thr Ser Tyr Val Lys Val Leu His His Met Val Lys Ile Ser Gly
1               5                   10                  15

<210> SEQ ID NO 203
<211> LENGTH: 14
<212> TYPE: PRT
<213> ORGANISM: Homo sapiens

<400> SEQUENCE: 203

Leu Leu Lys Tyr Arg Ala Arg Glu Pro Val Thr Lys Ala Glu
1               5                   10

<210> SEQ ID NO 204
<211> LENGTH: 16
<212> TYPE: PRT
<213> ORGANISM: Homo sapiens

<400> SEQUENCE: 204

Trp Asn Arg Gln Leu Tyr Pro Glu Trp Thr Glu Ala Gln Arg Leu Asp
1               5                   10                  15
```

<210> SEQ ID NO 205
<211> LENGTH: 16
<212> TYPE: PRT
<213> ORGANISM: Artificial Sequence
<220> FEATURE:
<223> OTHER INFORMATION: Artificially synthesized tetanus peptide

<400> SEQUENCE: 205

Ala Gln Tyr Ile Lys Ala Asn Ser Lys Phe Ile Gly Ile Thr Glu Leu
1               5                   10                  15

<210> SEQ ID NO 206
<211> LENGTH: 9
<212> TYPE: PRT
<213> ORGANISM: Homo sapiens

<400> SEQUENCE: 206

Lys Ile Phe Gly Ser Leu Ala Phe Leu
1               5

<210> SEQ ID NO 207
<211> LENGTH: 9
<212> TYPE: PRT
<213> ORGANISM: Homo sapiens

<400> SEQUENCE: 207

Tyr Leu Ser Gly Ala Asp Leu Asn Leu
1               5

<210> SEQ ID NO 208
<211> LENGTH: 9
<212> TYPE: PRT
<213> ORGANISM: Homo sapiens

<400> SEQUENCE: 208

Val Leu Arg Glu Asn Thr Ser Pro Lys
1               5

<210> SEQ ID NO 209
<211> LENGTH: 9
<212> TYPE: PRT
<213> ORGANISM: Homo sapiens

<400> SEQUENCE: 209

Glu Ile Trp Thr His Ser Tyr Lys Val
1               5

<210> SEQ ID NO 210
<211> LENGTH: 9
<212> TYPE: PRT
<213> ORGANISM: Homo sapiens

<400> SEQUENCE: 210

Ser Leu Phe Arg Ala Val Ile Thr Lys
1               5

<210> SEQ ID NO 211
<211> LENGTH: 9
<212> TYPE: PRT
<213> ORGANISM: Homo sapiens

<400> SEQUENCE: 211

His Leu Phe Gly Tyr Ser Trp Tyr Lys
1               5

<210> SEQ ID NO 212
<211> LENGTH: 9
<212> TYPE: PRT
<213> ORGANISM: Homo sapiens

<400> SEQUENCE: 212

Ala Pro Pro Ala Tyr Glu Lys Leu Ser
1               5

<210> SEQ ID NO 213
<211> LENGTH: 9
<212> TYPE: PRT
<213> ORGANISM: Homo sapiens

<400> SEQUENCE: 213

Pro Pro Ala Tyr Glu Lys Leu Ser Ala
1               5

<210> SEQ ID NO 214
<211> LENGTH: 9
<212> TYPE: PRT
<213> ORGANISM: Homo sapiens

<400> SEQUENCE: 214

Pro Ala Tyr Glu Lys Leu Ser Ala Glu
1               5

<210> SEQ ID NO 215
<211> LENGTH: 20
<212> TYPE: PRT
<213> ORGANISM: Homo sapiens
<220> FEATURE:
<221> NAME/KEY: MISC_FEATURE
<222> LOCATION: (12)..(12)
<223> OTHER INFORMATION: The amino acid at the noted position is
      optionally phosphorylated

<400> SEQUENCE: 215

Val Pro Asn Ala Pro Pro Ala Tyr Glu Lys Leu Ser Ala Glu Gln Ser
1               5                   10                  15

Pro Pro Pro Tyr
            20

<210> SEQ ID NO 216
<211> LENGTH: 12
<212> TYPE: PRT
<213> ORGANISM: Homo sapiens
<220> FEATURE:
<221> NAME/KEY: MISC_FEATURE
<222> LOCATION: (11)..(11)
<223> OTHER INFORMATION: The amino acid at the noted position is
      optionally phosphorylated

<400> SEQUENCE: 216

Pro Asn Ala Pro Pro Ala Tyr Glu Lys Leu Ser Ala
1               5                   10

<210> SEQ ID NO 217
<211> LENGTH: 12
<212> TYPE: PRT
<213> ORGANISM: Homo sapiens
<220> FEATURE:
<221> NAME/KEY: MISC_FEATURE
<222> LOCATION: (10)..(10)
<223> OTHER INFORMATION: The amino acid at the noted position is
      optionally phosphorylated

<400> SEQUENCE: 217

```
Asn Ala Pro Pro Ala Tyr Glu Lys Leu Ser Ala Glu
1               5                   10

<210> SEQ ID NO 218
<211> LENGTH: 12
<212> TYPE: PRT
<213> ORGANISM: Homo sapiens
<220> FEATURE:
<221> NAME/KEY: MISC_FEATURE
<222> LOCATION: (9)..(9)
<223> OTHER INFORMATION: The amino acid at the noted position is
      optionally phosphorylated

<400> SEQUENCE: 218

Ala Pro Pro Ala Tyr Glu Lys Leu Ser Ala Glu Gln
1               5                   10

<210> SEQ ID NO 219
<211> LENGTH: 15
<212> TYPE: PRT
<213> ORGANISM: Homo sapiens
<220> FEATURE:
<221> NAME/KEY: MISC_FEATURE
<222> LOCATION: (9)..(9)
<223> OTHER INFORMATION: The amino acid at the noted position is
      optionally phosphorylated

<400> SEQUENCE: 219

Ala Pro Pro Ala Tyr Glu Lys Leu Ser Ala Glu Gln Ser Pro Pro
1               5                   10                  15

<210> SEQ ID NO 220
<211> LENGTH: 16
<212> TYPE: PRT
<213> ORGANISM: Homo sapiens
<220> FEATURE:
<221> NAME/KEY: MISC_FEATURE
<222> LOCATION: (9)..(9)
<223> OTHER INFORMATION: The amino acid at the noted position is
      optionally phosphorylated

<400> SEQUENCE: 220

Ala Pro Pro Ala Tyr Glu Lys Leu Ser Ala Glu Gln Ser Pro Pro Pro
1               5                   10                  15

<210> SEQ ID NO 221
<211> LENGTH: 12
<212> TYPE: PRT
<213> ORGANISM: Homo sapiens
<220> FEATURE:
<221> NAME/KEY: MISC_FEATURE
<222> LOCATION: (8)..(8)
<223> OTHER INFORMATION: The amino acid at the noted position is
      optionally phosphorylated

<400> SEQUENCE: 221

Pro Pro Ala Tyr Glu Lys Leu Ser Ala Glu Gln Ser
1               5                   10

<210> SEQ ID NO 222
<211> LENGTH: 12
<212> TYPE: PRT
<213> ORGANISM: Homo sapiens
<220> FEATURE:
<221> NAME/KEY: MISC_FEATURE
<222> LOCATION: (7)..(7)
<223> OTHER INFORMATION: The amino acid at the noted position is
      optionally phosphorylated
```

<400> SEQUENCE: 222

Pro Ala Tyr Glu Lys Leu Ser Ala Glu Gln Ser Pro
1               5                   10

<210> SEQ ID NO 223
<211> LENGTH: 12
<212> TYPE: PRT
<213> ORGANISM: Homo sapiens
<220> FEATURE:
<221> NAME/KEY: MISC_FEATURE
<222> LOCATION: (6)..(6)
<223> OTHER INFORMATION: The amino acid at the noted position is
      optionally phosphorylated

<400> SEQUENCE: 223

Ala Tyr Glu Lys Leu Ser Ala Glu Gln Ser Pro Pro
1               5                   10

<210> SEQ ID NO 224
<211> LENGTH: 12
<212> TYPE: PRT
<213> ORGANISM: Homo sapiens

<400> SEQUENCE: 224

Tyr Glu Lys Leu Ser Ala Glu Gln Ser Pro Pro Pro
1               5                   10

<210> SEQ ID NO 225
<211> LENGTH: 16
<212> TYPE: PRT
<213> ORGANISM: Homo sapiens

<400> SEQUENCE: 225

Ala Pro Pro Ala Tyr Glu Lys Leu Ser Ala Glu Gln Ser Pro Pro Pro
1               5                   10                  15

<210> SEQ ID NO 226
<211> LENGTH: 17
<212> TYPE: PRT
<213> ORGANISM: Homo sapiens
<220> FEATURE:
<221> NAME/KEY: MISC_FEATURE
<222> LOCATION: (9)..(9)
<223> OTHER INFORMATION: The amino acid at the noted position is
      optionally phosphorylated

<400> SEQUENCE: 226

Ala Pro Pro Ala Tyr Glu Lys Leu Ser Ala Glu Gln Ser Pro Pro Pro
1               5                   10                  15

Tyr

<210> SEQ ID NO 227
<211> LENGTH: 12
<212> TYPE: PRT
<213> ORGANISM: Homo sapiens
<220> FEATURE:
<221> NAME/KEY: MISC_FEATURE
<222> LOCATION: (8)..(8)
<223> OTHER INFORMATION: The amino acid at the noted position is
      optionally phosphorylated

<400> SEQUENCE: 227

Val Ser Lys Val Met Ile Gly Ser Pro Lys Lys Val
1               5                   10

<210> SEQ ID NO 228

```
<211> LENGTH: 9
<212> TYPE: PRT
<213> ORGANISM: Homo sapiens
<220> FEATURE:
<221> NAME/KEY: MISC_FEATURE
<222> LOCATION: (5)..(5)
<223> OTHER INFORMATION: The amino acid at the noted position is
      optionally phosphorylated

<400> SEQUENCE: 228

Val Met Ile Gly Ser Pro Lys Lys Val
1               5

<210> SEQ ID NO 229
<211> LENGTH: 10
<212> TYPE: PRT
<213> ORGANISM: Homo sapiens
<220> FEATURE:
<221> NAME/KEY: MISC_FEATURE
<222> LOCATION: (3)..(3)
<223> OTHER INFORMATION: The amino acid at the noted position is
      optionally phosphorylated

<400> SEQUENCE: 229

Lys Tyr Ser Pro Gly Lys Leu Arg Gly Asn
1               5                   10

<210> SEQ ID NO 230
<211> LENGTH: 22
<212> TYPE: PRT
<213> ORGANISM: Homo sapiens
<220> FEATURE:
<221> NAME/KEY: MISC_FEATURE
<222> LOCATION: (21)..(21)
<223> OTHER INFORMATION: The amino acid at the noted position is
      optionally phosphorylated

<400> SEQUENCE: 230

Ser Lys Glu Asp Lys Asn Gly His Asp Gly Asp Thr His Gln Glu Asp
1               5                   10                  15

Asp Gly Glu Lys Ser Asp
            20

<210> SEQ ID NO 231
<211> LENGTH: 28
<212> TYPE: PRT
<213> ORGANISM: Homo sapiens
<220> FEATURE:
<221> NAME/KEY: MISC_FEATURE
<222> LOCATION: (21)..(21)
<223> OTHER INFORMATION: The amino acid at the noted position is
      optionally phosphorylated

<400> SEQUENCE: 231

Gly Ser Ala Leu Gly Gly Gly Gly Ala Gly Leu Ser Gly Arg Ala Ser
1               5                   10                  15

Gly Gly Ala Gln Ser Pro Leu Arg Tyr Leu His Val
            20                  25

<210> SEQ ID NO 232
<211> LENGTH: 25
<212> TYPE: PRT
<213> ORGANISM: Homo sapiens
<220> FEATURE:
<221> NAME/KEY: MISC_FEATURE
<222> LOCATION: (18)..(18)
<223> OTHER INFORMATION: The amino acid at the noted position is
      optionally phosphorylated
```

```
<400> SEQUENCE: 232

Leu Gly Gly Gly Gly Ala Gly Leu Ser Gly Arg Ala Ser Gly Gly Ala
1               5                   10                  15

Gln Ser Pro Leu Arg Tyr Leu His Val
            20                  25

<210> SEQ ID NO 233
<211> LENGTH: 14
<212> TYPE: PRT
<213> ORGANISM: Homo sapiens
<220> FEATURE:
<221> NAME/KEY: MISC_FEATURE
<222> LOCATION: (6)..(6)
<223> OTHER INFORMATION: The amino acid at the noted position is
      optionally phosphorylated

<400> SEQUENCE: 233

Ser Gly Gly Ala Gln Ser Pro Leu Arg Tyr Leu His Val Leu
1               5                   10

<210> SEQ ID NO 234
<211> LENGTH: 19
<212> TYPE: PRT
<213> ORGANISM: Homo sapiens
<220> FEATURE:
<221> NAME/KEY: MISC_FEATURE
<222> LOCATION: (4)..(4)
<223> OTHER INFORMATION: The amino acid at the noted position is
      optionally phosphorylated

<400> SEQUENCE: 234

Glu Glu Gly Ser Pro Thr Met Val Glu Lys Gly Leu Glu Pro Gly Val
1               5                   10                  15

Phe Thr Leu

<210> SEQ ID NO 235
<211> LENGTH: 18
<212> TYPE: PRT
<213> ORGANISM: Homo sapiens
<220> FEATURE:
<221> NAME/KEY: MISC_FEATURE
<222> LOCATION: (3)..(3)
<223> OTHER INFORMATION: The amino acid at the noted position is
      optionally phosphorylated

<400> SEQUENCE: 235

Glu Gly Ser Pro Thr Met Val Glu Lys Gly Leu Glu Pro Gly Val Phe
1               5                   10                  15

Thr Leu

<210> SEQ ID NO 236
<211> LENGTH: 17
<212> TYPE: PRT
<213> ORGANISM: Homo sapiens
<220> FEATURE:
<221> NAME/KEY: MISC_FEATURE
<222> LOCATION: (2)..(2)
<223> OTHER INFORMATION: The amino acid at the noted position is
      optionally phosphorylated

<400> SEQUENCE: 236

Gly Ser Pro Thr Met Val Glu Lys Gly Leu Glu Pro Gly Val Phe Thr
1               5                   10                  15

Leu
```

-continued

```
<210> SEQ ID NO 237
<211> LENGTH: 24
<212> TYPE: PRT
<213> ORGANISM: Homo sapiens
<220> FEATURE:
<221> NAME/KEY: MISC_FEATURE
<222> LOCATION: (10)..(10)
<223> OTHER INFORMATION: The amino acid at the noted position is
      optionally phosphorylated

<400> SEQUENCE: 237

Glu Glu Met Pro Glu Asn Ala Leu Pro Ser Asp Glu Asp Asp Lys Asp
1               5                   10                  15

Pro Asn Asp Pro Tyr Arg Ala Leu
            20

<210> SEQ ID NO 238
<211> LENGTH: 14
<212> TYPE: PRT
<213> ORGANISM: Homo sapiens
<220> FEATURE:
<221> NAME/KEY: MISC_FEATURE
<222> LOCATION: (8)..(8)
<223> OTHER INFORMATION: The amino acid at the noted position is
      optionally phosphorylated

<400> SEQUENCE: 238

Gln Ala Ala Ser Asn Phe Lys Ser Pro Val Lys Thr Ile Arg
1               5                   10

<210> SEQ ID NO 239
<211> LENGTH: 13
<212> TYPE: PRT
<213> ORGANISM: Homo sapiens
<220> FEATURE:
<221> NAME/KEY: MISC_FEATURE
<222> LOCATION: (7)..(7)
<223> OTHER INFORMATION: The amino acid at the noted position is
      optionally phosphorylated

<400> SEQUENCE: 239

Ala Ala Ser Asn Phe Lys Ser Pro Val Lys Thr Ile Arg
1               5                   10

<210> SEQ ID NO 240
<211> LENGTH: 11
<212> TYPE: PRT
<213> ORGANISM: Homo sapiens
<220> FEATURE:
<221> NAME/KEY: MISC_FEATURE
<222> LOCATION: (5)..(5)
<223> OTHER INFORMATION: The amino acid at the noted position is
      optionally phosphorylated

<400> SEQUENCE: 240

Ser Asn Phe Lys Ser Pro Val Lys Thr Ile Arg
1               5                   10

<210> SEQ ID NO 241
<211> LENGTH: 10
<212> TYPE: PRT
<213> ORGANISM: Homo sapiens
<220> FEATURE:
<221> NAME/KEY: MISC_FEATURE
<222> LOCATION: (4)..(4)
<223> OTHER INFORMATION: The amino acid at the noted position is
      optionally phosphorylated

<400> SEQUENCE: 241
```

```
Asn Phe Lys Ser Pro Val Lys Thr Ile Arg
1               5                   10
```

<210> SEQ ID NO 242
<211> LENGTH: 9
<212> TYPE: PRT
<213> ORGANISM: Homo sapiens
<220> FEATURE:
<221> NAME/KEY: MISC_FEATURE
<222> LOCATION: (3)..(3)
<223> OTHER INFORMATION: The amino acid at the noted position is
      optionally phosphorylated

<400> SEQUENCE: 242

```
Phe Lys Ser Pro Val Lys Thr Ile Arg
1               5
```

<210> SEQ ID NO 243
<211> LENGTH: 17
<212> TYPE: PRT
<213> ORGANISM: Homo sapiens
<220> FEATURE:
<221> NAME/KEY: MISC_FEATURE
<222> LOCATION: (8)..(8)
<223> OTHER INFORMATION: The amino acid at the noted position is
      optionally phosphorylated

<400> SEQUENCE: 243

```
Tyr Tyr Thr Ala Gly Ser Ser Ser Pro Thr His Ala Lys Ser Ala His
1               5                   10                  15
Val
```

<210> SEQ ID NO 244
<211> LENGTH: 12
<212> TYPE: PRT
<213> ORGANISM: Homo sapiens
<220> FEATURE:
<221> NAME/KEY: MISC_FEATURE
<222> LOCATION: (3)..(3)
<223> OTHER INFORMATION: The amino acid at the noted position is
      optionally phosphorylated

<400> SEQUENCE: 244

```
Ser Ser Ser Pro Thr His Ala Lys Ser Ala His Val
1               5                   10
```

<210> SEQ ID NO 245
<211> LENGTH: 17
<212> TYPE: PRT
<213> ORGANISM: Homo sapiens
<220> FEATURE:
<221> NAME/KEY: MISC_FEATURE
<222> LOCATION: (4)..(4)
<223> OTHER INFORMATION: The amino acid at the noted position is
      optionally phosphorylated

<400> SEQUENCE: 245

```
Val Arg Gln Ser Val Thr Ser Phe Pro Asp Ala Asp Ala Phe His His
1               5                   10                  15
Gln
```

<210> SEQ ID NO 246
<211> LENGTH: 12
<212> TYPE: PRT
<213> ORGANISM: Homo sapiens
<220> FEATURE:
<221> NAME/KEY: MISC_FEATURE
<222> LOCATION: (8)..(8)

```
<223> OTHER INFORMATION: The amino acid at the noted position is
      optionally phosphorylated

<400> SEQUENCE: 246

Phe Lys Met Pro Gln Glu Lys Ser Pro Gly Tyr Ser
1               5                   10

<210> SEQ ID NO 247
<211> LENGTH: 11
<212> TYPE: PRT
<213> ORGANISM: Homo sapiens
<220> FEATURE:
<221> NAME/KEY: MISC_FEATURE
<222> LOCATION: (4)..(4)
<223> OTHER INFORMATION: The amino acid at the noted position is
      optionally phosphorylated

<400> SEQUENCE: 247

Arg Val Ala Ser Pro Thr Ser Gly Val Lys Arg
1               5                   10

<210> SEQ ID NO 248
<211> LENGTH: 28
<212> TYPE: PRT
<213> ORGANISM: Homo sapiens
<220> FEATURE:
<221> NAME/KEY: MISC_FEATURE
<222> LOCATION: (14)..(14)
<223> OTHER INFORMATION: The amino acid at the noted position is
      optionally phosphorylated

<400> SEQUENCE: 248

Gln Val Ala Met Pro Val Lys Lys Ser Pro Arg Arg Ser Ser Ser Asp
1               5                   10                  15

Glu Gln Gly Leu Ser Tyr Ser Ser Leu Lys Asn Val
            20                  25

<210> SEQ ID NO 249
<211> LENGTH: 27
<212> TYPE: PRT
<213> ORGANISM: Homo sapiens
<220> FEATURE:
<221> NAME/KEY: MISC_FEATURE
<222> LOCATION: (13)..(13)
<223> OTHER INFORMATION: The amino acid at the noted position is
      optionally phosphorylated

<400> SEQUENCE: 249

Val Ala Met Pro Val Lys Lys Ser Pro Arg Arg Ser Ser Ser Asp Glu
1               5                   10                  15

Gln Gly Leu Ser Tyr Ser Ser Leu Lys Asn Val
            20                  25

<210> SEQ ID NO 250
<211> LENGTH: 17
<212> TYPE: PRT
<213> ORGANISM: Homo sapiens
<220> FEATURE:
<221> NAME/KEY: MISC_FEATURE
<222> LOCATION: (11)..(11)
<223> OTHER INFORMATION: The amino acid at the noted position is
      optionally phosphorylated

<400> SEQUENCE: 250

Ser Ser Asn Gly Lys Met Ala Ser Arg Arg Ser Glu Glu Lys Glu Ala
1               5                   10                  15

Gly
```

```
<210> SEQ ID NO 251
<211> LENGTH: 19
<212> TYPE: PRT
<213> ORGANISM: Homo sapiens
<220> FEATURE:
<221> NAME/KEY: MISC_FEATURE
<222> LOCATION: (11)..(11)
<223> OTHER INFORMATION: The amino acid at the noted position is
      optionally phosphorylated

<400> SEQUENCE: 251

Ser Ser Asn Gly Lys Met Ala Ser Arg Arg Ser Glu Glu Lys Glu Ala
1               5                   10                  15

Gly Glu Ile

<210> SEQ ID NO 252
<211> LENGTH: 24
<212> TYPE: PRT
<213> ORGANISM: Homo sapiens
<220> FEATURE:
<221> NAME/KEY: MISC_FEATURE
<222> LOCATION: (10)..(10)
<223> OTHER INFORMATION: The amino acid at the noted position is
      optionally phosphorylated

<400> SEQUENCE: 252

Lys Glu Gly Glu Glu Pro Thr Val Tyr Ser Asp Glu Glu Glu Pro Lys
1               5                   10                  15

Asp Glu Ser Ala Arg Lys Asn Asp
            20

<210> SEQ ID NO 253
<211> LENGTH: 23
<212> TYPE: PRT
<213> ORGANISM: Homo sapiens
<220> FEATURE:
<221> NAME/KEY: MISC_FEATURE
<222> LOCATION: (9)..(9)
<223> OTHER INFORMATION: The amino acid at the noted position is
      optionally phosphorylated

<400> SEQUENCE: 253

Glu Gly Glu Glu Pro Thr Val Tyr Ser Asp Glu Glu Glu Pro Lys Asp
1               5                   10                  15

Glu Ser Ala Arg Lys Asn Asp
            20

<210> SEQ ID NO 254
<211> LENGTH: 27
<212> TYPE: PRT
<213> ORGANISM: Homo sapiens
<220> FEATURE:
<221> NAME/KEY: MISC_FEATURE
<222> LOCATION: (22)..(22)
<223> OTHER INFORMATION: The amino acid at the noted position is
      optionally phosphorylated
<220> FEATURE:
<221> NAME/KEY: MISC_FEATURE
<222> LOCATION: (24)..(24)
<223> OTHER INFORMATION: The amino acid at the noted position is
      optionally phosphorylated

<400> SEQUENCE: 254

Ala Ser Lys Met Thr Gln Pro Gln Ser Lys Ser Ala Phe Pro Leu Ser
1               5                   10                  15

Arg Lys Asn Lys Gly Ser Gly Ser Leu Asp Gly
```

```
<210> SEQ ID NO 255
<211> LENGTH: 25
<212> TYPE: PRT
<213> ORGANISM: Homo sapiens
<220> FEATURE:
<221> NAME/KEY: MISC_FEATURE
<222> LOCATION: (13)..(13)
<223> OTHER INFORMATION: The amino acid at the noted position is
      optionally phosphorylated

<400> SEQUENCE: 255

Ala Pro Pro Pro Leu Val Pro Ala Pro Arg Pro Ser Ser Pro Pro Arg
1               5                   10                  15

Gly Pro Gly Pro Ala Arg Ala Asp Arg
            20                  25

<210> SEQ ID NO 256
<211> LENGTH: 22
<212> TYPE: PRT
<213> ORGANISM: Homo sapiens
<220> FEATURE:
<221> NAME/KEY: MISC_FEATURE
<222> LOCATION: (16)..(16)
<223> OTHER INFORMATION: The amino acid at the noted position is
      optionally phosphorylated

<400> SEQUENCE: 256

Ser Ala Ala Arg Glu Ser His Pro His Gly Val Lys Arg Ser Ala Ser
1               5                   10                  15

Pro Asp Asp Asp Leu Gly
            20

<210> SEQ ID NO 257
<211> LENGTH: 22
<212> TYPE: PRT
<213> ORGANISM: Homo sapiens
<220> FEATURE:
<221> NAME/KEY: MISC_FEATURE
<222> LOCATION: (1)..(1)
<223> OTHER INFORMATION: Ser-1 can be acetylated (Acetyl-Ser)
<220> FEATURE:
<221> NAME/KEY: MISC_FEATURE
<222> LOCATION: (16)..(16)
<223> OTHER INFORMATION: The amino acid at the noted position is
      optionally phosphorylated

<400> SEQUENCE: 257

Ser Ala Ala Arg Glu Ser His Pro His Gly Val Lys Arg Ser Ala Ser
1               5                   10                  15

Pro Asp Asp Asp Leu Gly
            20

<210> SEQ ID NO 258
<211> LENGTH: 13
<212> TYPE: PRT
<213> ORGANISM: Homo sapiens
<220> FEATURE:
<221> NAME/KEY: MISC_FEATURE
<222> LOCATION: (5)..(5)
<223> OTHER INFORMATION: The amino acid at the noted position is
      optionally phosphorylated

<400> SEQUENCE: 258

Ala Ser Lys Ala Ser Pro Thr Leu Asp Phe Thr Glu Arg
1               5                   10
```

```
<210> SEQ ID NO 259
<211> LENGTH: 16
<212> TYPE: PRT
<213> ORGANISM: Homo sapiens
<220> FEATURE:
<221> NAME/KEY: MISC_FEATURE
<222> LOCATION: (4)..(4)
<223> OTHER INFORMATION: The amino acid at the noted position is
      optionally phosphorylated

<400> SEQUENCE: 259

Gly Glu Arg Ser Pro Leu Leu Ser Gln Glu Thr Ala Gly Gln Lys Pro
1               5                   10                  15

<210> SEQ ID NO 260
<211> LENGTH: 17
<212> TYPE: PRT
<213> ORGANISM: Homo sapiens
<220> FEATURE:
<221> NAME/KEY: MISC_FEATURE
<222> LOCATION: (4)..(4)
<223> OTHER INFORMATION: The amino acid at the noted position is
      optionally phosphorylated

<400> SEQUENCE: 260

Gly Glu Arg Ser Pro Leu Leu Ser Gln Glu Thr Ala Gly Gln Lys Pro
1               5                   10                  15

Leu

<210> SEQ ID NO 261
<211> LENGTH: 15
<212> TYPE: PRT
<213> ORGANISM: Homo sapiens
<220> FEATURE:
<221> NAME/KEY: MISC_FEATURE
<222> LOCATION: (3)..(3)
<223> OTHER INFORMATION: The amino acid at the noted position is
      optionally phosphorylated

<400> SEQUENCE: 261

Glu Arg Ser Pro Leu Leu Ser Gln Glu Thr Ala Gly Gln Lys Pro
1               5                   10                  15

<210> SEQ ID NO 262
<211> LENGTH: 16
<212> TYPE: PRT
<213> ORGANISM: Homo sapiens
<220> FEATURE:
<221> NAME/KEY: MISC_FEATURE
<222> LOCATION: (3)..(3)
<223> OTHER INFORMATION: The amino acid at the noted position is
      optionally phosphorylated

<400> SEQUENCE: 262

Glu Arg Ser Pro Leu Leu Ser Gln Glu Thr Ala Gly Gln Lys Pro Leu
1               5                   10                  15

<210> SEQ ID NO 263
<211> LENGTH: 15
<212> TYPE: PRT
<213> ORGANISM: Homo sapiens
<220> FEATURE:
<221> NAME/KEY: MISC_FEATURE
<222> LOCATION: (9)..(9)
<223> OTHER INFORMATION: The amino acid at the noted position is
      optionally phosphorylated

<400> SEQUENCE: 263
```

```
Thr Ile Gly Glu Lys Lys Glu Pro Ser Asp Lys Ser Val Asp Ser
1               5                   10                  15

<210> SEQ ID NO 264
<211> LENGTH: 18
<212> TYPE: PRT
<213> ORGANISM: Homo sapiens
<220> FEATURE:
<221> NAME/KEY: MISC_FEATURE
<222> LOCATION: (11)..(11)
<223> OTHER INFORMATION: The amino acid at the noted position is
      optionally phosphorylated

<400> SEQUENCE: 264

Ser Gly Pro Lys Pro Leu Phe Arg Arg Met Ser Ser Leu Val Gly Pro
1               5                   10                  15

Thr Gln

<210> SEQ ID NO 265
<211> LENGTH: 11
<212> TYPE: PRT
<213> ORGANISM: Homo sapiens
<220> FEATURE:
<221> NAME/KEY: MISC_FEATURE
<222> LOCATION: (10)..(10)
<223> OTHER INFORMATION: The amino acid at the noted position is
      optionally phosphorylated

<400> SEQUENCE: 265

Gly Pro Lys Pro Leu Phe Arg Arg Met Ser Ser
1               5                   10

<210> SEQ ID NO 266
<211> LENGTH: 12
<212> TYPE: PRT
<213> ORGANISM: Homo sapiens
<220> FEATURE:
<221> NAME/KEY: MISC_FEATURE
<222> LOCATION: (10)..(10)
<223> OTHER INFORMATION: The amino acid at the noted position is
      optionally phosphorylated

<400> SEQUENCE: 266

Gly Pro Lys Pro Leu Phe Arg Arg Met Ser Ser Leu
1               5                   10

<210> SEQ ID NO 267
<211> LENGTH: 13
<212> TYPE: PRT
<213> ORGANISM: Homo sapiens
<220> FEATURE:
<221> NAME/KEY: MISC_FEATURE
<222> LOCATION: (10)..(10)
<223> OTHER INFORMATION: The amino acid at the noted position is
      optionally phosphorylated

<400> SEQUENCE: 267

Gly Pro Lys Pro Leu Phe Arg Arg Met Ser Ser Leu Val
1               5                   10

<210> SEQ ID NO 268
<211> LENGTH: 14
<212> TYPE: PRT
<213> ORGANISM: Homo sapiens
<220> FEATURE:
<221> NAME/KEY: MISC_FEATURE
<222> LOCATION: (10)..(10)
<223> OTHER INFORMATION: The amino acid at the noted position is
      optionally phosphorylated
```

```
<400> SEQUENCE: 268

Gly Pro Lys Pro Leu Phe Arg Arg Met Ser Ser Leu Val Gly
1               5                   10

<210> SEQ ID NO 269
<211> LENGTH: 15
<212> TYPE: PRT
<213> ORGANISM: Homo sapiens
<220> FEATURE:
<221> NAME/KEY: MISC_FEATURE
<222> LOCATION: (10)..(10)
<223> OTHER INFORMATION: The amino acid at the noted position is
      optionally phosphorylated

<400> SEQUENCE: 269

Gly Pro Lys Pro Leu Phe Arg Arg Met Ser Ser Leu Val Gly Pro
1               5                   10                  15

<210> SEQ ID NO 270
<211> LENGTH: 16
<212> TYPE: PRT
<213> ORGANISM: Homo sapiens
<220> FEATURE:
<221> NAME/KEY: MISC_FEATURE
<222> LOCATION: (10)..(10)
<223> OTHER INFORMATION: The amino acid at the noted position is
      optionally phosphorylated

<400> SEQUENCE: 270

Gly Pro Lys Pro Leu Phe Arg Arg Met Ser Ser Leu Val Gly Pro Thr
1               5                   10                  15

<210> SEQ ID NO 271
<211> LENGTH: 17
<212> TYPE: PRT
<213> ORGANISM: Homo sapiens
<220> FEATURE:
<221> NAME/KEY: MISC_FEATURE
<222> LOCATION: (10)..(10)
<223> OTHER INFORMATION: The amino acid at the noted position is
      optionally phosphorylated

<400> SEQUENCE: 271

Gly Pro Lys Pro Leu Phe Arg Arg Met Ser Ser Leu Val Gly Pro Thr
1               5                   10                  15

Gln

<210> SEQ ID NO 272
<211> LENGTH: 18
<212> TYPE: PRT
<213> ORGANISM: Homo sapiens
<220> FEATURE:
<221> NAME/KEY: MISC_FEATURE
<222> LOCATION: (10)..(10)
<223> OTHER INFORMATION: The amino acid at the noted position is
      optionally phosphorylated

<400> SEQUENCE: 272

Gly Pro Lys Pro Leu Phe Arg Arg Met Ser Ser Leu Val Gly Pro Thr
1               5                   10                  15

Gln Ser

<210> SEQ ID NO 273
<211> LENGTH: 16
<212> TYPE: PRT
<213> ORGANISM: Homo sapiens
```

```
<220> FEATURE:
<221> NAME/KEY: MISC_FEATURE
<222> LOCATION: (2)..(2)
<223> OTHER INFORMATION: The amino acid at the noted position is
      optionally phosphorylated

<400> SEQUENCE: 273

Ala Ser Pro Thr Ile Glu Ala Gln Gly Thr Ser Pro Ala His Asp Asn
1               5                   10                  15

<210> SEQ ID NO 274
<211> LENGTH: 17
<212> TYPE: PRT
<213> ORGANISM: Homo sapiens
<220> FEATURE:
<221> NAME/KEY: MISC_FEATURE
<222> LOCATION: (2)..(2)
<223> OTHER INFORMATION: The amino acid at the noted position is
      optionally phosphorylated

<400> SEQUENCE: 274

Ala Ser Pro Thr Ile Glu Ala Gln Gly Thr Ser Pro Ala His Asp Asn
1               5                   10                  15

Ile

<210> SEQ ID NO 275
<211> LENGTH: 18
<212> TYPE: PRT
<213> ORGANISM: Homo sapiens
<220> FEATURE:
<221> NAME/KEY: MISC_FEATURE
<222> LOCATION: (2)..(2)
<223> OTHER INFORMATION: The amino acid at the noted position is
      optionally phosphorylated

<400> SEQUENCE: 275

Ala Ser Pro Thr Ile Glu Ala Gln Gly Thr Ser Pro Ala His Asp Asn
1               5                   10                  15

Ile Ala

<210> SEQ ID NO 276
<211> LENGTH: 16
<212> TYPE: PRT
<213> ORGANISM: Homo sapiens
<220> FEATURE:
<221> NAME/KEY: MISC_FEATURE
<222> LOCATION: (3)..(3)
<223> OTHER INFORMATION: The amino acid at the noted position is
      optionally phosphorylated

<400> SEQUENCE: 276

Ser Ser Ser Trp Arg Ile Leu Gly Ser Lys Gln Ser Glu His Arg Pro
1               5                   10                  15

<210> SEQ ID NO 277
<211> LENGTH: 19
<212> TYPE: PRT
<213> ORGANISM: Homo sapiens
<220> FEATURE:
<221> NAME/KEY: MISC_FEATURE
<222> LOCATION: (1)..(1)
<223> OTHER INFORMATION: The amino acid at the noted position is
     optionally phosphorylated

<400> SEQUENCE: 277

Ser Pro Pro Phe Pro Val Pro Val Tyr Thr Arg Gln Ala Pro Lys Gln
1               5                   10                  15
```

```
Val Ile Lys

<210> SEQ ID NO 278
<211> LENGTH: 18
<212> TYPE: PRT
<213> ORGANISM: Homo sapiens
<220> FEATURE:
<221> NAME/KEY: MISC_FEATURE
<222> LOCATION: (10)..(10)
<223> OTHER INFORMATION: The amino acid at the noted position is
      optionally phosphorylated

<400> SEQUENCE: 278

Asp Pro Thr Arg Arg Phe Phe Lys Val Thr Pro Pro Gly Ser Gly
1               5                   10                  15

Pro Gln

<210> SEQ ID NO 279
<211> LENGTH: 18
<212> TYPE: PRT
<213> ORGANISM: Homo sapiens
<220> FEATURE:
<221> NAME/KEY: MISC_FEATURE
<222> LOCATION: (2)..(2)
<223> OTHER INFORMATION: The amino acid at the noted position is
      optionally phosphorylated

<400> SEQUENCE: 279

Arg Ser Pro Glu Asp Glu Tyr Glu Leu Leu Met Pro His Arg Ile Ser
1               5                   10                  15

Ser His

<210> SEQ ID NO 280
<211> LENGTH: 17
<212> TYPE: PRT
<213> ORGANISM: Homo sapiens
<220> FEATURE:
<221> NAME/KEY: MISC_FEATURE
<222> LOCATION: (1)..(1)
<223> OTHER INFORMATION: The amino acid at the noted position is
      optionally phosphorylated

<400> SEQUENCE: 280

Ser Pro Glu Asp Glu Tyr Glu Leu Leu Met Pro His Arg Ile Ser Ser
1               5                   10                  15

His

<210> SEQ ID NO 281
<211> LENGTH: 17
<212> TYPE: PRT
<213> ORGANISM: Homo sapiens
<220> FEATURE:
<221> NAME/KEY: MISC_FEATURE
<222> LOCATION: (15)..(15)
<223> OTHER INFORMATION: The amino acid at the noted position is
      optionally phosphorylated

<400> SEQUENCE: 281

Ser Pro Glu Asp Glu Tyr Glu Leu Leu Met Pro His Arg Ile Ser Ser
1               5                   10                  15

His

<210> SEQ ID NO 282
<211> LENGTH: 12
<212> TYPE: PRT
<213> ORGANISM: Homo sapiens
```

```
<220> FEATURE:
<221> NAME/KEY: MISC_FEATURE
<222> LOCATION: (9)..(9)
<223> OTHER INFORMATION: The amino acid at the noted position is
      optionally phosphorylated

<400> SEQUENCE: 282

Glu Leu Leu Met Pro His Arg Ile Ser Ser His Phe
1               5                   10

<210> SEQ ID NO 283
<211> LENGTH: 13
<212> TYPE: PRT
<213> ORGANISM: Homo sapiens
<220> FEATURE:
<221> NAME/KEY: MISC_FEATURE
<222> LOCATION: (9)..(9)
<223> OTHER INFORMATION: The amino acid at the noted position is
      optionally phosphorylated

<400> SEQUENCE: 283

Glu Leu Leu Met Pro His Arg Ile Ser Ser His Phe Leu
1               5                   10

<210> SEQ ID NO 284
<211> LENGTH: 19
<212> TYPE: PRT
<213> ORGANISM: Homo sapiens
<220> FEATURE:
<221> NAME/KEY: MISC_FEATURE
<222> LOCATION: (12)..(12)
<223> OTHER INFORMATION: The amino acid at the noted position is
      optionally phosphorylated

<400> SEQUENCE: 284

Thr Pro Asp Pro Ser Lys Phe Phe Ser Gln Leu Ser Ser Glu His Gly
1               5                   10                  15

Gly Asp Val

<210> SEQ ID NO 285
<211> LENGTH: 20
<212> TYPE: PRT
<213> ORGANISM: Homo sapiens
<220> FEATURE:
<221> NAME/KEY: MISC_FEATURE
<222> LOCATION: (1)..(1)
<223> OTHER INFORMATION: The amino acid at the noted position is
      optionally phosphorylated

<400> SEQUENCE: 285

Thr Pro Asp Pro Ser Lys Phe Phe Ser Gln Leu Ser Ser Glu His Gly
1               5                   10                  15

Gly Asp Val Gln
            20

<210> SEQ ID NO 286
<211> LENGTH: 12
<212> TYPE: PRT
<213> ORGANISM: Homo sapiens
<220> FEATURE:
<221> NAME/KEY: MISC_FEATURE
<222> LOCATION: (1)..(1)
<223> OTHER INFORMATION: The amino acid at the noted position is
      optionally phosphorylated

<400> SEQUENCE: 286

Ser Asp Phe His Ala Glu Arg Ala Ala Arg Glu Lys
1               5                   10
```

```
<210> SEQ ID NO 287
<211> LENGTH: 18
<212> TYPE: PRT
<213> ORGANISM: Homo sapiens
<220> FEATURE:
<221> NAME/KEY: MISC_FEATURE
<222> LOCATION: (1)..(1)
<223> OTHER INFORMATION: The amino acid at the noted position is
      optionally phosphorylated

<400> SEQUENCE: 287

Ser Pro Glu Arg Pro Phe Leu Ala Ile Leu Gly Gly Ala Lys Val Ala
1               5                   10                  15

Asp Lys

<210> SEQ ID NO 288
<211> LENGTH: 20
<212> TYPE: PRT
<213> ORGANISM: Homo sapiens
<220> FEATURE:
<221> NAME/KEY: MISC_FEATURE
<222> LOCATION: (1)..(1)
<223> OTHER INFORMATION: The amino acid at the noted position is
      optionally phosphorylated

<400> SEQUENCE: 288

Ser Pro Glu Arg Pro Phe Leu Ala Ile Leu Gly Gly Ala Lys Val Ala
1               5                   10                  15

Asp Lys Ile Gln
            20

<210> SEQ ID NO 289
<211> LENGTH: 18
<212> TYPE: PRT
<213> ORGANISM: Homo sapiens
<220> FEATURE:
<221> NAME/KEY: MISC_FEATURE
<222> LOCATION: (15)..(15)
<223> OTHER INFORMATION: The amino acid at the noted position is
      optionally phosphorylated

<400> SEQUENCE: 289

Thr Lys Asp Lys Tyr Met Ala Ser Arg Gly Gln Lys Ala Lys Ser Met
1               5                   10                  15

Glu Gly

<210> SEQ ID NO 290
<211> LENGTH: 13
<212> TYPE: PRT
<213> ORGANISM: Homo sapiens
<220> FEATURE:
<221> NAME/KEY: MISC_FEATURE
<222> LOCATION: (10)..(10)
<223> OTHER INFORMATION: The amino acid at the noted position is
      optionally phosphorylated

<400> SEQUENCE: 290

Val Pro His His Gly Phe Glu Asp Trp Ser Gln Ile Arg
1               5                   10

<210> SEQ ID NO 291
<211> LENGTH: 16
<212> TYPE: PRT
<213> ORGANISM: Homo sapiens
<220> FEATURE:
<221> NAME/KEY: MISC_FEATURE
```

```
<222> LOCATION: (6)..(6)
<223> OTHER INFORMATION: The amino acid at the noted position is
      optionally phosphorylated

<400> SEQUENCE: 291

Lys Ile Glu Lys Ile Tyr Ile Met Lys Ala Asp Thr Val Ile Val Gly
1               5                   10                  15

<210> SEQ ID NO 292
<211> LENGTH: 15
<212> TYPE: PRT
<213> ORGANISM: Homo sapiens
<220> FEATURE:
<221> NAME/KEY: MISC_FEATURE
<222> LOCATION: (4)..(4)
<223> OTHER INFORMATION: The amino acid at the noted position is
      optionally phosphorylated

<400> SEQUENCE: 292

Ile Glu Lys Ile Tyr Ile Met Lys Ala Asp Thr Val Ile Val Gly
1               5                   10                  15

<210> SEQ ID NO 293
<211> LENGTH: 10
<212> TYPE: PRT
<213> ORGANISM: Homo sapiens
<220> FEATURE:
<221> NAME/KEY: MISC_FEATURE
<222> LOCATION: (4)..(4)
<223> OTHER INFORMATION: The amino acid at the noted position is
      optionally phosphorylated

<400> SEQUENCE: 293

Glu Glu Ser Ser Asp Asp Gly Lys Lys Tyr
1               5                   10

<210> SEQ ID NO 294
<211> LENGTH: 8
<212> TYPE: PRT
<213> ORGANISM: Homo sapiens
<220> FEATURE:
<221> NAME/KEY: MISC_FEATURE
<222> LOCATION: (4)..(4)
<223> OTHER INFORMATION: The amino acid at the noted position is
      optionally phosphorylated

<400> SEQUENCE: 294

Lys Asn Arg Ser Trp Lys Tyr Asn
1               5

<210> SEQ ID NO 295
<211> LENGTH: 9
<212> TYPE: PRT
<213> ORGANISM: Homo sapiens
<220> FEATURE:
<221> NAME/KEY: MISC_FEATURE
<222> LOCATION: (4)..(4)
<223> OTHER INFORMATION: The amino acid at the noted position is
      optionally phosphorylated

<400> SEQUENCE: 295

Lys Asn Arg Ser Trp Lys Tyr Asn Gln
1               5

<210> SEQ ID NO 296
<211> LENGTH: 14
<212> TYPE: PRT
<213> ORGANISM: Homo sapiens
<220> FEATURE:
```

<221> NAME/KEY: MISC_FEATURE
<222> LOCATION: (4)..(4)
<223> OTHER INFORMATION: The amino acid at the noted position is
      optionally phosphorylated

<400> SEQUENCE: 296

Lys Asn Arg Ser Trp Lys Tyr Asn Gln Ser Ile Ser Leu Arg
1               5                   10

<210> SEQ ID NO 297
<211> LENGTH: 16
<212> TYPE: PRT
<213> ORGANISM: Homo sapiens
<220> FEATURE:
<221> NAME/KEY: MISC_FEATURE
<222> LOCATION: (4)..(4)
<223> OTHER INFORMATION: The amino acid at the noted position is
      optionally phosphorylated

<400> SEQUENCE: 297

Lys Asn Arg Ser Trp Lys Tyr Asn Gln Ser Ile Ser Leu Arg Arg Pro
1               5                   10                  15

<210> SEQ ID NO 298
<211> LENGTH: 13
<212> TYPE: PRT
<213> ORGANISM: Homo sapiens
<220> FEATURE:
<221> NAME/KEY: MISC_FEATURE
<222> LOCATION: (3)..(3)
<223> OTHER INFORMATION: The amino acid at the noted position is
      optionally phosphorylated

<400> SEQUENCE: 298

Asn Arg Ser Trp Lys Tyr Asn Gln Ser Ile Ser Leu Arg
1               5                   10

<210> SEQ ID NO 299
<211> LENGTH: 15
<212> TYPE: PRT
<213> ORGANISM: Homo sapiens
<220> FEATURE:
<221> NAME/KEY: MISC_FEATURE
<222> LOCATION: (3)..(3)
<223> OTHER INFORMATION: The amino acid at the noted position is
      optionally phosphorylated

<400> SEQUENCE: 299

Asn Arg Ser Trp Lys Tyr Asn Gln Ser Ile Ser Leu Arg Arg Pro
1               5                   10                  15

<210> SEQ ID NO 300
<211> LENGTH: 14
<212> TYPE: PRT
<213> ORGANISM: Homo sapiens
<220> FEATURE:
<221> NAME/KEY: MISC_FEATURE
<222> LOCATION: (2)..(2)
<223> OTHER INFORMATION: The amino acid at the noted position is
      optionally phosphorylated

<400> SEQUENCE: 300

Arg Ser Trp Lys Tyr Asn Gln Ser Ile Ser Leu Arg Arg Pro
1               5                   10

<210> SEQ ID NO 301
<211> LENGTH: 9
<212> TYPE: PRT
<213> ORGANISM: Homo sapiens

```
<220> FEATURE:
<221> NAME/KEY: MISC_FEATURE
<222> LOCATION: (6)..(6)
<223> OTHER INFORMATION: The amino acid at the noted position is
      optionally phosphorylated

<400> SEQUENCE: 301

Arg Ala Lys Ser Pro Ile Ser Leu Lys
1               5

<210> SEQ ID NO 302
<211> LENGTH: 13
<212> TYPE: PRT
<213> ORGANISM: Homo sapiens
<220> FEATURE:
<221> NAME/KEY: MISC_FEATURE
<222> LOCATION: (3)..(3)
<223> OTHER INFORMATION: The amino acid at the noted position is
      optionally phosphorylated

<400> SEQUENCE: 302

Glu Ser Ser Val Arg Ser Gln Glu Asp Gln Leu Ser Arg
1               5                   10

<210> SEQ ID NO 303
<211> LENGTH: 14
<212> TYPE: PRT
<213> ORGANISM: Homo sapiens
<220> FEATURE:
<221> NAME/KEY: MISC_FEATURE
<222> LOCATION: (3)..(3)
<223> OTHER INFORMATION: The amino acid at the noted position is
      optionally phosphorylated

<400> SEQUENCE: 303

Glu Ser Ser Val Arg Ser Gln Glu Asp Gln Leu Ser Arg Arg
1               5                   10

<210> SEQ ID NO 304
<211> LENGTH: 15
<212> TYPE: PRT
<213> ORGANISM: Homo sapiens
<220> FEATURE:
<221> NAME/KEY: MISC_FEATURE
<222> LOCATION: (4)..(4)
<223> OTHER INFORMATION: The amino acid at the noted position is
      optionally phosphorylated

<400> SEQUENCE: 304

Asp Lys Leu Ser Val Ile Ala Glu Asp Ser Glu Ser Gly Lys Gln
1               5                   10                  15

<210> SEQ ID NO 305
<211> LENGTH: 16
<212> TYPE: PRT
<213> ORGANISM: Homo sapiens
<220> FEATURE:
<221> NAME/KEY: MISC_FEATURE
<222> LOCATION: (4)..(4)
<223> OTHER INFORMATION: The amino acid at the noted position is
      optionally phosphorylated

<400> SEQUENCE: 305

Asp Lys Leu Ser Val Ile Ala Glu Asp Ser Glu Ser Gly Lys Gln Asn
1               5                   10                  15

<210> SEQ ID NO 306
<211> LENGTH: 17
<212> TYPE: PRT
```

```
<213> ORGANISM: Homo sapiens
<220> FEATURE:
<221> NAME/KEY: MISC_FEATURE
<222> LOCATION: (4)..(4)
<223> OTHER INFORMATION: The amino acid at the noted position is
      optionally phosphorylated

<400> SEQUENCE: 306

Asp Lys Leu Ser Val Ile Ala Glu Asp Ser Glu Ser Gly Lys Gln Asn
1               5                   10                  15

Pro

<210> SEQ ID NO 307
<211> LENGTH: 18
<212> TYPE: PRT
<213> ORGANISM: Homo sapiens
<220> FEATURE:
<221> NAME/KEY: MISC_FEATURE
<222> LOCATION: (4)..(4)
<223> OTHER INFORMATION: The amino acid at the noted position is
      optionally phosphorylated

<400> SEQUENCE: 307

Asp Lys Leu Ser Val Ile Ala Glu Asp Ser Glu Ser Gly Lys Gln Asn
1               5                   10                  15

Pro Gly

<210> SEQ ID NO 308
<211> LENGTH: 20
<212> TYPE: PRT
<213> ORGANISM: Homo sapiens
<220> FEATURE:
<221> NAME/KEY: MISC_FEATURE
<222> LOCATION: (4)..(4)
<223> OTHER INFORMATION: The amino acid at the noted position is
      optionally phosphorylated

<400> SEQUENCE: 308

Asp Lys Leu Ser Val Ile Ala Glu Asp Ser Glu Ser Gly Lys Gln Asn
1               5                   10                  15

Pro Gly Asp Ser
            20

<210> SEQ ID NO 309
<211> LENGTH: 15
<212> TYPE: PRT
<213> ORGANISM: Homo sapiens
<220> FEATURE:
<221> NAME/KEY: MISC_FEATURE
<222> LOCATION: (3)..(3)
<223> OTHER INFORMATION: The amino acid at the noted position is
      optionally phosphorylated

<400> SEQUENCE: 309

Lys Leu Ser Val Ile Ala Glu Asp Ser Glu Ser Gly Lys Gln Asn
1               5                   10                  15

<210> SEQ ID NO 310
<211> LENGTH: 16
<212> TYPE: PRT
<213> ORGANISM: Homo sapiens
<220> FEATURE:
<221> NAME/KEY: MISC_FEATURE
<222> LOCATION: (3)..(3)
<223> OTHER INFORMATION: The amino acid at the noted position is
      optionally phosphorylated

<400> SEQUENCE: 310
```

Lys Leu Ser Val Ile Ala Glu Asp Ser Glu Ser Gly Lys Gln Asn Pro
1               5                   10                  15

<210> SEQ ID NO 311
<211> LENGTH: 17
<212> TYPE: PRT
<213> ORGANISM: Homo sapiens
<220> FEATURE:
<221> NAME/KEY: MISC_FEATURE
<222> LOCATION: (3)..(3)
<223> OTHER INFORMATION: The amino acid at the noted position is
      optionally phosphorylated

<400> SEQUENCE: 311

Lys Leu Ser Val Ile Ala Glu Asp Ser Glu Ser Gly Lys Gln Asn Pro
1               5                   10                  15

Gly

<210> SEQ ID NO 312
<211> LENGTH: 21
<212> TYPE: PRT
<213> ORGANISM: Homo sapiens
<220> FEATURE:
<221> NAME/KEY: MISC_FEATURE
<222> LOCATION: (18)..(18)
<223> OTHER INFORMATION: The amino acid at the noted position is
      optionally phosphorylated

<400> SEQUENCE: 312

Asn Leu Glu Leu Ser Lys Phe Arg Met Pro Gln Pro Ser Ser Gly Arg
1               5                   10                  15

Glu Ser Pro Arg His
            20

<210> SEQ ID NO 313
<211> LENGTH: 18
<212> TYPE: PRT
<213> ORGANISM: Homo sapiens
<220> FEATURE:
<221> NAME/KEY: MISC_FEATURE
<222> LOCATION: (15)..(15)
<223> OTHER INFORMATION: The amino acid at the noted position is
      optionally phosphorylated

<400> SEQUENCE: 313

Leu Ser Lys Phe Arg Met Pro Gln Pro Ser Ser Gly Arg Glu Ser Pro
1               5                   10                  15

Arg His

<210> SEQ ID NO 314
<211> LENGTH: 21
<212> TYPE: PRT
<213> ORGANISM: Homo sapiens
<220> FEATURE:
<221> NAME/KEY: MISC_FEATURE
<222> LOCATION: (18)..(18)
<223> OTHER INFORMATION: The amino acid at the noted position is
      optionally phosphorylated

<400> SEQUENCE: 314

Pro Pro Leu Pro Glu Asp Ser Ile Lys Val Ile Arg Asn Met Arg Ala
1               5                   10                  15

Ala Ser Pro Pro Ala
            20

-continued

```
<210> SEQ ID NO 315
<211> LENGTH: 17
<212> TYPE: PRT
<213> ORGANISM: Homo sapiens
<220> FEATURE:
<221> NAME/KEY: MISC_FEATURE
<222> LOCATION: (5)..(5)
<223> OTHER INFORMATION: The amino acid at the noted position is
      optionally phosphorylated

<400> SEQUENCE: 315

Met Pro Arg Pro Ser Ile Lys Lys Ala Gln Asn Ser Gln Ala Ala Arg
1               5                   10                  15

Gln

<210> SEQ ID NO 316
<211> LENGTH: 20
<212> TYPE: PRT
<213> ORGANISM: Homo sapiens
<220> FEATURE:
<221> NAME/KEY: MISC_FEATURE
<222> LOCATION: (18)..(18)
<223> OTHER INFORMATION: The amino acid at the noted position is
      optionally phosphorylated
<220> FEATURE:
<221> NAME/KEY: MISC_FEATURE
<222> LOCATION: (19)..(19)
<223> OTHER INFORMATION: The amino acid at the noted position is
      optionally phosphorylated

<400> SEQUENCE: 316

Thr His Lys Gly Glu Ile Arg Gly Ala Ser Thr Pro Phe Gln Phe Arg
1               5                   10                  15

Ala Ser Ser Pro
            20

<210> SEQ ID NO 317
<211> LENGTH: 19
<212> TYPE: PRT
<213> ORGANISM: Homo sapiens
<220> FEATURE:
<221> NAME/KEY: MISC_FEATURE
<222> LOCATION: (17)..(17)
<223> OTHER INFORMATION: The amino acid at the noted position is
      optionally phosphorylated
<220> FEATURE:
<221> NAME/KEY: MISC_FEATURE
<222> LOCATION: (18)..(18)
<223> OTHER INFORMATION: The amino acid at the noted position is
      optionally phosphorylated

<400> SEQUENCE: 317

His Lys Gly Glu Ile Arg Gly Ala Ser Thr Pro Phe Gln Phe Arg Ala
1               5                   10                  15

Ser Ser Pro

<210> SEQ ID NO 318
<211> LENGTH: 10
<212> TYPE: PRT
<213> ORGANISM: Homo sapiens
<220> FEATURE:
<221> NAME/KEY: MISC_FEATURE
<222> LOCATION: (6)..(6)
<223> OTHER INFORMATION: The amino acid at the noted position is
      optionally phosphorylated

<400> SEQUENCE: 318

Ser Thr Ile Gln Asn Ser Pro Thr Lys Lys
1               5                   10
```

<210> SEQ ID NO 319
<211> LENGTH: 10
<212> TYPE: PRT
<213> ORGANISM: Homo sapiens
<220> FEATURE:
<221> NAME/KEY: MISC_FEATURE
<222> LOCATION: (4)..(4)
<223> OTHER INFORMATION: The amino acid at the noted position is
      optionally phosphorylated

<400> SEQUENCE: 319

Arg Ser Tyr Ser Pro Asp His Arg Gln Lys
1               5                   10

<210> SEQ ID NO 320
<211> LENGTH: 13
<212> TYPE: PRT
<213> ORGANISM: Homo sapiens
<220> FEATURE:
<221> NAME/KEY: MISC_FEATURE
<222> LOCATION: (9)..(9)
<223> OTHER INFORMATION: The amino acid at the noted position is
      optionally phosphorylated

<400> SEQUENCE: 320

Phe Asp Lys His Thr Leu Gly Asp Ser Asp Asn Glu Ser
1               5                   10

<210> SEQ ID NO 321
<211> LENGTH: 21
<212> TYPE: PRT
<213> ORGANISM: Homo sapiens
<220> FEATURE:
<221> NAME/KEY: MISC_FEATURE
<222> LOCATION: (4)..(4)
<223> OTHER INFORMATION: The amino acid at the noted position is
      optionally phosphorylated
<220> FEATURE:
<221> NAME/KEY: MISC_FEATURE
<222> LOCATION: (8)..(8)
<223> OTHER INFORMATION: The amino acid at the noted position is
      optionally phosphorylated

<400> SEQUENCE: 321

Glu Pro Ala Ser Pro Ala Ala Ser Ile Ser Arg Leu Ser Gly Glu Gln
1               5                   10                  15

Val Asp Gly Lys Gly
            20

<210> SEQ ID NO 322
<211> LENGTH: 18
<212> TYPE: PRT
<213> ORGANISM: Homo sapiens
<220> FEATURE:
<221> NAME/KEY: MISC_FEATURE
<222> LOCATION: (10)..(10)
<223> OTHER INFORMATION: The amino acid at the noted position is
      optionally phosphorylated

<400> SEQUENCE: 322

Ser Pro Ala Ala Ser Ile Ser Arg Leu Ser Gly Glu Gln Val Asp Gly
1               5                   10                  15

Lys Gly

<210> SEQ ID NO 323
<211> LENGTH: 15
<212> TYPE: PRT

```
<213> ORGANISM: Homo sapiens
<220> FEATURE:
<221> NAME/KEY: MISC_FEATURE
<222> LOCATION: (7)..(7)
<223> OTHER INFORMATION: The amino acid at the noted position is
      optionally phosphorylated

<400> SEQUENCE: 323

Ala Ser Ile Ser Arg Leu Ser Gly Glu Gln Val Asp Gly Lys Gly
1               5                   10                  15

<210> SEQ ID NO 324
<211> LENGTH: 15
<212> TYPE: PRT
<213> ORGANISM: Homo sapiens
<220> FEATURE:
<221> NAME/KEY: MISC_FEATURE
<222> LOCATION: (2)..(2)
<223> OTHER INFORMATION: The amino acid at the noted position is
      optionally phosphorylated
<220> FEATURE:
<221> NAME/KEY: MISC_FEATURE
<222> LOCATION: (7)..(7)
<223> OTHER INFORMATION: The amino acid at the noted position is
      optionally phosphorylated

<400> SEQUENCE: 324

Ala Ser Ile Ser Arg Leu Ser Gly Glu Gln Val Asp Gly Lys Gly
1               5                   10                  15

<210> SEQ ID NO 325
<211> LENGTH: 15
<212> TYPE: PRT
<213> ORGANISM: Homo sapiens
<220> FEATURE:
<221> NAME/KEY: MISC_FEATURE
<222> LOCATION: (2)..(2)
<223> OTHER INFORMATION: The amino acid at the noted position is
      optionally phosphorylated

<400> SEQUENCE: 325

Ala Ser Ile Ser Arg Leu Ser Gly Glu Gln Val Asp Gly Lys Gly
1               5                   10                  15

<210> SEQ ID NO 326
<211> LENGTH: 13
<212> TYPE: PRT
<213> ORGANISM: Homo sapiens
<220> FEATURE:
<221> NAME/KEY: MISC_FEATURE
<222> LOCATION: (4)..(4)
<223> OTHER INFORMATION: The amino acid at the noted position is
      optionally phosphorylated

<400> SEQUENCE: 326

Thr Thr Lys Ser Val Lys Ala Leu Ser Ser Leu His Gly
1               5                   10

<210> SEQ ID NO 327
<211> LENGTH: 15
<212> TYPE: PRT
<213> ORGANISM: Homo sapiens
<220> FEATURE:
<221> NAME/KEY: MISC_FEATURE
<222> LOCATION: (4)..(4)
<223> OTHER INFORMATION: The amino acid at the noted position is
      optionally phosphorylated

<400> SEQUENCE: 327

Thr Thr Lys Ser Val Lys Ala Leu Ser Ser Leu His Gly Asp Asp
```

<210> SEQ ID NO 328
<211> LENGTH: 16
<212> TYPE: PRT
<213> ORGANISM: Homo sapiens
<220> FEATURE:
<221> NAME/KEY: MISC_FEATURE
<222> LOCATION: (4)..(4)
<223> OTHER INFORMATION: The amino acid at the noted position is
      optionally phosphorylated

<400> SEQUENCE: 328

Thr Thr Lys Ser Val Lys Ala Leu Ser Ser Leu His Gly Asp Asp Gln
1               5                   10                  15

<210> SEQ ID NO 329
<211> LENGTH: 17
<212> TYPE: PRT
<213> ORGANISM: Homo sapiens
<220> FEATURE:
<221> NAME/KEY: MISC_FEATURE
<222> LOCATION: (4)..(4)
<223> OTHER INFORMATION: The amino acid at the noted position is
      optionally phosphorylated

<400> SEQUENCE: 329

Thr Thr Lys Ser Val Lys Ala Leu Ser Ser Leu His Gly Asp Asp Gln
1               5                   10                  15

Asp

<210> SEQ ID NO 330
<211> LENGTH: 18
<212> TYPE: PRT
<213> ORGANISM: Homo sapiens
<220> FEATURE:
<221> NAME/KEY: MISC_FEATURE
<222> LOCATION: (4)..(4)
<223> OTHER INFORMATION: The amino acid at the noted position is
      optionally phosphorylated

<400> SEQUENCE: 330

Thr Thr Lys Ser Val Lys Ala Leu Ser Ser Leu His Gly Asp Asp Gln
1               5                   10                  15

Asp Ser

<210> SEQ ID NO 331
<211> LENGTH: 14
<212> TYPE: PRT
<213> ORGANISM: Homo sapiens
<220> FEATURE:
<221> NAME/KEY: MISC_FEATURE
<222> LOCATION: (3)..(3)
<223> OTHER INFORMATION: The amino acid at the noted position is
      optionally phosphorylated

<400> SEQUENCE: 331

Thr Lys Ser Val Lys Ala Leu Ser Ser Leu His Gly Asp Asp
1               5                   10

<210> SEQ ID NO 332
<211> LENGTH: 15
<212> TYPE: PRT
<213> ORGANISM: Homo sapiens
<220> FEATURE:
<221> NAME/KEY: MISC_FEATURE
<222> LOCATION: (3)..(3)
<223> OTHER INFORMATION: The amino acid at the noted position is optionally phosphorylated

<400> SEQUENCE: 332

Thr Lys Ser Val Lys Ala Leu Ser Ser Leu His Gly Asp Asp Gln
1               5                   10                  15

<210> SEQ ID NO 333
<211> LENGTH: 16
<212> TYPE: PRT
<213> ORGANISM: Homo sapiens
<220> FEATURE:
<221> NAME/KEY: MISC_FEATURE
<222> LOCATION: (3)..(3)
<223> OTHER INFORMATION: The amino acid at the noted position is
      optionally phosphorylated

<400> SEQUENCE: 333

Thr Lys Ser Val Lys Ala Leu Ser Ser Leu His Gly Asp Asp Gln Asp
1               5                   10                  15

<210> SEQ ID NO 334
<211> LENGTH: 14
<212> TYPE: PRT
<213> ORGANISM: Homo sapiens
<220> FEATURE:
<221> NAME/KEY: MISC_FEATURE
<222> LOCATION: (2)..(2)
<223> OTHER INFORMATION: The amino acid at the noted position is
      optionally phosphorylated

<400> SEQUENCE: 334

Lys Ser Val Lys Ala Leu Ser Ser Leu His Gly Asp Asp Gln
1               5                   10

<210> SEQ ID NO 335
<211> LENGTH: 15
<212> TYPE: PRT
<213> ORGANISM: Homo sapiens
<220> FEATURE:
<221> NAME/KEY: MISC_FEATURE
<222> LOCATION: (2)..(2)
<223> OTHER INFORMATION: The amino acid at the noted position is
      optionally phosphorylated

<400> SEQUENCE: 335

Lys Ser Val Lys Ala Leu Ser Ser Leu His Gly Asp Asp Gln Asp
1               5                   10                  15

<210> SEQ ID NO 336
<211> LENGTH: 20
<212> TYPE: PRT
<213> ORGANISM: Homo sapiens
<220> FEATURE:
<221> NAME/KEY: MISC_FEATURE
<222> LOCATION: (18)..(18)
<223> OTHER INFORMATION: The amino acid at the noted position is
      optionally phosphorylated

<400> SEQUENCE: 336

Thr Thr Lys Ser Val Lys Ala Leu Ser Ser Leu His Gly Asp Asp Gln
1               5                   10                  15

Asp Ser Glu Asp
            20

<210> SEQ ID NO 337
<211> LENGTH: 21
<212> TYPE: PRT
<213> ORGANISM: Homo sapiens

```
<220> FEATURE:
<221> NAME/KEY: MISC_FEATURE
<222> LOCATION: (18)..(18)
<223> OTHER INFORMATION: The amino acid at the noted position is
      optionally phosphorylated

<400> SEQUENCE: 337

Thr Thr Lys Ser Val Lys Ala Leu Ser Ser Leu His Gly Asp Asp Gln
1               5                   10                  15

Asp Ser Glu Asp Glu
            20

<210> SEQ ID NO 338
<211> LENGTH: 19
<212> TYPE: PRT
<213> ORGANISM: Homo sapiens
<220> FEATURE:
<221> NAME/KEY: MISC_FEATURE
<222> LOCATION: (16)..(16)
<223> OTHER INFORMATION: The amino acid at the noted position is
      optionally phosphorylated

<400> SEQUENCE: 338

Lys Ser Val Lys Ala Leu Ser Ser Leu His Gly Asp Asp Gln Asp Ser
1               5                   10                  15

Glu Asp Glu

<210> SEQ ID NO 339
<211> LENGTH: 13
<212> TYPE: PRT
<213> ORGANISM: Homo sapiens
<220> FEATURE:
<221> NAME/KEY: MISC_FEATURE
<222> LOCATION: (9)..(9)
<223> OTHER INFORMATION: The amino acid at the noted position is
      optionally phosphorylated

<400> SEQUENCE: 339

Lys Leu Val Ser Phe His Asp Asp Ser Asp Glu Asp Leu
1               5                   10

<210> SEQ ID NO 340
<211> LENGTH: 12
<212> TYPE: PRT
<213> ORGANISM: Homo sapiens
<220> FEATURE:
<221> NAME/KEY: MISC_FEATURE
<222> LOCATION: (10)..(10)
<223> OTHER INFORMATION: The amino acid at the noted position is
      optionally phosphorylated

<400> SEQUENCE: 340

Ala Pro Ser Thr Tyr Ala His Leu Ser Pro Ala Lys
1               5                   10

<210> SEQ ID NO 341
<211> LENGTH: 17
<212> TYPE: PRT
<213> ORGANISM: Homo sapiens
<220> FEATURE:
<221> NAME/KEY: MISC_FEATURE
<222> LOCATION: (9)..(9)
<223> OTHER INFORMATION: The amino acid at the noted position is
      optionally phosphorylated

<400> SEQUENCE: 341

Ala Pro Ser Thr Tyr Ala His Leu Ser Pro Ala Lys Thr Pro Pro Pro
1               5                   10                  15
```

Pro

<210> SEQ ID NO 342
<211> LENGTH: 13
<212> TYPE: PRT
<213> ORGANISM: Homo sapiens
<220> FEATURE:
<221> NAME/KEY: MISC_FEATURE
<222> LOCATION: (8)..(8)
<223> OTHER INFORMATION: The amino acid at the noted position is
      optionally phosphorylated

<400> SEQUENCE: 342

Asn Arg Ala Met Arg Arg Val Ser Ser Val Pro Ser Arg
1               5                   10

<210> SEQ ID NO 343
<211> LENGTH: 15
<212> TYPE: PRT
<213> ORGANISM: Homo sapiens
<220> FEATURE:
<221> NAME/KEY: MISC_FEATURE
<222> LOCATION: (8)..(8)
<223> OTHER INFORMATION: The amino acid at the noted position is
      optionally phosphorylated

<400> SEQUENCE: 343

Asn Arg Ala Met Arg Arg Val Ser Ser Val Pro Ser Arg Ala Gln
1               5                   10                  15

<210> SEQ ID NO 344
<211> LENGTH: 19
<212> TYPE: PRT
<213> ORGANISM: Homo sapiens
<220> FEATURE:
<221> NAME/KEY: MISC_FEATURE
<222> LOCATION: (4)..(4)
<223> OTHER INFORMATION: The amino acid at the noted position is
      optionally phosphorylated
<220> FEATURE:
<221> NAME/KEY: MISC_FEATURE
<222> LOCATION: (6)..(6)
<223> OTHER INFORMATION: The amino acid at the noted position is
      optionally phosphorylated

<400> SEQUENCE: 344

Arg Pro Ala Ser Pro Thr Ala Ile Arg Arg Ile Gly Ser Val Thr Ser
1               5                   10                  15

Arg Gln Thr

<210> SEQ ID NO 345
<211> LENGTH: 19
<212> TYPE: PRT
<213> ORGANISM: Homo sapiens
<220> FEATURE:
<221> NAME/KEY: MISC_FEATURE
<222> LOCATION: (1)..(1)
<223> OTHER INFORMATION: The amino acid at the noted position is
      optionally phosphorylated

<400> SEQUENCE: 345

Ser Gly Gly Asp Asp Asp Trp Thr His Leu Ser Ser Lys Glu Val Asp
1               5                   10                  15

Pro Ser Thr

<210> SEQ ID NO 346
<211> LENGTH: 20

```
<212> TYPE: PRT
<213> ORGANISM: Homo sapiens
<220> FEATURE:
<221> NAME/KEY: MISC_FEATURE
<222> LOCATION: (1)..(1)
<223> OTHER INFORMATION: The amino acid at the noted position is
      optionally phosphorylated

<400> SEQUENCE: 346

Ser Gly Gly Asp Asp Asp Trp Thr His Leu Ser Ser Lys Glu Val Asp
1               5                   10                  15

Pro Ser Thr Gly
            20

<210> SEQ ID NO 347
<211> LENGTH: 21
<212> TYPE: PRT
<213> ORGANISM: Homo sapiens
<220> FEATURE:
<221> NAME/KEY: MISC_FEATURE
<222> LOCATION: (1)..(1)
<223> OTHER INFORMATION: The amino acid at the noted position is
      optionally phosphorylated

<400> SEQUENCE: 347

Ser Gly Gly Asp Asp Asp Trp Thr His Leu Ser Ser Lys Glu Val Asp
1               5                   10                  15

Pro Ser Thr Gly Glu
            20

<210> SEQ ID NO 348
<211> LENGTH: 22
<212> TYPE: PRT
<213> ORGANISM: Homo sapiens
<220> FEATURE:
<221> NAME/KEY: MISC_FEATURE
<222> LOCATION: (1)..(1)
<223> OTHER INFORMATION: The amino acid at the noted position is
      optionally phosphorylated

<400> SEQUENCE: 348

Ser Gly Gly Asp Asp Asp Trp Thr His Leu Ser Ser Lys Glu Val Asp
1               5                   10                  15

Pro Ser Thr Gly Glu Leu
            20

<210> SEQ ID NO 349
<211> LENGTH: 23
<212> TYPE: PRT
<213> ORGANISM: Homo sapiens
<220> FEATURE:
<221> NAME/KEY: MISC_FEATURE
<222> LOCATION: (1)..(1)
<223> OTHER INFORMATION: The amino acid at the noted position is
      optionally phosphorylated

<400> SEQUENCE: 349

Ser Gly Gly Asp Asp Asp Trp Thr His Leu Ser Ser Lys Glu Val Asp
1               5                   10                  15

Pro Ser Thr Gly Glu Leu Gln
            20

<210> SEQ ID NO 350
<211> LENGTH: 17
<212> TYPE: PRT
<213> ORGANISM: Homo sapiens
<220> FEATURE:
```

```
<221> NAME/KEY: MISC_FEATURE
<222> LOCATION: (10)..(10)
<223> OTHER INFORMATION: The amino acid at the noted position is
      optionally phosphorylated

<400> SEQUENCE: 350

Gly Gly Asp Asp Asp Trp Thr His Leu Ser Ser Lys Glu Val Asp Pro
1               5                   10                  15

Ser

<210> SEQ ID NO 351
<211> LENGTH: 19
<212> TYPE: PRT
<213> ORGANISM: Homo sapiens
<220> FEATURE:
<221> NAME/KEY: MISC_FEATURE
<222> LOCATION: (10)..(10)
<223> OTHER INFORMATION: The amino acid at the noted position is
      optionally phosphorylated

<400> SEQUENCE: 351

Gly Gly Asp Asp Asp Trp Thr His Leu Ser Ser Lys Glu Val Asp Pro
1               5                   10                  15

Ser Thr Gly

<210> SEQ ID NO 352
<211> LENGTH: 14
<212> TYPE: PRT
<213> ORGANISM: Homo sapiens
<220> FEATURE:
<221> NAME/KEY: MISC_FEATURE
<222> LOCATION: (9)..(9)
<223> OTHER INFORMATION: The amino acid at the noted position is
      optionally phosphorylated

<400> SEQUENCE: 352

Gly Asp Asp Asp Trp Thr His Leu Ser Ser Lys Glu Val Asp
1               5                   10

<210> SEQ ID NO 353
<211> LENGTH: 15
<212> TYPE: PRT
<213> ORGANISM: Homo sapiens
<220> FEATURE:
<221> NAME/KEY: MISC_FEATURE
<222> LOCATION: (9)..(9)
<223> OTHER INFORMATION: The amino acid at the noted position is
      optionally phosphorylated

<400> SEQUENCE: 353

Gly Asp Asp Asp Trp Thr His Leu Ser Ser Lys Glu Val Asp Pro
1               5                   10                  15

<210> SEQ ID NO 354
<211> LENGTH: 16
<212> TYPE: PRT
<213> ORGANISM: Homo sapiens
<220> FEATURE:
<221> NAME/KEY: MISC_FEATURE
<222> LOCATION: (9)..(9)
<223> OTHER INFORMATION: The amino acid at the noted position is
      optionally phosphorylated

<400> SEQUENCE: 354

Gly Asp Asp Asp Trp Thr His Leu Ser Ser Lys Glu Val Asp Pro Ser
1               5                   10                  15
```

-continued

```
<210> SEQ ID NO 355
<211> LENGTH: 18
<212> TYPE: PRT
<213> ORGANISM: Homo sapiens
<220> FEATURE:
<221> NAME/KEY: MISC_FEATURE
<222> LOCATION: (9)..(9)
<223> OTHER INFORMATION: The amino acid at the noted position is
      optionally phosphorylated

<400> SEQUENCE: 355

Gly Asp Asp Asp Trp Thr His Leu Ser Ser Lys Glu Val Asp Pro Ser
1               5                   10                  15

Thr Gly

<210> SEQ ID NO 356
<211> LENGTH: 15
<212> TYPE: PRT
<213> ORGANISM: Homo sapiens
<220> FEATURE:
<221> NAME/KEY: MISC_FEATURE
<222> LOCATION: (8)..(8)
<223> OTHER INFORMATION: The amino acid at the noted position is
      optionally phosphorylated

<400> SEQUENCE: 356

Asp Asp Asp Trp Thr His Leu Ser Ser Lys Glu Val Asp Pro Ser
1               5                   10                  15

<210> SEQ ID NO 357
<211> LENGTH: 17
<212> TYPE: PRT
<213> ORGANISM: Homo sapiens
<220> FEATURE:
<221> NAME/KEY: MISC_FEATURE
<222> LOCATION: (8)..(8)
<223> OTHER INFORMATION: The amino acid at the noted position is
      optionally phosphorylated

<400> SEQUENCE: 357

Asp Asp Asp Trp Thr His Leu Ser Ser Lys Glu Val Asp Pro Ser Thr
1               5                   10                  15

Gly

<210> SEQ ID NO 358
<211> LENGTH: 14
<212> TYPE: PRT
<213> ORGANISM: Homo sapiens
<220> FEATURE:
<221> NAME/KEY: MISC_FEATURE
<222> LOCATION: (7)..(7)
<223> OTHER INFORMATION: The amino acid at the noted position is
      optionally phosphorylated

<400> SEQUENCE: 358

Asp Asp Trp Thr His Leu Ser Ser Lys Glu Val Asp Pro Ser
1               5                   10

<210> SEQ ID NO 359
<211> LENGTH: 13
<212> TYPE: PRT
<213> ORGANISM: Homo sapiens
<220> FEATURE:
<221> NAME/KEY: MISC_FEATURE
<222> LOCATION: (6)..(6)
<223> OTHER INFORMATION: The amino acid at the noted position is
      optionally phosphorylated

<400> SEQUENCE: 359
```

Asp Trp Thr His Leu Ser Ser Lys Glu Val Asp Pro Ser
1               5                   10

<210> SEQ ID NO 360
<211> LENGTH: 15
<212> TYPE: PRT
<213> ORGANISM: Homo sapiens
<220> FEATURE:
<221> NAME/KEY: MISC_FEATURE
<222> LOCATION: (6)..(6)
<223> OTHER INFORMATION: The amino acid at the noted position is
      optionally phosphorylated

<400> SEQUENCE: 360

Asp Trp Thr His Leu Ser Ser Lys Glu Val Asp Pro Ser Thr Gly
1               5                   10                  15

<210> SEQ ID NO 361
<211> LENGTH: 12
<212> TYPE: PRT
<213> ORGANISM: Homo sapiens
<220> FEATURE:
<221> NAME/KEY: MISC_FEATURE
<222> LOCATION: (5)..(5)
<223> OTHER INFORMATION: The amino acid at the noted position is
      optionally phosphorylated

<400> SEQUENCE: 361

Trp Thr His Leu Ser Ser Lys Glu Val Asp Pro Ser
1               5                   10

<210> SEQ ID NO 362
<211> LENGTH: 14
<212> TYPE: PRT
<213> ORGANISM: Homo sapiens
<220> FEATURE:
<221> NAME/KEY: MISC_FEATURE
<222> LOCATION: (5)..(5)
<223> OTHER INFORMATION: The amino acid at the noted position is
      optionally phosphorylated

<400> SEQUENCE: 362

Trp Thr His Leu Ser Ser Lys Glu Val Asp Pro Ser Thr Gly
1               5                   10

<210> SEQ ID NO 363
<211> LENGTH: 13
<212> TYPE: PRT
<213> ORGANISM: Homo sapiens
<220> FEATURE:
<221> NAME/KEY: MISC_FEATURE
<222> LOCATION: (2)..(2)
<223> OTHER INFORMATION: The amino acid at the noted position is
      optionally phosphorylated

<400> SEQUENCE: 363

Gly Thr Leu Arg Arg Ser Asp Ser Gln Gln Ala Val Lys
1               5                   10

<210> SEQ ID NO 364
<211> LENGTH: 14
<212> TYPE: PRT
<213> ORGANISM: Homo sapiens
<220> FEATURE:
<221> NAME/KEY: MISC_FEATURE
<222> LOCATION: (2)..(2)
<223> OTHER INFORMATION: The amino acid at the noted position is
      optionally phosphorylated

```
<400> SEQUENCE: 364

Gly Thr Leu Arg Arg Ser Asp Ser Gln Gln Ala Val Lys Ser
1               5                   10

<210> SEQ ID NO 365
<211> LENGTH: 16
<212> TYPE: PRT
<213> ORGANISM: Homo sapiens
<220> FEATURE:
<221> NAME/KEY: MISC_FEATURE
<222> LOCATION: (2)..(2)
<223> OTHER INFORMATION: The amino acid at the noted position is
      optionally phosphorylated

<400> SEQUENCE: 365

Gly Thr Leu Arg Arg Ser Asp Ser Gln Gln Ala Val Lys Ser Pro Pro
1               5                   10                  15

<210> SEQ ID NO 366
<211> LENGTH: 12
<212> TYPE: PRT
<213> ORGANISM: Homo sapiens
<220> FEATURE:
<221> NAME/KEY: MISC_FEATURE
<222> LOCATION: (7)..(7)
<223> OTHER INFORMATION: The amino acid at the noted position is
      optionally phosphorylated
<220> FEATURE:
<221> NAME/KEY: MISC_FEATURE
<222> LOCATION: (8)..(8)
<223> OTHER INFORMATION: The amino acid at the noted position is
      optionally phosphorylated

<400> SEQUENCE: 366

Val Leu Lys Ser Arg Lys Ser Ser Val Thr Glu Glu
1               5                   10

<210> SEQ ID NO 367
<211> LENGTH: 12
<212> TYPE: PRT
<213> ORGANISM: Artificial Sequence
<220> FEATURE:
<223> OTHER INFORMATION: Artificially synthesized peptide
<220> FEATURE:
<221> NAME/KEY: MISC_FEATURE
<222> LOCATION: (3)..(3)
<223> OTHER INFORMATION: Xaa can be any naturally occurring amino acid

<400> SEQUENCE: 367

Ala Lys Xaa Val Ala Ala Trp Thr Leu Lys Ala Ala
1               5                   10

<210> SEQ ID NO 368
<211> LENGTH: 15
<212> TYPE: PRT
<213> ORGANISM: Clostridium tetani

<400> SEQUENCE: 368

Gln Tyr Ile Lys Ala Asn Ser Lys Phe Ile Gly Ile Thr Glu Leu
1               5                   10                  15
```